US006428955B1

(12) United States Patent
Köster et al.

(10) Patent No.: US 6,428,955 B1
(45) Date of Patent: *Aug. 6, 2002

(54) DNA DIAGNOSTICS BASED ON MASS SPECTROMETRY

(75) Inventors: Hubert Köster, Concord; Kai Tang, Brighton, both of MA (US); Dong-Jing Fu, San Diego, CA (US); Carsten W. Siegert, Hamburg (DE); Daniel P. Little; Andreas Braun, both of San Diego, CA (US); Brigitte Darnhofer-Demar; Christian Jurinke, both of Hamburg (DE); Dirk Van den Boom, Dreieich (DE)

(73) Assignee: Sequenom, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/744,481

(22) Filed: Nov. 6, 1996

Related U.S. Application Data

(63) Continuation-in-part of application No. 08/617,256, filed on Mar. 18, 1996, which is a continuation-in-part of application No. 08/406,199, filed on Mar. 17, 1995.

(51) Int. Cl.$^7$ ............................. C12Q 1/68; C12P 19/34
(52) U.S. Cl. ........................................ 435/6; 435/91.2
(58) Field of Search ..................................... 435/6, 91.2

(56) References Cited

U.S. PATENT DOCUMENTS

| | | | | |
|---|---|---|---|---|
| 3,568,735 A | 3/1971 | Lancaster | ................... | 141/238 |
| 3,776,700 A | 12/1973 | Gallant | ...................... | 422/65 |
| 3,807,235 A | 4/1974 | Lefkovitz | ................ | 73/863.32 |
| 3,999,689 A | 12/1976 | Ciantro et al. | .............. | 222/108 |
| 4,139,346 A | 2/1979 | Rabbani | ..................... | 422/56 |
| 4,442,354 A | 4/1984 | Hurst et al. | ................. | 250/281 |
| 4,461,328 A | 7/1984 | Kenney | ..................... | 422/100 |
| 4,548,245 A | 10/1985 | Crandell et al. | ........... | 141/237 |
| 4,554,839 A | 11/1985 | Hewett et al. | ........... | 73/864.16 |
| 4,582,789 A | 4/1986 | Sheldon, III et al. | ........... | 435/6 |
| 4,683,194 A | 7/1987 | Saiki et al. | ..................... | 435/6 |
| 4,683,195 A | 7/1987 | Mullis et al. | .................. | 435/6 |
| 4,725,677 A | 2/1988 | Köster et al. | ................. | 536/27 |
| 4,729,947 A | 3/1988 | Middendorf et al. | ........... | 435/6 |
| 4,731,335 A | 3/1988 | Brigati | ....................... | 436/180 |
| 4,757,141 A | 7/1988 | Fung et al. | ................... | 536/27 |
| 4,779,467 A | 10/1988 | Rainin et al. | ............ | 73/864.17 |
| 4,797,355 A | 1/1989 | Stabinsky | ...................... | 435/6 |
| 4,798,706 A | 1/1989 | Brigati | ....................... | 422/102 |
| 4,806,546 A | 2/1989 | Carrico et al. | ................. | 536/27 |
| 4,844,298 A | 7/1989 | Ohoka et al. | ................. | 222/58 |
| 4,855,225 A | 8/1989 | Fung et al. | ..................... | 435/6 |
| 4,877,745 A | 10/1989 | Hayes et al. | ................. | 436/166 |

(List continued on next page.)

FOREIGN PATENT DOCUMENTS

| | | |
|---|---|---|
| DE | 4431174 | 3/1996 |
| DE | 4438630 | 5/1996 |
| EP | 0268237 | 5/1988 |
| EP | 0269520 | 6/1988 |
| EP | 0339781 | 11/1989 |
| EP | 0360677 | 3/1990 |
| EP | 0396116 | 11/1990 |
| EP | 0412883 | 2/1991 |
| EP | 0455905 | 11/1991 |
| EP | 0500506 | 8/1992 |
| EP | 0593789 | 4/1994 |
| EP | 0655501 | 5/1995 |
| EP | 0785278 | 7/1997 |
| EP | 0648280 | 5/1999 |
| GB | 2017105 | 3/1979 |
| GB | 2260811 | 4/1993 |
| JP | 63230086 | 9/1988 |
| JP | 2215399 | 8/1990 |
| JP | 6294796 | 10/1994 |
| JP | 8290377 | 11/1996 |
| WO | 8402579 | 7/1984 |
| WO | 8903432 | 4/1989 |
| WO | 8906700 | 7/1989 |

(List continued on next page.)

OTHER PUBLICATIONS

Khrapko et al, DNA Sequence—J. DNA Sequencing 1:375–388 & Mapping, 1991.*

Schlesinger (editor) Macromolecular Sequencing pp. 127–149, 1988.*

Siegert et al. "Matrix–assisted laser desorption/ionization time–of–flight mass spectrometry for the detection of polymerase chain reaction products containing 7–deazapurine moieties" *Anal. Biochem.* 243:55–65 (1996).

Ardrey, "Electrospray mass spectrometry", *Spectroscopy Europe* 4(4):10–18 (1992).

Arshady, Reza, Beaded polymer supports and gels: I. Manufacturing techniques, *Journal of Chromatography*, 586:181–197 (1991).

Arshady, Reza, Beaded polymer supports and gels: II. Physico–chemical criteria and functionalization, *Journal of Chromatography*, 586:199–219 (1991).

Barany, F., Genentic disease detection and DNA amplification using cloned thermostable ligase, *Proc. Natl. Acad. Sci.* 88:189–193 (1991).

Barrell B., "DNA sequencing: present limitations and prospects for the future", *FASEB Journal* 5:40–45 (1991).

(List continued on next page.)

*Primary Examiner*—Eggerton A. Campbell
(74) *Attorney, Agent, or Firm*—Stephanie L. Seidman; Heller Ehrman White & McAuliffe LLP

(57) ABSTRACT

The invention provides fast and highly accurate mass spectrometer based processes for detecting a particular nucleic acid sequence in a biological sample. Depending on the sequence to be detected, the processes can be used, for example, to diagnose a genetic disease or chromosomal abnormality; a predisposition to a disease or condition, infection by a pathogenic organism, or for determining identity or heredity.

18 Claims, 88 Drawing Sheets

U.S. PATENT DOCUMENTS

| | | | | |
|---|---|---|---|---|
| 4,882,127 | A | 11/1989 | Rosenthal et al. | 422/50 |
| 4,902,481 | A | 2/1990 | Clark et al. | 422/101 |
| 4,925,629 | A | 5/1990 | Schramm | 422/82.05 |
| 4,931,400 | A | 6/1990 | Jitsukawa | 435/287 |
| 4,948,442 | A | 8/1990 | Manns | 156/73.1 |
| 4,948,882 | A | 8/1990 | Ruth | 536/27 |
| 4,952,518 | A | 8/1990 | Johnson et al. | 436/518 |
| 4,983,521 | A | 1/1991 | Lingappa et al. | 435/172.3 |
| 4,994,373 | A | 2/1991 | Stavrianopoulos et al. | 435/6 |
| 5,000,921 | A | 3/1991 | Hanaway et al. | 422/100 |
| 5,003,059 | A | 3/1991 | Brennan | 536/27 |
| 5,023,187 | A | 6/1991 | Koebler et al. | 436/180 |
| 5,045,694 | A | 9/1991 | Beavis et al. | 250/287 |
| 5,047,215 | A | 9/1991 | Manns | 422/101 |
| 5,064,754 | A | 11/1991 | Mills | 435/6 |
| 5,077,210 | A | 12/1991 | Eigler et al. | 435/176 |
| 5,082,935 | A | 1/1992 | Cruickshank | 536/27 |
| 5,108,703 | A | 4/1992 | Pfost et al. | 422/65 |
| 5,118,937 | A | 6/1992 | Hillenkamp et al. | 250/282 |
| 5,135,870 | A | 8/1992 | Williams et al. | 436/86 |
| 5,143,854 | A | 9/1992 | Pirrung et al. | 436/518 |
| 5,149,625 | A | 9/1992 | Church et al. | 435/6 |
| 5,195,657 | A | 3/1993 | Wells | 222/330 |
| 5,210,412 | A | 5/1993 | Levis et al. | 250/288 |
| 5,221,518 | A | 6/1993 | Mills | 422/62 |
| 5,234,824 | A | 8/1993 | Mullis | 435/91 |
| 5,237,016 | A | 8/1993 | Ghosh et al. | 525/329.4 |
| 5,242,974 | A | 9/1993 | Holmes | 525/54.1 |
| 5,262,128 | A | 11/1993 | Leighton et al. | 422/100 |
| 5,283,342 | A | 2/1994 | Gustavson et al. | 548/304.1 |
| 5,288,644 | A | 2/1994 | Beavis et al. | 436/94 |
| 5,312,233 | A | 5/1994 | Tanny et al. | 417/316 |
| 5,338,688 | A | 8/1994 | Deeg et al. | 436/180 |
| 5,380,833 | A | 1/1995 | Urdea | 536/22.1 |
| 5,403,711 | A | 4/1995 | Walder et al. | 435/6 |
| 5,410,068 | A | 4/1995 | Coull et al. | 548/545 |
| 5,430,136 | A | 7/1995 | Urdea et al. | 536/243 |
| 5,436,327 | A | 7/1995 | Southern et al. | 536/25.34 |
| 5,439,649 | A | 8/1995 | Tseung et al. | 422/99 |
| 5,457,041 | A | 10/1995 | Ginaven et al. | 435/172.1 |
| 5,474,895 | A | 12/1995 | Ishii et al. | 435/6 |
| 5,478,893 | A | 12/1995 | Ghosh et al. | 525/329.4 |
| 5,484,701 | A | 1/1996 | Cocuzza et al. | 435/6 |
| 5,492,817 | A | 2/1996 | Thompson et al. | 435/68.1 |
| 5,503,980 | A | 4/1996 | Cantor | 435/6 |
| 5,506,348 | A | 4/1996 | Pieles | 536/23.1 |
| 5,512,295 | A | 4/1996 | Kornberg et al. | 424/450 |
| 5,512,439 | A | 4/1996 | Hornes et al. | 435/6 |
| 5,514,548 | A | 5/1996 | Krebber et al. | 436/6 |
| 5,527,675 | A | 6/1996 | Coull et al. | 435/6 |
| 5,541,313 | A | 7/1996 | Ruth | 536/24.3 |
| 5,545,539 | A | 8/1996 | Miller | 435/91.2 |
| 5,547,835 | A | 8/1996 | Köster et al. | 435/6 |
| 5,571,669 | A | 11/1996 | Lu et al. | 435/6 |
| 5,580,733 | A | 12/1996 | Levis et al. | 435/6 |
| 5,589,136 | A | 12/1996 | Northrup et al. | 422/102 |
| 5,599,500 | A | 2/1997 | Jones | 422/62 |
| 5,601,982 | A | 2/1997 | Sargent et al. | 435/6 |
| 5,604,099 | A | 2/1997 | Erlich et al. | 435/6 |
| 5,605,662 | A | 2/1997 | Heller | 422/68.1 |
| 5,605,798 | A | 2/1997 | Köster et al. | 435/6 |
| 5,612,474 | A | 3/1997 | Patel | 536/27.14 |
| 5,622,824 | A | 4/1997 | Köster et al. | 435/6 |
| 5,622,829 | A | 4/1997 | King et al. | 435/6 |
| 5,624,711 | A | 4/1997 | Sundberg et al. | 427/261 |
| 5,631,134 | A | 5/1997 | Cantor | 435/6 |
| 5,641,959 | A | 6/1997 | Holle et al. | 250/287 |
| 5,643,722 | A | 7/1997 | Rothschild et al. | 435/6 |
| 5,643,798 | A | 7/1997 | Beavis et al. | 436/94 |
| 5,654,545 | A | 8/1997 | Holle et al. | 250/287 |
| 5,663,242 | A | 9/1997 | Shanker et al. | 525/329.4 |
| 5,670,322 | A | 9/1997 | Eggers et al. | 435/6 |
| 5,670,381 | A | 9/1997 | Jou et al. | 436/518 |
| 5,677,195 | A | 10/1997 | Winkler et al. | 436/518 |
| 5,688,642 | A | 11/1997 | Chrisey et al. | 435/6 |
| 5,691,141 | A | 11/1997 | Köster et al. | 435/6 |
| 5,700,642 | A | 12/1997 | Monforte et al. | 435/6 |
| 5,710,028 | A | 1/1998 | Eyal et al. | 435/91.1 |
| 5,742,049 | A | 4/1998 | Holle et al. | 250/282 |
| 5,746,373 | A | 5/1998 | Sanada | 239/102.2 |
| 5,757,392 | A | 5/1998 | Zhang | 347/14 |
| 5,795,714 | A | 8/1998 | Cantor et al. | 435/6 |
| 5,807,522 | A | 9/1998 | Brown et al. | 422/50 |
| 5,830,655 | A | 11/1998 | Monforte et al. | 435/6 |
| 5,846,710 | A | 12/1998 | Bajaj | 435/6 |
| 5,856,092 | A | 1/1999 | Dale et al. | 435/6 |
| 5,869,242 | A | 2/1999 | Kamb | 435/6 |
| 5,965,363 | A | 10/1999 | Monforte et al. | 435/6 |
| 5,976,798 | A | 11/1999 | Parker et al. | 435/6 |

FOREIGN PATENT DOCUMENTS

| | | |
|---|---|---|
| WO | 8907149 | 8/1989 |
| WO | 8909282 | 10/1989 |
| WO | 8909406 | 10/1989 |
| WO | 8910786 | 11/1989 |
| WO | 8911270 | 11/1989 |
| WO | 8912694 | 12/1989 |
| WO | 9001564 | 2/1990 |
| WO | 9003382 | 4/1990 |
| WO | 9007582 | 7/1990 |
| WO | 9014148 | 11/1990 |
| WO | 9113075 | 9/1991 |
| WO | 9115600 | 10/1991 |
| WO | 9207879 | 5/1992 |
| WO | 9210092 | 6/1992 |
| WO | 9213629 | 8/1992 |
| WO | 9215712 | 9/1992 |
| WO | 9306925 | 4/1993 |
| WO | 9309668 | 5/1993 |
| WO | 9320236 | 10/1993 |
| WO | 9323563 | 11/1993 |
| WO | 9400562 | 1/1994 |
| WO | 9411529 | 5/1994 |
| WO | 9411530 | 5/1994 |
| WO | 9411735 | 5/1994 |
| WO | 9416101 | 7/1994 |
| WO | 9421822 | 9/1994 |
| WO | 9504524 | 2/1995 |
| WO | 9513381 | 5/1995 |
| WO | 9513538 | 5/1995 |
| WO | 9515400 | 6/1995 |
| WO | 9530773 | 11/1995 |
| WO | 9531429 | 11/1995 |
| WO | 9605323 | 2/1996 |
| WO | 9610648 | 4/1996 |
| WO | 9615262 | 5/1996 |
| WO | 9617080 | 6/1996 |
| WO | 9619587 | 6/1996 |
| WO | 9629431 | 9/1996 |
| WO | 9630545 | 10/1996 |
| WO | 9632504 | 10/1996 |
| WO | WO 9632504 | * 10/1996 |
| WO | 9636731 | 11/1996 |
| WO | 9637630 | 11/1996 |
| WO | 9627681 | 12/1996 |
| WO | 9708306 | 3/1997 |
| WO | 9716699 | 5/1997 |
| WO | 9733000 | 9/1997 |
| WO | 9737041 | 10/1997 |
| WO | 9742348 | 11/1997 |
| WO | 9743617 | 11/1997 |

| WO | 9812355 | 3/1998 |
| WO | 9820020 | 5/1998 |
| WO | 9820166 | 5/1998 |
| WO | 9854571 | 12/1998 |
| WO | 9854751 | 12/1998 |

OTHER PUBLICATIONS

Batista–Viera et al., A new method for reversible immobilization of thiol biomolecules bsed on solid–phase bound thiolsulfonate groups, *App. Biochem and Biotech*, 31:175–195 (1991).

Beck and Koster, "Applications of dioxetance chemiluminescent probes tomolecular biology", *Anal. Chem.* 62:2258–2270 (1990).

Beck et al., "Chemiluminescent detection of DNA: Application of DNA sequencing and hybridization", *Nucleic Acids Res.* 17(13):5115–5123 (1989).

Braun et al., "Improved Analysis of Microsatellites Using Mass Spectrometry", *Genomics* 46:18–23 (1997).

Broude, Natalie E. et al., "Enhanced DNA sequencing by hybridization (streptavidin/biotin/stacking interaction/T4 DNA ligase/DNA polymerase)", *Proc. Natl. Acad. Sci.*, 91:3072–3076 (1994).

Brown, et al., "A single–bead decode strategy using electrospray ionization mass spectrometry and a new photolabile linker: 3–amino–3–(2–nitrophenyl) propionic acid", *Mol. Diversity* 1:4–12(1995).

Certified English translation of Japanese patent 6–294796, Nucleic acid analysis method.

Certified English translation of European patent 0412883A1, Fast screening and/or identification of a single base on a nucleic acid sequence, including applications.

Chakraborti et al., Sequence of simian immunodeficiency virus from macaque and its relationship to other human and simian retrovirues, *Nature* 328:543–547 (1987).

Chrisey et al., Covalent attachment of synthetic DNA to self–assembled monlayer films, *Nucl. Acids Res.* 24:3031–3039 (1996).

Chrisey et al., Fabrication of patterned DNA surfaces, *Nucl. Acids. Res.* 24:3040–3047 (1996).

Church et al., "Multiplex DNA Sequencing", *Science* 240:185–188 (1988).

Connolly, B. A., "Oligonucleotides containing modified bases", *Oligonucleotides and Analogues, A Practical Approach*, Edited by F. Eckstein, Oxford University Press, Ch. 7, pp. 40–45 (1991).

Crain, "Mass spectrometric techniques in nucleic acid research", *Mass Spectr. Rev.* 9:505–554 (1990).

Damha, Mased J. e al.; An improved procedure for derivatization of controlled–pore glass beads for solid–phase oligonucleotide synthesis; *Nucleic Acids Research* 18(13):3813–3821 (1990).

Database WPI, Derwent Publications #199703, citing Japanese Patent No. 8290377 published Nov. 5, 1996.

Database WPI, Derwent Publication #198822, citing European Patent No. 269520 A, New HIV–2 retrovirus causing AIDS—and new antigenic proteins, antibodies and complementary nucleic acid sequences.

Database WPI, Derwent Publications #198942, citing International PCT Application No. WO 89/09406 published Oct. 5, 1989.

Database WPI, Derwent Publication, AN90–302767, Japanese Patent, JP2215399 A, Method detect DNA single strand combination DNA prime correspond base sequence forming replica.

Database WPI, Derwent Publication #199015, citing European Patent No. 0360677, Identification of sub–units in complex moles.—by mass spectrometry, especially in nucleic acid sequencing.

Database WPI, Derwent Publication, AN88–311964, JP63230086 A 880926 DW8844, Carry immobilise physiological active substance comprise bind chain form di sulphide compound epoxy group latex contain polymer particle.

Drmanac, et al., "Sequencing of megabase plus DNA by hybridization: theory of the method", *Genomics* 4:114–128 (1989).

Eggers et al., "A microchip for quantitative detection of molecules utilizing luminescent and radioisotope reporter groups", *Bio Techniques* 17:516–524 (1994).

Ferrie et al., Development, multiplexing, and application of Arms tests for common mutations in the CFTR gene, *Am. J. Hum. Genet.* 51:251–262 (1992).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu, et al., "A DNA suquencing strategy that requires only five bases of known terminal sequence for priming (primer extention/stacking interaction/fluorescein/solid state/duplex probe)", *Proc. Natl. Acad. Sci. USA* 92:10162–10166 (1995).

Ganem, "Detection of oligonucleotide duplex forms by ion–spray mass spectrometry", *Tetrahedron Letters* 34(9):1445–1448 (1993).

*Genetics in Medicine*, Thompson, J.S. and M.W. Thompson, eds., W.B. Saunders Co., Philadelphia, PA (1986).

Ghosh, et al., "Covalent attachment of oligonucleotides to solid supports", *Nuc. Acids Res.* 15)13):5353–5372 (1987).

Gildea et al., A versatile acid–labile linker for modification of synthetic biomolecules, *Tetrahedron Letters* 31:7095–7098 (1990).

Greene and Wuts, *Protective Groups in Organic Synthesis*, 2nd Edition, Wiley & Sons (1991).

Gust et al., Taxomonic classifcation of Hepatiti A virus *Intervirology* 20:1–7 (1983).

Guyader, et al., "Genome organization and transactivation of the human immunodeficiency virus type 2", *Nature* 326:662–669 (1987).

Hayashi, et al., "Immobilization of Thiol Proteases onto porous poly(vinyl alcohol) beads", *Polymer Journal*, 25(5):489–497 (1993).

Heermann, et al., "Liquid–phase hybridization and capture of hepatitis B virus DNA with magnetic beads and fluorescence detection of PCR product", *J. of Virol. Methods* 50:43–58 (1994).

Hermanson, *Bioconjugate Techniques*, Academic Press (1996).

Higuchi et al., Kinetic PCR analysis: Real–time monitoring of DNA amplification reactions, Bio/Technology 11:1026–1030 (1993).

Hillencamp et al., Matrix Assisted UV–Laser Desorption/Ionization: A New Approach to Mass Spectrometry of Large Biomolecules, *Biological Mass Spectrometry*, Editors: A. L. Burlingame and J. A. McCloskey, Elsevier Science Publishers, B. V., Amsterdam, pp. 49–61 (1989).

Hillenkamp and Ehring, Laser desorption mass spectrometry Part 1: Basic mechanisms and techniques, *Mass Spectrometry in the Biological Sciences: A tutorial*, pp. 165–179 (1992).

Human Gene Mutations, D.N. Cooper and M. Krawczak, BIOS Publishers, (1993).

Jacobson, et al., "Applications of mass spectrometry to DNA sequencing", *GATA* 8(8):223–229 (1991).

Jett et al., "High–Speed DNA Sequencing: An Approach Based Upon fluorescence Detection of Single Molecules", *J. Bio Strut & Dynam.* 7(2):301–09 (1989).

Khrapko et al., "A method for DNA sequencing by hybridization with oligonucleotide matrix", *J. DNA Seq. and Mapping* 1:375–388 (1991).

Köster, et al., "Oligonucleotide synthesis and multiplex DNA sequencing using chemiluminescent detection", *Nucleic Acids Research*, Symposium Series No. 24, 318–321 (1991).

Köster et al., "Well–Defined Insoluble Primers for the Enzymatic Synthesis of Oligo–and Polynucleotides", *Hoppe–Seyler's Z. Physiol. Chem.* 359:1579–1589 (1978).

Köster et al., N–acyl protecting groups for deoxynucleotides: A quantitative and comparative study, *Tetrahedron* 37:363–369 (1981).

Köster et al., "A strategy for rapid and efficient DNA sequencing by mass spectrometry", *Nature Bio* 14:1123–1128 (1996).

Kozal et al., "Extensive polymorphisms observed in HIV–1 clade B protease gene using high–density oligonucleotide arrays", *Nature Medicine*, 2(7):753–759 (1996).

Kuppuswamy, et al., "Single nucleotide primer extension to detect gentic diseases: experimental application to hemophilia B (factor IX) and cystic fibrosis genes", *Proc. Natl. Acad. Sci. USA* 88:1143–1147 (1991).

Lamture et al., "Direct detection of nucleic acid hybridization on the surface of a charge coupled device", *Nucl. Acids Res.* 22:2121–2125 (1994).

Landegren et al., "DNA Diagnostics—Molecular techniques and automation", *Science* 242:229–237 (1988).

Li et al., "Analysis of single mammalian cell lysates by mass spectrometry", *J. Am. Chem. Soc. 118*:11662–11663 (1996).

Li et al., "High–Resolution MALDI Fourier Transform Mass Spectrometry of Oligonucleotides", *Anal Chem* 68(13):2090–2096 (1996).

Liss, Alan R. "Macromolecular sequencing and synthesis selected methods and applications", Edited by David H. Schlesinger, Department of Experimental Medicine and Cell Biology, New York University Medical Center, New York, New York (1988).

Little et al., "Mass spectrometry from miniaturized arrays for full comparative DNA analysis", *Nature Med* 3(12):1413–1416 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Little et al., "Direct detection of synthetic and biologically generated double–stranded DNA by MALDI–TOF MS", *J. Mass Spec* 17:1–8 (1997).

Lopez–Galindez, et al., "Characterization of genetic variation and 3'–azido–3'–deoxythymidine–resistance mutations of human immunodeficiency virus by the RNase A mismatch cleavage method", *Proc. Natl. Acad. Sci, USA* 88:4280–4284 (1991).

Lund, Vera et al., "Assessment of methods for covalent binding of nucleic acids to magnetic beads, dynabeads, and the characteistics of the bound nucleic acids in hybridization reactions", *Nucleic Acids Res.* 16(22) (1988).

Manoharan et al., A 2'–O–thiol tether in the ribose moiety of nucleic acids for conjugation chemistry, *Gene*, 149:147–156 (1994).

Martin, "New technologies for large–genome sequencing", *Genome* 31:1073–1080 (1989).

Matthews, et al., "Analytical strategies for the use of DNA probes", *Analytical Biochemistry* 169:1–25 (1988).

McCray and Trentham, "Properties and uses of photoreactive caged compounds", *Annu. Rev. Biophys. Biophys. Chem.*18:239–270 (1989).

Mizusawa, et al., "Improvement of the dideoxy chain termination method of DNA sequencing by use of deoxy–7–deazaguanosine triphosphate in place of dGTP", *Nucleic Acids Res.* 14(3):1319–1325 (1986).

Moini et al., "A Moving Belt Device to Couple High–Performance Liquid Chromatography and Chemical Reaction Interface Mass Spectrometry", *Bio Mass Spect* 20:308–312 (1991).

Nelson et al., "Volatilization of High Molecular Weight DNA by Pulsed Laser Ablation of Frozen Aqueous Solutions", *Science* 246:1585–1587 (1989).

Nelson et al., Time–of–flight mass spectrometry of nucleic acids by laser ablation and ionization from a frozen aqueous matrix, *Rapid Communications in Mass Spectrometry* 4:348–351 (1990).

Newton et al., "The production of PCR products with 5' single–straned tails using primers that incorporate novel phosphoramidite intermediates", *Nucl. Acids. Res.* 21:1155–1162 (1993).

Nikiforov and Rogers, "The use of 96–well polystyrene plates for DNA hybridization–based assays: An evaluatin of different approaches to oligonucleotide immobilization", *Anal. Biochm.* 227:201–209 (1995).

Nordhoff et al., "Ion stability of nucleic acids in infrared matrix–assised laser desorption/ionization mass spectrometry", *Nuc Acids Res.* 21(15):3347–3357 (1993).

Nordoff et al., "Matrix–assisted laser desorption/ionization mass spectrometry of nucleic acids with wavelength in the ultraviolet and infrared", *Rapid Comm. Mass Spectrom.* 6:771–776 (1992).

O'Donnell et al., "High–Density, Covalent Attachment of DNA to Siliocn Wafers for Analysis by MALDI–TOF Mass Spectrometry", *Analytical Chemistry* 69(13):2438–2443 (1997).

O'Donnell et al., "MassArray as an Enabling Technology for the Industrial–Scale Analysis of DNA", *Genetic Engineering News* 17(21) (1997).

O'Donnell–Maloney et al., "Microfabrication and array technologies for DNA sequencing and diagnostics", *Genetic Analysis: Biomolecular Engineering* 13:151–157 (1996).

Olejnik et al., "Photocleavable biotin phosphoramidite for 5'–end–labeling, affinity purification and phosphorylation of synthetic oligonucleotides", *Nucleic Acids Res.* 24:351–366 (1996).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial* 181–197 (1992).

PCR, C.R. Newton and A. Graham, BIOS Publishers, (1994).

Pieles et al., Matrix–assisted desorption ionization time–of–flight mass spectrometry: a powerful tool for the mass and sequence analysis of natural and modified oligonucleotides, *Nucleic Acids Res.* 21(14):3191–3196 (1993).

Pierce Catalog, pp. T123–T154, 1994.

Pon, et al., Derivation of controlled pore glass beads for solid phase oligonucleotide synthesis, *BioTechniques*, 6:8, 770–775 (1988).

Rasmussen et al., "Covalent immobilization of DNA onto polystyrene microwells: The molecules ar eonly bound at the 5' end", *Anal. Biochem.* 198:138–142 (1991).

Ratner et al., Complete nucleotide sequence of the AIDS virus, HTLV–III, *Nature* 313:227–284 (1985).

Rolfs et al., *PCR: Clinical Diagnostics and Research*, Springer–Verlag (1992).

Running and Urdea, "A procedure for productive coupling of synthetic oligonucleotides to polystyrene microtiter wells for hybridization capture", *Biotechniques* 8:276–277 (1990).

Ruppert et al., "Preparation of plasmid DNA as Sequencing Templates in a Microtiter Plate Format", Paper presented, Cold Spring Harbor Laboratory.

Ruppert et al., "A rapid and high throughout method for plasmid isolations", Presented: Automation in Mapping and DNA Sequencing Conference, Aug. 31–Sep. 2, 1994.

Saiki, et al., "Genetic analysis of amplified DNA with immobilized sequence–specific oligonucleotide probes", *Proc. Natl. Acad. Sci. USA* 86:6230–6234 (1989).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Schram, Karl H., "Mass Spectrometry of Nucleic Acid Components", *Bio Appl of Mass Spect.* 34:203–287 (1990).

Seela and Kehne, Palindromic octa–and dodecanucleotides containing 2'–deoxytubercidin: Synthesis, hairpin formation, and recognition by the endodeoxyribonuclease EcoRI, *Biochemistry* 26:222–2238 (1987).

Sequenom Advances the Industrial Genomics Revolution with the Launch of Its DNA MassArray™ Automated Process Line, Press Release: Sep. 28, 1998, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Reports On Use of Its DNA MassArray™ Technology to Analyze Genes Associated with Alzheimer's Disease adn Arteriosclerosis: Technology Has Applications in Drug Development, Press Release: Sep. 22, 1997, http://www.sequenom.com/pressrelease.htm.

Sequenom Uses DNA MassArray™ to Sequence Section of Human Cancer–Related p53 Gene, Press Release: Mar. 27, 1998, http://www.sequenom.com/pressrelease.htm.

Sequenom Reports DNA MassArray™ Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Shaler et al., "Effect of Impurities on the matrix–Assisted Laser Desorption Mass Spectra of Single–Stranded Oligodeoxynucleotides", *Anal. Chem.* 68:576–579 (1996).

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Siuzdak, Gary, "The emergence of mass spectrometry in biochemical research", *Proc. natl. Acad. Sci. USA* 91:11290–11297 (1994).

Smith R. D., "New Developments in Biochemical Mass Spectrometry: Electrospray Ionization", *Anal. Chem.* 62:882–899 (1990).

Smith, Cassandra L., "cDNA Fingerprinting of Breast Cancer Tumor Cells", Boston Univ., MA (1996).

Stahl, et al., "Soid phase DNA sequencing using the biotin–avidin system", *Nucleic Acids Res.* 16(7):3025–3039 (1988).

Strezoska, et al., "DNA sequencing by hybridization: 100 bases read by a non–gel–based method", *Proc. Natl. Acad. Sci. USA* 88:10089–10093 (1991).

Tang et al., "Matrix–assisted laser desorption/ionization mass spectrometry of immobilized duplex DNA probes", *Nucleic Acids Research* 23:3126–3131 (1995).

Tang et al., Detection of 500–nucleotide DNA by laser desorption mass spectrometry, *Rapid Commun. Mass Spectrom.* 8:727–730 (1994).

Tang et al., Matrix–assisted laser desorption/ionization of restriction enzyme–digested DNA, *Rapid Commun. Mass Spectrom.* 8:183–186 (1994).

Tang, et al., "Improving mass resolution in MALDI/TOF analysis of DNA".

Tomer et al., "Coaxial Continuous Flow Fast Atom Bombardment for Higher–Molecular–Weight Peptides: Comparison with Static Fast Atom Bombardment and electrospray Ionization", *Bio Mass Spect* 20:783–788 (1991).

Trainor, "DNA Sequencing, Automation, and the Human Genome", *Anal. Chem.* 62:418–426 (1990).

Valaskovic et al., "Attomole protein characterization by capillary electrophoresis–mass spectrometry", *Science* 273:1199–1202 (1996).

Wain–Hobson et al., Nucleotide sequence of the AIDS virus, LAV, *Cell* 40:9–17 (1985).

Walker et al., Multiplex strand displacement amplification (SDA) and detection of DNA sequences from *Mycobacterium tuberculosis* and other mycobacteria, *Nucleic Acids Res.* 22(13):2670–2677 (1994).

Wallace, "Ink–jet based fluid microdispensing in biochemical applications", Microfab Technologies, Inc., Laboratory Automation News, 1(5):6–9 (1996).

Wang, Solid phase synthesis of protected peptides via photolytic cleavage of the α–methylphenacyl ester anchoring linkage, *J. Org. Chem.* 41(20):3258–3261 (1976).

Wiedmann M. et al., Ligase chain reaction (LCR)—overview and applications, *PCR Methods Appl.* 3(4):S51–S64 (1994).

Williams, Time of flight mass spectrometry of DNA laser-ablated from frozen aqueous solutions: applications to the Human Genome Project, *Intl. J. Mass Spectrom. and Ion Processes* 131:335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry* 14:111–116 (1987).

Wong, Ch. 12: Conjugation of proteins to solid matrices, *Chemistry of Protein Conjugation and Cross Linking* 12:295–317 (1993).

Wu et al., "Time–of–Flight Mass Spectrometry of Underivatized Single–Stranded DNA Oligomers by Matrix–Assisted Laser Desorption", *Anal. Chem.* 66:1637–1645 (1994).

Wu et al., "Matrix–assisted Laser Desorption Time–of–flight Mass Spectrometry of Oligonucleotides Using 3–Hydroxypicolinic Acid as an Ultraviolet–sensitive Matrix", *Rapid Comm Mass Spec* 7:142–146 (1993).

Yang, et al., "Detection of hepatitis B virus in plasma using cytometric analyses of polymerase chain reaction–amplified DNA incorporating digoxigenin–11–dUTP", *Blood* 81(4):1083–1088 (1993).

Zhang et al., "Single–base mutational analysis of cancer and genetic disease using membrane bound modified oligonucleotides", *Nucl. Acids Res.* 19:3929–3933 (1991).

Zukermann et al., Efficient methods for attachment of thiol specific probes to the 3'–ends of synthetic oligodeoxyribonucleotides, *Nucleic Acids Research*, 15:13, 5305–5321 (1987).

Chee, Enzymatic multiples DNA sequencing, *Nucleic Acids Res.* 19(12):3301–3305.

Palejwala et al., Quantitative Multiplex Sequence Analysis of Mutational Hot Spots. Frequency and Specificity of Mutations Induced by a Site–Specific Ethenocytosine in M13 Viral DNA, *Biochemistry* 32:4105–4111 (1993).

Database WPI, WPI Acc. No. 96140362/199615, citing German Patent No. DE4431174 published Mar.7, 1996.

Database WPI, WPI Acc. No. 96222896/199623, citing German Patent No. DE4438630 published May 2, 1996.

Feng et al., The RNA Component of Human Telomerase, *Science* 269(5228):1236–1241 (1995).

Naito et al., Detection of Tyrosine Hydroxylase mRNA and Minimal Neuroblastoma Cells by the Reverse Transcription– Polymerase Chain Reaction, *European Journal of Cancer* 27:762–765 (1991).

Ordoukhanian et al., Design and Synthesis of a Versatile Photocleavable DNA Building Block. Application to Phototriggered Hybridization, *J. Am. Chem. Soc.* 117:9570–9571 (1995).

Pasini et al., RET mutations in human disease, *Trends in Genetics* 12(4):138–144 (1996).

Syvanen et al., Detection of Point Mutations by Solid–Phase Methods, *Human Mutation* 3(3):172–179 (1994).

Tang et al., Matrix–assisted Laser Desorption/Ionization of Restriction Enzyme–digested DNA, *Rapid Communications in Mass Spectrometry* 8(2):183–186 (1994).

Chen et al., "Laser mass spectrometry for DNA fingerprinting for forensic applications", *Annual Meeting of the Society of Photo Optical Instrumentation Engineers*, Jul. 24–29, 1994.

Jacobson et al., "Applications of mass spectrometry to DNA fingerprinting and DNA sequencing", *International Symposium on the Forensic Aspects of DNA Analysis*, pp. 1–18, Mar. 29–Apr. 2, 1993, (Abstract).

Doktycz et al., "Analysis of Polymerase Chain Reaction–Amplified DNA Products by Mass Spectrometry Using Matrix Assisted Laser Desorption and Ekectrospray: Current Status" *Anal. Biochem*, 230:205–214 (1995).

Andersen, et al., Electrospray ionization and matrix assisted laser desorption/ionization mass spectrometry: Powerful analytical tools in recombinant protein chemistry, *Nature Biotech.* 14:449–457 (1996).

Arlinghaus et al., "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Braun et al., Detecting CFTR gene mutations by using primer oligo base extension and mass spectrometry, *Clinical Chemistry* 43:1151–1158 (1997).

Covey, et al., The determination of protein, oligonucleotide and peptide molecular weights by ion–spray mass spectrometry, *Rapid Comm. Mass Spectrom.* 2:249–256 (1988).

Eckstein (ed.), *Oligonucleotides and Analogues*, IRL Press, Oxford (1991).

Edmonds et al., Thermospray liquid chromatography–mass spectrometry of nucleosides and of enzymatic hydrolysates of nucleic acids, *Nucleic Acids Research* 13:8197–8206 (1985).

Ehring et al., Photochemical versus thermal mechanisms in matrix–assisted laser desorption/ionization probed by back side desorption, *Rapid Comm in Mass Spect* 10:821–824 (1996).

Fu et al., A DNA sequencing strategy which requires only five bases of known terminal sequence for priming, Paper presented, Genome Mapping and Sequencing, Cold Spring Harbor Laboratory.

Fu et al., Efficient preparation of short DNA sequence ladders potentially suitable for MALDI–TOF DNA sequencing, *Genetic Analysis* 12:137–142 (1996).

Fu et al., Sequencing double–stranded DNA by strand displacement, *Nucl. Acids Res* 25:677–679 (1997).

Fu et al., Sequencing exons 5 to 8 of the p53 gene by MALDI–TOF mass spectrometry, *Nat Biotechnol* 16:381–4 (1998).

Haglund et al., Matrix–assisted laser–desorption mass spectrometry on DNA using an infrared free–electron laser, *SPIE* 1854:117–128.

Hsiung et al., A new simpler photoaffinity analogue of peptidyl rRNA, *Nucl Acids Res* 1:1753–1762 (1974).

Huth–Fehre et al., Matrix–assisted laser desorption mass spectrometry of oligodeoxythymidylic acids, *Rapid Comm in Mass Spect* 6:209–213 (1992).

Ji et al., Two–dimensional electrophoretic analysis of proteins expressed by normal and cancerous human crypts: Applications of mass spectrometry to peptide–mass fingerprinting, *Electrophoresis* 15:391–405 (1994).

Juhasz et al., Applications of delayed extraction matrix–assisted laser desorption ionization time–of–flight mass spectrometry to oligonucleotide analysis, *Analy Chem* 68:941–946 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Jurinke et al., Application of nested PCR and mass spectrometry for DNA–based virus detection: HBV–DNA detected in the majority of isolated anti–HBc positive sera, *Genetic Analysis* 14:97–102 (1998).

Jurinke et al., Analysis of ligase chain reaction products via matrix–assisted laser desorption/ionization time–of–flight–mass spectrometry, *Analy Biochem* 237:174–181 (1996).

Jurinke et al., Detection of hepatitis B virus DNA in serum samples via nested PCR and MALDI–TOF mass spectrometry, *Genetic Analysis* 13:67–71 (1996).

Köster et al., Polymer support oligonucleotide synthesis—XV[1,2], *Tetrahedron* 40:102–112 (1984).

Köster et al., Some improvements in the synthesis of DNA of biological interest, *Nucl Acids Res* 7:39–59 (1980).

Little et al., Identification of apolipoprotein E polymorphisms using temperature cycled primer oligo base extension and mass spectrometry, *Short Communiation*.

Little et al., Verification of 50–to 100–mer DNA and RNA sequences with high–resolution mass spectrometry, *Proc. Natl. Acad. Sci. USA* 92:2318–2322 (1995).

Little et al., Detection of RET proto–oncogene codon 634 mutations using mass spectrometry, *J. Mol Med.* 75:745–750 (1997).

Little et al., Mass spectrometry from miniaturized arrays for full comparative DNA analysis, *Nature Med* 3:1413–1416 (1997).

Nikiforov et al., Genetic bit analysis: a solid phase method for typing single nucleotide polymorphisms, *Nucleic Acids Res* 22(20):4167–4175 (1994).

Pomerantz et al., Determination of oligonucleotide composition from mass spectrometrically measured molecular weight, *Am. Soc. Mass Spectrom.* 4:204–09 (1993).

Ruppert et al., A filtration method for plasmid isolation using microtiter filter plates, *Anal. Biochem.* 230:130–134 (1995).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Smith et al., Capillary zone electrophoresis–mass spectrometry using an electrospray ionization interface, *Anal. Chem.* 60:436–441 (1988).

Sproat et al., The synthesis of protected 5'–amino–2', 6'–dideoxyribonucleoside–3'–O–phosphoramidites; applications of 5'–amino–oligodeoxyribonucleotides, *Nucleic Acids Res.* 15:6181–6196 (1987).

Vorm et al., Improved resolution and very high sensitivity in MALDI TOF of matrix surfaces made by fast evaportion, *Anal. Chem.* 66:3281–3287 (1994).

Wu et al., Allele–specific enzymatic amplification of β–globin genomic DNA for diagnosis of sickle cell anemia, *Proc. Natl. Acad. Sci. USA* 86:2757–2760 (1989).

Yamashita et al., Electrospray ion source. Another variation on the free–jet theme, *J. Phys. Chem.* 88:4451–4459, (1984).

"Time of Flight Mass Spectrometry of DNA for Rapid Sequence Determination. Technical Progress Report, Jul. 31, 1991–Jul. 31, 1992" Arizona State University., Tempe.

Liu et al., "Use of a Nitrocellulose Film Substrate in Matrix–Assisted Laser Desorption/Ionization Mass Spectrometry for DNA Mapping and Screening", *Anal. Chem.* 67: 3482–3490 (1995).

Elov et al., Synthesis of RNA using T7 RNA polymerase and immobilized DNA in a stream type reactor, *Bioorganicheskala Khhimia*, 17(6) 789–794 (1991).

English Language translation of Elov et al., *Bioorganischeskala Khhimia*, 17(6) 789–794 (1991).

* cited by examiner

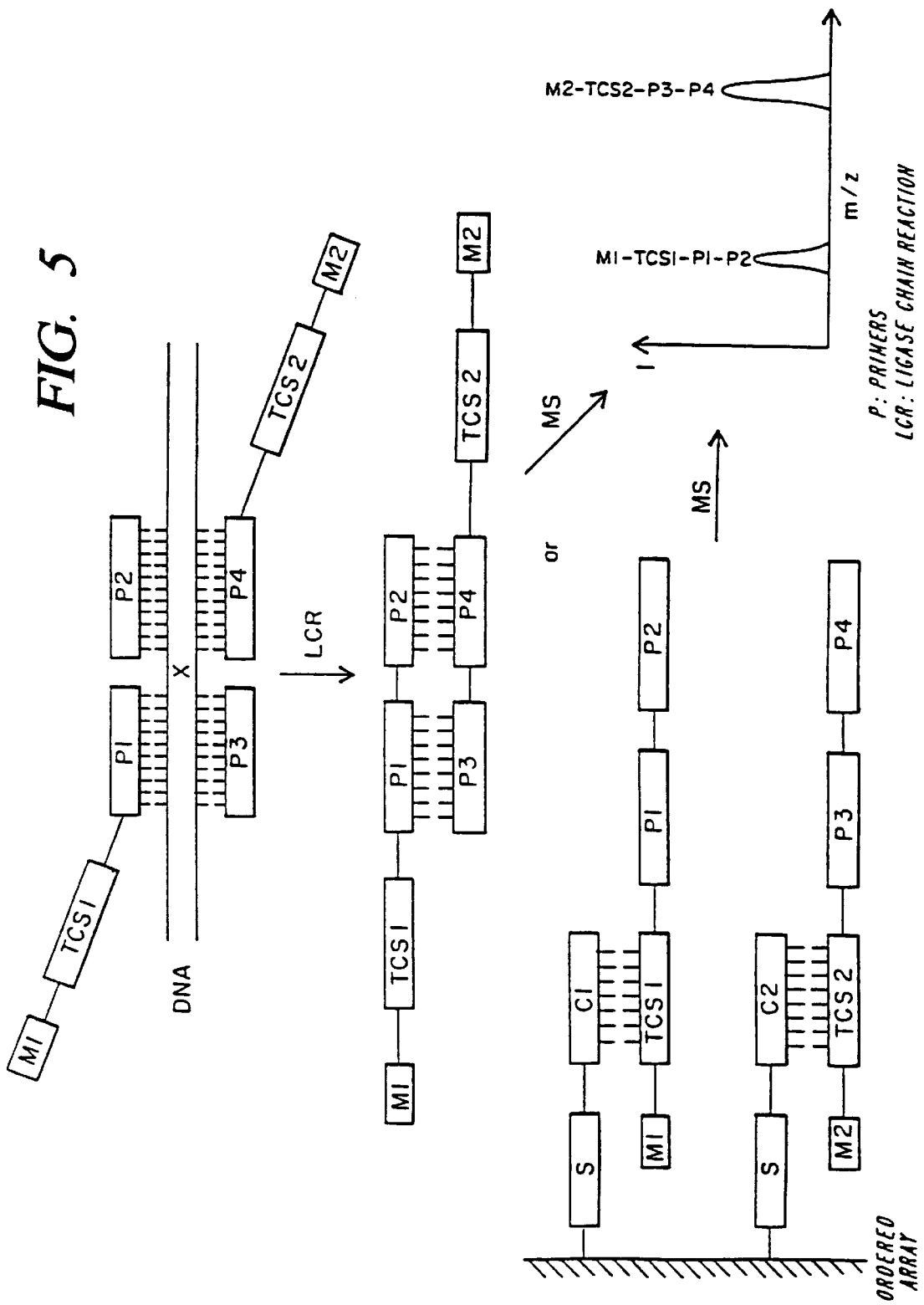

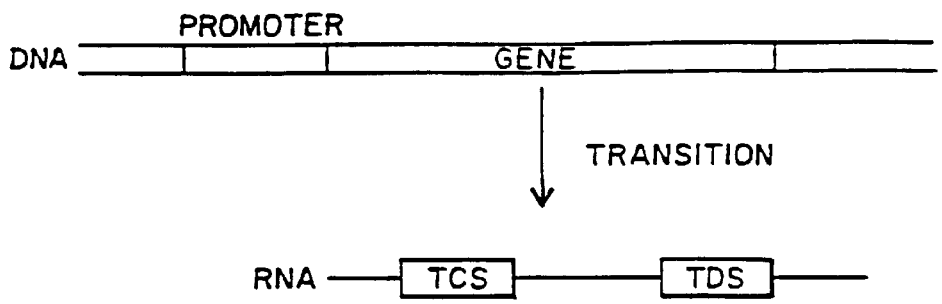
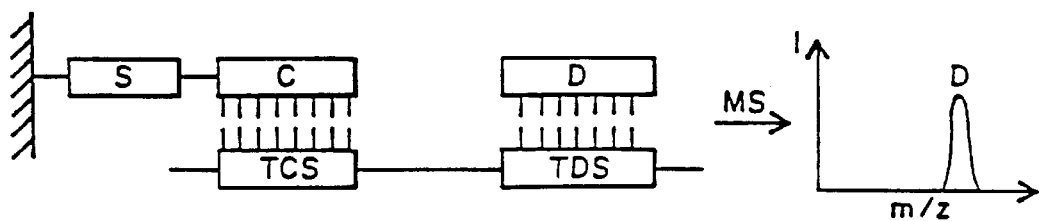
FIG. 6A
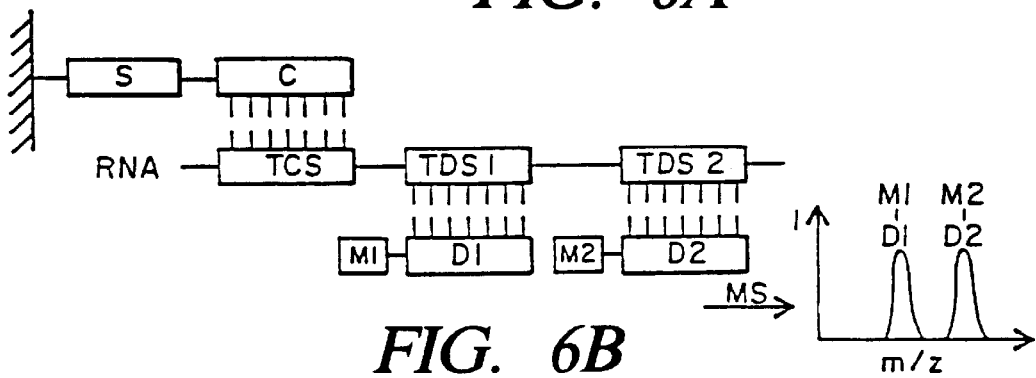
FIG. 6B
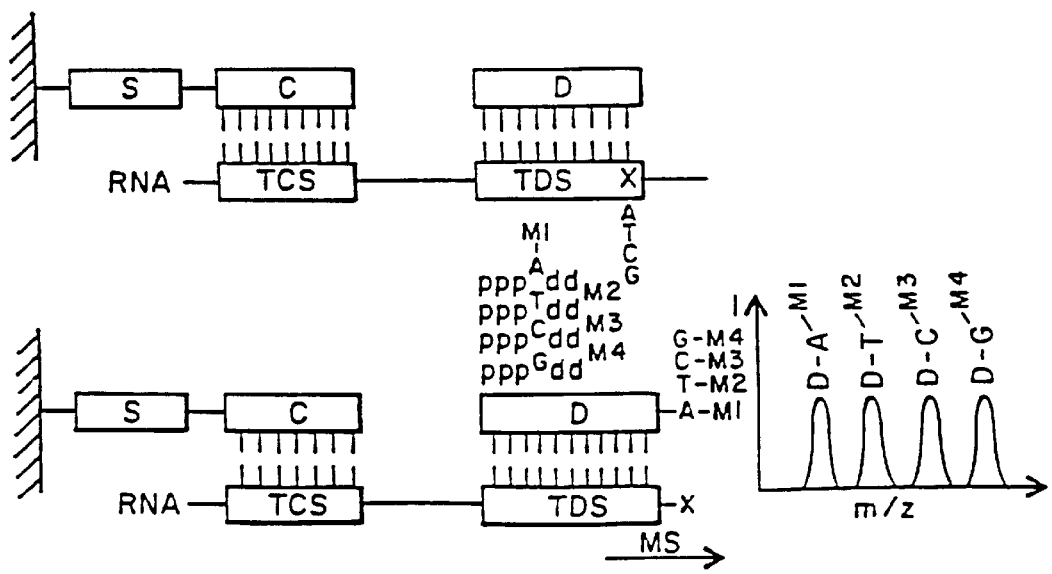
FIG. 6C

MOLECULAR WEIGHT OF THE VARIABLE FRAGMENTS IN Da:

| | | | ε2/ε2 | ε3/ε3 | ε4/ε4 | ε2/ε3 | ε2/ε4 | ε3/ε4 |
|---|---|---|---|---|---|---|---|---|
| 91 bp | SENSE | 28421 | X | X | | X | X | X |
| | ANTISENSE | 27864 | | | | | | |
| 83 bp | SENSE | 25747 | X | | | X | X | |
| | ANTISENSE | 25591 | | | | | | |
| 72 bp | SENSE | 22440 | | | X | | X | X |
| | ANTISENSE | 21494 | | | | | | |
| 48 bp | SENSE | 14844 | | X | X | X | X | X |
| | ANTISENSE | 14857 | | | | | | |
| 35 bp | SENSE | 10921 | | X | X | X | X | X |
| | ANTISENSE | 10751 | | | | | | |

```
          5065O75O8
          IleIlePhe
ACCATTAAAGAAAAATATCATCTTTGGTGTTCCTATGATGAATATAGAAGCGTCATC
primer                ACCACAAAGGATACTACTTATATC  (7289,8)
wildtype       TAGAAACCACAAAGGATACTACTACTTATATC  (8846,8)
ΔF508          TA---ACCACAAAGGATACTACTACTTATATC  (7891,2)
ΔI507       TAG---AAACCACAAAGGATACTACTACTTATATC  (8846,8)
```

FIG. 34A

```
          5065O75O8
          IleIlePhe
ACCATTAAAGAAAAATATCATCTTTGGTGTTTGGTGTTCCTATGATGAATATAGAAGCGTCATC
primer                    ACCACAAAGGATACTACTTATATC   (7289,8)
wildtype       CTTTTATAGTAGAAACCACAAAGGATACTACTACTTATATC   (11612,6)
ΔF508          CTTTTATAGTA---ACCACAAAGGATACTACTACTTATATC   (10657,0)
ΔI507       CTTTTATAG---AAACCACAAAGGATACTACTACTTATATC   (10666,0)
506Ser         CGTAGAAACCACAAAGGATACTACTACTTATATC   (9465,2)
```

FIG. 34B

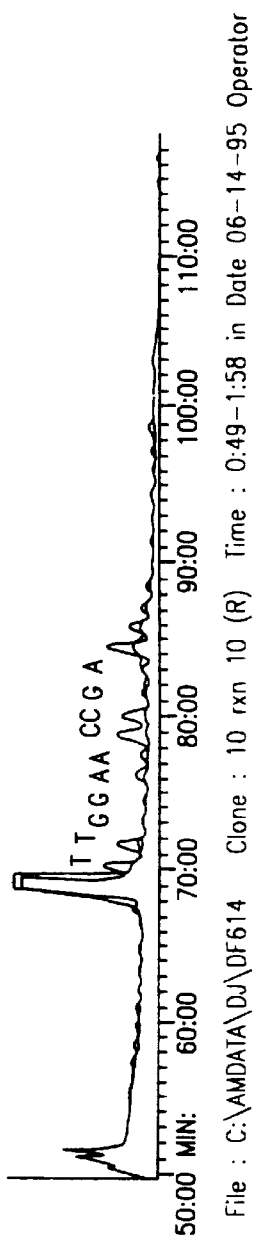
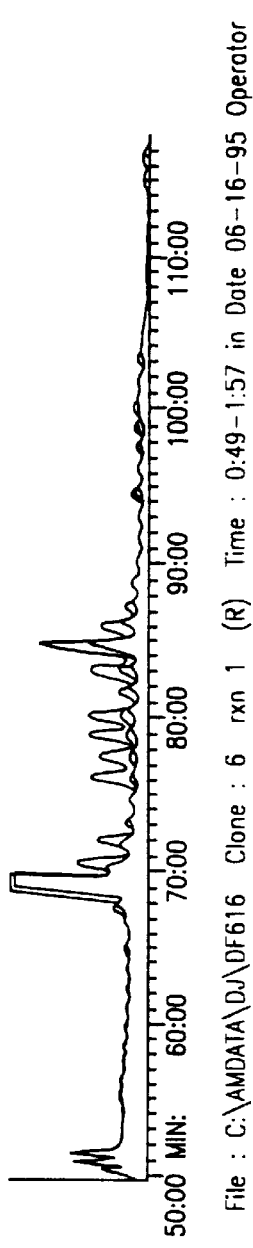
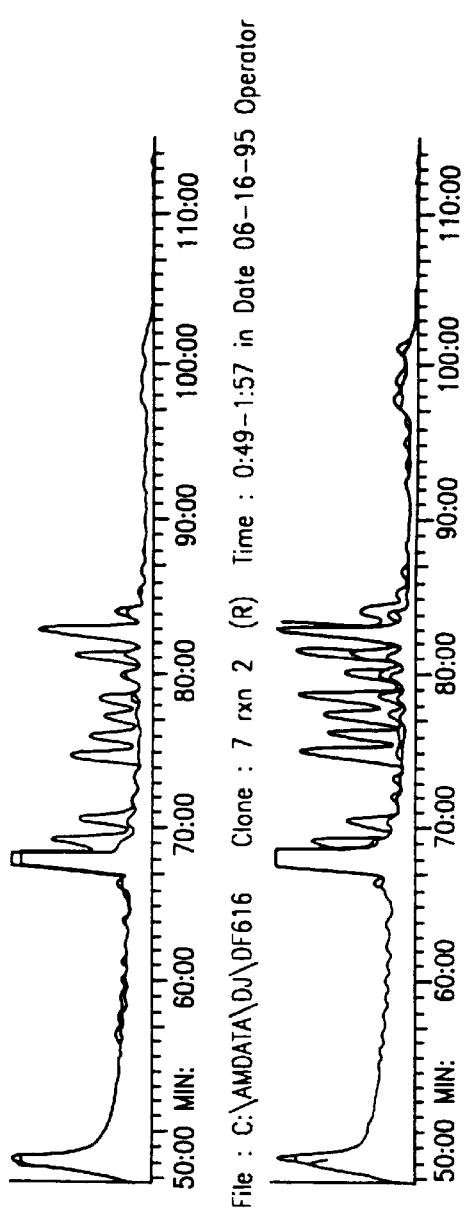
FIG. 48A
FIG. 48B
FIG. 48C
FIG. 48D

PARTIAL SEQUENCE OF THE β-GLOBIN TEMPLATE
3'-(H)$_n$-ACCACGTGGACTGAG GACACCTCTT CAGACGGCAA TGACGOGACA CCCCGTTCCA CTTGCACCTA-(N)$_n$-5'

| 5'-TGCACCTGACTC | 3' (PRIME) |
| 5'-TGCACCTGACTC | C-3' |
| 5'-TGCACCTGACTC | CT-3' |
| 5'-TGCACCTGACTC | CTG-3' |
| 5'-TGCACCTGACTC | CTGT-3' |
| 5'-TGCACCTGACTC | CTGTG-3' |
| 5'-TGCACCTGACTC | CTGTGG-3' |
| 5'-TGCACCTGACTC | CTGTGGA-3' |
| 5'-TGCACCTGACTC | CTGTGGAG-3' |
| 5'-TGCACCTGACTC | CTGTGGAGA-3' |
| 5'-TGCACCTGACTC | CTGTGGAGAA-3' |

| 5'-TGCACCTGACTC | CTGTGGAGAA G-3' |
| 5'-TGCACCTGACTC | CTGTGGAGAA GT-3' |
| 5'-TGCACCTGACTC | CTGTGGAGAA GTC-3' |
| 5'-TGCACCTGACTC | CTGTGGAGAA GTCT-3' |
| 5'-TGCACCTGACTC | CTGTGGAGAA GTCTG-3' |
| 5'-TGCACCTGACTC | CTGTGGAGAA GTCTGC-3' |
| 5'-TGCACCTGACTC | CTGTGGAGAA GTCTGCC-3' |
| 5'-TGCACCTGACTC | CTGTGGAGAA GTCTGCCG-3' |
| 5'-TGCACCTGACTC | CTGTGGAGAA GTCTGCCGT-3' |
| 5'-TGCACCTGACTC | CTGTGGAGAA GTCTGCCGTT-3' |

| 5'-TGCACCTGACTC | CTGTGGAGAA GTCTGCCGTT A-3' |
| 5'-TGCACCTGACTC | CTGTGGAGAA GTCTGCCGTT AC-3' |
| 5'-TGCACCTGACTC | CTGTGGAGAA GTCTGCCGTT ACT-3' |
| 5'-TGCACCTGACTC | CTGTGGAGAA GTCTGCCGTT ACTG-3' |
| 5'-TGCACCTGACTC | CTGTGGAGAA GTCTGCCGTT ACTGC-3' |
| 5'-TGCACCTGACTC | CTGTGGAGAA GTCTGCCGTT ACTGCC-3' |
| 5'-TGCACCTGACTC | CTGTGGAGAA GTCTGCCGTT ACTGCCC-3' |
| 5'-TGCACCTGACTC | CTGTGGAGAA GTCTGCCGTT ACTGCCCT-3' |
| 5'-TGCACCTGACTC | CTGTGGAGAA GTCTGCCGTT ACTGCCCTG-3' |
| 5'-TGCACCTGACTC | CTGTGGAGAA GTCTGCCGTT ACTGCCCTGT-3' |

| 5'-TGCACCTGACTC | CTGTGGAGAA GTCTGCCGTT ACTGCCCTGT G-3' |
| 5'-TGCACCTGACTC | CTGTGGAGAA GTCTGCCGTT ACTGCCCTGT GG-3' |
| 5'-TGCACCTGACTC | CTGTGGAGAA GTCTGCCGTT ACTGCCCTGT GGG-3' |
| 5'-TGCACCTGACTC | CTGTGGAGAA GTCTGCCGTT ACTGCCCTGT GGGG-3' |
| 5'-TGCACCTGACTC | CTGTGGAGAA GTCTGCCGTT ACTGCCCTGT GGGGC-3' |
| 5'-TGCACCTGACTC | CTGTGGAGAA GTCTGCCGTT ACTGCCCTGT GGGGCA-3' |
| 5'-TGCACCTGACTC | CTGTGGAGAA GTCTGCCGTT ACTGCCCTGT GGGGCAA-3' |
| 5'-TGCACCTGACTC | CTGTGGAGAA GTCTGCCGTT ACTGCCCTGT GGGGCAAG-3' |
| 5'-TGCACCTGACTC | CTGTGGAGAA GTCTGCCGTT ACTGCCCTGT GGGGCAAGG-3' |
| 5'-TGCACCTGACTC | CTGTGGAGAA GTCTGCCGTT ACTGCCCTGT GGGGCAAGGT-3' |

12 met PRIMER

FIG. 50A

| \multicolumn{4}{c}{REACTION STOPPED WITH} |
| ddATP | ddCTP | ddGTP | ddTTP |
| --- | --- | --- | --- |
| 3581.4 da | 3581.4 da | 3581.4 da | 3581.4 da |
|  | 3854.6 da |  |  |
|  |  |  | 4158.9 da |
|  |  | 4488.0 da |  |
|  |  |  | 4791.2 da |
|  |  | 5120.4 da |  |
|  |  | 5448.6 da |  |
| 5760.8 da |  |  |  |
|  |  | 6089.0 da |  |
| 6401.2 da |  |  |  |
| 6713.4 da |  |  |  |
|  |  | 7041.6 da |  |
|  |  |  | 7344.8 da |
|  | 7634.0 da |  |  |
|  |  |  | 7938.2 da |
|  |  | 8267.4 da |  |
|  | 8555.6 da |  |  |
|  | 8844.8 da |  |  |
|  |  | 9174.0 da |  |
|  |  |  | 9477.2 da |
|  |  |  | 9781.4 da |
| 10094.6 da |  |  |  |
|  | 10382.8 da |  |  |
|  |  |  | 10687.0 da |
|  |  | 11016.2 da |  |
|  | 11304.4 da |  |  |
|  | 11593.6 da |  |  |
|  | 11652.8 da |  |  |
|  |  |  | 12187.0 da |
|  |  | 12516.2 da |  |
|  |  |  | 12819.4 da |
|  |  | 13148.6 da |  |
|  |  | 13476.8 da |  |
|  |  | 13805.0 da |  |
|  |  | 14133.2 da |  |
|  | 14421.4 da |  |  |
| 14734.6 da |  |  |  |
| 15146.8 da |  |  |  |
|  |  | 15375.0 da |  |
|  |  | 15703.2 da |  |
|  |  |  | 16006.4 da |

*FIG. 50B*

SEQUENCE OF THE AMPLIFIED 209 bp PCR-PRODUCT OF THE β-GLOBIN GENE

FORWARD PRIMER: β2
CATTTGCTTC TGACACAACT GTGTTCACTA GCAACCTCAA ACAGACACCA
    12mer PRIMER
TGC TGCACCT GACTC CTGTG GAGAAGTCTG CCGTTACTGC CCTGTGGGGC

AAGGTGAACG TGGATGAAGT TGGTGGTGAG GCCCTGGGCA GGTTGGTATC

AAGGTTACAA GACAGGTTTA AGGAGACCAA TAGAAACTGG GCATGTGGAG

ACAGAGAAG
REVERSE PRIMER β11

*FIG. 51*

```
                    1     2     3     4     5     6     7     8     9    10    11    12    13
                          c           g
5'-gcattctttcttttactt  attt  attt  attt  attt  attt  attt  attt  attt  attt  attt  attt  attt  attt  ttgagacagagtctca-3'
3'-cgtaagaaagaaaatgaa  taaa  taaa  taaa  taaa  taaa  taaa  taaa  taaa  taaa  taaa  taaa  taaa  taaa  aactctgtctcagagt-5
                          g                                      c
```

| ALLELE NUMBER OF REPEATS | THEORETICALLY CALCULATED MOLECULAR MASS | | |
|---|---|---|---|
| | ddG | ddC | ddG AND ddC |
| TRUNCATED | 19440.60 | 11643.60 | 11643.60 |
| 8xAAAT | 15718.20 | 21033.60 | 15718.20 |
| 9xAAAT | 16959.00 | 22274.40 | 16959.00 |
| 10xAAAT | 18199.80 | 23515.20 | 18199.80 |
| 11xAAAT | 19440.60 | 24756.00 | 19440.60 |
| 12xAAAT | 20681.40 | 25996.80 | 20681.40 |
| 13xAAAT | 21922.20 | 27237.60 | 21922.20 |

FIG. 52

```
5' -GTGTGTGTGTGTGTGTGTTTTT (TT) (TT) AACAGGGATTTGGGGAATTATTTGAGA-3'
   PRIMER                             TTGTCCCTAAACCCCTT (4448.0)
   T5 ALLELE      CAAAAA -- --        TTGTCCCTAAACCCCTT (6890.6)
   T7 ALLELE      CAAAAA AA --        TTGTCCCTAAACCCCTT (7515.0)
   T9 ALLELE      CAAAAA AA AA        TTGTCCCTAAACCCCTT (8139.4)
```

*FIG. 55*

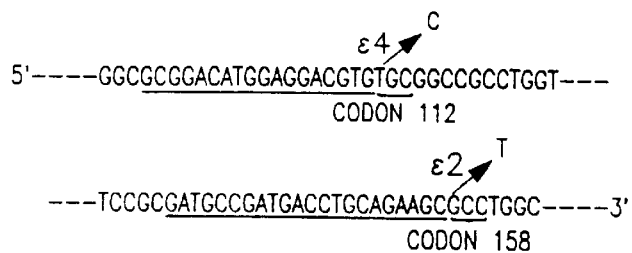
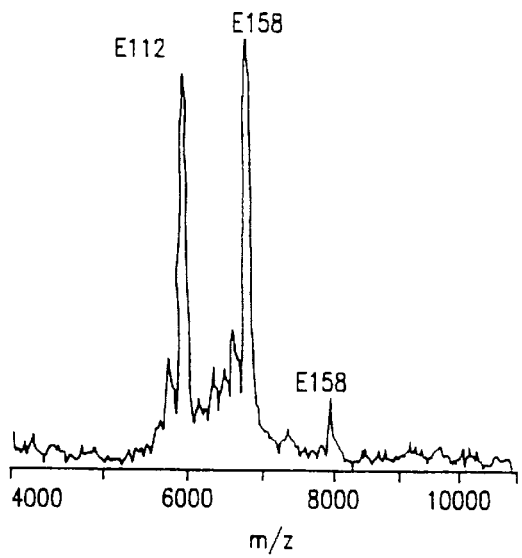
FIG. 61A
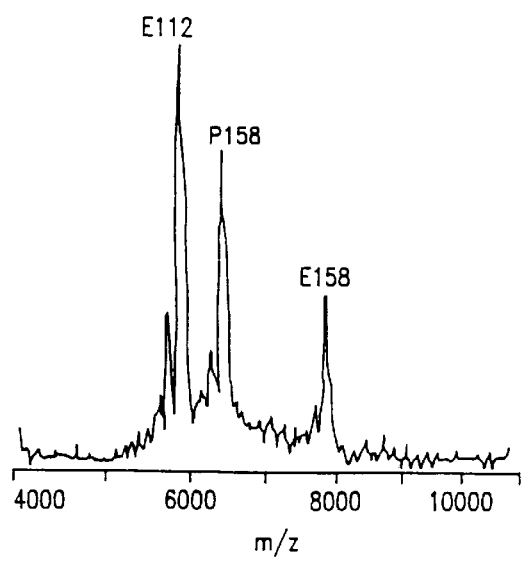
FIG. 61B
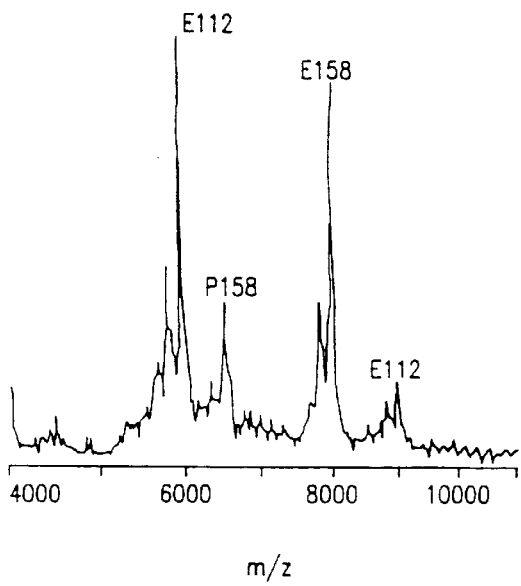
FIG. 61C
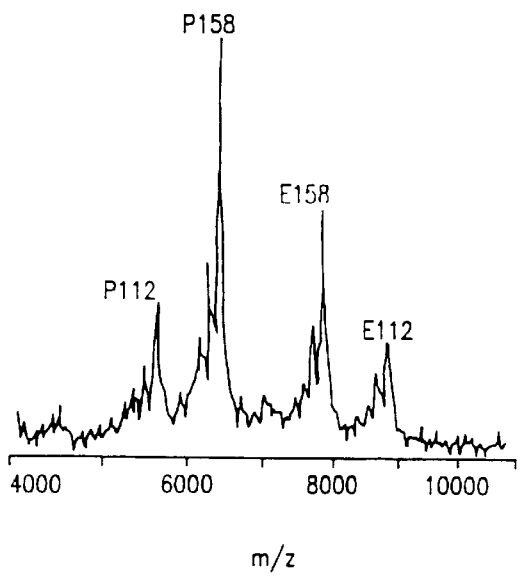
FIG. 61D

| ddTTP + dNTP (N=A,C,G) | ddATP + dNTP (N=C,T,G) |
|---|---|
| CGG CTG CGA TCA CCG TGC GG C ACA GCT | CGG CTG CGA TGA CCG TGC GG C A |
| WILDTYPE 8246 Da | WILDTYPE 6721 Da |
| CGG CTG CGA TGA CCG TGC GG T | CGG CTG CGA TGA CCG TGC GG T A |
| 6423 Da | 6736 Da |
| CGG CTG CGA TGA CCG TGC GG A ACA GCT | CGG CTG CGA TCA CCG TGC GG A |
| 8270 Da | 6432 Da |

$R^1$=OMe,H
$R^2$=OMe,H
$R^3$=O,NH

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

GCAAGTGAAT CCTGAGCGTG                                                    20

(2) INFORMATION FOR SEQ ID NO:2:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

GTGTGAAGGG TTCATATGC                                                     19

(2) INFORMATION FOR SEQ ID NO:3:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

ATCTATATTC ATCATAGGAA ACACCACA                                           28

(2) INFORMATION FOR SEQ ID NO:4:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

GTATCTATAT TCATCATAGG AAACACCATT                                         30

(2) INFORMATION FOR SEQ ID NO:5:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

```
GCTTTGGGGC ATGGACATTG ACCCGTATAA                                          30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CTGACTACTA ATTCCCTGGA TGCTGGGTCT                                          30

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TTGCCTGAGT GCAGTATGGT                                                     20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGCTCTATAT CGGGAAGCCT                                                     20

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TTGTGCCACG CGGTTGGGAA TGTA                                                24

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AGCAACGACT GTTTGCCCGC CAGTTG                                              26
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TACATTCCCA ACCGCGTGGC ACAAC                                                 25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

AACTGGCGGG CAAACAGTCG TTGCT                                                 25

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCAAGTGAAT CCTGAGCGTG                                                          20

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GTGTGAAGGG CGTG                                                                  14

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTATATTCAT CATAGGAAAC ACCA                                                  24

(2) INFORMATION FOR SEQ ID NO:16:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GTCACCCTCG ACCTGCAG                                                18

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TTGTAAAACG ACGGCCAGT                                               19

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CTTCCACCGC GATGTTGA                                                18

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CAGGAAACAG CTATGAC                                                 17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GTAAAACGAC GGCCAGT                                                 17

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear -continued (ii) MOLECULE TYPE: cDNA (ix) FEATURE:
              (A) NAME/KEY: misc_feature
              (B) LOCATION: 19
              (D) OTHER INFORMATION: /note= "g: RiboG"

(xi) SEQUENCE DESCRIPTION: SEQ ID NO:21:

GTCACCCTCG ACCTGCAgC                                                 19

(2) INFORMATION FOR SEQ ID NO:22:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 19
              (D) OTHER INFORMATION: /note= "g: RiboG"

(xi) SEQUENCE DESCRIPTION: SEQ ID NO:22:

GTTGTAAAAC GAGGGCCAgT                                                20

(2) INFORMATION FOR SEQ ID NO:23:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:23:

TCTGGCCTGG TGCAGGGCCT ATTGTAGTTG TGACGTACA                            39

(2) INFORMATION FOR SEQ ID NO:24:

(i) SEQUENCE CHARACTERISTICS:
              (A) LENGTH: 14 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:24:

TCAACACTGC ATGT                                                      14

(2) INFORMATION FOR SEQ ID NO:25:

(i) SEQUENCE CHARACTERISTICS:
              (A) LENGTH: 78 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:25:

AAGATCTGAC CAGGGATTCG GTTAGCGTGA CTGCTGCTGC TGCTGCTGCT GCTGGATGAT    60
CCGACGCATC AGATCTGG                                                  78

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CTACTAGGCT GCGTAGTC                                                      18

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GATGATCCGA CGCATCACAG CTC                                                23

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

CTACTAGGCT GCGTAGTGTC GAGAACCTTG GCT                                     33

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GATGATCCGA CGCATCACAG CTC                                                23

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GTGATGCGTC GGATCATC                                                      18

(2) INFORMATION FOR SEQ ID NO:31:

(i) SEQUENCE CHARACTERISTICS:
        (A) LENGTH: 15 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

TCGGTTCCAA GAGCT                                                    15

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

CATTTGCTTC TGACACAACT G                                             21

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CTTCTCTGTC TCCACATG                                                 18

(2) INFORMATION FOR SEQ ID NO:34:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TGCACCTGAC TC                                                       12

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TGCTTACTTA ACCCAGTGTG                                               20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CACACTATGT AATACTATGC                                              20

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GAAAATATCT GACAAACTCA TC                                           22

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CATGGACACC AAATTAAGTT C                                            21

(2) INFORMATION FOR SEQ ID NO:39:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TGAGACTCTG TCTC                                                    14

(2) INFORMATION FOR SEQ ID NO:40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

TTCCCCAAAT CCCTG                                                   15

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
GGCACGGCTG TCCAAGGAG                                                    19

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

AGGCCGCGCT CGGCGCCCTC                                                   20

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

GCGGACATGG AGGACGTG                                                     18

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GATGCCGATG ACCTGCAGAA G                                                 21

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

CCCTTACCCT TACCCTTACC CTAA                                              24

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

AATCCGTGCA GCAGAGTT                                                     18

(2) INFORMATION FOR SEQ ID NO:47:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:47:

TGTCAGAGCT GGACAAGTGT                                       20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GATATTGTCT TCCCGGTAGC                                       20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

CTCGGACCAG GTGTACCGCC                                       20

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

CCTGTACTGG AAGGCGATCT C                                     21

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

CATGAGGCAG AGCATACGCA                                       20

(2) INFORMATION FOR SEQ ID NO:52:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:52:
GACAGCAGCA CCGAGACGAT                                               20

(2) INFORMATION FOR SEQ ID NO:53:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:53:

CGGCTGCGAT CACCGTGCGG                                               20

(2) INFORMATION FOR SEQ ID NO:54:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:54:

GATCCACTGT GCGACGAGC                                                19

(2) INFORMATION FOR SEQ ID NO:55:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:55:

GCGGCTGCGA TCACCGTGC                                                19
```

DNA DIAGNOSTICS BASED ON MASS SPECTROMETRY

RELATED APPLICATIONS

This application is a continuation-in-part of U.S. patent application Ser. No. 08/617,256 filed on Mar. 18, 1996, which itself is a continuation-in-part of U.S. Pat. Ser. No. 08/406,199 filed on Mar. 17, 1995, the contents of both patent applications are hereby incorporated by reference.

BACKGROUND OF THE INVENTION

The genetic information of all living organisms (e.g. animals, plants and microorganisms) is encoded in deoxyribonucleic acid (DNA). In humans, the complete genome is comprised of about 100,000 genes located on 24 chromosomes (The Human Genome, T. Strachan, BIOS Scientific Publishers, 1992). Each gene codes for a specific protein which after its expression via transcription and translation, fulfills a specific biochemical function within a living cell. Changes in a DNA sequence are known as mutations and can result in proteins with altered or in some cases even lost biochemical activities; this in turn can cause genetic disease. Mutations include nucleotide deletions, insertions or alterations (i.e. point mutations). Point mutations can be either "missense", resulting in a change in the amino acid sequence of a protein or "nonsense" coding for a stop codon and thereby leading to a truncated protein.

More than 3000 genetic diseases are currently known (Human Genome Mutations, D. N. Cooper and M. Krawczak, BIOS Publishers, 1993), including hemophilias, thalassemias, Duchenne Muscular Dystrophy (DMD), Huntington's Disease (HD), Alzheimer's Disease and Cystic Fibrosis (CF). In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Further, there is growing evidence that certain DNA sequences may predispose an individual to any of a number of diseases such as diabetes, arteriosclerosis, obesity, various autoimmune diseases and cancer (e.g. colorectal, breast, ovarian, lung).

Viruses, bacteria, fungi and other infectious organisms contain distinct nucleic acid sequences, which are different from the sequences contained in the host cell. Therefore, infectious organisms can also be detected and identified based on their specific DNA sequences.

Since the sequence of about 16 nucleotides is specific on statistical grounds even for the size of the human genome, relatively short nucleic acid sequences can be used to detect normal and defective genes in higher organisms and to detect infectious microorganisms (e.g. bacteria, fungi, protists and yeast) and viruses. DNA sequences can even serve as a fingerprint for detection of different individuals within the same species. (Thompson, J. S. and M. W. Thompson, eds., *Genetics in Medicine*, W. B. Saunders Co., Philadelphia, Pa. (1991)).

Several methods for detecting DNA are currently being used. For example, nucleic acid sequences can be identified by comparing the mobility of an amplified nucleic acid fragment with a known standard by gel electrophoresis, or by hybridization with a probe, which is complementary to the sequence to be identified. Identification, however, can only be accomplished if the nucleic acid fragment is labeled with a sensitive reporter function (e.g. radioactive ($^{32}$P, $^{35}$S), fluorescent or chemiluminescent). However, radioactive labels can be hazardous and the signals they produce decay over time. Non-isotopic labels (e.g. fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structures and interactions with the gel matrix are causing artefacts.

In general, mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Many applications of mass spectrometric methods are known in the art, particularly in biosciences, and can be found summarized in *Methods in Enzymology*, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); and P. F. Crain, "Mass Spectrometric Techniques in Nucleic Acid Research," *Mass Spectrometry Reviews* 9, 505–554 (1990).

However, nucleic acids are very polar biopolymers that are very difficult to volatilize. Consequently, mass spectrometric detection has been limited to low molecular weight synthetic oligonucleotides by determining the mass of the parent molecular ion and through this, confirming the already known oligonucleotide sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Wolter et al. *Biomedical Environmental Mass Spectrometry* 14, 111–116 (1987)).

Two more recent ionization/desorption techniques are electrospray/ionspray (ES) and matrix-assisted laser desorption/ionization (MALDI). ES mass spectrometry has been introduced by Yamashita et al. (*J. Phys. Chem.* 88, 4451–59 (1984); PCT Application No. WO 90/14148) and current applications are summarized in recent review articles (R. D. Smith et al., *Anal. Chem.* 62, 882–89 (1990) and B.

Ardrey, Electrospray Mass Spectrometry, *Spectroscopy Europe*, 4, 10–18 (1992)). The molecular weights of a tetradecanucleotide (Covey et al. "The Determination of Protein, Oligonucleotide and Peptide Molecular Weights by Ionspray Mass Spectrometry," *Rapid Communications in Mass Spectrometry*, 2, 249–256 (1988)), and of a 21-mer (*Methods in Enzymology*, 193, "Mass Spectrometry" (McCloskey, editor), p. 425, 1990, Academic Press, New York) have been published. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. ("Matrix Assisted UV-Laser Desorption/Ionization: A New Approach to Mass Spectrometry of Large Biomolecules," *Biological Mass Spectrometry* (Burlingame and McCloskey, editors), Elsevier Science Publishers, Amsterdam, pp. 49–60, 1990.) Since, in most cases, no multiple molecular ion peaks are produced with this technique, the mass spectra, in principle, look simpler compared to ES mass spectrometry.

Although DNA molecules up to a molecular weight of 410,000 daltons have been desorbed and volatilized (Williams et al., "Volatilization of High Molecular Weight DNA by Pulsed Laser Ablation of Frozen Aqueous Solutions," *Science*, 246, 1585–87 (1989)), this technique has so far only shown very low resolution (oligothymidylic acids up to 18 nucleotides, Huth-Fehre et al., *Rapid Communications in Mass Spectrometry*, 6, 209–13 (1992); DNA fragments up to 500 nucleotides in length K. Tang et al., *Rapid Communications in Mass Spectrometry*, 8, 727–730 (1994); and a double-stranded DNA of 28 base pairs (Williams et al., "Time-of-Flight Mass Spectrometry of Nucleic Acids by Laser Ablation and Ionization from a Frozen Aqueous Matrix," *Rapid Communications in Mass Spectrometry*, 4, 348–351 (1990)).

Japanese Patent No. 59-131909 describes an instrument, which detects nucleic acid fragments separated either by electrophoresis, liquid chromatography or high speed gel filtration. Mass spectrometric detection is achieved by incorporating into the nucleic acids, atoms which normally do not occur in DNA such as S, Br, I or Ag, Au, Pt, Os, Hg.

SUMMARY OF THE INVENTION

The instant invention provides mass spectrometric processes for detecting a particular nucleic acid sequence in a biological sample. Depending on the sequence to be detected, the processes can be used, for example, to diagnose (e.g. prenatally or postnatally) a genetic disease or chromosomal abnormality; a predisposition to or an early indication of a gene influenced disease or condition (e.g. obesity, artherosclerosis, cancer), an infection by a pathogenic organism (e.g. virus, bacteria, parasite or fungus); or to provide information relating to identity (e.g., mini- and micro-satellites) heredity, or compatibility (e.g. HLA phenotyping).

In a first embodiment, a nucleic acid molecule containing the nucleic acid sequence to be detected (i.e. the target) is initially immobilized to a solid support. Immobilization can be accomplished, for example, based on hybridization between a portion of the target nucleic acid molecule, which is distinct from the target detection site and a capture nucleic acid molecule, which has been previously immobilized to a solid support. Alternatively, immobilization can be accomplished by direct bonding of the target nucleic acid molecule and the solid support. Preferably, there is a spacer (e.g. a nucleic acid molecule) between the target nucleic acid molecule and the support. A detector nucleic acid molecule (e.g. an oligonucleotide or oligonucleotide mimetic), which is complementary to the target detection site can then be contacted with the target detection site and formation of a duplex, indicating the presence of the target detection site can be detected by mass spectrometry. In preferred embodiments, the target detection site is amplified prior to detection and the nucleic acid molecules are conditioned. In a further preferred embodiment, the target detection sequences are arranged in a format that allows multiple simultaneous detections (multiplexing), as well as parallel processing using oligonucleotide arrays ("DNA chips").

In a second embodiment, immobilization of the target nucleic acid molecule is an optional rather than a required step. Instead, once a nucleic acid molecule has been obtain from a biological sample, the target detection sequence is amplified and directly detected by mass spectrometry. In preferred embodiments, the target detection site and/or the detector oligonucleotides are conditioned prior to mass spectrometric detection. In another preferred embodiment, the amplified target detection sites are arranged in a format that allows multiple simultaneous detections (multiplexing), as well as parallel processing using oligonucleotide arrays ("DNA chips").

In a third embodiment, nucleic acid molecules which have been replicated from a nucleic acid molecule obtained from a biological sample can be specifically digested using one or more nucleases (using deoxyribonucleases for DNA or ribonucleases for RNA) and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. Further, the fragments generated can be ordered to provide the sequence of the larger target fragment.

Examples of preferred methods for generating specifically terminated fragments include: 1) using a base-specific ribonuclease (e.g. the G-specific $T_1$, the A-specific $U_2$, the A/U specific PhyM and U/C specific ribonuclease A) e.g., after a transcription reaction; 2) performing a combined amplification and base-specific termination reaction (e.g. using two appropriate polymerases); and 3) contacting an appropriate amount of the target nucleic acid with a specific endonuclease (e.g., a restriction enzyme).

In preferred embodiments, the 5' and/ or 3' end of the target nucleic acid is tagged to facilitate the ordering of fragments. Tagging of the 3' end is also useful to rule out or compensate for the influence of 3' heterogeneity, premature termination and nonspecific elongation. In other preferred embodiments, modified nucleotides are included in the transcription reaction with unmodified nucleotides. Most preferably, the modified nucleotides and unmodified nucleotides are added to the transcription reaction at appropriate concentrations, so that both moieties are incorporated at a preferential rate of about 1:1. Alternatively, two separate transcriptions of the target DNA sequence, one with the modified and one with the unmodified nucleotides can be performed and the results compared.

In a fourth embodiment, at least one primer with 3' terminal base complementarity to an allele (mutant or normal) is hybridized with a target nucleic acid molecule, which contains the allele. An appropriate polymerase and a complete set of nucleoside triphosphates or only one of the nucleoside triphosphates are used in separate reactions to furnish a distinct extension of the primer. Only if the primer is appropriately annealed (i.e. no 3' mismatch) and if the correct (i.e. complementary) nucleotide is added, will the primer be extended. Products can be resolved by molecular weight shifts as determined by mass spectrometry.

In a fifth embodiment, a nucleic acid molecule containing the nucleic acid sequence to be detected (i.e. the target) is initially immobilized to a solid support.

Immobilization can be accomplished, for example, based on hybridization between a portion of the target nucleic acid molecule, which is distinct from the target detection site and a capture nucleic acid molecule, which has been previously immobilized to a solid support. Alternatively, immobilization can be accomplished by direct bonding of the target nucleic acid molecule and the solid support. Preferably, there is a spacer (e.g. a nucleic acid molecule) between the target nucleic acid molecule and the support. A nucleic acid molecule that is complementary to a portion of the target detection site that is immediately 5' of the site of a potential mutation (X) is then hybridized with the target nucleic acid molecule. The addition of a complete set of dideoxynucleosides or 3'-deoxynucleoside triphosphates (e.g. pppAdd, pppTdd, pppCdd and pppGdd) and a DNA dependent DNA or RNA polymerase allows for the addition only of the one dideoxynucleoside or 3'-deoxynucleoside triphosphate that is complementary to X. The hybridization product can then be detected by mass spectrometry.

In a sixth embodiment, a target nucleic acid is hybridized with a complementary oligonucleotides that hybridize to the target within a region that includes a mutation M. The heteroduplex is then contacted with an agent that can specifically cleave at an unhybridized portion (e.g. a single strand specific endonuclease), so that a mismatch, indicating the presence of a mutation, results in the cleavage of the target nucleic acid. The two cleavage products can then be detected by mass spectrometry.

In a seventh embodiment, which is based on the ligase chain reaction (LCR), a target nucleic acid is hybridized with a set of ligation educts and a thermostable DNA ligase, so that the ligation educts become covalently linked to each other, forming a ligation product. The ligation product can then be detected by mass spectrometry and compared to a known value. If the reaction is performed in a cyclic manner, the ligation product obtained can be amplified to better facilitate detection of small amounts of the target nucleic acid. Selection between wildtype and mutated primers at the ligation point can result in the detection of a point mutation.

In an eighth embodiment, at least one primer with 3'-terminal base is hybridized to the target nucleic acid near a site where possible mutations are to be detected. An appropriate polymerase and a set of three nucleoside triphosphates (NTPs) and the fourth added as a terminator are reacted. The extension reaction products are measured by mass spectrometry and are indicative of the presence and the nature of a mutation. The set of three NTPs and one dd NTP (or three NTPs and one 3'-deoxy NTP), will be varied to be able to discriminate between several mutations (including compound heterozygotes) in the target nucleic acid sequnce.

The processes of the invention provide for increased accuracy and reliability of nucleic acid detection by mass spectrometry. In addition, the processes allow for rigorous controls to prevent false negative or positive results. The processes of the invention avoid electrophoretic steps; labeling and subsequent detection of a label. In fact it is estimated that the entire procedure, including nucleic acid isolation, amplification, and mass spectrometry analysis requires only about 2–3 hours. Therefore the instant disclosed processes of the invention are faster and less expensive to perform than existing DNA detection systems. In addition, because the instant disclosed processes allow the nucleic acid fragments to be identified and detected at the same time by their specific molecular weights (an unambiguous physical standard), the disclosed processes are also much more accurate and reliable than currently available procedures.

Other features and advantages of the invention will be further described with reference to the following Detailed Description and Claims.

BRIEF DESCRIPTION OF THE FIGURES

FIG. 5 is a diagram showing how amplification (here ligase chain reaction (LCR)) products can be prepared and detected by mass spectrometry. Mass differentiation can be achieved by the mass modifying functionalities (M1 and M2) attached to primers (P1 and P4 respectively). Detection by mass spectrometry can be accomplished directly (i.e. without employing immobilization and target capturing sites (TCS)). Multiple LCR reactions can be performed in parallel by providing an ordered array of capturing sequences (C). This format allows separation of the ligation products and spot by spot identification via mass spectrometry or multiplexing if mass differentiation is sufficient.

FIG. 6A is a diagram showing mass spectrometric analysis of a nucleic acid molecule, which has been amplified by a transcription amplification procedure. An RNA sequence is captured via its TCS sequence, so that wildtype and mutated target detection sites can be detected as above by employing appropriate detector oligonucleotides (D).

FIG. 6B is a diagram showing multiplexing to detect two different (mutated) sites on the same RNA in a simultaneous fashion using mass-modified detector oligonucleotides M1–D1 and M2–D2.

FIG. 6C is a diagram of a different multiplexing procedure for detection of specific mutations by employing mass modified dideoxynucleoside or 3'-deoxynucleoside triphosphates and an RNA dependent DNA polymerase. Alternatively, DNA dependent RNA polymerase and ribonucleotide triphosphates can be employed. This format allows for simultaneous detection of all four base possibilities at the site of a mutation (X).

FIG. 34 is a schematic presentation of the oligo base extension of the mutation detection primer as described in Example 7, using ddTTP (A) or ddCTP (B) in the reaction mix, respectively. The theoretical mass calculation is given in parenthesis. The sequence shown is part of the exon 10 of the CFTR gene that bears the most common cystic fibrosis mutation ΔF508 and more rare mutations ΔI507 as well as Ile506Ser.

FIG. 48 shows a stacking flurogram of the same products obtained from the reaction described in FIG. 47, but run on a conventional DNA sequencer.

FIG. 50 shows a schematic representation of the sequencing ladder generated in FIG. 49 with the corresponding calculated molecular masses up to 40 bases after the primer. For the calculation, the following masses were used: 3581.4Da for the primer, 312.2 Da for 7-deaza-dATP, 304.2 Da for dTTP, 289.2 Da for dCTP and 328.2 Da for 7-deaza-dGTP.

FIG. 51 shows the sequence of the amplified 209 bp PCR product within the β-globin gene, which was used as a template for sequencing. The sequences of the appropriate PCR primer and the location of the 12 mer sequencing primer is also shown. This sequence represents a homozygote mutant at the position 4 bases after the primer. In a wildtype sequence this T would be replaced by an A.

FIG. 52 shows a sequence which is part of the intron 5 of the interferon-receptor gene that bears the AluVpA polymorphism as further described in Example 11. The scheme presents the primer oligo base extension (PROBE) using ddGTP, ddCTP, or both for termination, respectively. The polymorphism detection primer (IFN) is underlined, the termination nucleotides are marked in bold letters. The theoretical mass values from the alleles found in 28 unrelated individuals and a five member family are given in the table. Both second site mutations found in most 13 units allele, but not all, are indicated.

FIG. 55 shows a schematic presentation of the PROBE method for detection of different alleles in the polyT tract at the 3'-end of intron 8 of the CFTR gene with pppCdd as terminator (Example 11).

FIG. 61 shows the multiplex (codons 112 and 158) mass spectrum PROBE results for a) $\epsilon2/\epsilon3$, b)$\epsilon3/\epsilon3$, c) $\epsilon3/\epsilon4$ and d) $\epsilon4/\epsilon4$ genotypes. E: extension products; P: unextended primer. Top: codon 112 and 158 regions, with polymorphic sites bold and primer sequences underlined.

FIG. 65 (b) shows the expected PROBE products for ddT and ddA reactions for wildtype, C→T, and C→A antisense strands.

DETAILED DESCRIPTION OF THE INVENTION

Figure 1A:
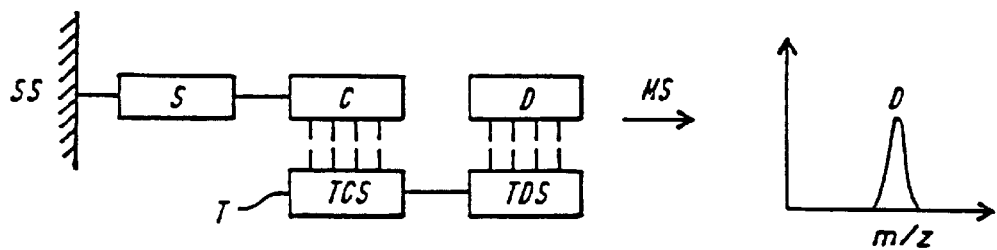
FIG. 1A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on the target nucleic acid molecule (T), known as the target capture site (TCS). The spacer (S) facilitates unhindered hybridization. A detector nucleic acid sequence (D), which is complementary to the TDS is then contacted with the TDS. Hybridization between D and the TDS can be detected by mass spectrometry.

In general, the instant invention provides mass spectrometric processes for detecting a particular nucleic acid sequence in a biological sample. As used herein, the term "biological sample" refers to any material obtained from any living source (e.g. human, animal, plant, bacteria, fungi, protist, virus). For use in the invention, the biological sample should contain a nucleic acid molecule. Examples of appropriate biological samples for use in the instant invention include: solid materials (e.g tissue, cell pellets, biopsies) and biological fluids (e.g. urine, blood, saliva, amniotic fluid, mouth wash).

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994)).

To obtain an appropriate quantity of a nucleic acid molecules on which to perform mass spectrometry, amplification may be necessary. Examples of appropriate amplification procedures for use in the invention include: cloning (Sambrook et al., Molecular Cloning : A Laboratory Manual, Cold Spring Harbor Laboratory Press, 1989), polymerase chain reaction (PCR) (C. R. Newton and A. Graham, PCR, BIOS Publishers, 1994), ligase chain reaction (LCR) (Wiedmann, M., et. al., (1994) *PCR Methods Appl.* Vol. 3, Pp. 57–64; F. Barany *Proc. Natl. Acad. Sci USA* 88, 189–93 (1991), strand displacement amplification (SDA) (G. Terrance Walker et al., *Nucleic Acids Res.* 22, 2670–77 (1994)) and variations such as RT-PCR (Higuchi, et al., *Bio/*

*Technology* 11:1026–1030 (1993)), allele-specific amplification (ASA) and transcription based processes.

As used herein, the phrases "chain-elongating nucleotides" and "chain-terminating nucleotides" are used in accordance with their art recognized meaning. For example, for DNA, chain-elongating nucleotides include 2'-deoxyribonucleotides (e.g. dATP, dCTP, dGTP and dTTP) and chain-terminating nucleotides include 2', 3'-dideoxyribonucleotides (e.g. ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g. 3'dA, 3'dC, 3'dG and 3'dU). A complete set of chain elongating nucleotides refers to dATP, dCTP, dGTP and dTTP. The term "nucleotide" is also well known in the art. For the purposes of this invention, nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

To facilitate mass spectrometric analysis, a nucleic acid molecule containing a nucleic acid sequence to be detected can be immobilized to an insoluble (i.e., a solid) support. Examples of appropriate solid supports include beads (e.g. silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g. silicon wafers) with or without filter plates.

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected (FIG. 1A). So that hybridization between the complementary nucleic acid molecules is not hindered by the support, the capture nucleic acid can include an e.g., spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al, *Science*, 254, 1497 (1991)) which render the base sequence less susceptible to enzymatic degradation and hence increases overall stability of the solid support-bound capture base sequence.

Figure 1B:
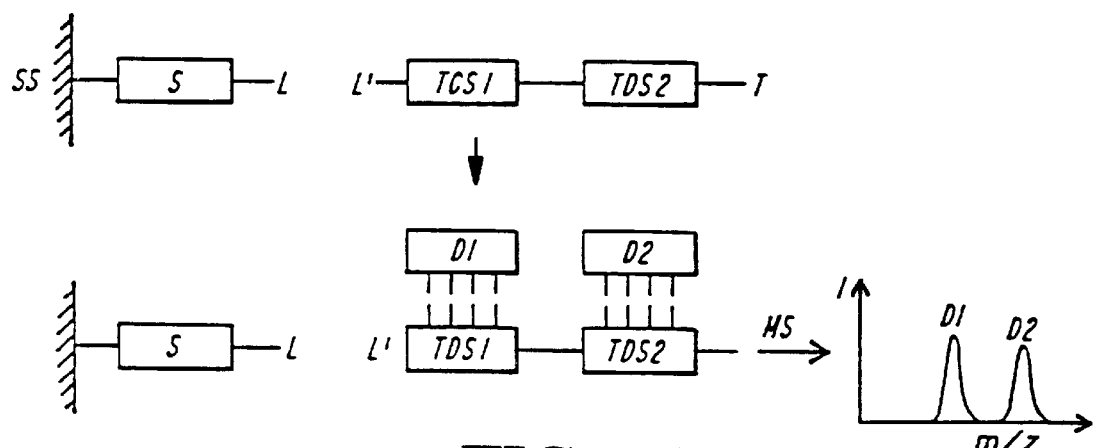
FIG. 1B is a diagram showing a process for performing mass spectrometric analysis on at least one target detection site (here TDS1 and TDS 2) via direct linkage to a solid support. The target sequence (T) containing the target detection site (TDS1 and TDS 2) is immobilized to a solid support via the formation of a reversible or irreversible bond formed between an appropriate functionality (L') on the target nucleic acid molecule (T) and an appropriate functionality (L) on the solid support. Detector nucleic acid sequences (here D1 and D2), which are complementary to a target detection site (TDS1 or TDS 2) are then contacted with the TDS. Hybridization between TDS1 and D1 and/or TDS 2 and D2 can be detected and distinguished based on molecular weight differences.

Alternatively, a target detection site can be directly linked to a solid support via a reversible or irreversible bond between an appropriate functionality (L') on the target nucleic acid molecule (T) and an appropriate functionality (L) on the capture molecule (FIG. 1B). A reversible linkage can be such that it is cleaved under the conditions of mass spectrometry (i.e., a photocleavable bond such as a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

By way of example, the L-L' chemistry can be of a type of disulfide bond (chemically cleavable, for example, by mercaptoethanol or dithioerythrol), a biotin/streptavidin system, a heterobifunctional derivative of a trityl ether group (Gildea et al., "A Versatile Acid-Labile Linker for Modification of Synthetic Biomolecules," *Tetrahedron Letters* 31, 7095 (1990)) which can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L,' can also form a charge transfer complex and thereby form the temporary L-L' linkage. Since in many cases the "charge-transfer band" can be determined by UV/vis spectrometry (see e.g. *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g. *Reactive Molecules* by C. Wentrup, John Wiley & Sons, 1984).

Figure 4:
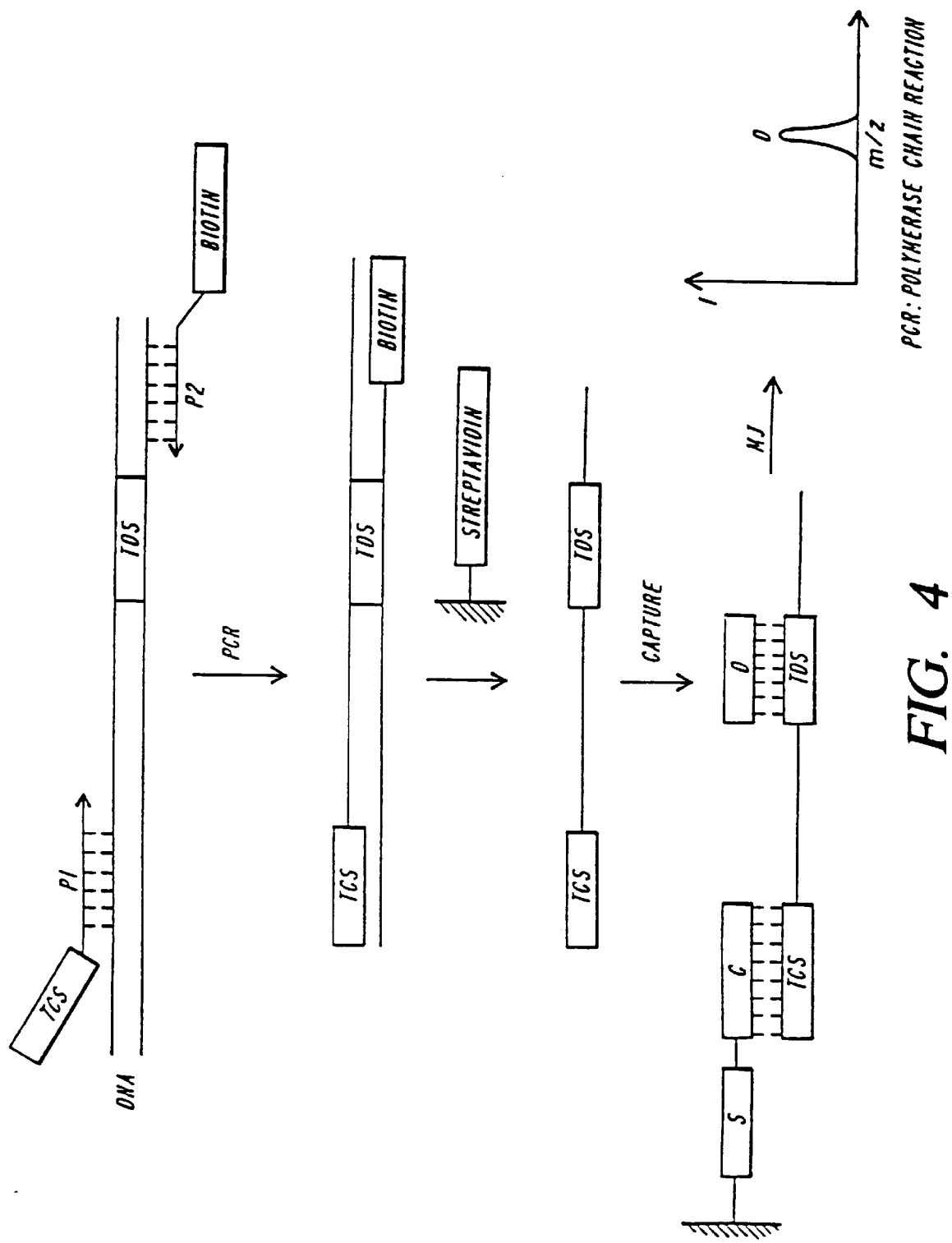
FIG. 4 is a diagram showing a format wherein a predesigned target capture site (TCS) is incorporated into the target sequence using PCR amplification. Only one strand is captured, the other is removed (e.g., based on the interaction between biotin and streptavidin coated magnetic beads). If the biotin is attached to primer 1 the other strand can be appropriately marked by a TCS. Detection is as described above through the interaction of a specific detector oligonucleotide D with the corresponding target detection site TDS via mass spectrometry.
Figure 7A:
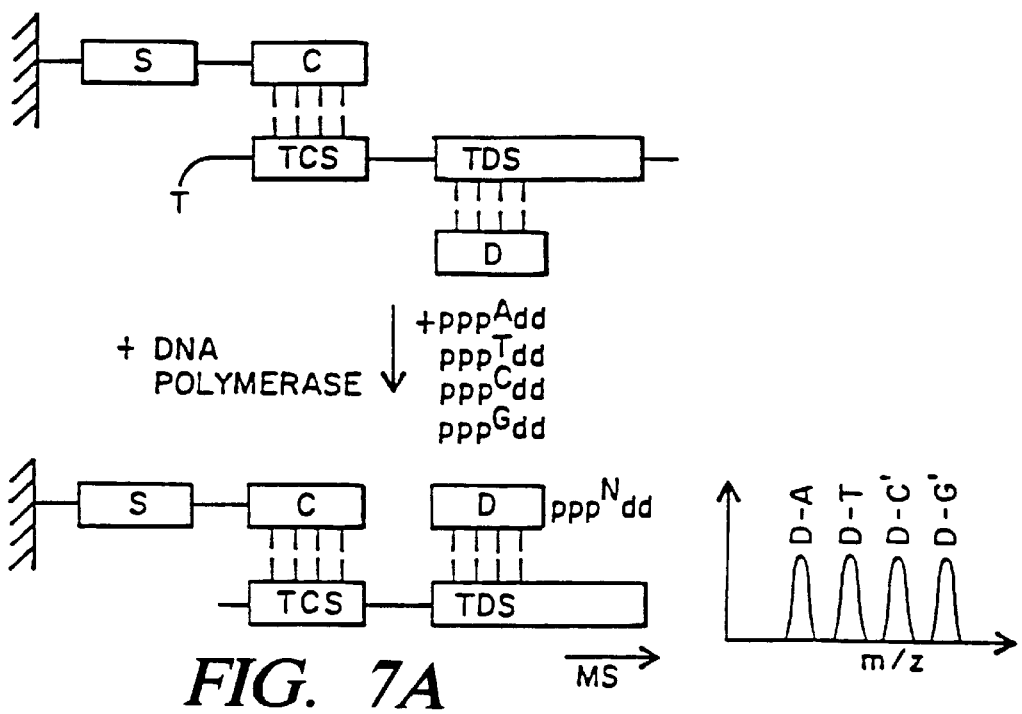
FIG. 7A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on T known as the target capture site (TCS). A nucleic acid molecule that is complementary to a portion of the TDS is hybridized to the TDS 5' of the site of a mutation (X) within the TDS. The addition of a complete set of dideoxynucleosides or 3'-deoxynucleoside triphosphates (e.g. pppAdd, pppTdd, pppCdd and pppGdd) and a DNA dependent DNA or RNA polymerase allows for the addition only of the one dideoxynucleoside or 3'-deoxynucleoside triphosphate that is complementary to X.
Figure 7B:
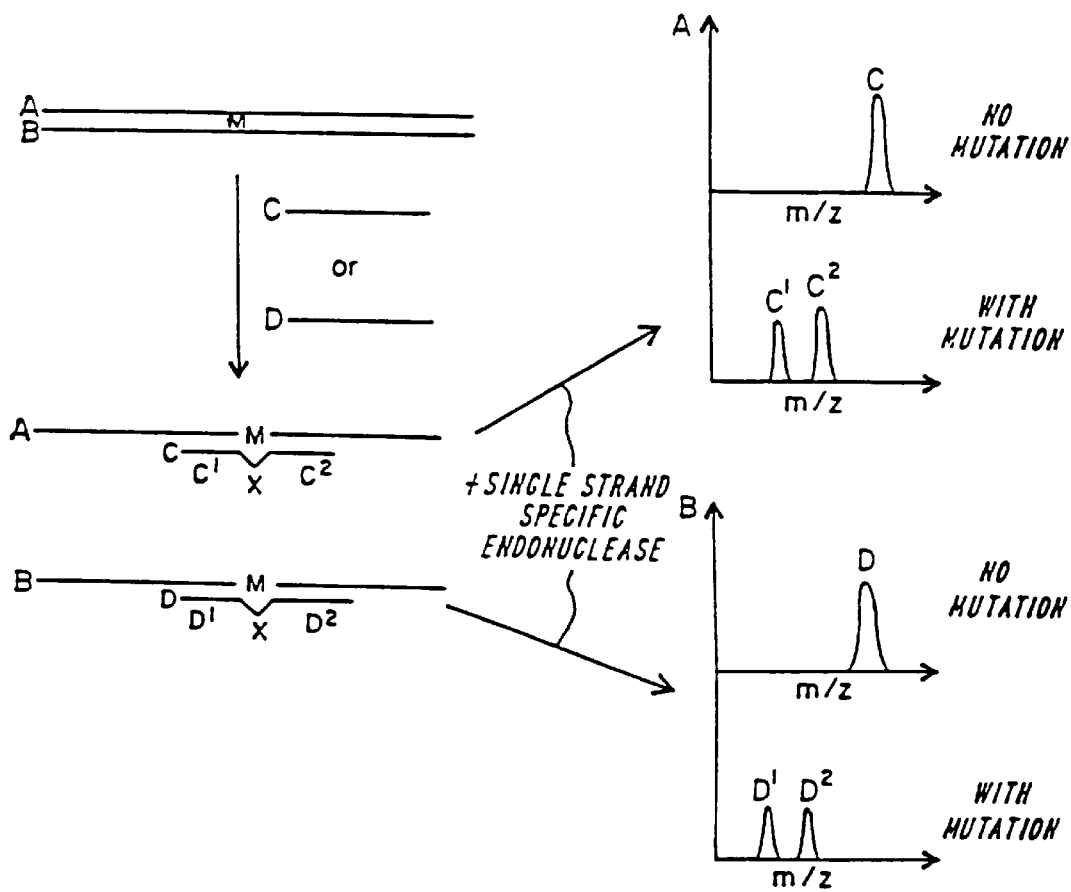
FIG. 7B is a diagram showing a process for performing mass spectrometric analysis to determine the presence of a mutation at a potential mutation site (M) within a nucleic acid molecule. This format allows for simultaneous analysis of both alleles (A) and (B) of a double stranded target nucleic acid molecule, so that a diagnosis of homozygous normal, homozygous mutant or heterozygous can be provided. Allele A and B are each hybridized with complementary oligonucleotides ((C) and (D) respectively), that hybridize to A and B within a region that includes M. Each heteroduplex is then contacted with a single strand specific endonuclease, so that a mismatch at M, indicating the presence of a mutation, results in the cleavage of (C) and/or (D), which can then be detected by mass spectrometry.
Figure 8:
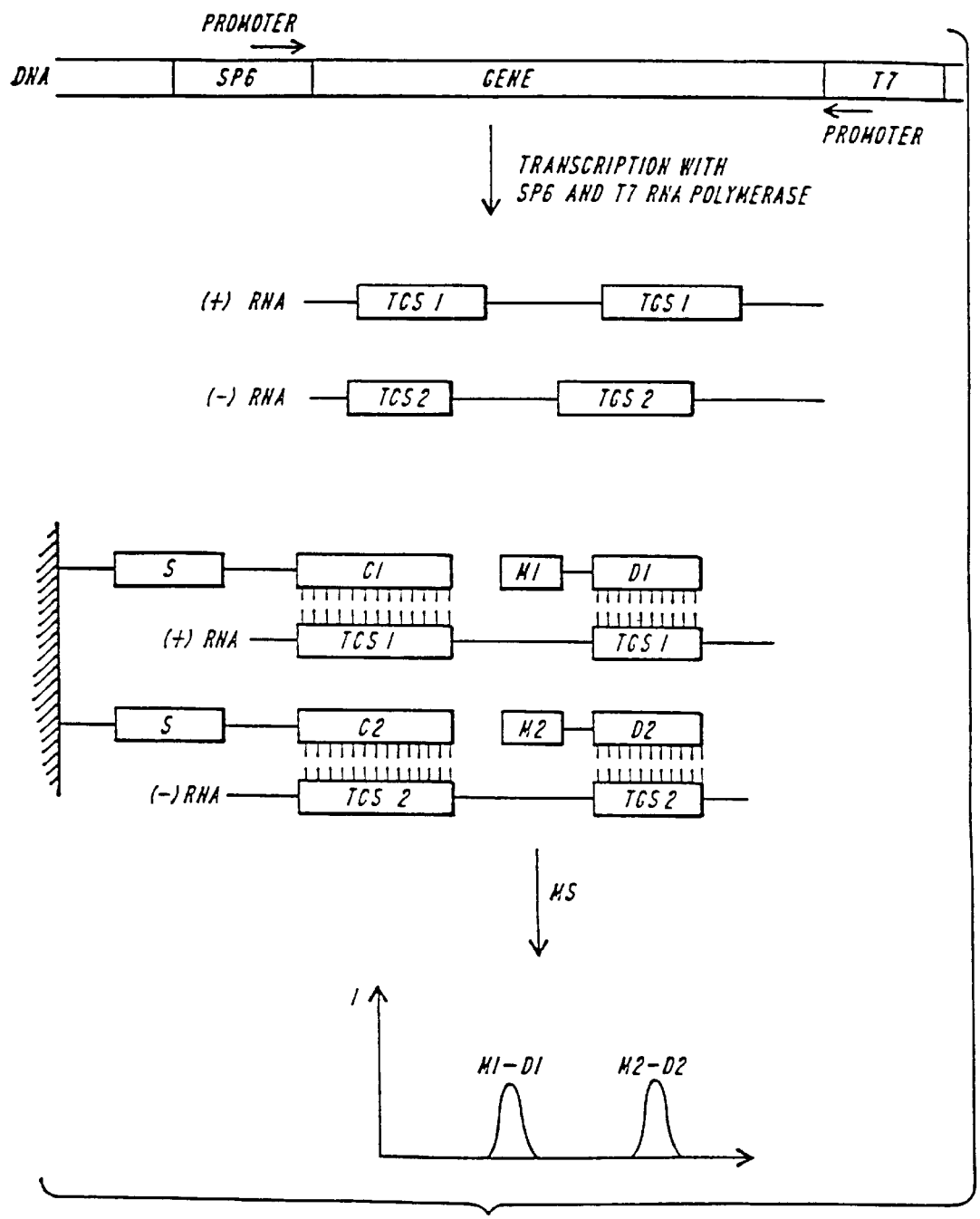
FIG. 8 is a diagram showing how both strands of a target DNA can be prepared for detection using transcription vectors having two different promoters at opposite locations (e.g. the SP6 and the T7 promoter). This format is particularly useful for detecting heterozygous target detection sites (TDS). Employing the SP6 or the T7 RNA polymerase both strands could be transcribed separately or simultaneously. Both RNAs can be specifically captured and simultaneously detected using appropriately mass-differentiated detector oligonucleotides. This can be accomplished either directly in solution or by parallel processing of many target sequences on an ordered array of specifically immobilized capturing sequences.

An anchoring function L' can also be incorporated into a target capturing sequence (TCS) by using appropriate primers during an amplification procedure, such as PCR (FIG. 4), LCR (FIG. 5) or transcription amplification (FIG. 6A).

Prior to mass spectrometric analysis, it may be useful to "condition" nucleic acid molecules, for example to decrease the laser energy required for volatization and/or to minimize fragmentation. Conditioning is preferably performed while a target detection site is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as alkyliodide, iodoacetamide, β-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depurination (fragmentation during MS) e.g., a purine analog such as N7- or N9-deazapurine nucleotides, or RNA building blocks or using oligonucleotide triesters or incorporating phosphorothioate functions which are alkylated or employing oligonucleotide mimetics such as PNA.

Figure 2:
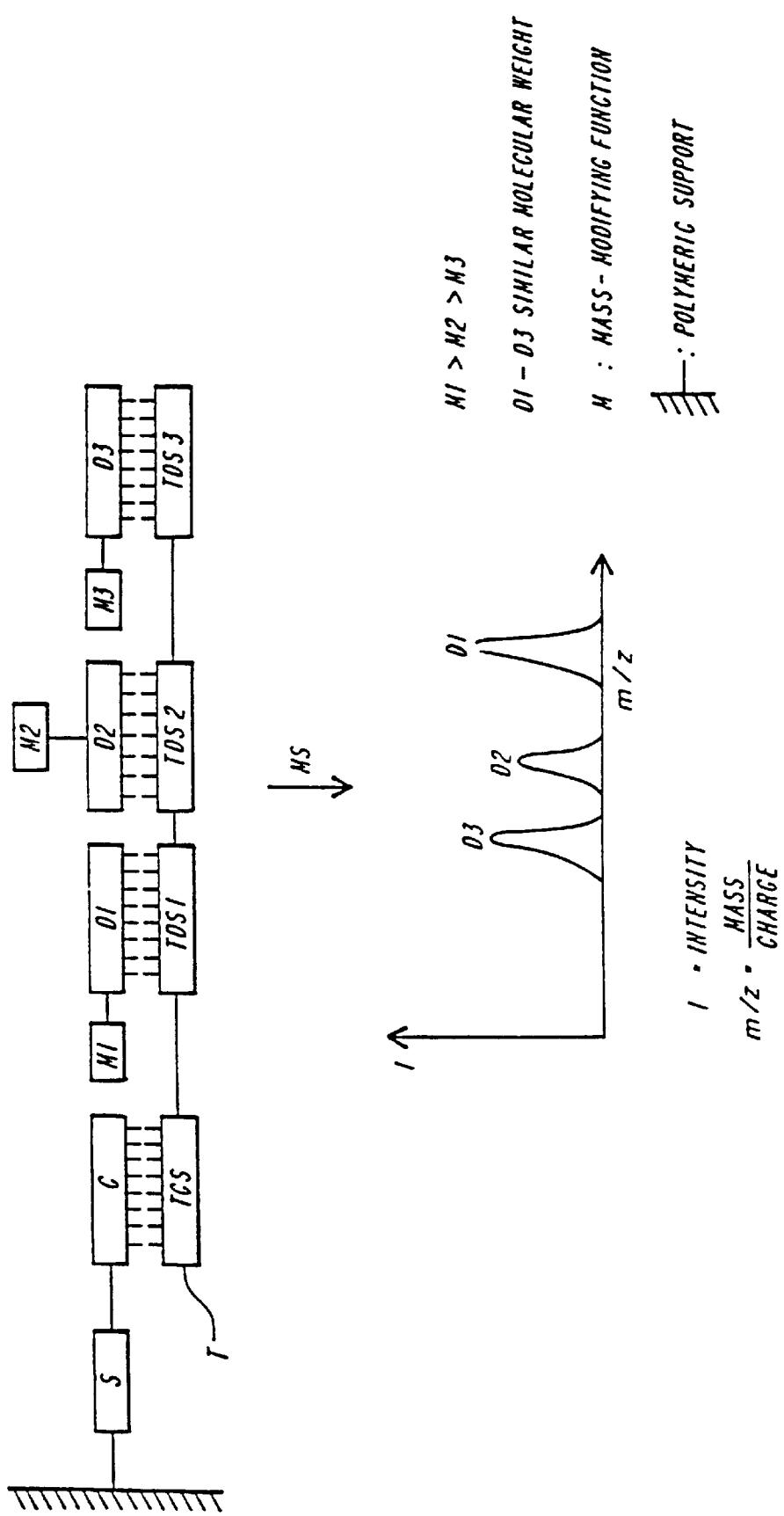
FIG. 2 is a diagram showing a process in which several mutations are simultaneously detected on one target sequence by employing corresponding detector oligonucleotides. The molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide.

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector (probe) molecules (e.g. oligonucleotides or oligonucleotide mimetics). However, the molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1–M3 into the detector oligonucleotide.(FIG. 2)

Mass modifying moieties can be attached, for instance, to either the 5'-end of the oligonucleotide ($M^1$), to the nucleobase (or bases) ($M^2$, $M^7$), to the phosphate backbone ($M^3$), to the 2'-position of the nucleoside (nucleosides) ($M^4$, $M^6$) and/or to the terminal 3'-position ($M^5$). Examples of mass modifying moieties include, for example, a halogen, an azido, or of the type, XR, wherein X is a linking group and R is a mass-modifying functionality. The mass-modifying functionality can thus be used to introduce defined mass increments into the oligonucleotide molecule.

In accordance with this invention, the mass-modifying functionality can be located at different positions within the nucleotide moiety (See also H. Köster, U.S. Pat. No. 5,547,835 and H. Köster, International Patent Application Serial No. WO 94/21822 for further examples and synthesis chemistries). For example, the mass-modifying moiety, M, can be attached either to the nucleobase, $M^2$ (in case of the $c^7$-deazanucleosides also to C-7, $M^7$), to the triphosphate group at the alpha phosphate, $M^3$, or to the 2'-position of the sugar ring of the nucleoside triphosphate, $M^4$ and $M^6$. Modifications introduced at the phosphodiester bond (M4), such as with alpha-thio nucleoside triphosphates, have the advantage that these modifications do not interfere with accurate Watson-Crick base-pairing and additionally allow for the one-step post-synthetic site-specific modification of the complete nucleic acid molecule e.g. via alkylation reactions (K. L. Nakamaye, G. Gish, F. Eckstein and H. -P. Vossberg, (1988) *Nucleic Acids Res.*, 16:9947–59). Particularly preferred mass-modifying functionalities are boron-modified nucleic acids since they are better incorporated into nucleic acids by polymerases. (Porter, K. W. et al., (1995) *Biochemistry* 34:11963–11969; Hasan, A. et al., (1996) *Nucleic Acids Res.* 24:2150–2157; Li, H. et al., (1995) *Nucleic Acids Res.* 23:4495–4501).

Furthermore, the mass-modifying functionality can be added so as to affect chain termination, such as by attaching it to the 3'-position of the sugar ring in the nucleoside triphosphate, $M^5$. For those skilled in the art, it is clear that many combinations can serve the purpose of the invention equally well. In the same way, those skilled in the art will recognize that chain-elongating nucleoside triphosphates can also be mass-modified in a similar fashion with numerous variations and combinations in functionality and attachment positions.

Without limiting the scope of the invention, the mass-modification, M, can be introduced for X in XR as well as using oligo-/polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid molecule (e.g. detector oligonucleotide (D) or the nucleoside triphosphates (FIG. 6(C)), respectively). The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds, as for example, those described recently in *Oligonucleotides and Analogues, A Practical Approach*, F. Eckstein, editor, IRL Press, Oxford, 1991.

In yet another embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as CN, SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g. detector (D)) or nucleoside triphosphates. One example, useful in generating mass-modified species with a mass increment of 57, is the attachment of oligoglycines, e.g., mass-modifications of 74 (r=1, m=0), 131 (r=1, m=1), 188 (r=1, m=2), 245 (r=1, m=3) are achieved. Simple oligoamides also can be used, e.g., mass-modifications of 74 (r=1, m=0), 88 (r=2, m=0), 102 (r=3, m=0), 116 (r=4, m=0), etc. are obtainable. For those skilled in the art, it will be obvious that there are numerous possibilities in addition to those mentioned above.

As used herein, the superscript 0–i designates i+1 mass differentiated nucleotides, primers or tags. In some instances, the superscript 0 can designate an unmodified species of a particular reactant, and the superscript i can designate the i-th mass-modified species of that reactant. If, for example, more than one species of nucleic acids are to be concurrently detected, then i+1 different mass-modified detector oligonucleotides ($D^0$, $D^1$, . . . $D^i$) can be used to distinguish each species of mass modified detector oligonucleotides (D) from the others by mass spectrometry.

Different mass-modified detector oligonucleotides can be used to detect all possible variants/mutants simultaneously (FIG. 6B). Alternatively, all four base permutations at the site of a mutation can be detected by designing and positioning a detector oligonucleotide, so that it serves as a primer for a DNA/RNA polymerase with varying combinations of elongating and terminating nucleoside triphosphates (FIG. 6C). For example, mass modifications also can be incorporated during the amplification process.

Figure 3:
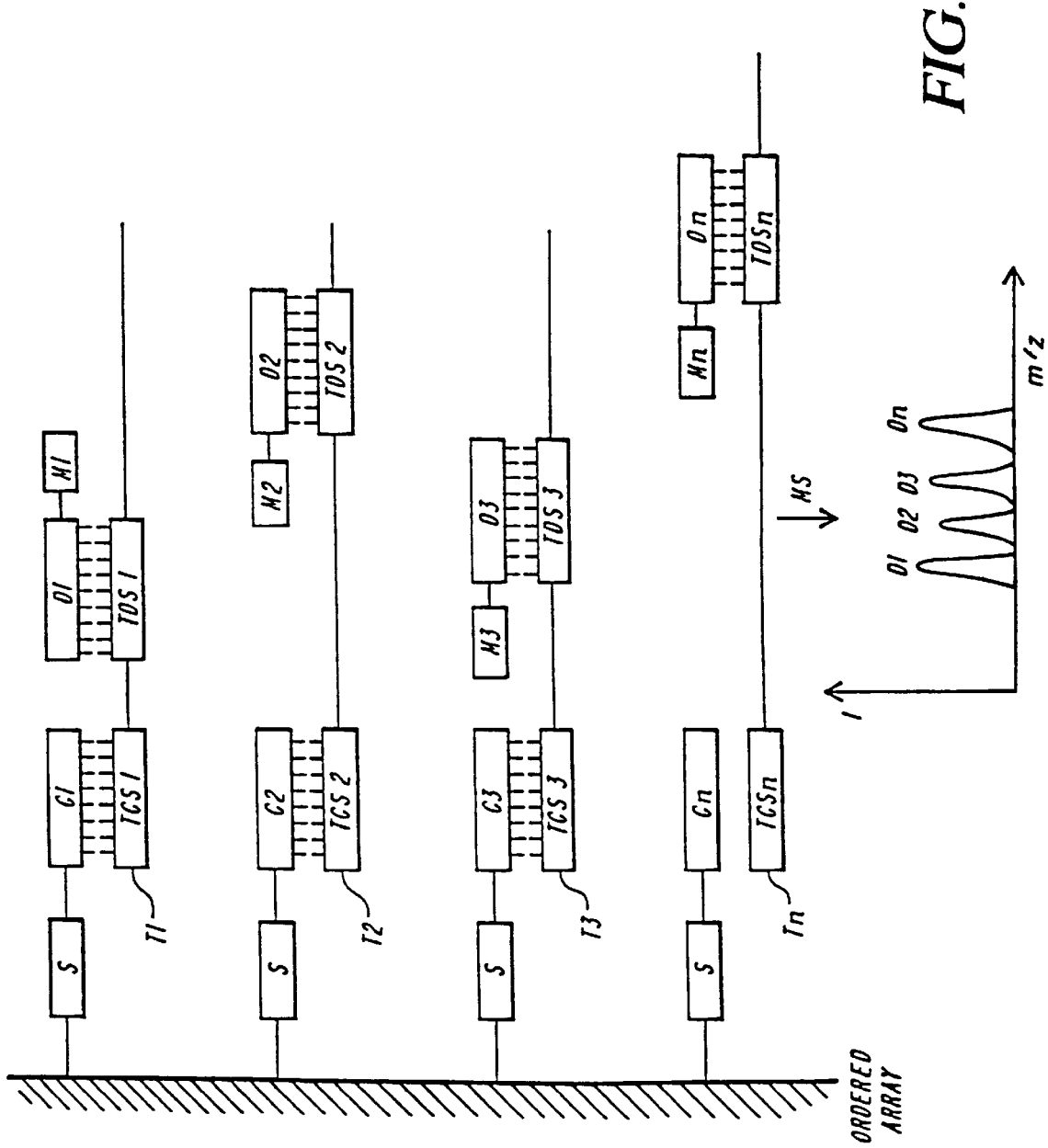
FIG. 3 is a diagram showing still another multiplex detection format. In this embodiment, differentiation is accomplished by employing different specific capture sequences which are position-specifically immobilized on a flat surface (e.g., a 'chip array'). If different target sequences T1–Tn are present, their target capture sites TCS1–TCSn will interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

FIG. 3 shows a different multiplex detection format, in which differentiation is accomplished by employing different specific capture sequences which are position-specifically immobilized on a flat surface (e.g, a 'chip array'). If different target sequences T1–Tn are present, their target capture sites TCS1–TCSn will specifically interact with complementary immobilized capture sequences C1–Cn. Detection is achieved by employing appropriately mass differentiated detector oligonucleotides D1–Dn, which are mass differentiated either by their sequences or by mass modifying functionalities M1–Mn.

Amenable mass spectrometric formats for use in the invention include the ionization (I) techniques, such as matrix assisted laser desorption (MALDI), electrospray (ESI) (e.g. continuous or pulsed); and related methods (e. g. Ionspray, Thermospray), and massive cluster impact (MCI); these ion sources can be matched with detection formats including linear or reflector (with linear or non-linear fields) time-of-flight (TOF), single or multiple quadrupole, single or multiple magnetic sector, Fourier transform ion cyclotron resonance (FTICR), ion trap, or combinations of these to give a hybrid detector (e. g. ion trap—time of flight). For ionization, numerous matrix/wavelength combinations including frozen analyte preparation (MALDI) or solvent combinations (ESI) can be employed.

Since a normal DNA molecule is only comprised of four nucleotide units (A, T, C, G), and the mass of each of these is unique (monoisotopic masses 313.06, 304.05, 289.05, 329.05 Da, respectively), an accurate mass determination can define or constrain the possible base compositions of that DNA. Only above 4900 Da does each unit molecular weight have at least one allowable composition; among all 5-mers there is only one non-unique nominal molecular weight, among 8-mers, 20. For these and larger oligonucleotides, such mass overlaps can be resolved with the $\sim 1/10^5$ ($\sim 10$ part per million, ppm) mass accuracy available with high resolution FTICR MS. For the 25-mer $A_5T_{20}$, the 20 composition degeneracies when measured at $\pm 0.5$ Da is reduced to three ($A_5T_{20}$, $T_4C_{12}G_9$, $AT_3C_4G_{16}$) when measured with 2 ppm accuracy. Given composition constraints (e. g. the presence or absence of one of the four bases in the strand) can reduce this further (see below).

Medium resolution instrumentation, including but not exclusively curved field reflectron or delayed extraction time-of-flight MS instruments, can also result in improved DNA detection for sequencing or diagnostics. Either of these are capable of detecting a 9 Da ($\Delta m$ (A–T)) shift in $\geq 30$-mer strands generated from for example primer oligo base extension (PROBE), or competitive oligonucleotide single base extension (COSBE), sequencing, or direct detection of small PCR products.

As described in detail in the following Example 11, the primer oligo base extension (PROBE) method combined with mass spectrometry identifies both the exact number of repeat units (i.e. the number of nucleotides in homogenous stretches) as well as second site mutations within a polymorphic region, which are otherwise only detectable by sequencing. Thus, the PROBE technique increases the total number of detectable alleles at a distinct genomic site, leading to a higher polymorphism information content (PIC) and yielding a far more definitive identification in for instance statistics-based analyses in paternity or forensics applications.

The method is based on the extension of a detection primer that anneals adjacent to a variable nucleotide tandem repeat (VNTR) or a polymorphic mononucleotide stretch using a DNA polymerase in the presence of a mixture of deoxyNTPs and those dideoxyNTPs which are not present in the deoxy form. The resulting products are evaluated and resolved by MALDI-TOF mass spectrometry without further labeling of the DNA. In a simulated routine application with 28 unrelated individuals, the mass error of this procedure using external calibration was in the worst case 0.38% (56-mer), which is comparable to approximately 0.1 base accuracy; routine standard mass deviations are in the range of 0.1% (0.03 bases). Such accuracy with conventional electrophoretic methods is not realistic , underscoring the value of PROBE and mass spectrometry in forensic medicine and paternity testing.

The ultra-high resolution of Fourier Transform mass spectrometry makes possible the simultaneous measurement of all reactions of a Sanger or Maxam Gilbert sequencing experiment, since the sequence may be read from mass differences instead of base counting from 4 tubes. Additionally, the mass differences between adjacent bases generated from an exonuclease sequencing experiment can be used to read the entire sequence of fragments generated.

New mutation screening over entire PCR product can be achieved by searching for mass shifted fragments generated in an endonuclease digestion as described in detail in the following Examples 4 and 12.

Partial sequence information obtained from tandem mass spectrometry (MSn) can place composition constraints as described in the preceding paragraph. For the 25-mer above, generation of two fragment ions formed by collisionally activated dissociation (CAD) which differ by 313 Da discounts $T_4C_{12}G_9$, which contains no A nucleotides; confirming more than a single A eliminates $AT_3C_4G_{16}$ as a possible composition.

$MS^n$ can also be used to determined full or partial sequences of larger DNAs; this could be used to detect, locate, and identify new mutations in a given gene region. Enzymatic digest products whose masses are correct need not be further analyzed; those with mass shifts could be isolated in real time from the complex mixture in the mass spectrometer and partially sequenced to locate the new mutation.

The mass spectrometric processes described above can be used, for example, to diagnose any of the more than 3000 genetic diseases currently known (e.g hemophilias, thalassemias, Duchenne Muscular Dystrophy (DMD), Huntington's Disease (HD), Alzheimer's Disease and Cystic Fibrosis (CF)) or to be identified.

The following Example 3 provides a mass spectrometer method for detecting a mutation ($\Delta F508$) of the cystic fibrosis transmembrane conductance regulator gene (CFTR), which differs by only three base pairs (900 daltons) from the wild type of CFTR gene. As described further in Example 3, the detection is based on a single-tube, competitive oligonucleotide single base extension (COSBE) reaction using a pair of primers with the 3'-terminal base complementary to either the normal or mutant allele. Upon hybridization and addition of a polymerase and the nucleoside triphosphate one base downstream, only those primers properly annealed (i.e., no 3'-terminal mismatch) are extended; products are resolved by molecular weight shifts as determined by matrix assisted laser desorption ionization time-of-flight mass spectrometry. For the cystic fibrosis $\Delta F508$ polymorphism, 28-mer 'normal' (N) and 30-mer 'mutant' (M) primers generate 29- and 31-mers for N and M homozygotes, respectively, and both for heterozygotes. Since primer and product molecular weights are relatively low (<10 kDa) and the mass difference between these are at least that of a single ~300 Da nucleotide unit, low resolution instrumentation is suitable for such measurements.

Thermosequence cycle sequencing, as further described in Example 11, is also useful for detecting a genetic disease.

In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Here, "house-keeping" genes encoded by the chromosome in question are present in different quantity and the different amount of an amplified fragment compared to the amount in a normal chromosomal configuration can be determined by mass spectrometry.

Further, there is growing evidence that certain DNA sequences may predispose an individual to any of a number of diseases such as diabetes, arteriosclerosis, obesity, various autoimmune diseases and cancer (e.g. colorectal, breast, ovarian, lung. Also, the detection of "DNA fingerprints", e.g. polymorphisms, such as "mini- and micro-satellite sequences", are useful for determining identity or heredity (e.g. paternity or maternity).

The following Examples 4 and 12 provide mass spectometer based methods for identifying any of the three different isoforms of human apolipoprotein E, which are coded by the E2, E3 and E4 alleles. For example, the molecular weights of DNA fragments obtained after restriction with appropriate restriction endonucleases can be used to detect the presence of a mutation and/or a specific allele.

The invention also discloses preferred mass spectrometer based methods for providing an early indication of the existence of a tumor or a cancer. For example, as described in Example 13, the telomeric repeat amplification protocol (TRAP) in conjunction with telomerase specific extension of a substrate primer and a subsequent amplification of the telomerase specific extension products by a PCR step using a second primer complementary to the repeat structure was used to obtain extension ladders, that were easily detected by MALDI-TOF mass spectrometry as an indication of telomerase activity and therefor tumorigenesis.

Alternatively, as described in Example 14, expression of a tumor or cancer associated gene (e.g. human tyrosine 5-hydroxylase) via RT-PCR and analysis of the PCR products by mass spectrometry can be used to detect the tumor or cancer (e.g. biosynthesis of catecholamine via tyrosine 5-hydroxylase is a characteristic of neuroblastoma).

Further, a primer oligo base extension reaction and detection of products by mass spectrometry provides a rapid means for detecting the presence of oncogenes, such as the RET protooncogene codon 634, which is related to causing multiple endocrine neoplasia, type II (MEN II), as described in Example 15.

Depending on the biological sample, the diagnosis for a genetic disease, chromosomal aneuploidy or genetic predisposition can be preformed either pre- or post-natally.

Viruses, bacteria, ftmgi and other infectious organisms contain distinct nucleic acid sequences, which are different from the sequences contained in the host cell. Detecting or quantitating nucleic acid sequences that are specific to the infectious organism is important for diagnosing or monitoring infection. Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, See Ratner, L. et al., *Nature*, Vol. 313, Pp. 227–284 (1985); Wain Hobson, S. et al, *Cell*, Vol. 40: Pp. 9–17 (1985)); HIV-2 (See Guyader et al., *Nature*, Vol. 328, Pp. 662–669 (1987); European Patent Publication No. 0 269 520; Chakraborti et al., *Nature*, Vol. 328, Pp. 543–547 (1987); and European Patent Application No. 0 655 501); and other isolates, such as HIV-LP (International Publication No. WO 94/00562 entitled *"A Novel Human Immunodeficiency Virus"*; Picornaviridae (e.g., polio viruses, hepatitis A virus, (Gust, I. D., et al., *Intervirology*, Vol. 20, Pp. 1–7 (1983); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae, Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia,* Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis,* Streptococcus (anaerobic sps.), *Streptococcus pneumoniae,* pathogenic Campylobacter sp., Enterococcus sp., *Haemophilus influenzae, Bacillus antracis, corynebacterium diphtheriae,* corynebacterium sp., *Erysipelothrix rhusiopathiae, Clostridium perfringers, Clostridium tetani, Enterobacter aerogenes, Klebsiella pneumoniae, Pasturella multocida,* Bacteroides sp., *Fusobacterium nucleatum, Streptobacillus moniliformis, Treponema pallidium, Treponema pertenue,* Leptospira, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium falciparum* and *Toxoplasma gondii.*

The following Example 5 provides a nested PCR and mass spectrometer based method that was used to detect hepatitis B virus (HBV) DNA in blood samples. Similarly, other blood-borne viruses (e.g., HIV-1, HIV-2, hepatitis C virus (HCV), hepatitis A virus (HAV) and other hepatitis viruses (e.g., non-A-non-B hepatitis, hepatitis G, hepatits E), cytomegalovirus, and herpes simplex virus (HSV)) can be detected each alone or in combination based on the methods described herein.

Figures 1, 10A:
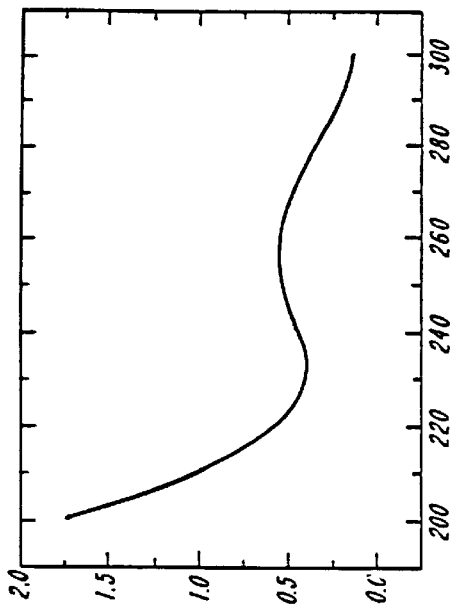
FIG. 10A shows UV spectra resulting from the experiment described in the following Example 1. Panel i) shows the absorbance of the 26-mer before hybridization. Panel ii) shows the filtrate of the centrifugation after hybridization. Panel iii) shows the results after the first wash with 50 mM ammonium citrate. Panel iv) shows the results after the second wash with 50 mM ammonium citrate.
Figures 2, 10A:
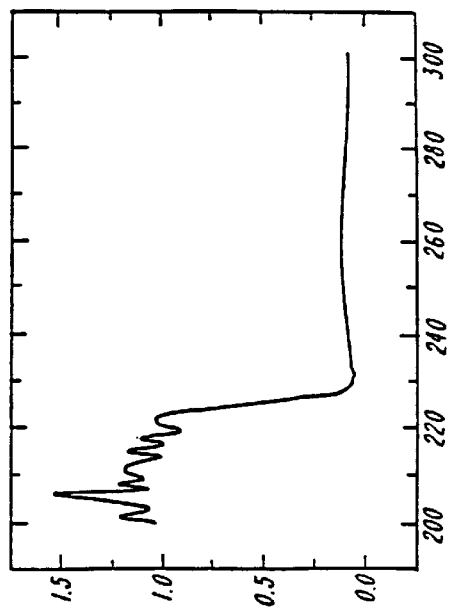
Figures 3, 10A:
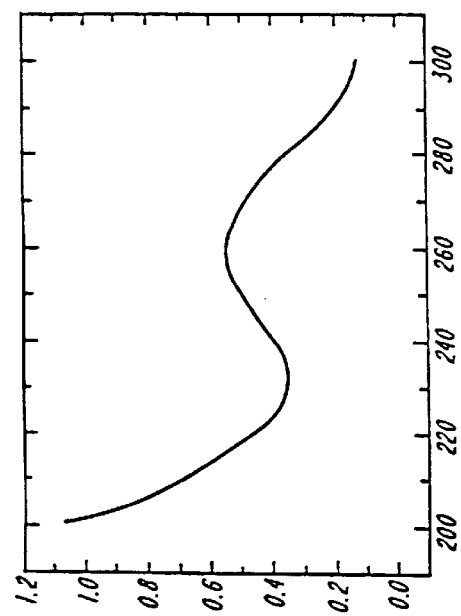
Figures 4, 10A:
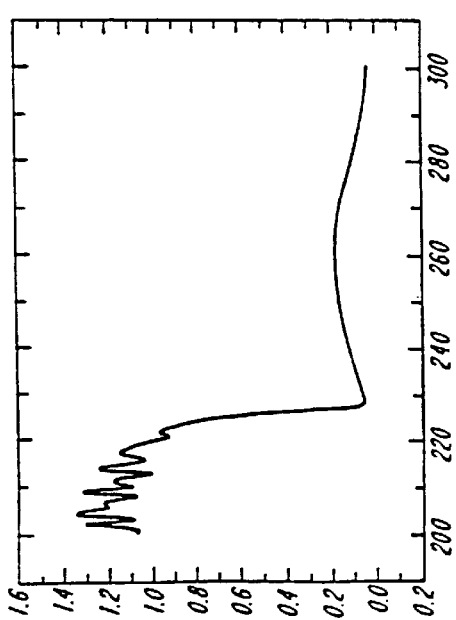
Figure 10B:
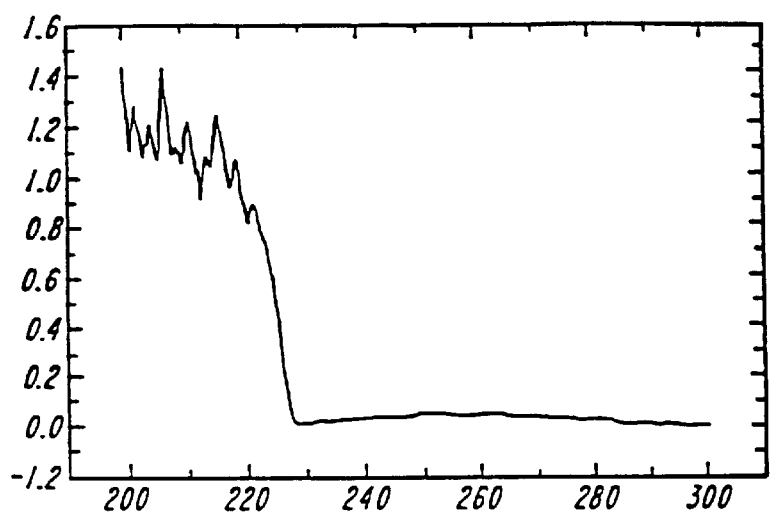
FIG. 10B shows a mass spectrum resulting from the experiment described in the following Example 1 after three washing/centrifugation steps.

Since the sequence of about 16 nucleotides is specific on statistical grounds (even for a genome as large as the human genome), relatively short nucleic acid sequences can be used to detect normal and defective genes in higher organisms and to detect infectious microorganisms (e.g. bacteria, fungi, protists and yeast) and viruses. In microorganisms also RNA, especially specific regions in ribsomal RNA can be used for indentification by using formats as described herein (e.g., FIG. 1). DNA sequences can even serve as a fingerprint for detection of different individuals within the same species. (Thompson, J. S. and M. W. Thompson, eds., *Genetics in Medicine,* W. B. Saunders Co., Philadelphia, Pa. (1986).

Figure 1C:
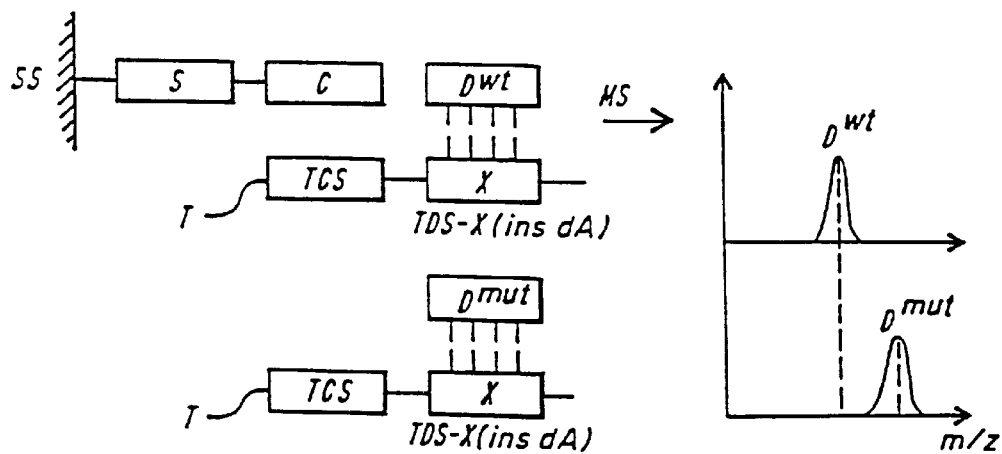
FIG. 1C is a diagram showing a process for detecting a wildtype ($D^{wt}$) and/or a mutant ($D^{mut}$) sequence in a target (T) nucleic acid molecule. As in FIG. 1A, a specific capture sequence (C) is attached to a solid support (SS) via a spacer (S). In addition, the capture sequence is chosen to specifically interact with a complementary sequence on the target sequence (T), the target capure site (TCS) to be detected through hybridization. However, if the target detection site (TDS) includes a mutation, X, which changes the molecular weight, mutated target detection sites can be distinguished from wildtype by mass spectrometry. Preferably, the detector nucleic acid molecule (D) is designed so that the mutation is in the middle of the molecule and therefore would not lead to a stable hybrid if the wildtype detector oligonucleotide ($D^{wt}$) is contacted with the target detector sequence, e.g. as a control. The mutation can also be detected if the mutated detector oligonucleotide ($D^{mut}$) with the matching base at the mutated position is used for hybridization. If a nucleic acid molecule obtained from a biological sample is heterozygous for the particular sequence (i.e. contain both $D^{wt}$ and $D^{mut}$), both $D^{wt}$ and $D^{mut}$ will be bound to the appropriate strand and the mass difference allows both $D^{wt}$ and $D^{mut}$ to be detected simultaneously.

One process for detecting a wildtype ($D^{wt}$) and/ or a mutant ($D^{mut}$) sequence in a target (T) nucleic acid molecule is shown in FIG. 1C. A specific capture sequence (C) is attached to a solid support (ss) via a spacer (S). In addition, the capture sequence is chosen to specifically interact with a complementary sequence on the target sequence (T), the target capture site (TCS) to be detected through hybridization. However, if the target detection site (TDS) includes a mutation, X, which increases or decreases the molecular weight, mutated TDS can be distinguished from wildtype by mass spectrometry. For example, in the case of an adenine base (dA) insertion, the difference in molecular weights between $D^{wt}$ and $D^{mut}$ would be about 314 daltons.

Preferably, the detector nucleic acid (D) is designed such that the mutation would be in the middle of the molecule and the flanking regions are short enough so that a stable hybrid would not be formed if the wildtype detector oligonucleotide ($D^{wt}$) is contacted with the mutated target detector sequence as a control. The mutation can also be detected if the mutated detector oligonucleotide ($D^{mut}$) with the matching base at the mutated position is used for hybridization. If a nucleic acid obtained from a biological sample is heterozygous for the particular sequence (i.e. contain both $D^{wt}$ and $D^{mut}$), both $D^{wt}$ and $D^{mut}$ will be bound to the appropriate strand and the mass difference allows both $D^{wt}$ and $D^{mut}$ to be detected simultaneously.

Figure 9:
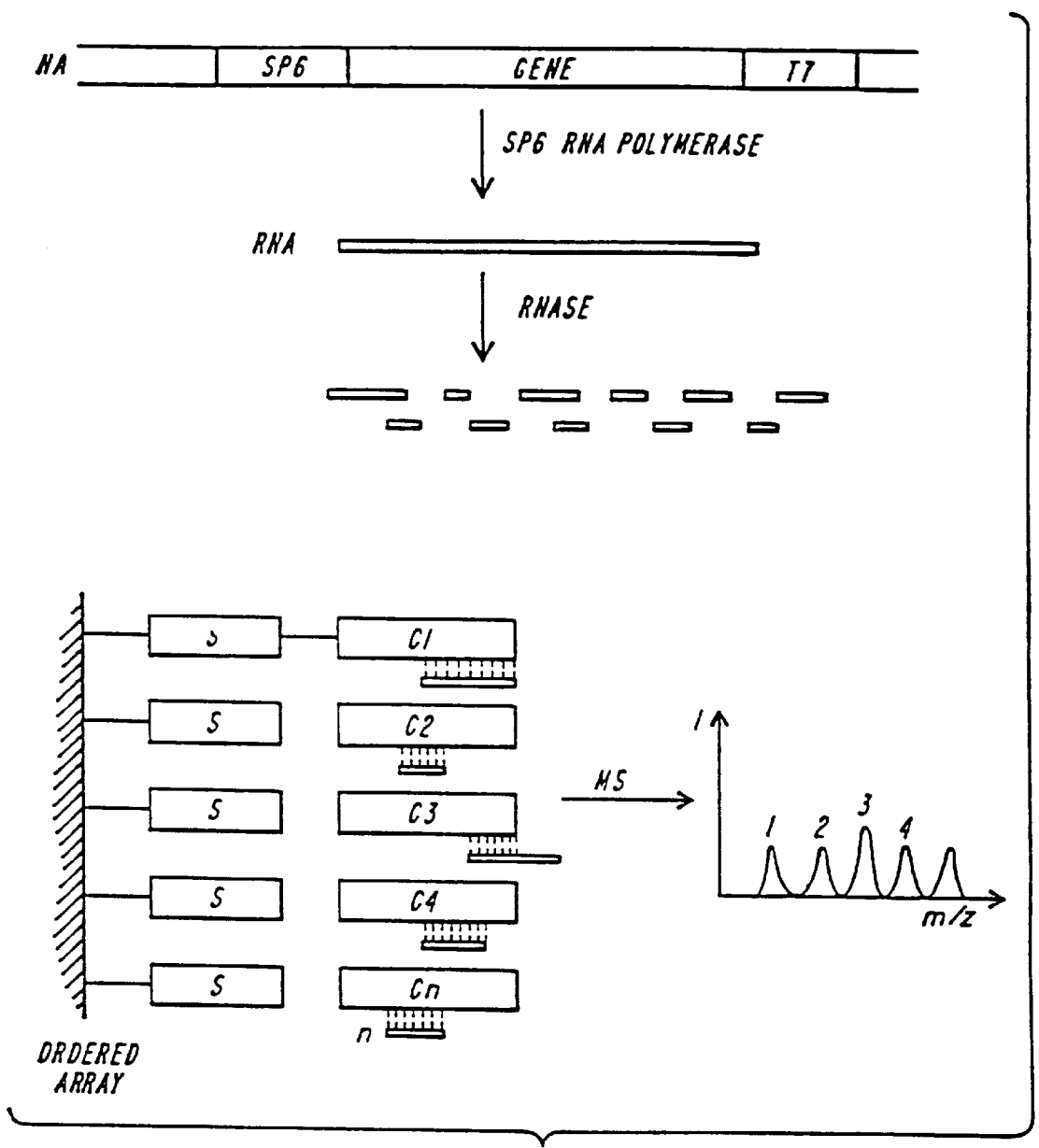
FIG. 9 is a diagram showing how RNA prepared as described in FIGS. 6, 7 and 8 can be specifically digested using one or more ribonucleases and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases. Mutations can be detected by different molecular weights of specific, individual fragments compared to the molecular weights of the wildtype fragments.

The process of this invention makes use of the known sequence information of the target sequence and known mutation sites. Although new mutations can also be detected. For example, as shown in FIG. 9, transcription of a nucleic acid molecule obtained from a biological sample can be specifically digested using one or more nucleases and the fragments captured on a solid support carrying the corresponding complementary nucleic acid sequences. Detection of hybridization and the molecular weights of the captured target sequences provide information on whether and where in a gene a mutation is present. Alternatively, DNA can be cleaved by one or more specific endonucleases to form a mixture of fragments. Comparison of the molecular weights between wildtype and mutant fragment mixtures results in mutation detection.

In another embodiment, an accurate sequence determination of a relatively large target nucleic acid, can be obtained by generating specifically terminated fragments from the target nucleic acid, determining the mass of each fragment by mass spectrometry and ordering the fragments to determine the sequence of the larger target nucleic acid. In a preferred embodiment, the specifically terminated fragments are partial or complete base-specifically terminated fragments.

One method for generating base specifically terminated fragments involves using a base-specific ribonuclease after e.g., a transcription reaction. Preferred base-specific ribonucleases are selected from the group consisting of: $T_1$-ribonuclease (G-specific), $U_2$-ribonuclease (A-specific), PhyM-ribonuclease U specific and ribonuclease A (U/C specific). Other efficient and base-specific ribonucleases can be identified using the assay described in Example 16. Preferably modified nucleotides are included in the transcription reaction with unmodified nucleotides. Most preferably, the modified nucleotides and unmodified nucleotides are added to the transcription reaction at appropriate concentrations, so that both moieties are incorporated at a preferential rate of about 1:1. Alternatively, two separate transcriptions of the target DNA sequence, one with the modified and one with the unmodified nucleotides can be performed and the results compared. Preferred modified nucleotides include: boron or bromine modified nucleotides (Porter, K. W. et al., (1995) *Biochemistry* 34:11963–11969; Hasan, A. et al., (1996) *Nucleic Acids Res.* 24:2150–2157; Li, H. et al., (1995) *Nucleic Acids Res.* 23:4495–4501), α-thio-modified nucleotides, as well as mass-modified nucleotides as described above.

Another method for generating base specifically terminated fragments involves performing a combined amplification and base-specific termination reaction. For example, a combined amplification and termination reaction can be performed using at least two different polymerase enzymes, each having a different affinity for the chain terminating nucleotide, so that polymerization by an enzyme with relatively low affinity for the chain terminating nucleotide leads to exponential amplification whereas an enzyme with relatively high affinity for the chain terminating nucleotide terminates the polymerization and yields sequencing products.

The combined amplification and sequencing can be based on any amplification procedure that employs an enzyme with polynucleotide synthetic ability (e.g. polymerase). One preferred process, based on the polymerase chain reaction (PCR), is comprised of the following three thermal steps: 1) denaturing a double stranded (ds) DNA molecule at an appropriate temperature and for an appropriate period of time to obtain the two single stranded (ss) DNA molecules (the template: sense and antisense strand); 2) contacting the template with at least one primer that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides, (ii) at least one chain terminating nucleotide, (iii) a first DNA polymerase, which has a relatively low affinity towards the chain terminating nucleotide; and (iv) a second DNA polymerase, which has a relatively high affinity towards the chain terminating nucleotide.

Steps 1)–3) can be sequentially performed for an appropriate number of times (cycles) to obtain the desired amount of amplified sequencing ladders. The quantity of the base specifically terminated fragment desired dictates how many cycles are performed. Although an increased number of cycles results in an increased level of amplification, it may also detract from the sensitivity of a subsequent detection. It is therefore generally undesirable to perform more than about 50 cycles, and is more preferable to perform less than about 40 cycles (e.g. about 20–30 cycles).

Another preferred process for simultaneously amplifying and chain terminating a nucleic acid sequence is based on strand displacement amplification (SDA) (G. Terrance Walker et al., *Nucleic Acids Res.* 22:2670–77 (1994); European Patent Publication No. 0 684 315 entitled Strand Displacement Amplification Using Thermophilic Enzymes). In essence, this process involves the following three steps, which altogether comprise a cycle: 1) denaturing a double stranded (ds) DNA molecule containing the sequence to be amplified at an appropriate temperature and for an appropriate period of time to obtain the two single stranded (ss) DNA molecules (the template: sense and antisense strand); 2) contacting the template with at least one primer (P), that contains a recognition/cleavage site for a restriction endonuclease (RE) and that hybridizes to at least one ss DNA template at an appropriate temperature and for an appropriate period of time to obtain a primer containing ss DNA template; 3) contacting the primer containing template at an appropriate temperature and for an appropriate period of time with (i) a complete set of chain elongating nucleotides; (ii) at least one chain terminating nucleotide; (iii) a first DNA polymerase, which has a relatively low affinity towards the chain terminating nucleotide; (iv) a second DNA polymerase, which has a relatively high affinity towards the chain terminating nucleotide; and (v) an RE that nicks the primer recognition/cleavage site.

Steps 1)–3) can be sequentially performed for an appropriate number of times (cycles) to obtain the desired amount of amplified sequencing ladders. As with the PCR based process, the quantity of the base specifically terminated fragment desired dictates how many cycles are performed. Preferably, less than 50 cycles, more preferably less than about 40 cycles and most preferably about 20 to 30 cycles are performed.

Preferably about 0.5 to about 3 units of polymerase is used in the combined amplification and chain termination reaction. Most preferably about 1 to 2 units is used. Particularly preferred polymerases for use in conjunction with PCR or other thermal amplification process are thermostable polymerases, such as Taq DNA polymerase (Boehringer Mannheim), AmpliTaq FS DNA polymerase (Perkin-Elmer), Deep Vent (exo-), Vent, Vent (exo-) and Deep Vent DNA polymerases (New England Biolabs), Thermo Sequenase (Amersham) or exo(-) *Pseudococcus furiosus* (Pfu) DNA polymerase (Stratagene, Heidelberg, Germany). AmpliTaq, Ultman, 9 degree Nm, Tth, Hot Tub, and *Pyrococcus furiosus*. In addition, preferably the polymerase does not have 5'-3'exonuclease activity.

In addition to polymerases, which have a relatively high and a relatively low affinity to the chain terminating nucleotide, a third polymerase, which has proofreading capacity (e.g. *Pyrococcus woesei* (Pwo)) DNA polymerase may also be added to the amplification mixture to enhance the fidelity of amplification.

Yet another method for generating base specifically terminated fragments involves contacting an appropriate amount of the target nucleic acid with a specific endonuclease or exonuclease.

Preferably, the original 5' and/or 3' end of the nucleic acid is tagged to facilitate the ordering of fragments. Tagging of the 3' end is particularly preferred when in vitro nucleic acid transcripts are being analyzed, so that the influence of 3' heterogeneity, premature termination and nonspecific elongation can be minimized. 5' and 3' tags can be natural (e.g. a 3' poly A tail or 5' or 3' heterogeneity ) or artificial. Preferred 5' and/or 3'tags are selected from the group consisting of the molecules described for mass-modification above.

The present invention is further illustrated by the following examples which should not be construed as limiting in any way. The contents of all cited references (including literature references, issued patents, published patent applications (including U.S. Pat. No. 5,547,835 and international patent application Publication Number WO 94/16101, entitled DNA Sequencing by Mass Spectrometry by H. Köster; and international patent application Publication Number WO 94/21822 entitled "DNA Sequencing by Mass Spectrometry Via Exonuclease Degradation" by H. Köster), and co-pending patent applications, (including U.S. patent application Ser. No. 08/406,199, entitled DNA Diagnostics Based on Mass Spectrometry by H. Köster), as cited throughout this application are hereby expressly incorporated by reference.

EXAMPLE 1

Figure 11:
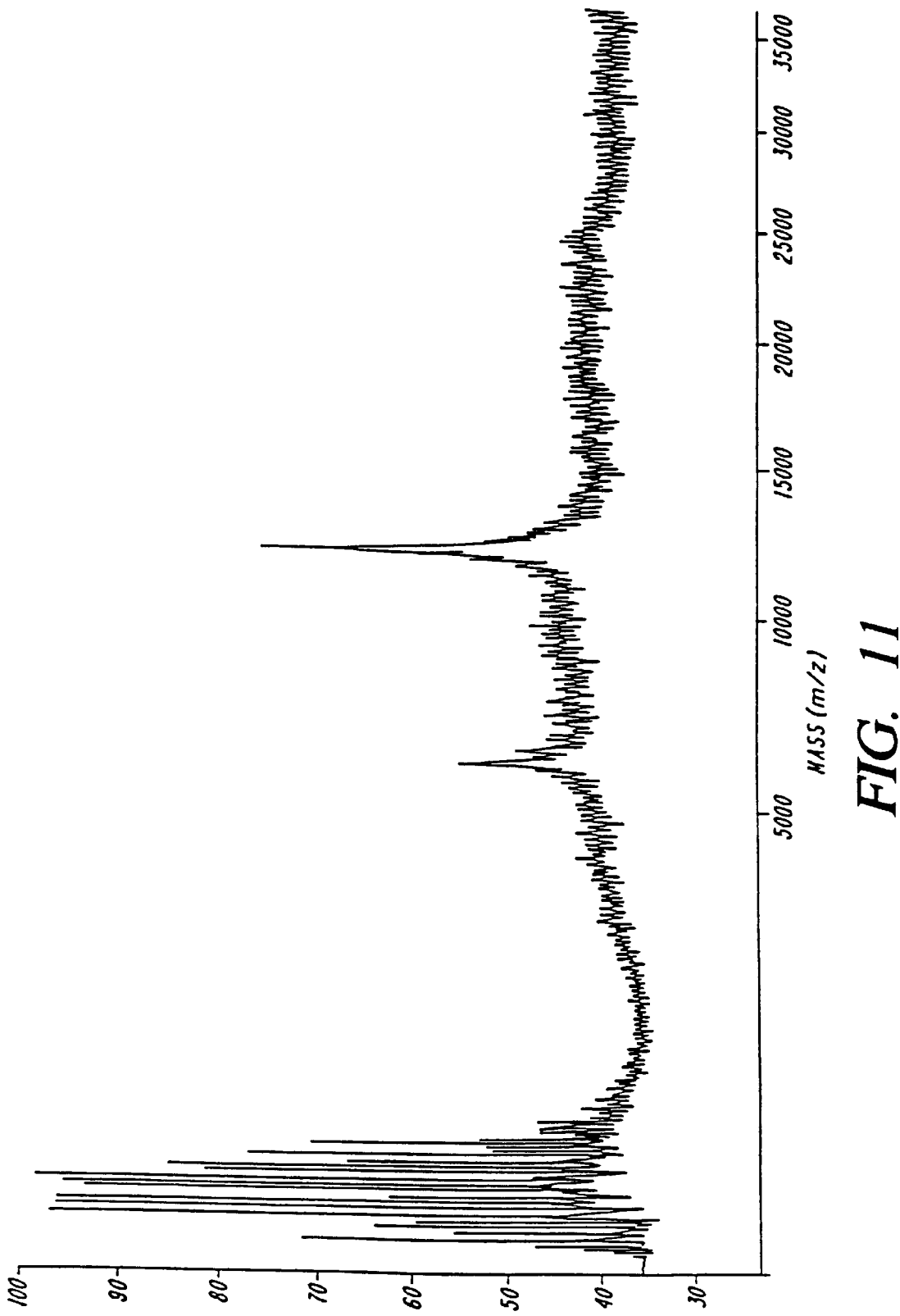
FIG. 11 shows a mass spectrum resulting from the experiment described in the following Example 1 showing the giving proof of an experiment as schematically depicted in FIG. 1B successful desorption of the hybridized 40 mer. The efficiency of detection suggests that fragments much longer than 40 mers can also be desorbed.

MALDI-TOF Desorption of Oligonucleotides Directly on Solid Supports 1 g CPG (Controlled Pore Glass) was functionalized with 3-(triethoxysilyl)-epoxypropan to form OH-groups on the polymer surface. A standard oligonucleotide synthesis with 13 mg of the OH-CPG on a DNA synthesizer (Milligen, Model 7500) employing β-cyanoethyl-phosphoamidites (Sinha et al., Nucleic Acids Res., 12, 4539 (1994)) and TAC N-protecting groups (Köster et al., Tetrahedron, 37, 362 (1981)) was performed to synthesize a 3'-$T_5$-50mer oligonucleotide sequence in which 50 nucleotides are complementary to a "hypothetical" 50mer sequence. $T_5$ serves as a spacer. Deprotection with saturated ammonia in methanol at room temperature for 2 hours furnished according to the determination of the DMT group CPG which contained about 10 umol 55 mer/g CPG. This 55 mer served as a template for hybridizations with a 26 mer (with 5'-DMT group) and a 40 mer (without DMT group). The reaction volume is 100 µl and contains about lnmol CPG bound 55 mer as template, an equimolar amount of oligonucleotide in solution (26 mer or 40 mer) in 20niM Tris-HCl, pH 7.5, 10 mM $MgCl_2$ and 25mM NaCl. The mixture was heated for 10' at 65° C. and cooled to 37° C. during 30' (annealing). The oligonucleotide which has not been hybridized to the polymer-bound template were removed by centrifugation and three subsequent washing/centrifugation steps with 100 ul each of ice-cold 50mM ammoniumcitrate. The beads were air-dried and mixed with matrix solution (3-hydroxypicolinic acid/10mM ammonium citrate in acetonitril/water, 1:1), and analyzed by MALDI-TOF mass spectrometry. The results are presented in FIGS. 10 and 11.

EXAMPLE 2

Electrospray (ES) Desorption and Differentiation of an 18-mer and 19-mer

DNA fragments at a concentration of 50 pmole/ul in 2-propanol/10 mM ammoniumcarbonate (1/9, v/v) were analyzed simultaneously by an electrospray mass spectrometer.

Figure 12A:
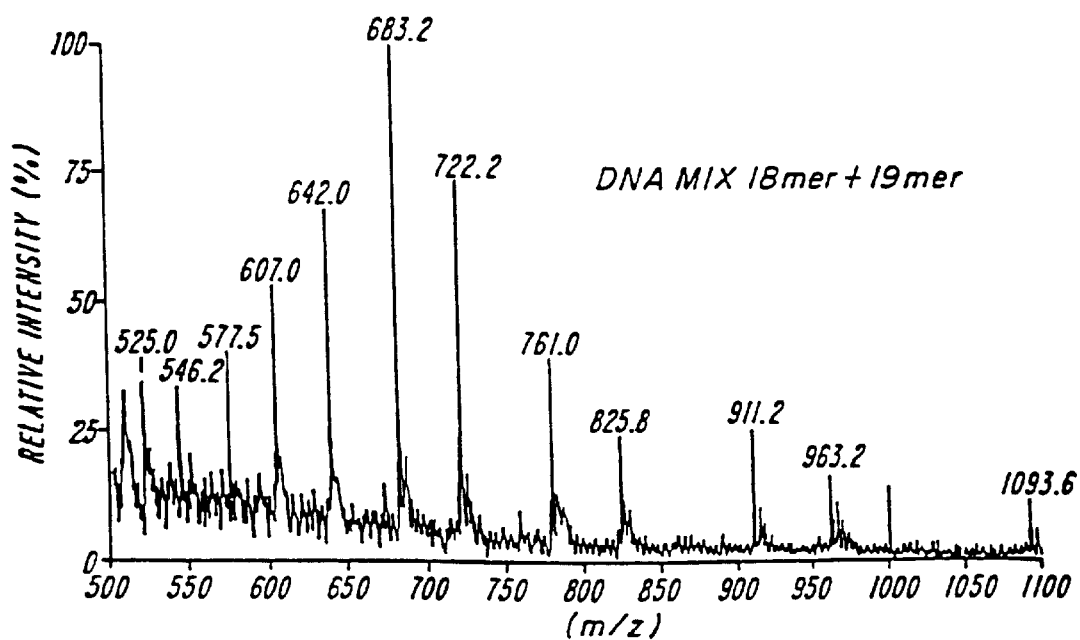
FIG. 12 shows mass spectrum resulting from the experiment described in the following Example 2 showing the successful desorption and differentiation of an 18-mer and 19-mer by electrospray mass spectrometry, the mixture (top), peaks resulting from 18-mer emphasized (middle) and peaks resulting from 19-mer emphasized (bottom)
Figure 10C:
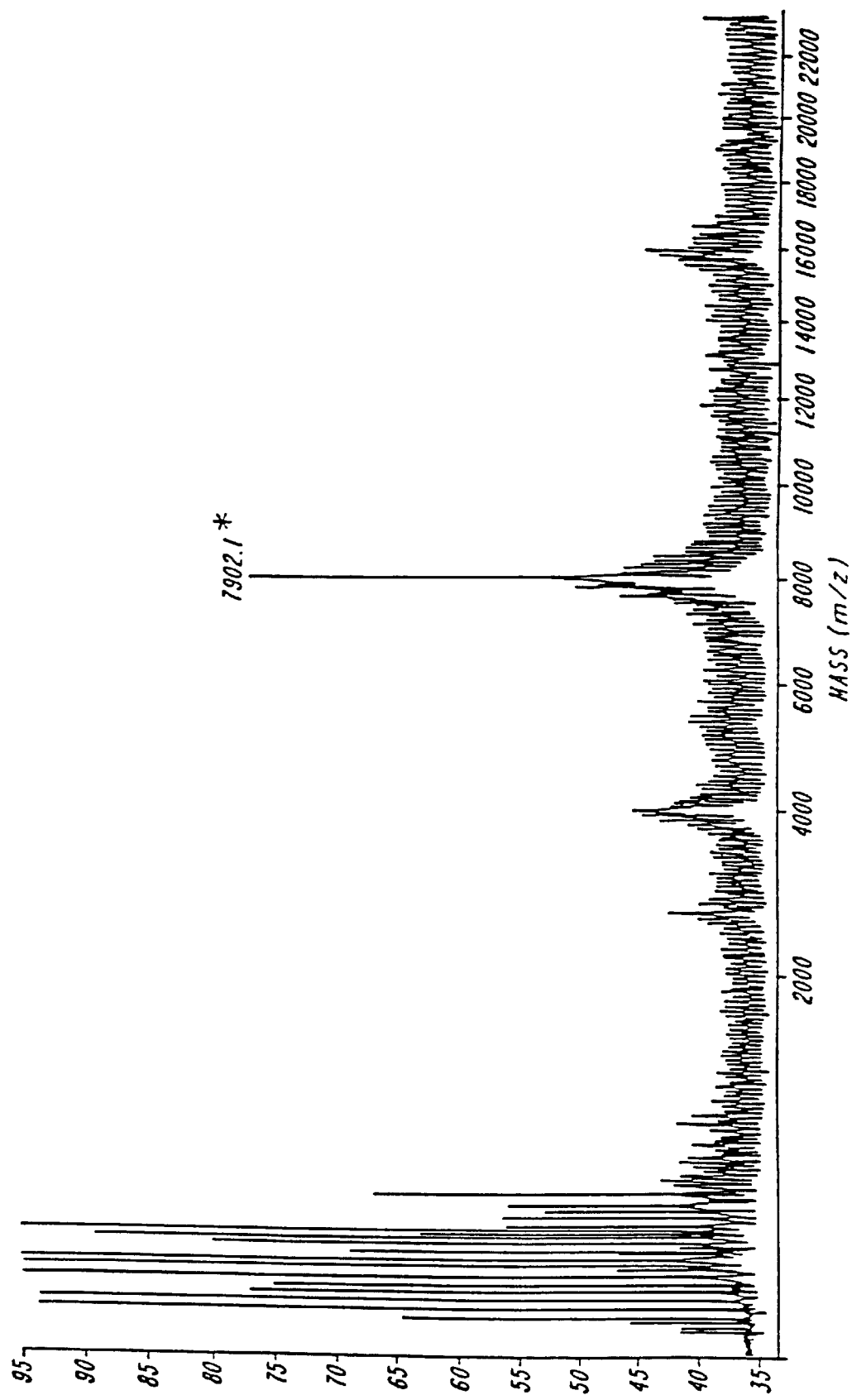
FIG. 10C shows a mass spectrum resulting from the experiment described in the following Example 1 showing the successful desorption of the hybridized 26mer off of beads in accordance with the format depicted schematically in FIG. 1B.
Figure 12B:
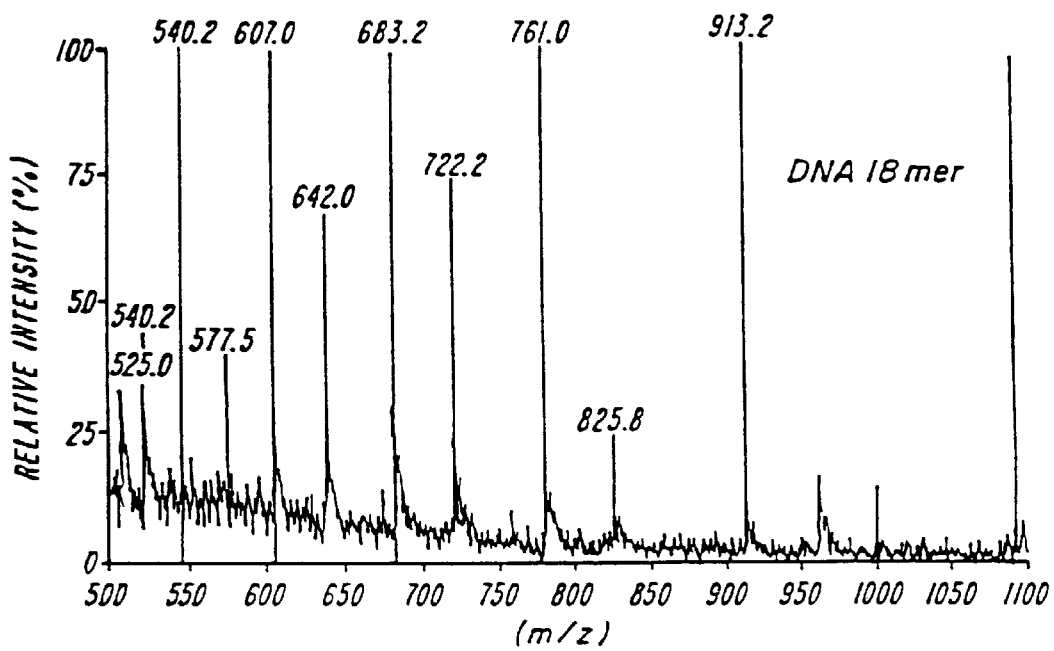
Figure 12C:
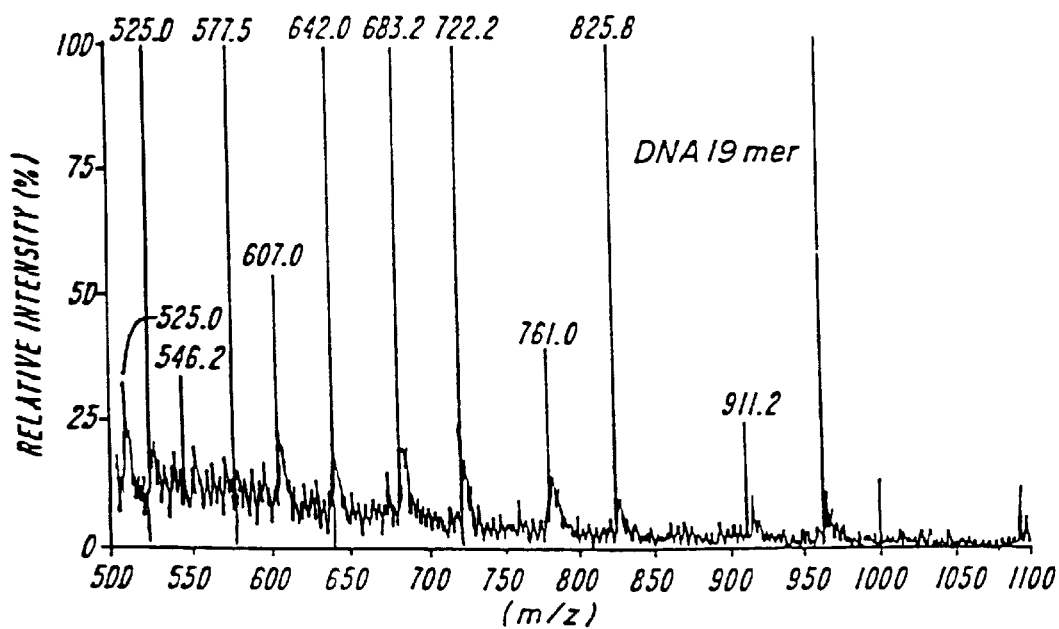

The successful desorption and differentiation of an 18-mer and 19-mer by electrospray mass spectrometry is shown in FIG. 12.

EXAMPLE 3

Detection of The Cystic Fibrosis Mutation, ΔF508, by Single Step Dideoxy Extension and Analysis by MALDI-TOF Mass Spectrometry (Competitive Oligonucleotide Simple Base Extension=COSBE)

Figure 13:
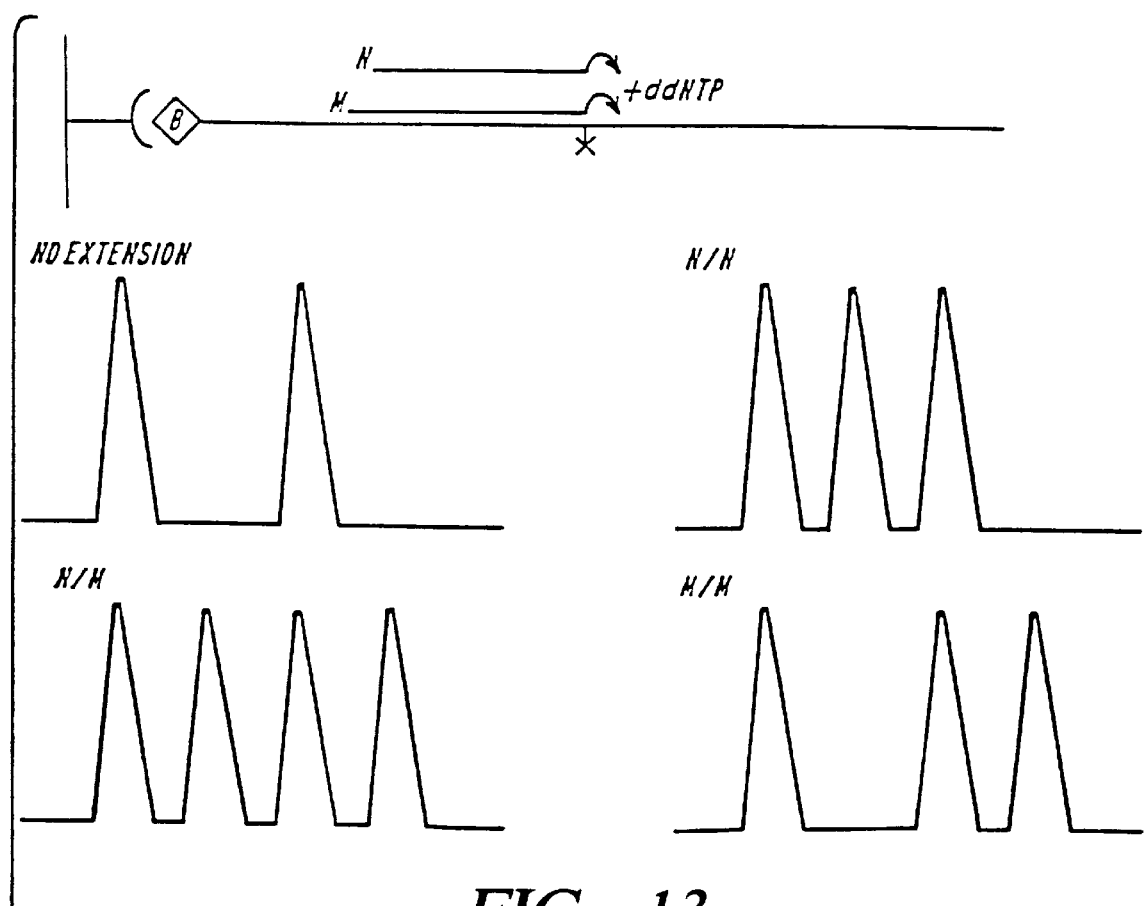
FIG. 13 is a graphic representation of the process for detecting the Cystic Fibrosis mutation ΔF508 as described in Example 3.
Figure 14:
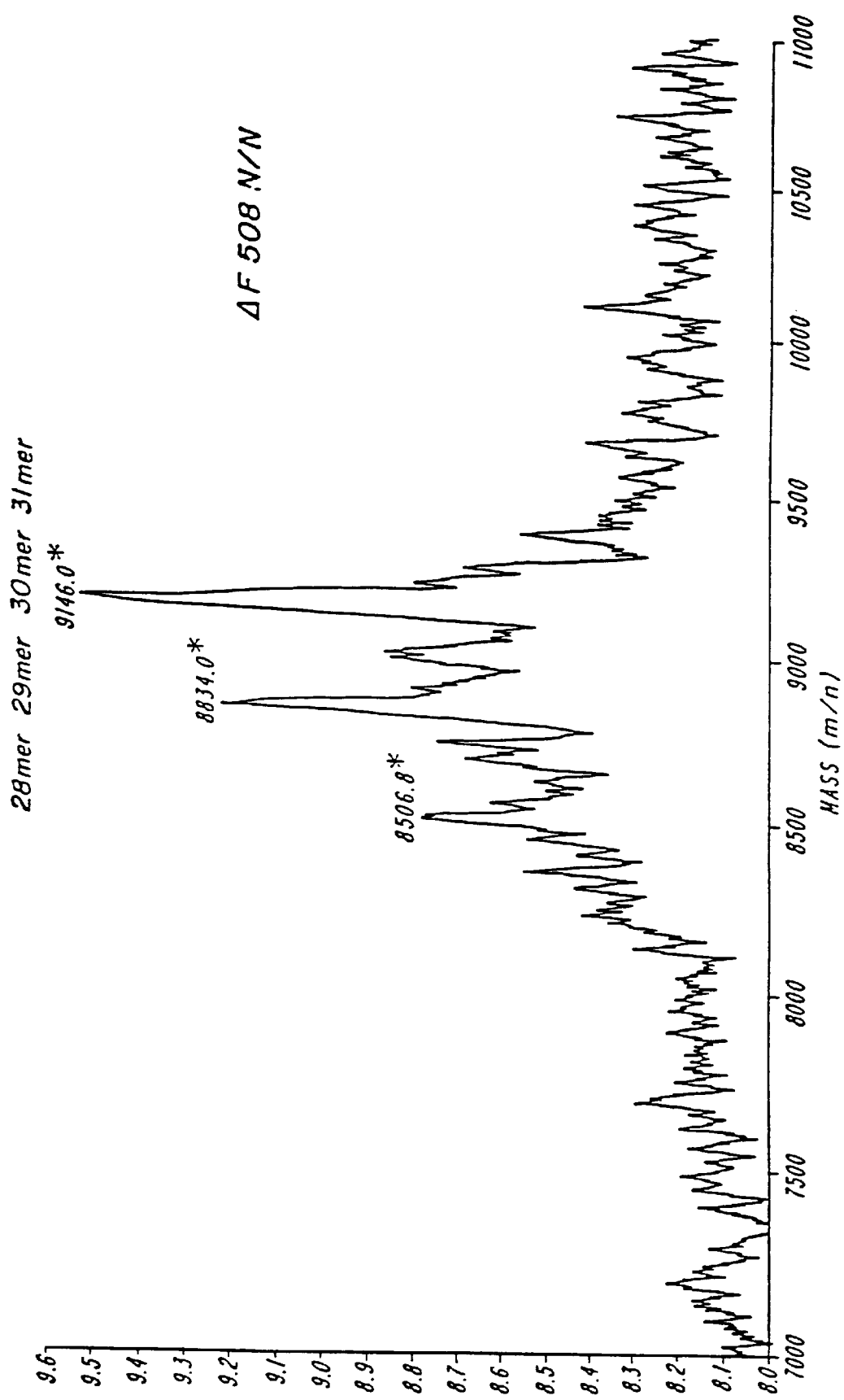
FIG. 14 is a mass spectrum of the DNA extension product of a ΔF508 homozygous normal of Example 3.
Figure 15:
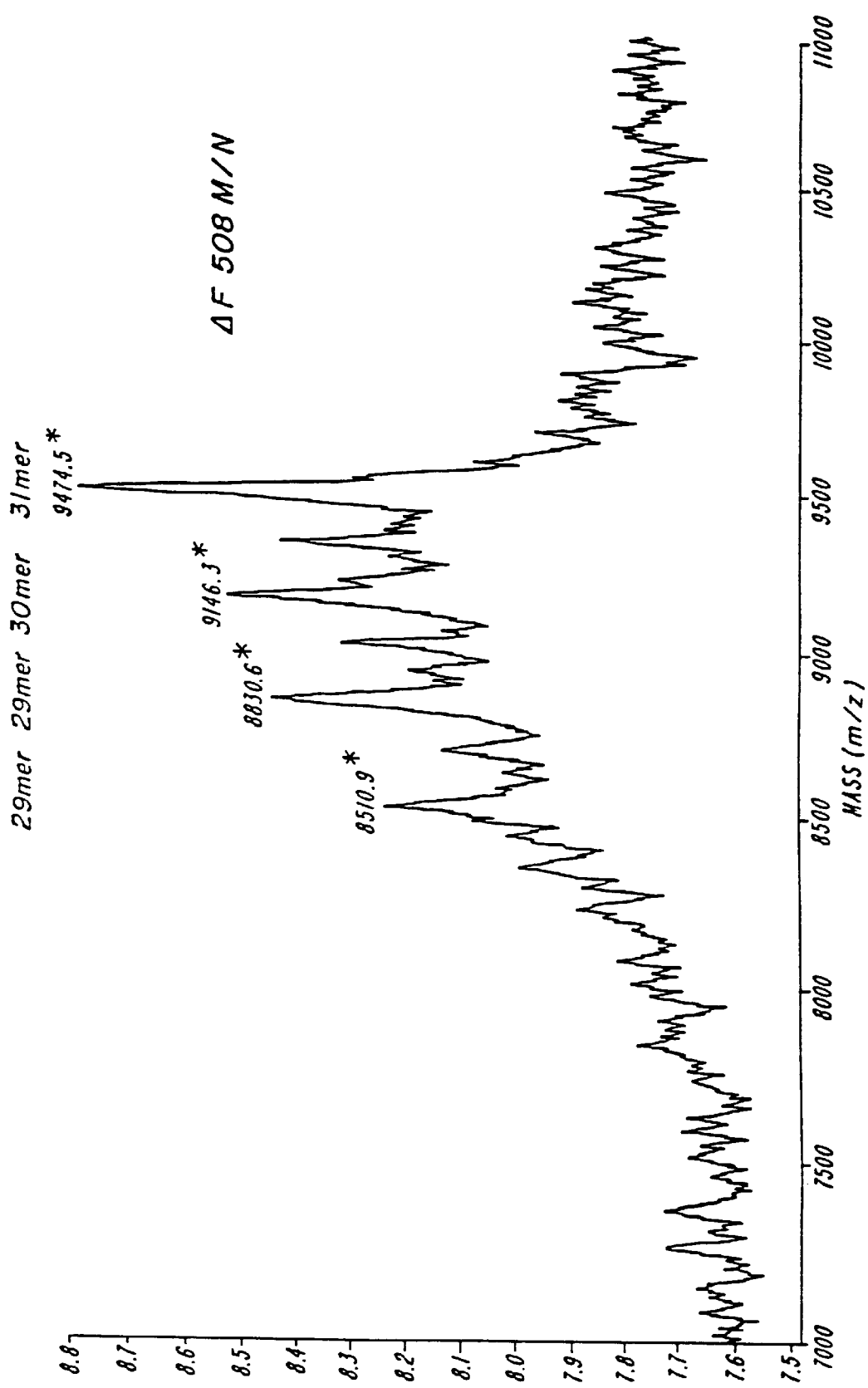
FIG. 15 is a mass spectrum of the DNA extension product of a ΔF508 heterozygous mutant of Example 3.
Figure 16:
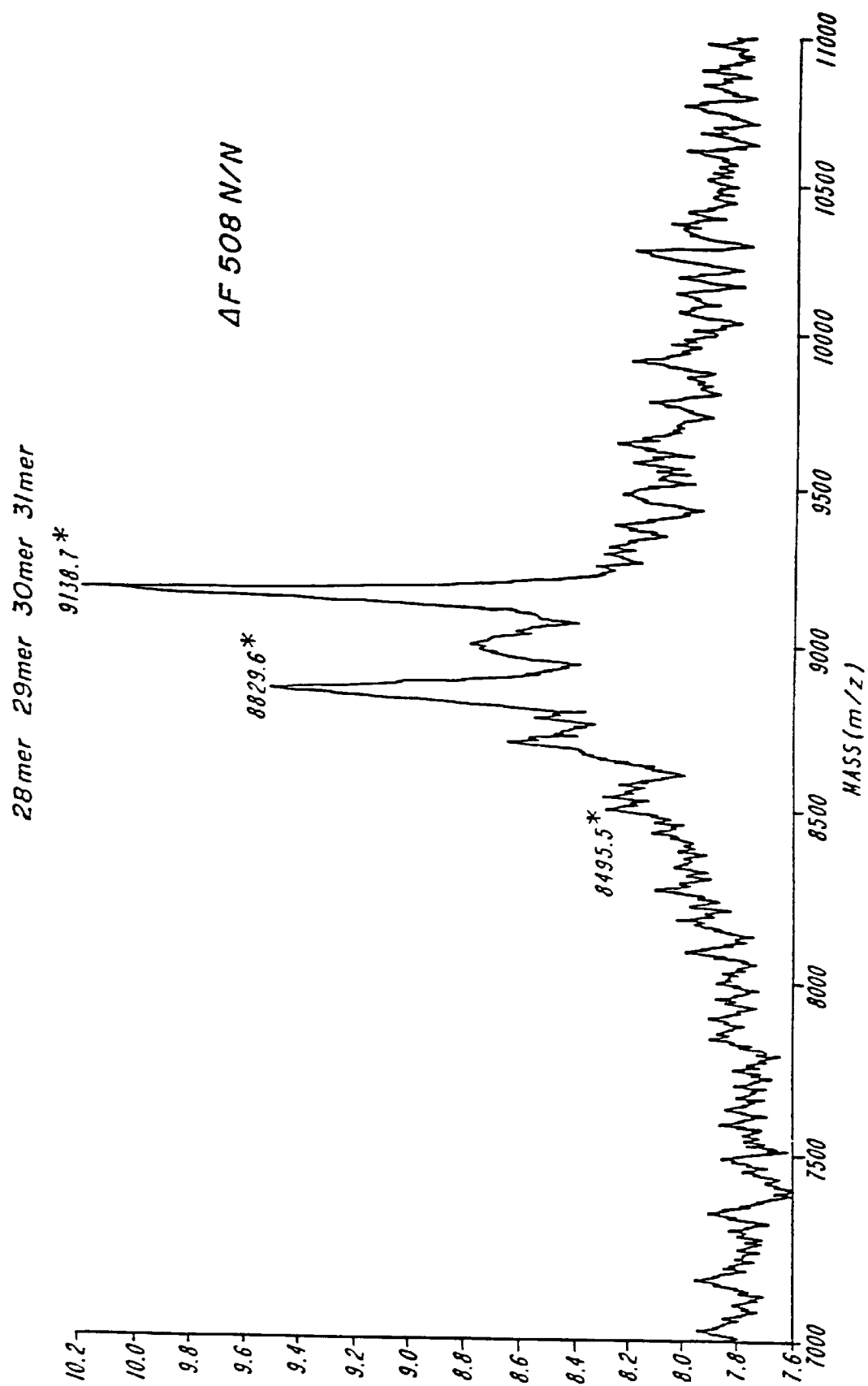
FIG. 16 is a mass spectrum of the DNA extension product of a ΔF508 homozygous normal of Example 3.
Figure 17:
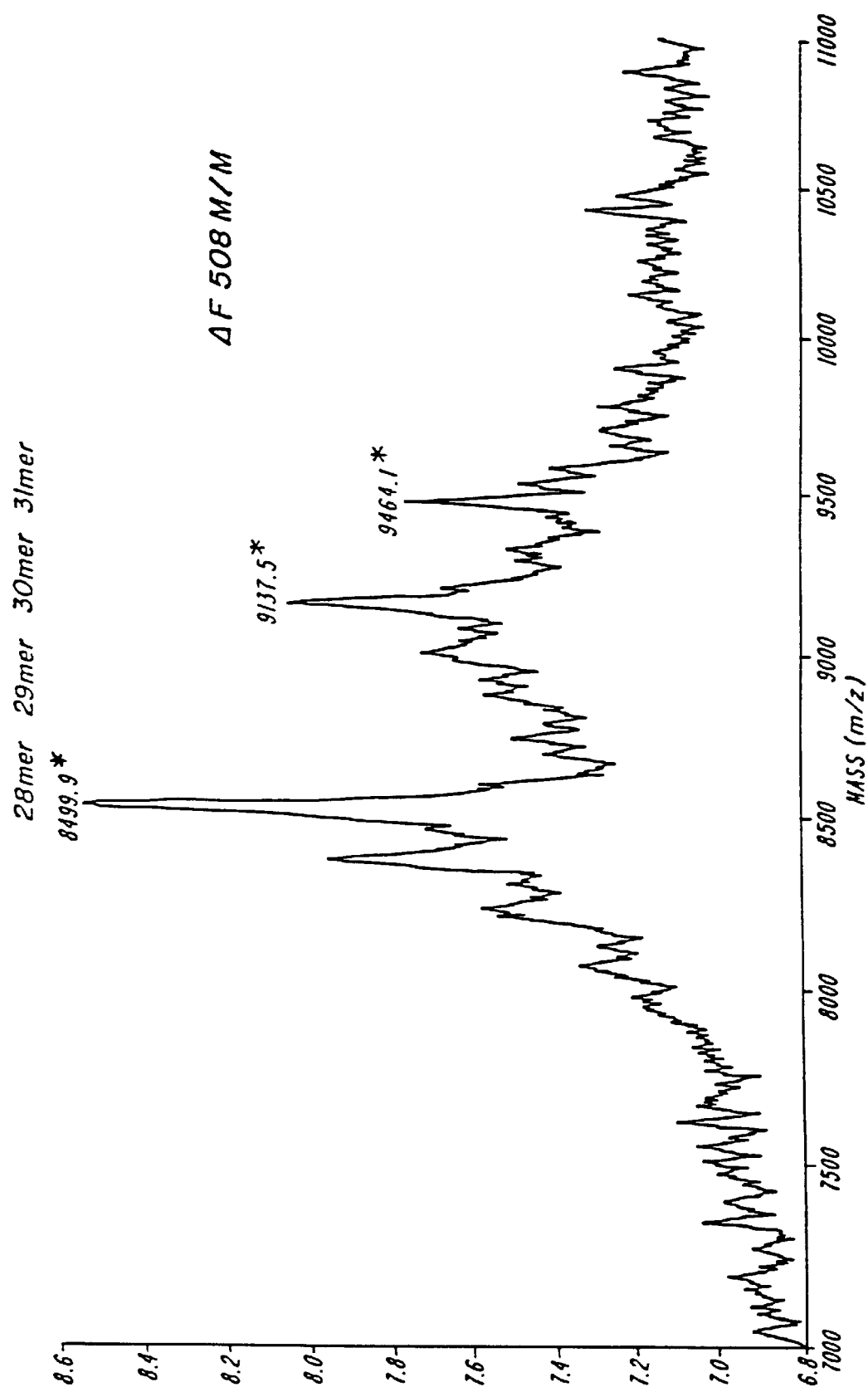
FIG. 17 is a mass spectrum of the DNA extension product of a ΔF508 homozygous mutant of Example 3.
Figure 18:
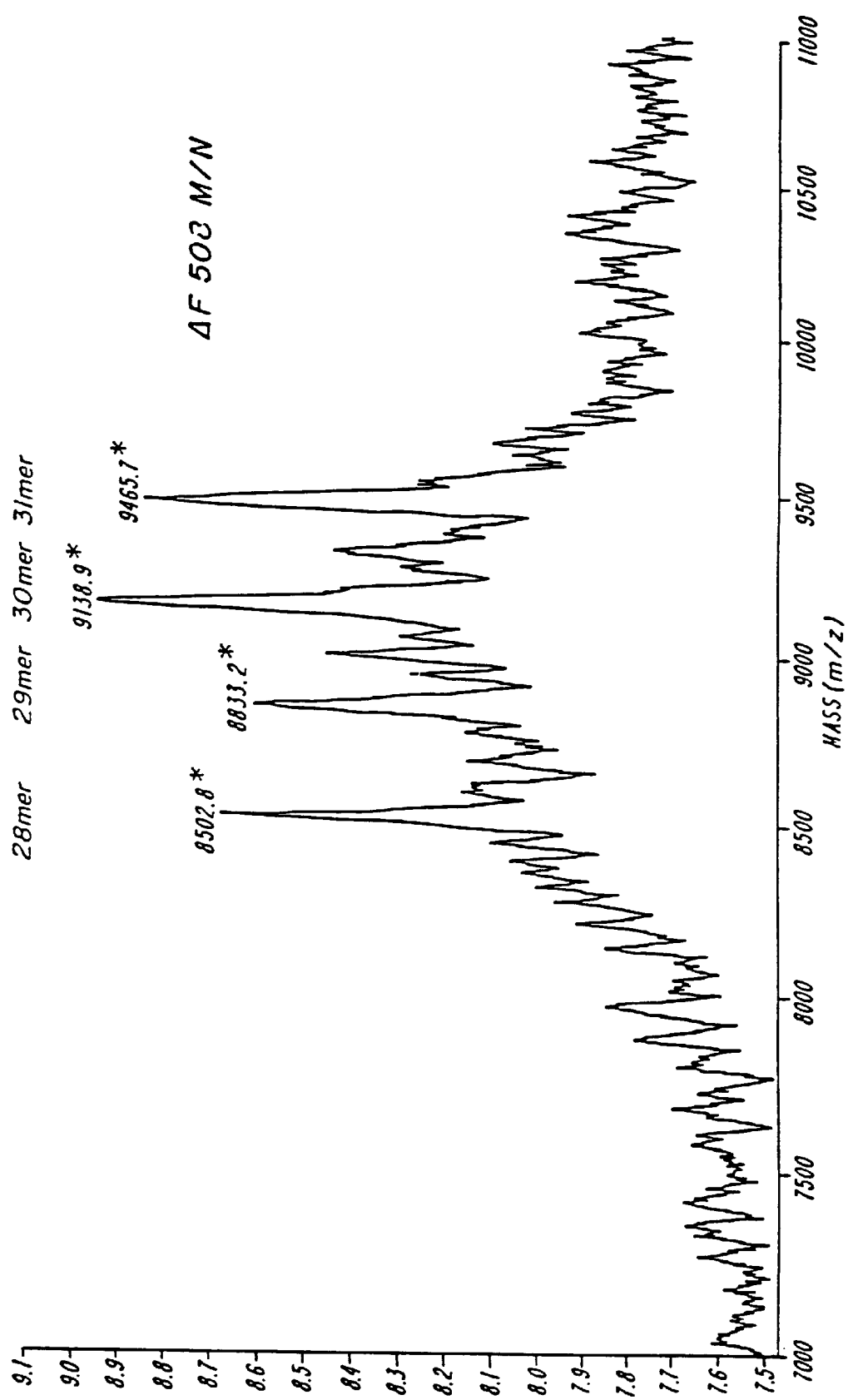
FIG. 18 is a mass spectrum of the DNA extension product of a ΔF508 heterozygous mutant of Example 3.

The principle of the COSBE method is shown in FIG. 13, N being the normal and M the mutation detection primer, respectively.

Materials and Methods

PCR Amplification and Strand Immobilization. Amplification was carried out with exon 10 specific primers using standard PCR conditions (30 cycles: 1'@95° C., 1'@55° C., 2'@72° C.); the reverse primer was 5' labelled with biotin and column purified (Oligopurification Cartridge, Cruachem). After amplification the PCR products were purified by column separation (Qiagen Quickspin) and immobilized on streptavidin coated magnetic beads (Dynabeads, Dynal, Norway) according to their standard protocol; DNA was denatured using 0.1M NaOH and washed with 0.1M NaOH, 1×B+W buffer and TE buffer to remove the non-biotinylated sense strand.

COSBE Conditions. The beads containing ligated antisense strand were resuspended in 18 µl of Reaction mix 1 (2 µl 10×Taq buffer, 1 µL (1 unit) Taq Polymerase, 2 µL of 2 mM dGTP, and 13 µL H₂O) and incubated at 80° C. for 5' before the addition of Reaction mix 2 (100 ng each of COSBE primers). The temperature was reduced to 60° C. and the mixtures incubated for a 5' annealing/extension period; the beads were then washed in 25 mM triethylammonium acetate (TEAA) followed by 50 mM ammonium citrate.

Primer Sequences. All primers were synthesized on a Perseptive Biosystems Expedite 8900 DNA Synthesizer using conventional phosphoramidite chemistry (Sinha et al. (1984) *Nucleic Acids Res.* 12:4539). COSBE primers (both containing an intentional mismatch one base before the 3'-terminus) were those used in a previous ARMS study (Ferrie et al., (1992) *Am J Hum Genet* 51:251–262) with the exception that two bases were removed from the 5'-end of the normal:

Ex10 PCR (Forward): 5'-BIO-GCA AGT GAA TCC TGA GCG TG-3' (SEQ ID No. 1)

Ex10 PCR (Reverse): 5'-GTG TGA AGG GTT CAT ATG C-3' (SEQ ID No. 2)

COSBE ΔF508-N 5'-ATC TAT ATT CAT CAT AGG AAA CAC CAC A-3' (28-mer) (SEQ ID No. 3)

COSBE ΔF508-M 5¹-GTA TCT ATA TTC ATC ATA GGA AAC ACC ATT-3' (30-mer) (SEQ ID No. 4)

Mass Spectrometry. After washing, beads were resuspended in 1 µL 18 Mohm/cm H₂O. 300 nL each of matrix (Wu et al., 1993) solution (0.7 M 3-hydroxypicolinic acid, 0.7 M dibasic ammonium citrate in 1:1 H₂O:CH₃CN) and resuspended beads (Tang et al. (1995) *Rapid Commun Mass Spectrom* 8:727–730) were mixed on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular weights ($M_r$(calc)) were calculated from atomic compositions. Vendor provided software was used to determine peak centroids using external calibration; 1.08 Da has been subtracted from these to correct for the charge carrying proton mass to yield the text $M_r$(exp) values.

Scheme. Upon annealing to the bound template, the N and M primers (8508.6 and 9148.0 Da, respectively) are presented with dGTP; only primers with proper Watson-Crick base paring at the variable (V) position are extended by the polymerase. Thus if V pairs with the 3'-terminal base of N, N is extended to a 8837.9 Da product (N+1). Likewise, if V is properly matched to the M terminus, M is extended to a 9477.3 Da M+1 product.

Results

FIGS. 14–18 show the representative mass spectra of COSBE reaction products. Better results were obtained when PCR products were purified before the biotinylated anti-sense strand was bound.

EXAMPLE 4

Differentiation of Human Apolipoprotein E Isoforms by Mass Spectrometry

Apolipoprotein E (Apo E), a protein component of lipoproteins, plays an essential role in lipid metabolism. For example, it is involved with cholesterol transport, metabolism of lipoprotein particles, immunoregulation and activation of a number of lipolytic enzymes.

There are three common isoforms of human Apo E (coded by E2, E3 and E4 alleles). The most common is the E3 allele. The E2 allele has been shown to decrease the cholesterol level in plasma and therefore may have a protective effect against the development of atherosclerosis. Finally, the E4 isoform has been correlated with increased levels of cholesterol, conferring predisposition to atherosclerosis. Therefore, the identity of the apo E allele of a particular individual is an important determinant of risk for the development of cardiovascular disease.

Figure 19:
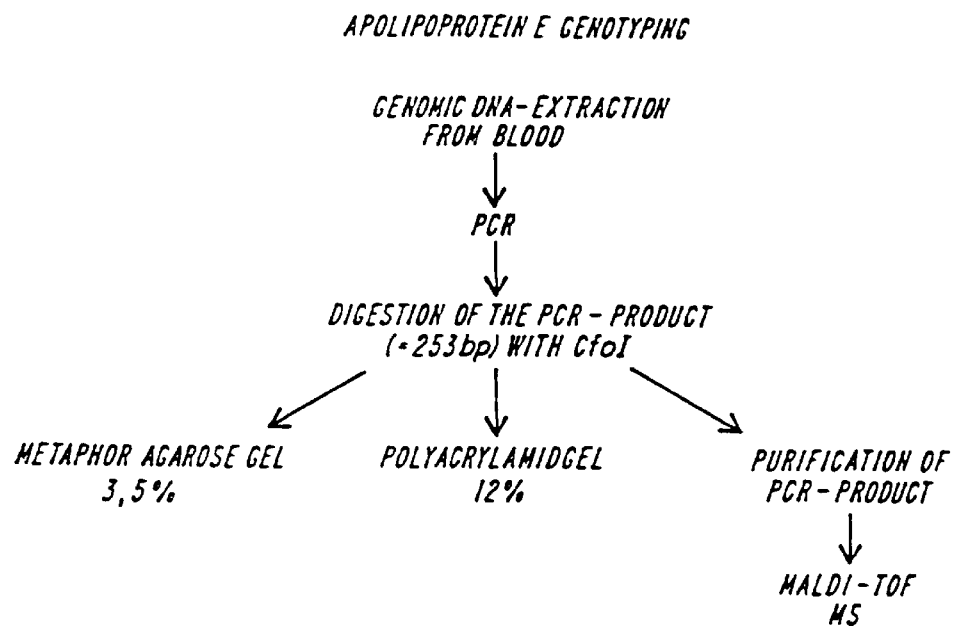
FIG. 19 is a graphic representation of various processes for performing apolipoprotein E genotyping of Example 4.
Figure 20A:
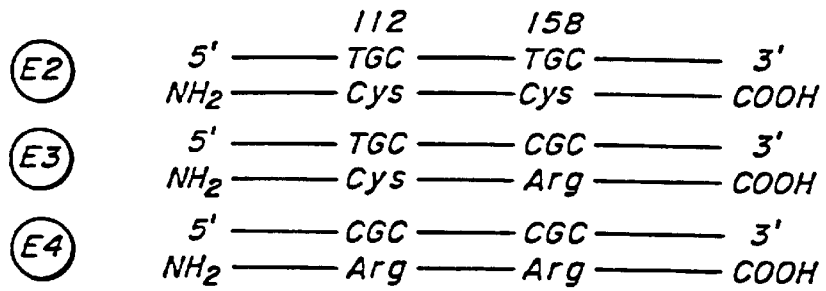
FIG. 20 shows the nucleic acid sequence of normal apolipoprotein E (encoded by the E3 allele, FIG. 20B) and other isotypes encoded by the E2 and E4 alleles (FIG. 20A).
Figure 20B:
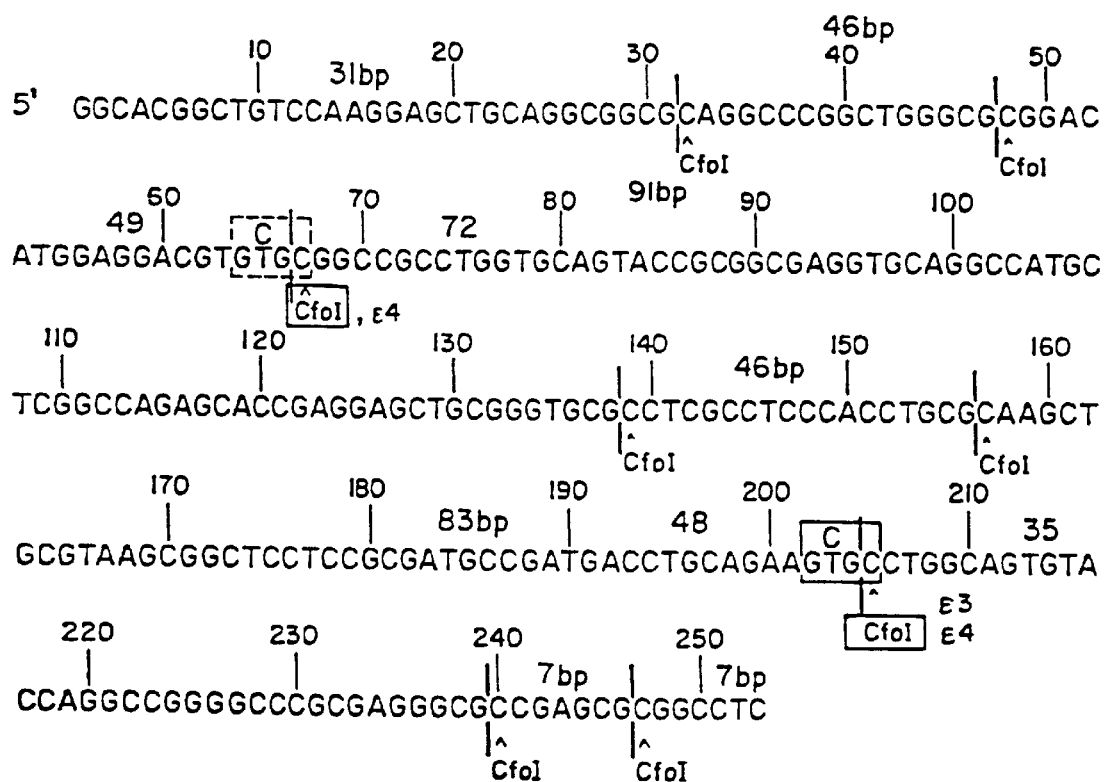

As shown in FIG. 19, a sample of DNA encoding apolipoprotein E can be obtained from a subject, amplified (e.g. via PCR); and the PCR product can be digested using an appropriate enzyme (e.g. CfoI). The restriction digest obtained can then be analyzed by a variety of means. As shown in FIG. 20, the three isotypes of apolipoprotein E (E2, E3 and E4 have different nucleic acid sequences and therefore also have distinguishable molecular weight values.

Figure 21A:
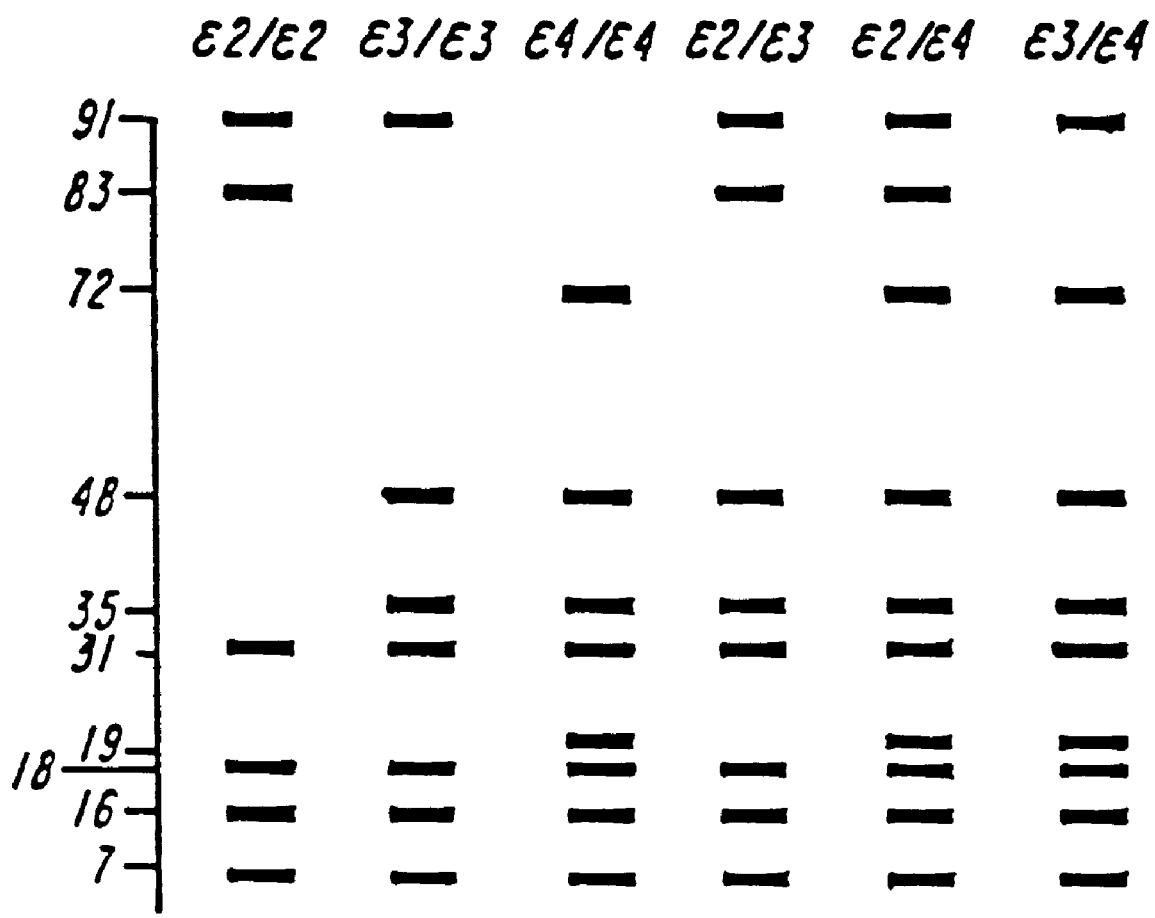
FIG. 21A shows a composite restriction pattern for various genotypes of apolipoprotein E using the Cfo I restriction endonuclease.
Figure 21B:
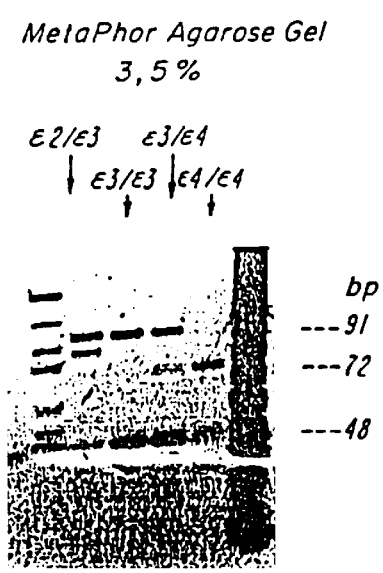
FIG. 21B shows the restriction pattern obtained in a 3.5% MetPhor Agarose Gel for various genotypes of apolipoprotein E.
Figure 21C:
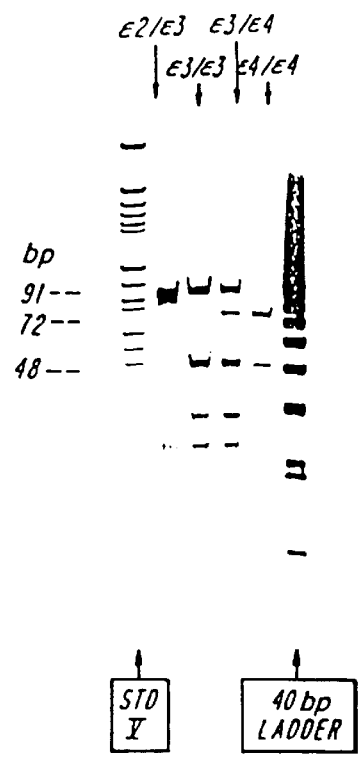
FIG. 21C shows the restriction pattern obtained in a 12% polyacrylamide gel for various genotypes of apolipoprotein E.
Figures 22A, 22B:
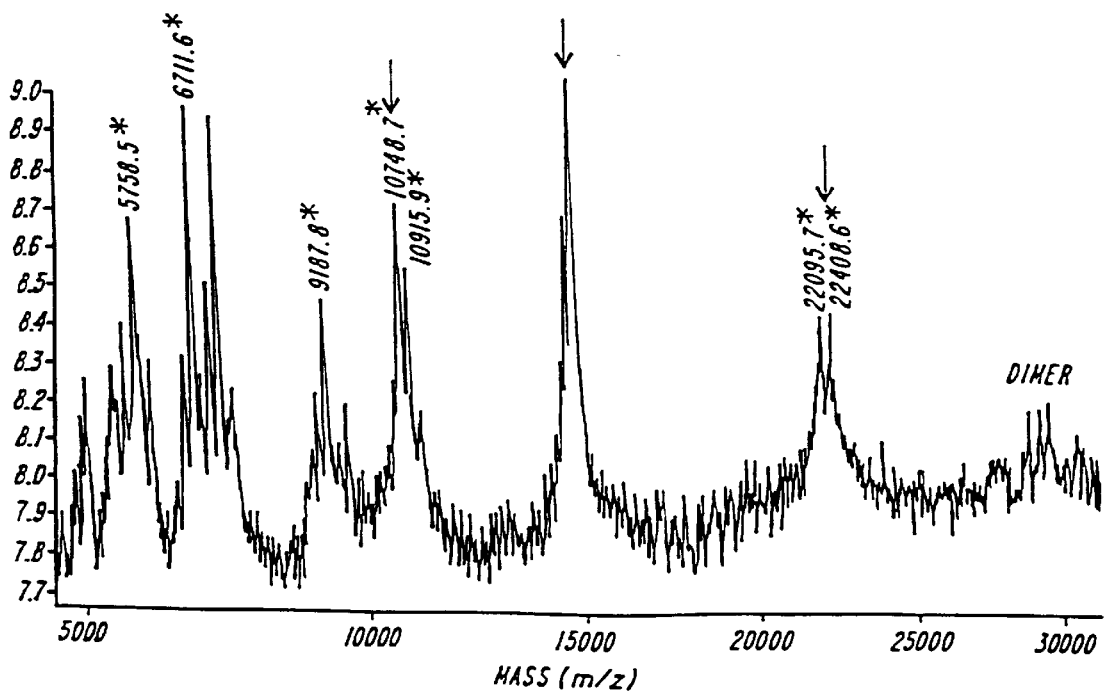
FIG. 22A is a chart showing the molecular weights of the 91, 83, 72, 48 and 35 base pair fragments obtained by restriction enzyme cleavage of the E2, E3 and E4 alleles of apolipoprotein E.
FIG. 22B is the mass spectra of the restriction product of a homozygous E4 apolipoprotein E genotype.
Figure 23A:
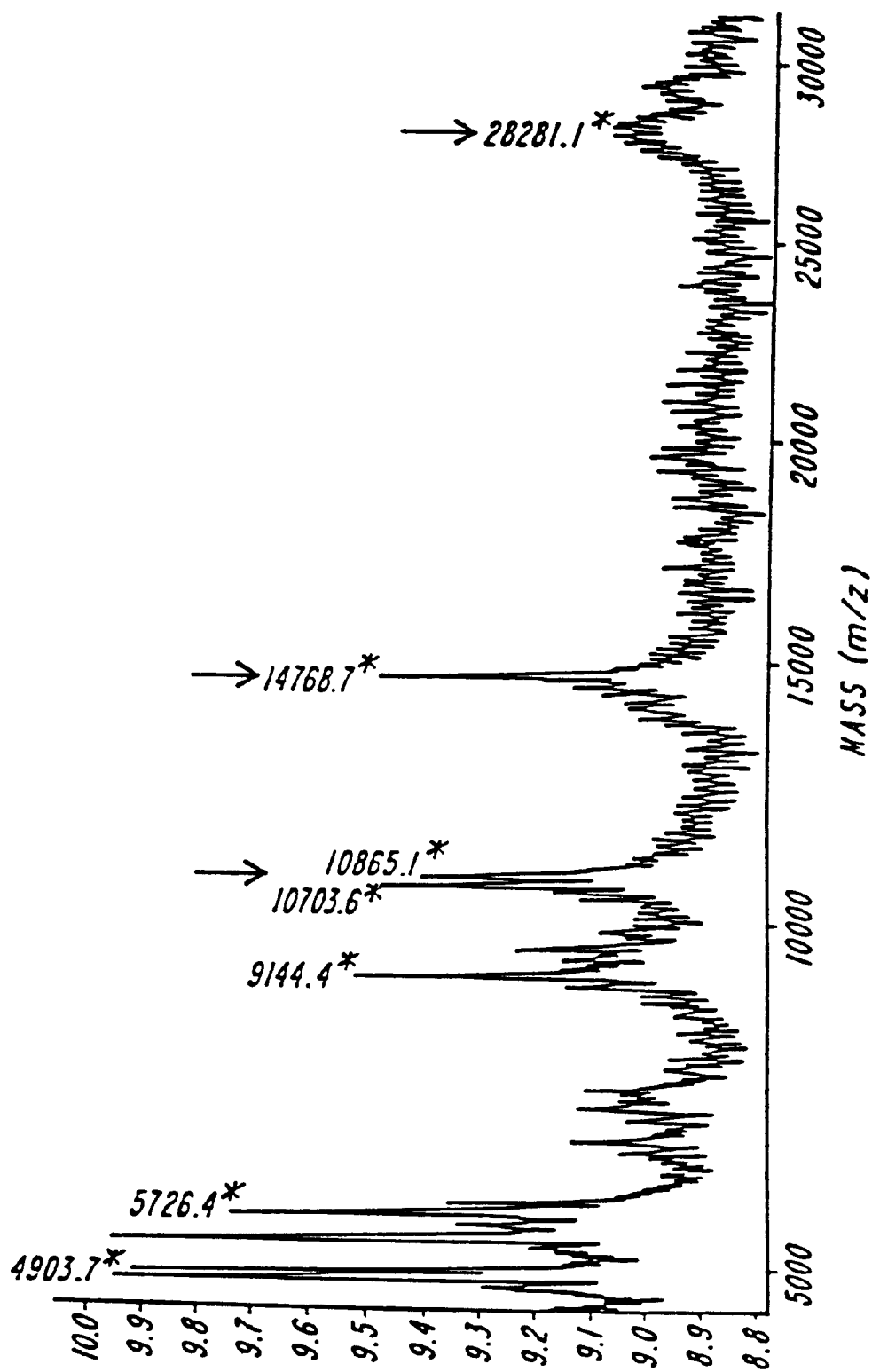
FIG. 23A is the mass spectrum of the restriction product of a homozygous E3 apolipoprotein E genotype.
Figure 23B:
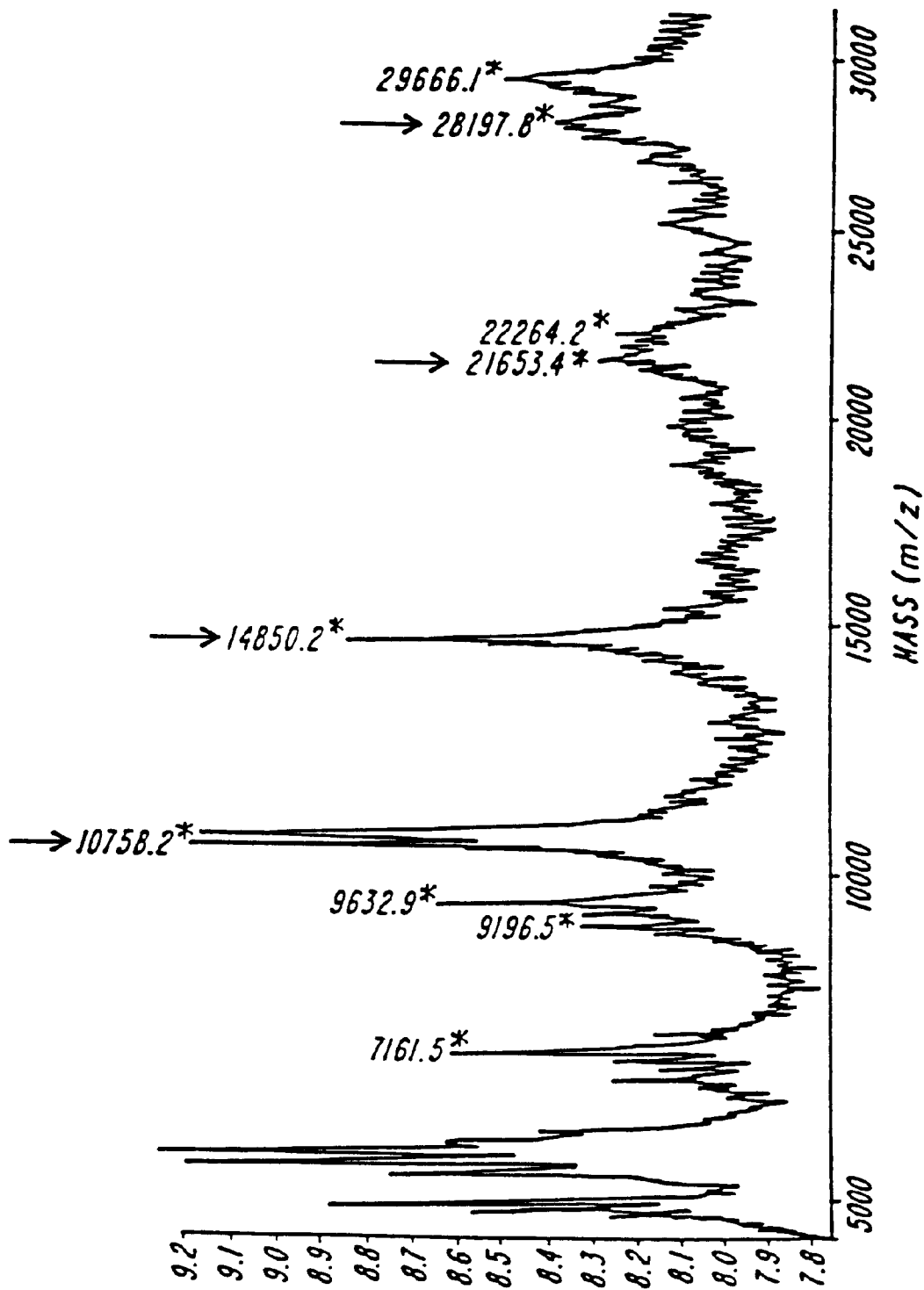
FIG. 23B is the mass spectrum of the restriction product of a E3/E4 apolipoprotein E genotype.

As shown in FIG. 21 A–C, different Apolipoprotein E genotypes exhibit different restriction patterns in a 3.5% MetPhor Agarose Gel or 12% polyacrylamide gel. As shown in FIGS. 22 and 23, the various apolipoprotein E genotypes can also be accurately and rapidly determined by mass spectrometry.

EXAMPLE 5

Detection of Hepatitis B Virus in Serum Samples.

Materials and Methods

Sample Preparation

Phenol/choloform extraction of viral DNA and the final ethanol precipitation was done according to standard protocols.

First PCR:

Each reaction was performed with 5 µl of the DNA preparation from serum. 15 pmol of each primer and 2 units Taq DNA polymerase (Perkin Elmer, Weiterstadt, Germany) were used. The final concentration of each dNTP was 200 µM, the final volume of the reaction was 50 µl. 10×PCR buffer (Perkin Elmer, Weiterstadt, Germany) contained 100 mM Tris-HCl, pH 8.3, 500 mM KCl, 15 mM MgCl₂, 0.01% gelatine (w/v).

Primer sequences:

Primer 1:
5'-GCTTTGGGGCATGGACATTGACCCGTATAA-3' (SEQ ID NO.5)

Primer 2:
5'-CTGACTACTAATTCCCTGGATGCTGGGTCT-3' (SEQ ID NO.6)

Nested PCR:

Each reaction was performed either with 1 µl of the first reaction or with a 1:10 dilution of the first PCR as template, respectively. 100 pmol of each primer, 2.5u Pfu(exo−) DNA polymerase (Stratagene, Heidelberg, Germany), a final concentration of 200 µM of each dNTPs and 5 µl 10×Pfu buffer (200 mM Tris-HCl, pH 8.75, 100 mM KCl, 100 mM (NH₄)₂SO₄, 20 mM MgSO₄, 1% Triton X-100, 1 mg/ml BSA, (Stratagene, Heidelberg, Germany) were used in a final volume 50 µl. The reactions were performed in a thermocycler (OmniGene, MWG-Biotech, Ebersberg, Germany) using the following program: 92° C. for 1 minute, 60° C. for 1 minute and 72° C. for 1 minute with 20 cycles. Sequence of oligodeoxynucleotides (purchased HPLC-purified from MWG-Biotech, Ebersberg, Germany):

HBV13: 5'-TTGCCTGAGTGCAGTATGGT-3' (SEQ ID NO.7)

HBV15bio: Biotin-5'-AGCTCTATATCGGGAAGCCT-3' (SEQ ID NO.8)

Purification of PCR Products.

For the recording of each spectrum, one PCR, 50 µl, (performed as described above) was used. Purification was done according to the following procedure: Ultrafiltration was done using Ultrafree-MC filtration units (Millipore, Eschborn, Germany) according to the protocol of the provider with centrifugation at 8000 rpm for 20 minutes. 25 µl (10 µg/µl) streptavidin Dynabeads (Dynal, Hamburg, Germany) were prepared according to the instructions of the manufacturer and resuspended in 25 µl of B/W buffer (10 mM Tris-HCl, pH7.5, 1 mM EDTA, 2 M NaCl). This suspension was added to the PCR samples still in the filtration unit and the mixture was incubated with gentle shaking for 15 minutes at ambient temperature. The suspension was transferred in a 1.5 ml Eppendorf tube and the supernatant was removed with the aid of a Magnetic Particle Collector, MPC, (Dynal, Hamburg, Germany). The beads were washed twice with 50 µl of 0.7 M ammonium citrate solution, pH 8.0 (the supernatant was removed each time using the MPC). Cleavage from the beads can be accomplished by using formamide at 90° C. The supernatant was dried in a speedvac for about an hour and resuspended in 4 µl of ultrapure water (MilliQ UF plus Millipore, Eschborn, Germany). This preparation was used for MALDI-TOF MS analysis.

MALDI-TOF MS:

Half a microliter of the sample was pipetted onto the sample holder, then immediately mixed with 0.5 µl matrix solution (0.7 M 3-hydroxypicolinic acid 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron (5 keV ion source, 20 keV postacceleration) and a 337 nm nitrogen laser. Calibration was done with a mixture of a 40 mer and a 100 mer. Each sample was measured with different laser energies. In the negative samples, the PCR product was detected neither with less nor with higher laser energies. In the positive samples the PCR product was detected at different places of the sample spot and also with varying laser energies.

Results

A nested PCR system was used for the detection of HBV DNA in blood samples employing oligonucleotides complementary to the c region of the HBV genome (primer 1: beginning at map position 1763, primer 2 beginning at map position 2032 of the complementary strand) encoding the HBV core antigen (HBVcAg). DNA was isolated from patients serum according to standard protocols. A first PCR was performed with the DNA from these preparations using a first set of primers. If HBV DNA was present in the sample a DNA fragment of 269 bp was generated.

In the second reaction, primers which were complementary to a region within the PCR fragment generated in the first PCR were used. If HBV related PCR products were present in the first PCR a DNA fragment of 67 bp was generated (see FIG. 25A) in this nested PCR. The usage of a nested PCR system for detection provides a high sensitivity and also serves as a specificity control for the external PCR (Rolfs, A. et al., PCR: Clinical Diagnostics and Research, Springer, Heidelberg, 1992). A further advantage is that the amount of fragments generated in the second PCR is high enough to ensure an unproblematic detection although purification losses can not be avoided.

The samples were purified using ultrafiltration to remove the primers prior to immobilization on streptavidin Dynabeads. This purification was done because the shorter primer fragments were immobilized in higher yield on the beads due to steric reasons. The immobilization was done directly on the ultrafiltration membrane to avoid substance losses due to unspecific absorption on the membrane. Following immobilization, the beads were washed with ammonium citrate to perform cation exchange (Pieles, U. et al., (1993) Nucleic Acids Res 21:3191–3196). The immobilized DNA was cleaved from the beads using 25% ammonia which allows cleavage of DNA from the beads in a very short time, but does not result in an introduction of sodium or other cations.

The nested PCRs and the MALDI TOF analysis were performed without knowing the results of serological analysis. Due to the unknown virus titer, each sample of the first PCR was used undiluted as template and in a 1:10 dilution, respectively.

Sample 1 was collected from a patient with chronic active HBV infection who was positive in HBs- and HBe-antigen tests but negative in a dot blot analysis. Sample 2 was a serum sample from a patient with an active HBV infection and a massive viremia who was HBV positive in a dot blot analysis. Sample 3 was a denatured serum sample therefore no serologicial analysis could be performed but an increased level of transaminases indicating liver disease was detected. In autoradiograph analysis (FIG. 24), the first PCR of this sample was negative. Nevertheless, there was some evidence of HBV infection. This sample is of interest for MALDI-TOF anlaysis, because it demonstrates that even low-level amounts of PCR products can be detected after the purification procedure. Sample 4 was from a patient who was cured of HBV infection. Samples 5 and 6 were collected from patients with a chronic active HBV infection.

Figure 24:
FIG. 24 is an autoradiograph of Example 5 of a 7.5% polyacrylamide gel in which 10% (5 μl) of each PCR was loaded. sample M: pBR322 AluI digested; sample 1: HBV positive in serological analysis; sample 2: also HBV positive; sample 3: without serological analysis but with an increased level of transaminases, indicating liver disease; sample 4: HBV negative containing HCV; sample 5: HBV positive by serological analysis; sample 6: HBV negative (−) negative control; (+) positive control). Staining was done with ethidium bromide.

FIG. 24 shows the results of a PAGE analysis of the nested PCR reaction. A PCR product is clearly revealed in samples 1, 2, 3, 5 and 6. In sample 4 no PCR product was generated, it is indeed HBV negative, according to the serological analysis. Negative and positive controls are indicated by +and –, respectively. Amplification artifacts are visible in lanes 2, 5, 6 and + if non-diluted template was used. These artifacts were not generated if the template was used in a 1:10 dilution. In sample 3, PCR product was merely detectable if the template was not diluted. The results of PAGE analysis are in agreement with the data obtained by serological analysis except for sample 3 as discussed above.

Figure 25A:
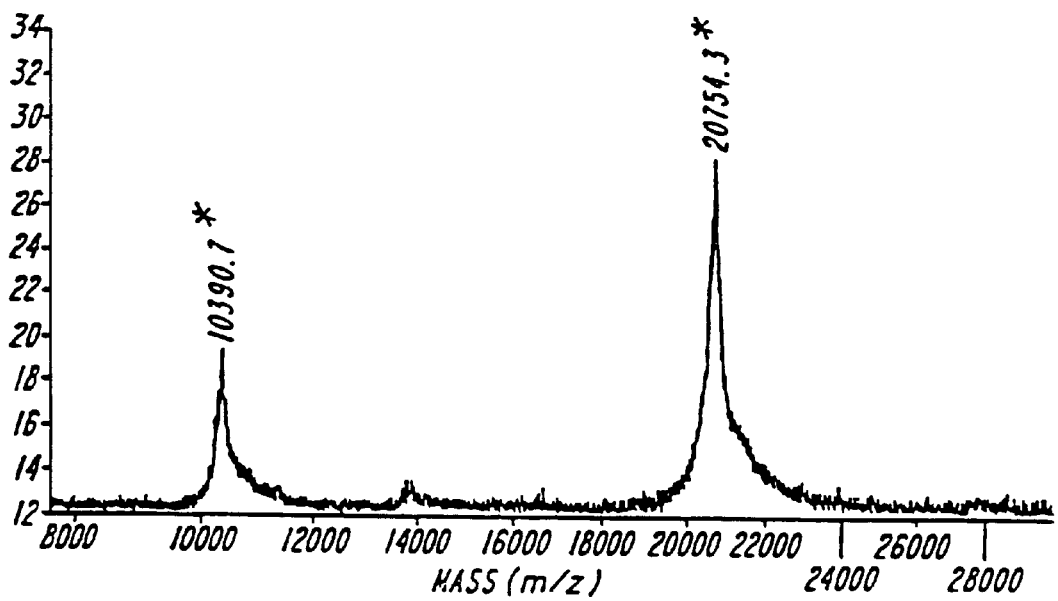
FIG. 25A is a mass spectrum of sample 1, which is HBV positive. The signal at 20754 Da represents the HBV related PCR product (67 nucleotides, calculated mass: 20735 Da). The mass signal at 10390 Da represents the $[M+2H]^{2+}$ signal (calculated: 10378 Da).

FIG. 25A shows a mass spectrum of a nested PCR product from sample number 1 generated and purified as described above. The signal at 20754 Da represents the single stranded PCR product (calculated: 20735 Da, as the average mass of both strands of the PCR product cleaved from the beads). The mass difference of calculated and obtained mass is 19 Da (0.09%). As shown in FIG. 25A, sample number 1 generated a high amount of PCR product, resulting in an unambiguous detection.

Figure 25B:
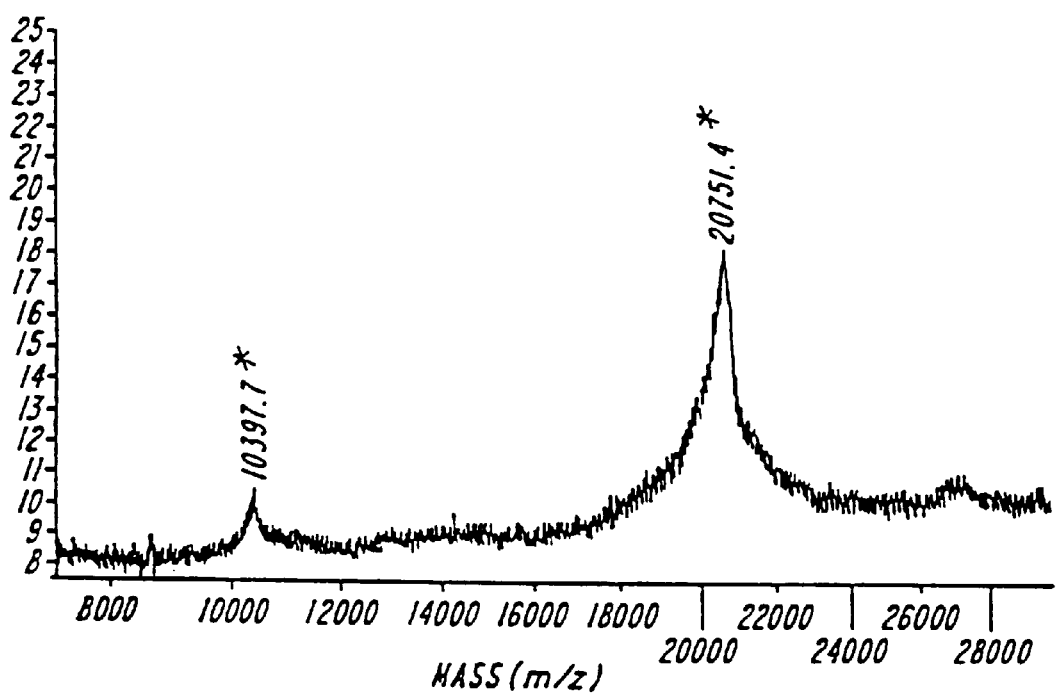
FIG. 25B is a mass spectrum of sample 3, which is HBV negative corresponding to PCR, serological and dot blot based assays. The PCR product is generated only in trace amounts. Nevertheless it is unambiguously detected at 20751 Da (calculated: 20735 Da). The mass signal at 10397 Da represents the $[M+2H]^{2+}$ molecule ion (calculated: 10376 Da).
Figure 25C:
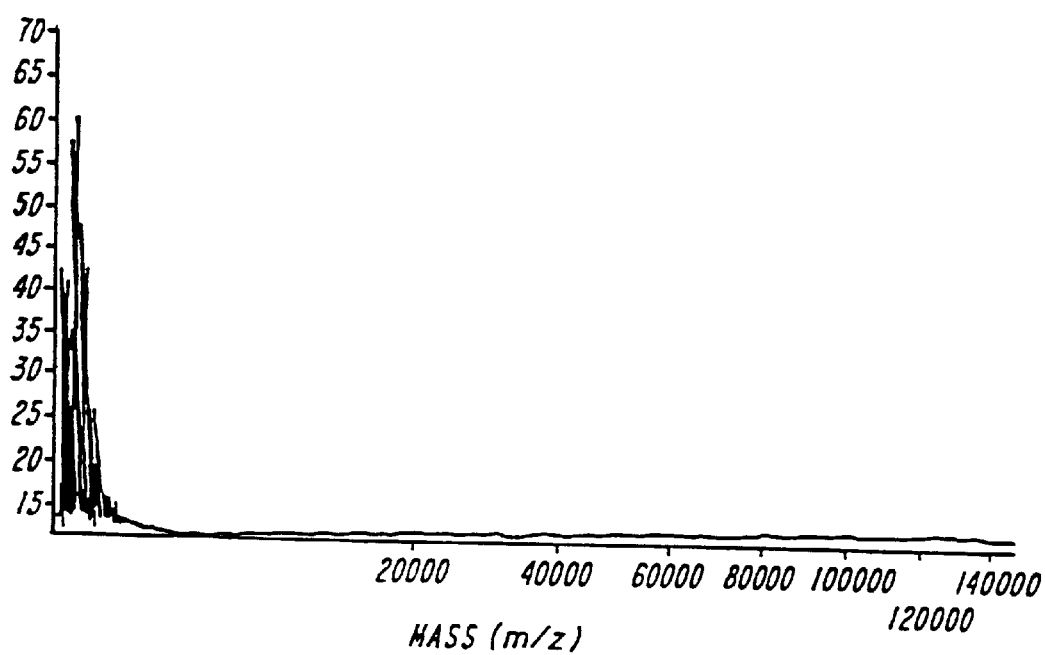
FIG. 25C is a mass spectrum of sample 4, which is HBV negative, but HCV positive. As expected, no HBV specific signals could be obtained.

FIG. 25B shows a spectrum obtained from sample number 3. As depicted in FIG. 24, the amount of PCR product generated in this section is significantly lower than that from sample number 1. Nevertheless, the PCR product is clearly revealed with a mass of 20751 Da (calculated 20735). The mass difference is 16 Da (0.08%). The spectrum depicted in FIG. 25C was obtained from sample number 4 which is HBV negative (as is also shown in FIG. 24). As expected no signals corresponding to the PCR product could be detected. All samples shown in FIG. 25 were analyzed with MALDI-TOF MS, whereby PCR product was detected in all HBV positive samples, but not in the HBV negative samples. These results were reproduced in several independent experiments.

EXAMPLE 6

Analysis of Ligase Chain Reaction Products Via MALDI-TOF Mass Spectrometry

Materials and Methods

Oligodeoxynucleotides

Except the biotinylated one and all other oligonucleotides were synthesized in a 0.2 μmol scale on a MilliGen 7500 DNA Synthesizer (Millipore, Bedford, Mass., USA) using the β-cyanoethylphosphoamidite method (Sinha, N. D. et al., (1984) *Nucleic Acids Res.*, Vol. 12, Pp. 4539–4577). The oligodeoxynucleotides were RP-HPLC-purified and deprotected according to standard protocols. The biotinylated oligodeoxynucleotide was purchased (HPLC-purified) from Biometra, Gottingen, Germany).

Sequences and calculated masses of the oligonucleotides used:

Oligodeoxynucleotide A: 5'-p-TTGTGCCACGCGGTTGGGAATGTA (7521 Da) (SEQ ID No. 9)

Oligodeoxynucleotide B: 5'-p-AGCAACGACTGTTTGCCCGCCAGTTG (7948 Da) (SEQ ID No. 10)

Oligodeoxynucleotide C: 5'-bio-TACATTCCCAACCGCGTGGCACAAC (7960 Da) (SEQ ID No. 11)

Oligodeoxynucleotide D: 5'-p-AACTGGCGGGCAAACAGTCGTTGCT (7708 Da) (SEQ ID No. 12)

5'-Phosphorylation of Oligonucleotides A and D

This was performed with polynucleotide kinase (Boehringer, Mannheim, Germany) according to published procedures, the 5'-phosphorylated oligonucleotides were used unpurified for LCR.

Ligase Chain Reaction

The LCR was performed with Pfu DNA ligase and a ligase chain reaction kit (Stratagene, Heidelberg, Germany) containing two different pBluescript KII phagemids. One carrying the wildtype form of the *E.coli* lacI gene and the other one a mutant of this gene with a single point mutation at bp 191 of the lacI gene.

The following LCR conditions were used for each reaction: 100 pg template DNA (0.74 fmol) with 500 pg sonified salmon sperm DNA as carrier, 25 ng (3.3 pmol) of each 5'-phosphorylated oligonucleotide, 20 ng (2.5 pmol) of each non-phosphorylated oligonucleotide, 4 U Pfu DNA ligase in a final volume of 20 μl buffered by Pfu DNA ligase reaction buffer (Stratagene, Heidelberg, Germany). In a model experiment a chemically synthesized ss 50-mer was used (1 fmol) as template, in this case oligo C was also biotinylated. All reactions were performed in a thermocycler (OmniGene, MWG-Biotech, Ebersberg, Germany) with the following program: 4 minutes 92° C., 2 minutes 60° C. and 25 cycles of 20 seconds 92° C., 40 seconds 60° C. Except for HPLC analysis the biotinylated ligation educt C was used. In a control experiment the biotinylated and non-biotinylated oligonucleotides revealed the same gel electrophoretic results. The reactions were analyzed on 7.5% polyacrylamide gels. Ligation product 1 (oligo A and B) calculated mass: 15450 Da, ligation product 2 (oligo C and D) calculated mass: 15387 Da.

SMART-HPLC

Ion exchange HPLC (IE HPLC) was performed on the SMART-system (Pharmacia, Freiburg, Germany) using a Pharmacia Mono Q, PC 1.6/5 column. Eluents were buffer A (25 mM Tris-HCl, 1 mM EDTA and 0.3 M NaCl at pH 8.0) and buffer B (same as A, but 1 M NaCl). Starting with 100% A for 5 minutes at a flow rate of 50 μl/min. a gradient was applied from 0 to 70% B in 30 minutes, then increased to 100% B in 2 minutes and held at 100% B for 5 minutes. Two pooled LCR volumes (40 μl) performed with either wildtype or mutant template were injected.

Sample Preparation for MALDI-TOF-MS

Preparation of immobilized DNA: For the recording of each spectrum two LCRs (performed as described above) were pooled and diluted 1:1 with 2×B/W buffer (10 mM Tris-HCl, pH 7.5, 1 mM EDTA, 2 M NaCl). To the samples 5 μl streptavidin DynaBeads (Dynal, Hamburg, Germany) were added, the mixture was allowed to bind with gentle shaking for 15 minutes at ambient temperature. The supernatant was removed using a Magnetic Particle Collector, MPC, (Dynal, Hamburg, Germany) and the beads were washed twice with 50 μl of 0.7 M ammonium citrate solution (pH 8.0) (the supernatant was removed each time using the MPC). The beads were resuspended in 1 μl of ultrapure water (MilliQ, Millipore, Bedford, Mass., USA). This suspension was directly used for MALDI-TOF-MS analysis as described below.

Combination of ultrafiltration and streptavidin Dyna-Beads: For the recording of spectrum two LCRs (performed as described above) were pooled, diluted 1:1 with 2×B/W buffer and concentrated with a 5000 NMWL Ultrafree-MC filter unit (Millipore, Eschborn, Germany) according to the instructions of the manufacturer. After concentration the samples were washed with 300 μl 1×B/W buffer to streptavidin DynaBeads were added. The beads were washed once on the Ultrafree-MC filtration unit with 300 μl of 1×B/W buffer and processed as described above. The beads were resuspended in 30 to 50 μl of 1×B/W buffer and transferred in a 1.5 ml Eppendorf tube. The supernatant was removed and the beads were washed twice with 50 μl of 0.7 M ammonium citrate (pH 8.0). Finally, the beads were washed once with 30 μl of acetone and resuspended in 1 μl of ultrapure water. The ligation mixture after immobilization on the beads was used for MALDS-TOF-MS analysis as described below.

MALDI-TOF-MS

A suspension of streptavidin-coated magnetic beads with the immobilized DNA was pipetted onto the sample holder, then immediately mixed with 0.5 Pl matrix solution (0.7 M 3-hydroxypicolinic acid in 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron (5 keV ion source, 20 keV postacceleration) and a nitrogen laser (337 nm). For the analysis of Pfu DNA ligase 0.5 μl of the solution was mixed on the sample holder with 1 μl of matrix solution and prepared as described above. For the analysis of unpurified LCRs 1 μl of an LCR was mixed with 1 μl matrix solution.

Results

Figure 26:
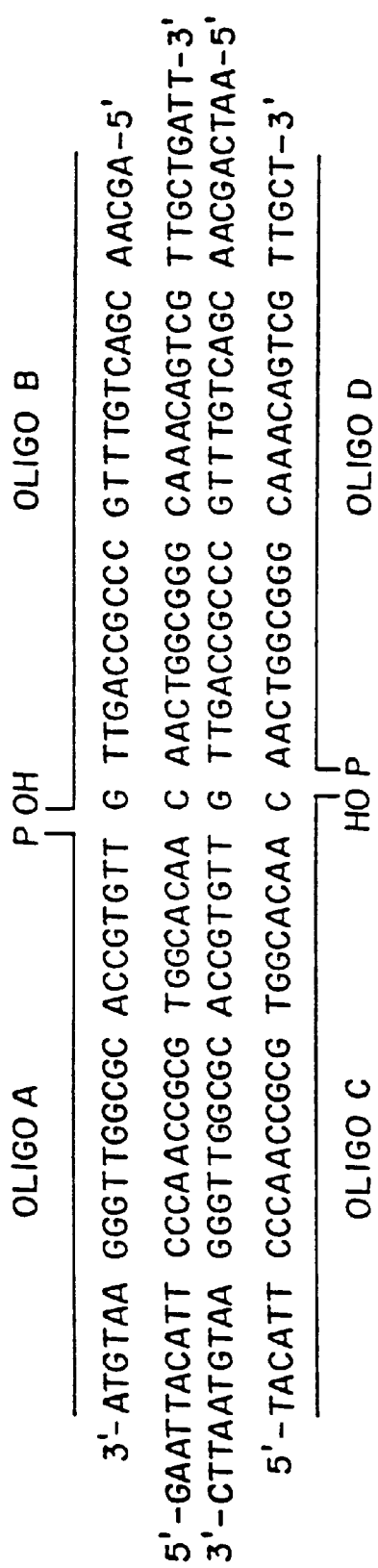
FIG. 26 shows a part of the *E. coli* lacI gene with binding sites of the complementary oligonucleotides used in the ligase chain reaction (LCR) of Example 6. Here the wildtype sequence is displayed. The mutant contains a point mutation at bp 191 which is also the site of ligation (bold). The mutation is a C to T transition (G to A, respectively). This leads to a T-G mismatch with oligo B (and A-C mismatch with oligo C, respectively).

The *E. coli* lacI gene served as a simple model system to investigate the suitability of MALDI-TOF-MS as detection method for products generated in ligase chain reactions. This template system consists of an *E.coli* lacI wildtype gene in a pBluescript KII phagemid and an *E. coli* lacI gene carrying a single point mutation at bp 191 (C to T transition) in the same phagemid. Four different oligonucleotides were used, which were ligated only if the *E. coli* lacI wildtype gene was present (FIG. 26).

Figure 27:
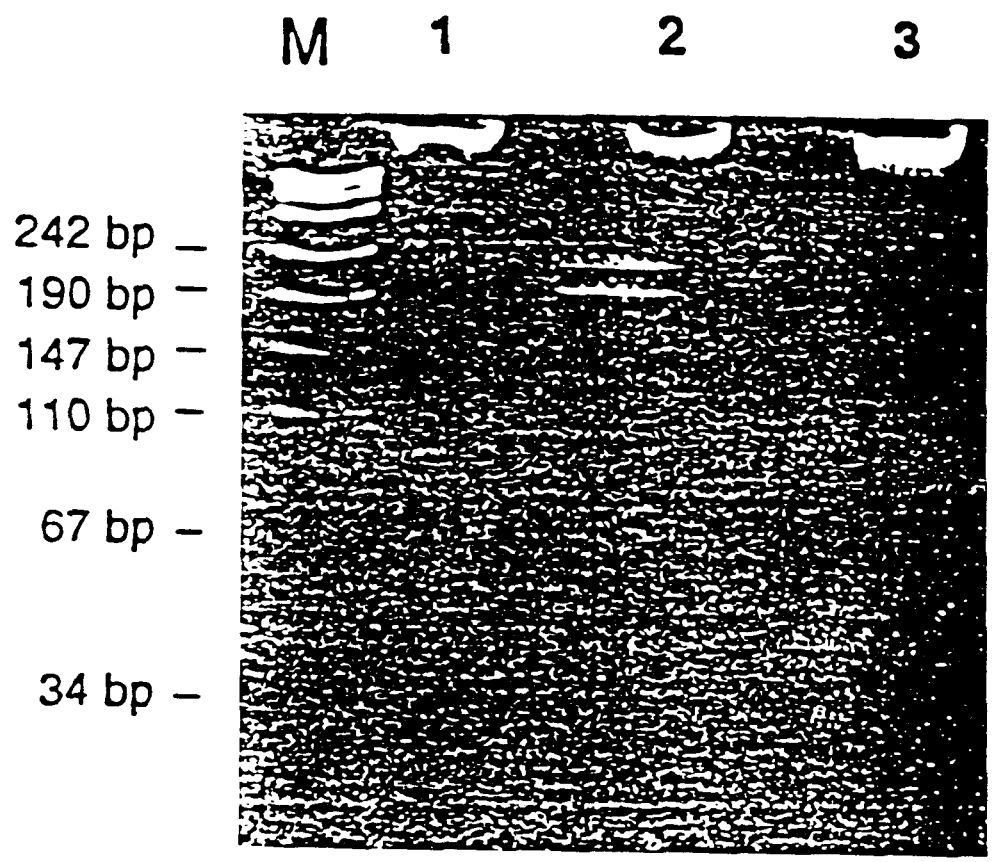
FIG. 27 is a 7.5% polyacrylamide gel of Example 6 stained with ethidium bromide. M: chain length standard (pUC19 DNA, MspI digested). Lane 1: LCR with wildtype template. Lane 2: LCR with mutant template. Lane 3: (control) LCR without template. The ligation product (50 bp) was only generated in the positive reaction containing wildtype template.
Figure 28:
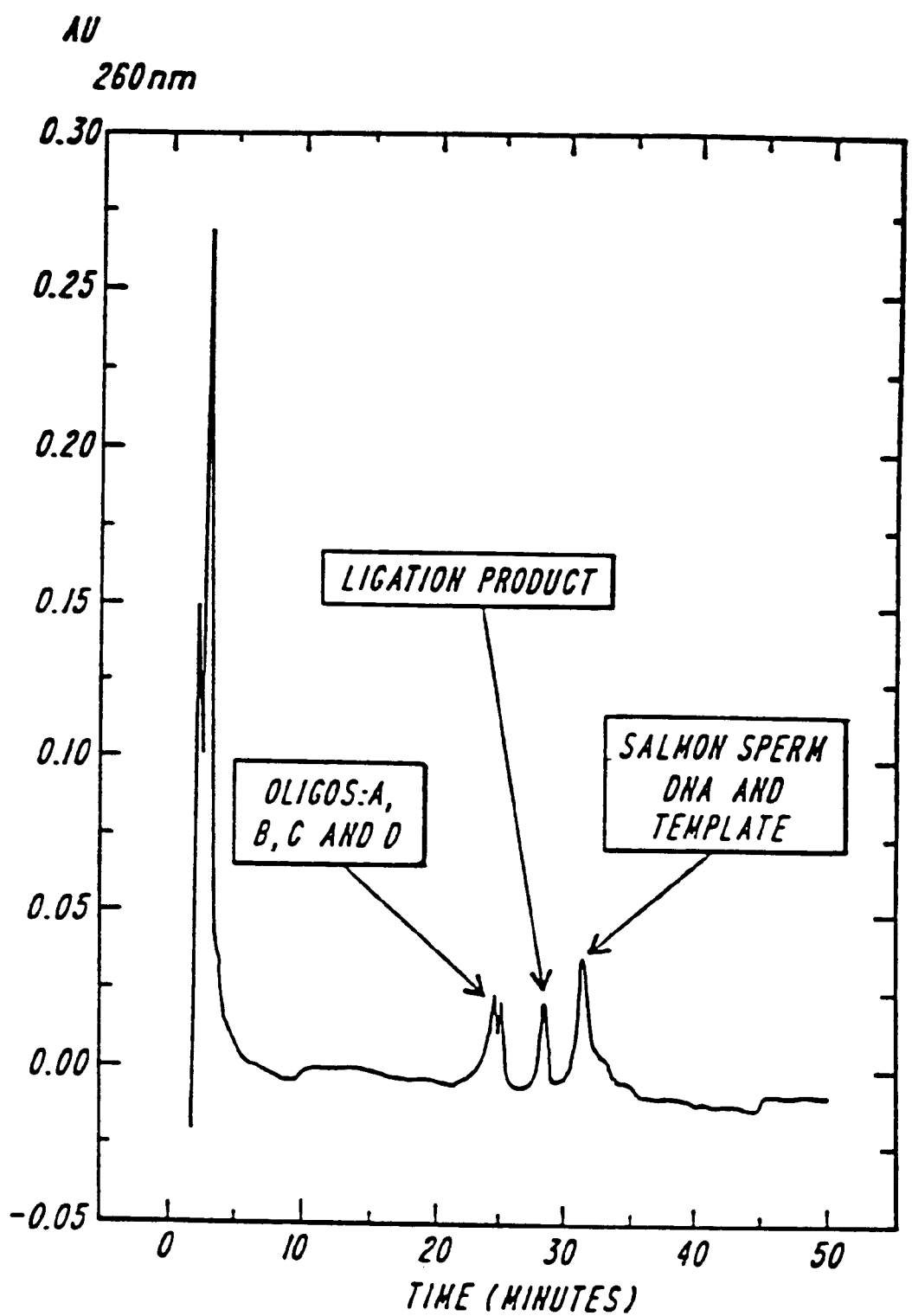
FIG. 28 is an HPLC chromatogram of two pooled positive LCRs.
Figure 29:
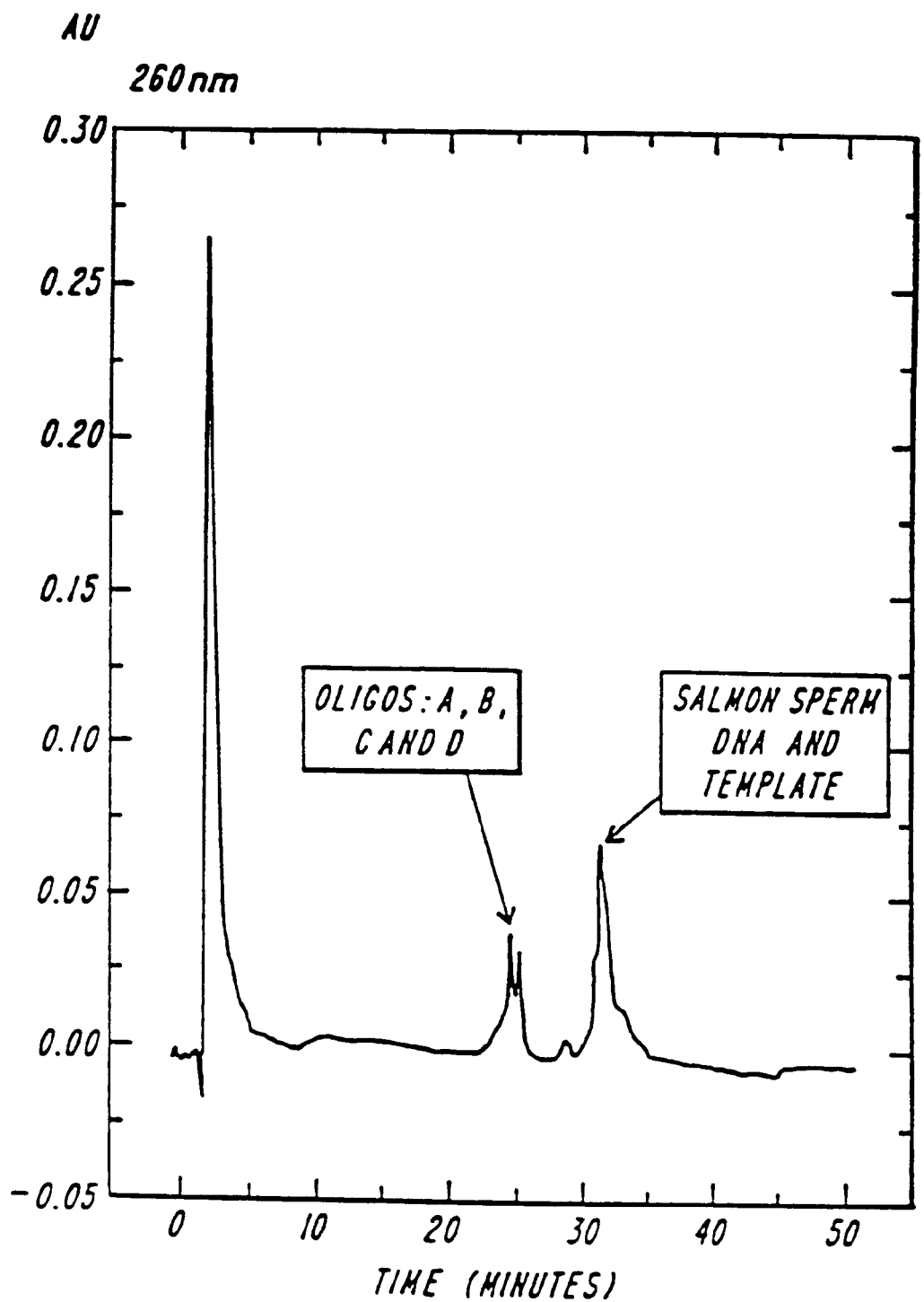
FIG. 29 shows an HPLC chromatogram the same conditions but mutant template were used. The small signal of the ligation product is due to either template-free ligation of the educts or to a ligation at a (G-T, A-C) mismatch. The 'false positive' signal is significantly lower than the signal of ligation product with wildtype template depicted in FIG. 28. The analysis of ligation educts leads to 'double -peaks' because two of the oligonucleotides are 5'- phosphorylated.

LCR conditions were optimized using Pfu DNA ligase to obtain at least 1 pmol ligation product in each positive reaction. The ligation reactions were analyzed by polyacrylamide gel electrophoresis (PAGE) and HPLC on the SMART system (FIGS. 27, 28 and 29). FIG. 27 shows a PAGE of a positive LCR with wildtype template (lane 1), a negative LCR with mutant template (1 and 2) and a negative control which contains enzyme, oligonucleotides and no template but salmon sperm DNA. The gel electrophoresis clearly shows that the ligation product (50 bp) was produced only in the reaction with wildtype template whereas neither the template carrying the point mutation nor the control reaction with salmon sperm DNA generated amplification products. In FIG. 28, HPLC was used to analyze two pooled LCRs with wildtype template performed under the same conditions. The ligation product was clearly revealed. FIG. 29 shows the results of a HPLC in which two pooled negative LCRs with mutant template were analyzed. These chromatograms confirm the data shown in FIG. 27 and the results taken together clearly demonstrate, that the system generates ligation products in a significant amount only if the wildtype template is provided.

Appropriate control runs were performed to determine retention times of the different compounds involved in the LCR experiments. These include the four oligonucleotides (A, B, C, and D), a synthetic ds 50-mer (with the same sequence as the ligation product), the wildtype template DNA, sonicated salmon sperm DNA and the Pfu DNA ligase in ligation buffer.

Figure 30A:
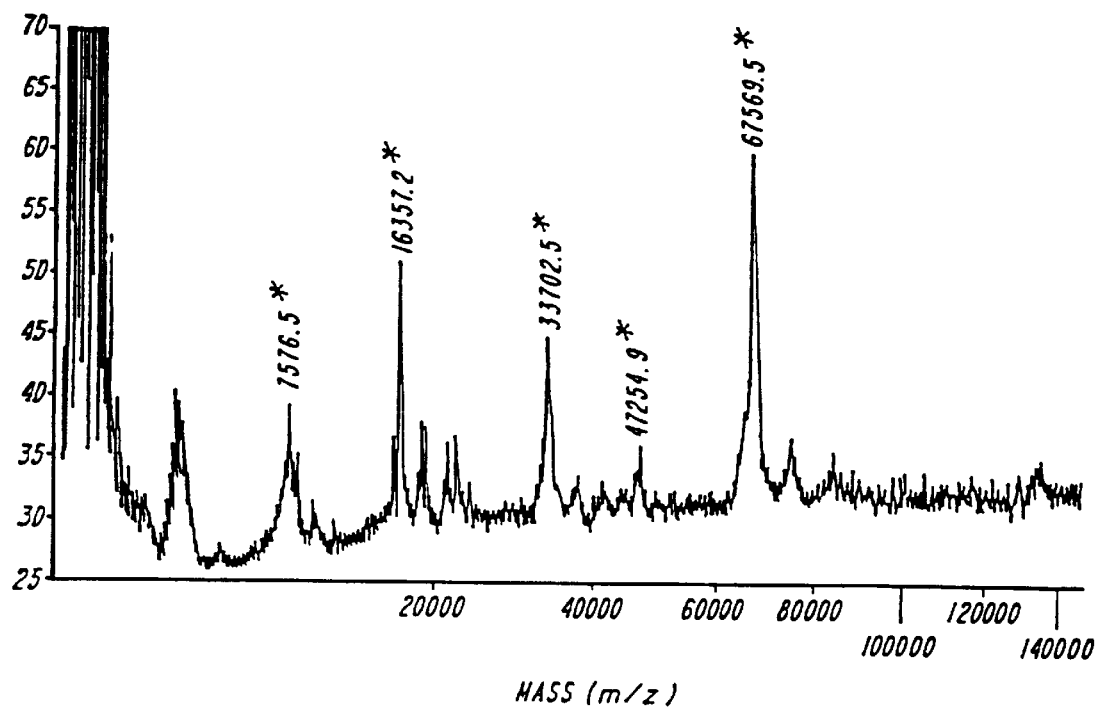
FIG. 30 In (b) the complex signal pattern obtained by MALDI-TOF-MS analysis of Pfu DNA-ligase solution of Example 6 is depicted. In (a) a MALDI-TOF-spectrum of an unpurified LCR is shown. The mass signal 67569 Da probably represents the Pfu DNA ligase.
Figure 30B:
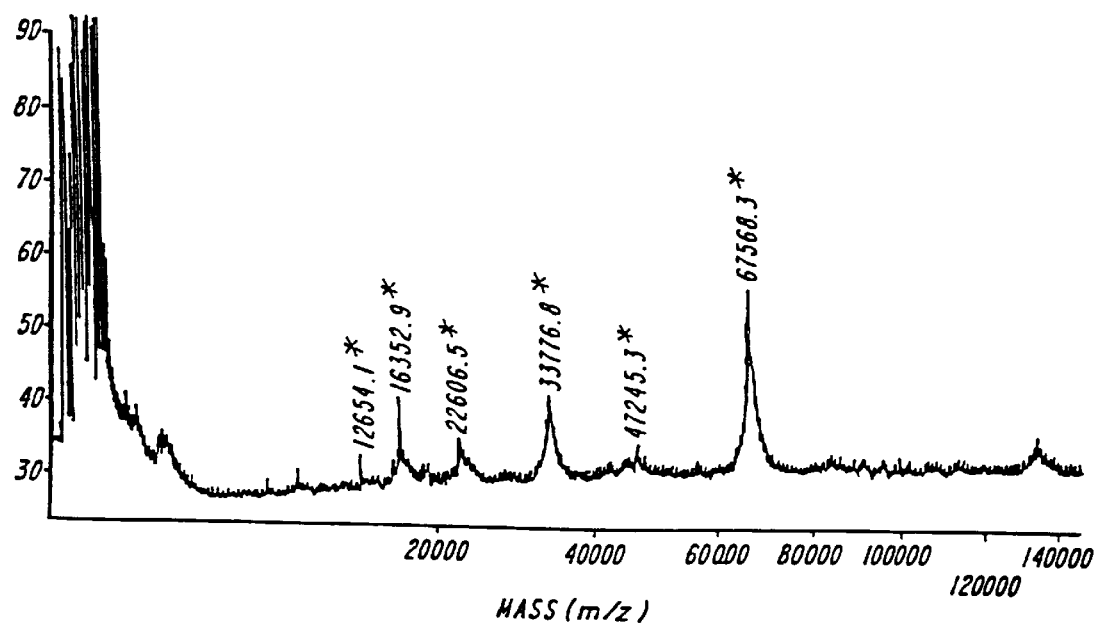

In order to test which purification procedure should be used before a LCR reaction can be analyzed by MALDI-TOF-MS, aliquots of an unpurified LCR (FIG. 30A) and aliquots of the enzyme stock solution (FIG. 30B) were analyzed with MALDI-TOF-MS. It turned out that appropriate sample preparation is absolutely necessary since all signals in the unpurified LCR correspond to signals obtained in the MALDI-TOF-MS analysis of the Pfu DNA ligase. The calculated mass values of oligo A and the ligation product are 7521 Da and 15450 Da, respectively. The data in FIG. 30 show that the enzyme solution leads to mass signals which do interfere with the expected signals of the ligation educts and products and therefore makes an unambiguous signal assignment impossible. Furthermore, the spectra showed signals of the detergent Tween20 being part of the enzyme storage buffer which influences the crystallization behavior of the analyte/matrix mixture in an unfavorable way.

In one purification format streptavidin-coated magnetic beads were used. As was shown in a recent paper, the direct desorption of DNA immobilized by Watson-Crick base pairing to a complementary DNA fragment covalently bound to the beads is possible and the non-biotinylated strand will be desorbed exclusively (Tang, K et al., (1995) Nucleic Acids Res. 23:3126–3131). This approach in using immobilized ds DNA ensures that only the non-biotinylated strand will be desorbed. If non-immobilized ds DNA is analyzed both strands are desorbed (Tang, K. et. al., (1994) Rapid Comm. Mass Spectrom. 7: 183–186) leading to broad signals depending on the mass difference of the two single strands. Therefore, employing this system for LCR only the non-ligated oligonucleotide A, with a calculated mass of 7521 Da, and the ligation product from oligo A and oligo B (calculated mass: 15450 Da) will be desorbed if oligo C is biotinylated at the 5'-end and immobilized on steptavidin-coated beads. This results in a simple and unambiguous identification of the LCR educts and products.

Figure 31A:
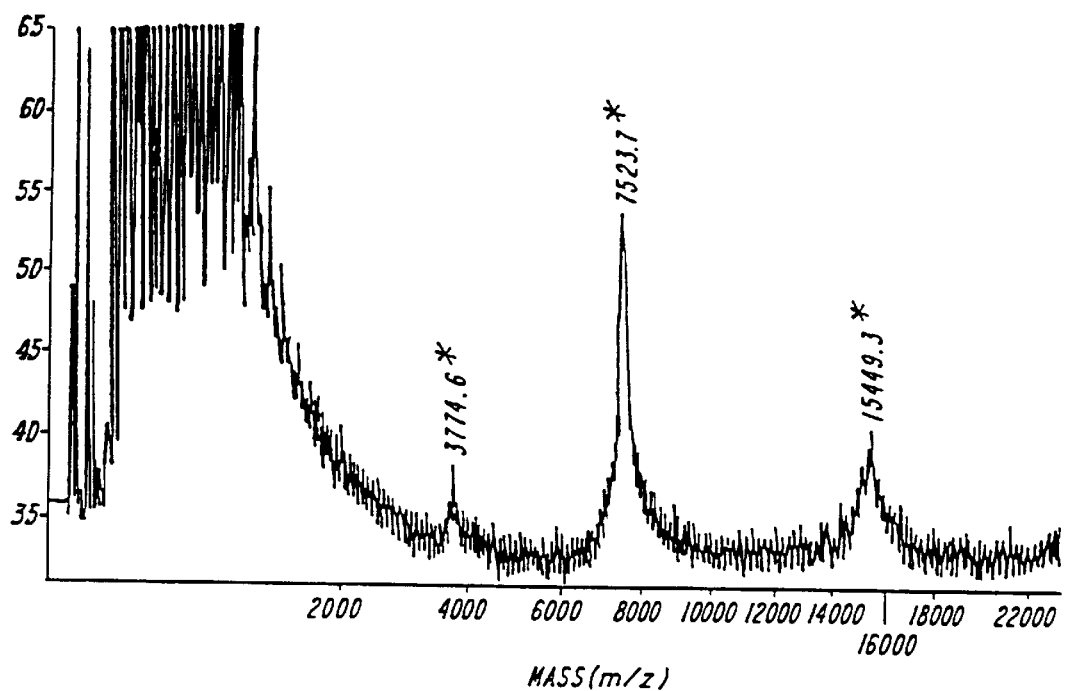
FIG. 31 shows a MALDI-TOF spectrum of two pooled positive LCRs (a). The signal at 7523 Da represents unligated oligo A (calculated: 7521 Da) whereas the signal at 15449 Da represents the ligation product (calculated: 15450 Da). The signal at 3774 Da is the $[M+2H]^{2+}$ signal of oligo A. The signals in the mass range lower than 2000 Da are due to the matrix ions. The spectrum corresponds to lane 1 in FIG. 27 and to the chromatogram in FIG. 28. In (b) a spectrum of two pooled negative LCRs (mutant template) is shown. The signal at 7517 Da represents oligo A (calculated: 7521 Da).
Figure 31B:
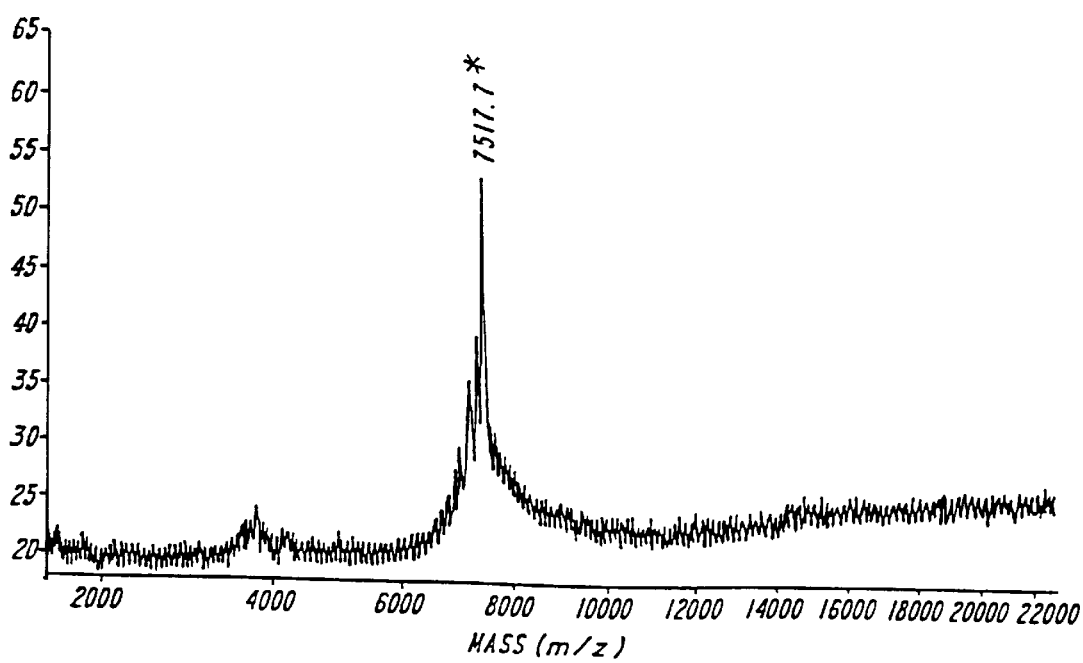
Figure 32:
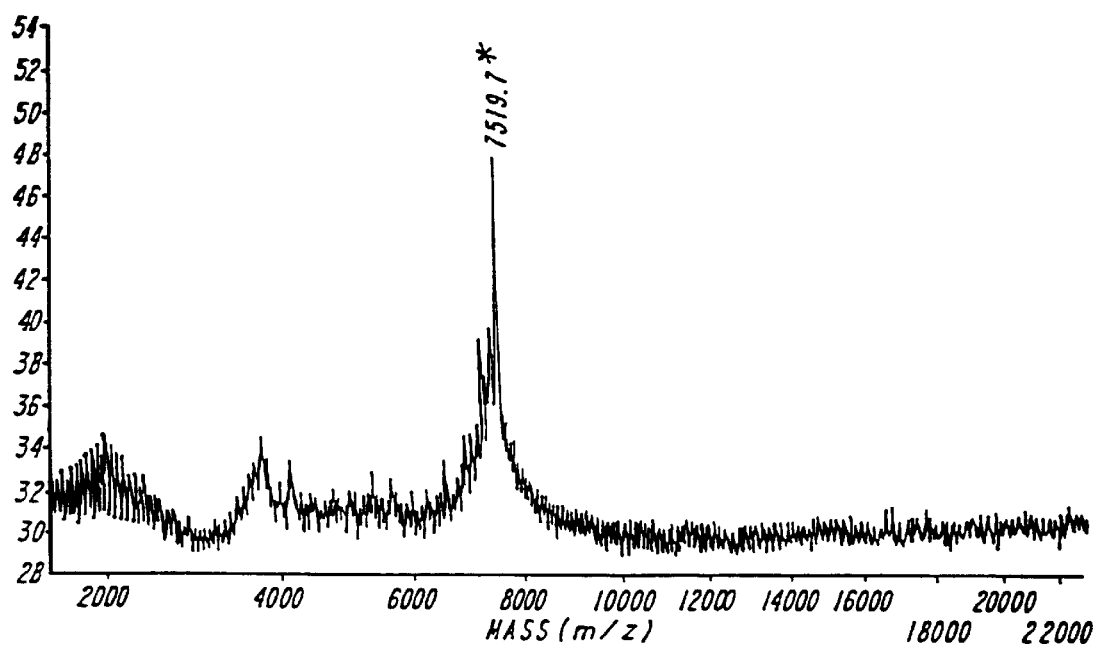
FIG. 32 shows a spectrum of two pooled control reactions (with salmon sperm DNA as template). The signals in the mass range around 2000 Da are due to Tween20, only oligo A could be detected, as expected.

FIG. 31A shows a MALDI-TOF mass spectrum obtained from two pooled LCRs (performed as described above) purified on streptavidin DynaBeads and desorbed directly from the beads showed that the purification method used was efficient (compared with FIG. 30). A signal which represents the unligated oligo A and a signal which corresponds to the ligation product could be detected. The agreement between the calculated and the experimentally found mass values is remarkable and allows an unambiguous peak assignment and accurate detection of the ligation product. In contrast, no ligation product but only oligo A could be detected in the spectrum obtained from two pooled LCRs with mutated template (FIG. 31B). The specificity and selectivity of the LCR conditions and the sensitivity of the MALDI-TOF detection is further demonstrated when performing the ligation reaction in the absence of a specific template. FIG. 32 shows a spectrum obtained from two pooled LCRs in which only salmon sperm DNA was used as a negative control, only oligo A could be detected, as expected.

While the results shown in FIG. 31A can be correlated to lane 1 of the gel in FIG. 27, the spectrum shown in FIG. 31B is equivalent to lane 2 in FIG. 27, and finally also the spectrum in FIG. 32 corresponds to lane 3 in FIG. 27. The results are in congruence with the HPLC analysis presented in FIGS. 28 and 29. While both gel electrophoresis (FIG. 27) and HPLC (FIGS. 28 and 29) reveal either an excess or almost equal amounts of ligation product over ligation educts, the analysis by MALDI-TOF mass spectrometry produces a smaller signal for the ligation product (FIG. 31A).

The lower intensity of the ligation product signal could be due to different desorption/ionization efficiencies between 24- and a 50-mer. Since the $T_{hd}$ $m$ value of a duplex with 50 compared to 24 base pairs is significantly higher, more 24-mer could be desorbed. A reduction in signal intensity can also result from a higher degree of fragmentation in case of the longer oligonucleotides.

Regardless of the purification with streptavidin DynaBeads, FIG. 32 reveals traces of Tween20 in the region around 2000 Da. Substances with a viscous consistence, negatively influence the process of crystallization and therefore can be detrimental to mass spectrometer analysis. Tween20 and also glycerol which are part of enzyme storage buffers therefore should be removed entirely prior to mass spectrometer analysis. For this reason an improved purification procedure which includes an additional ultrafiltration step prior to treatment with DynaBeads was investigated. Indeed, this sample purification resulted in a significant improvement of MALDI-TOF mass spectrometric performance.

Figure 33A:
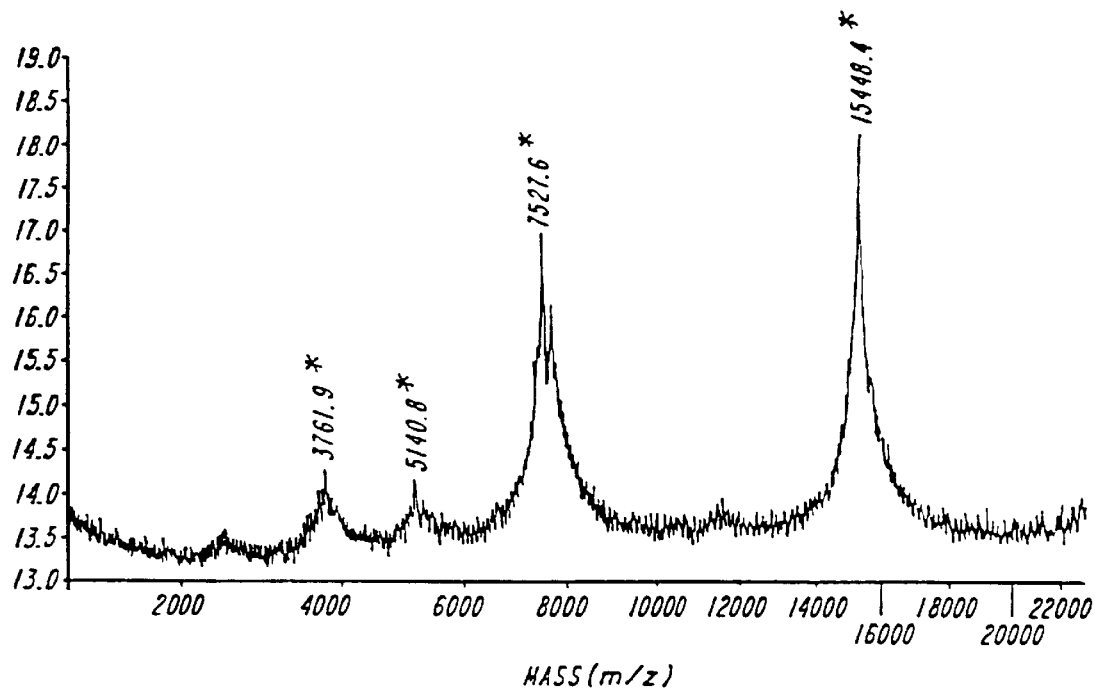
FIG. 33 shows a spectrum of two pooled positive LCRs (a). The purification was done with a combination of ultra-filtration and streptavidin DynaBeads as described in the text. The signal at 15448 Da represents the ligation product (calculated: 15450 Da). The signal at 7527 represents oligo A (calculated: 7521 Da). The signals at 3761 Da is the $[M+2H]^{2+}$ signal of oligo A, whereas the signal at 5140 Da is the $[M+3H]^{2+}$ signal of the ligation product. In (b) a spectrum of two pooled negative LCRs (without template) is shown. The signal at 7514 Da represents oligo A (calculated: 7521 Da).
Figure 33B:
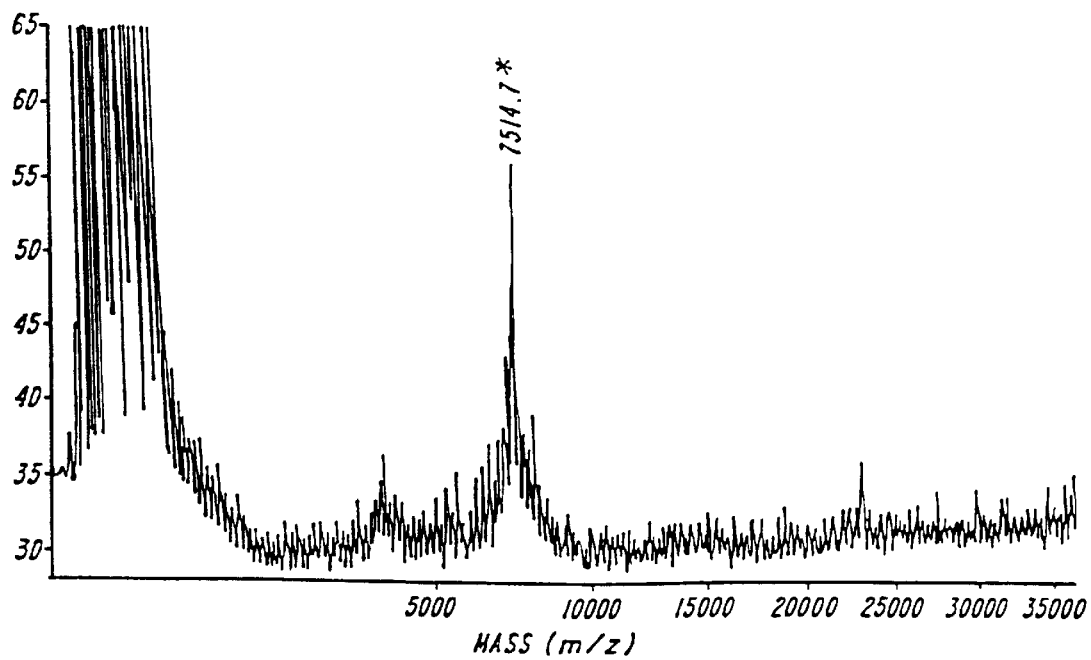
Figure 35A:
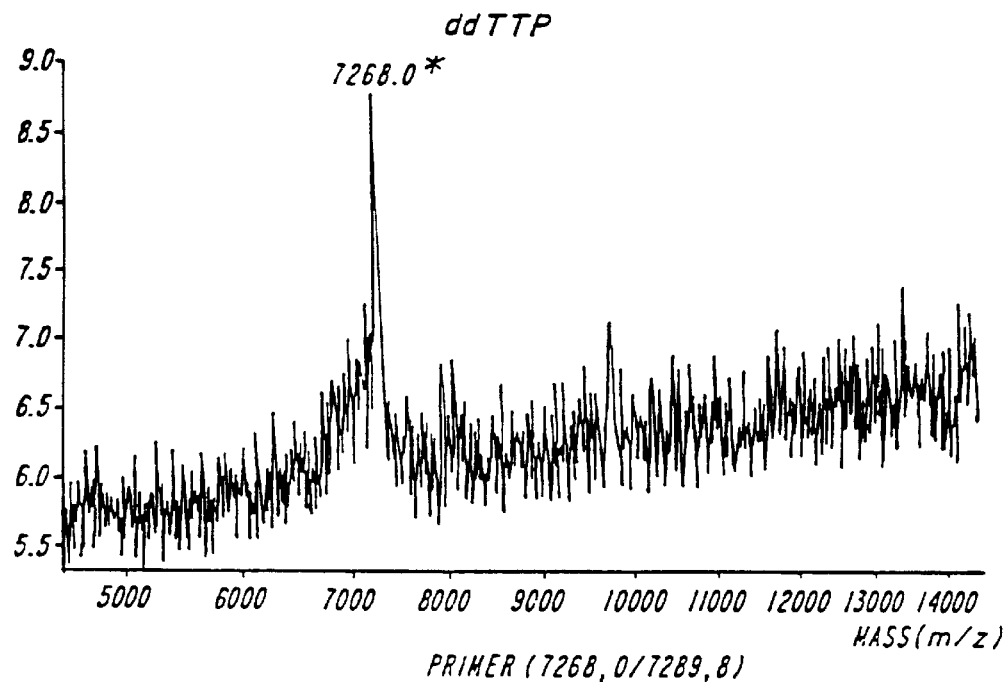
FIG. 35 is a MALDI-TOF-MS spectrum recorded directly from precipitated oligo base extended primers for mutation detection. The spectrum in (A) and (B), respectively show the annealed primer (CF508) without further extension reaction. Panel C displays the MALDI-TOF spectrum of the wild type by using pppTdd in the extension reaction and D a heterozygotic extension products carrying the 506S mutation when using pppCdd as terminator. Panels E and F show a heterozygote with ΔF508 mutation with pppTdd and pppCdd as terminators in the extension reaction. Panels G and H represent a homozygous ΔF508 mutation with either pppTdd or pppCdd as terminators. The template of diagnosis is pointed out below each spectrum and the observed/ expected molecular mass are written in parenthesis.
Figure 35B:
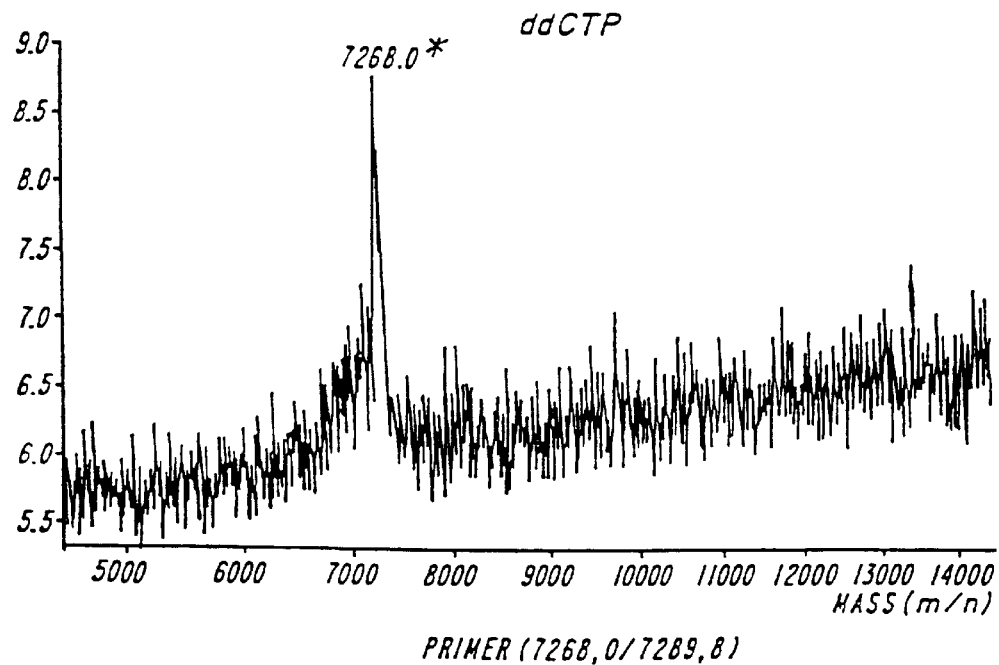
Figure 35C:
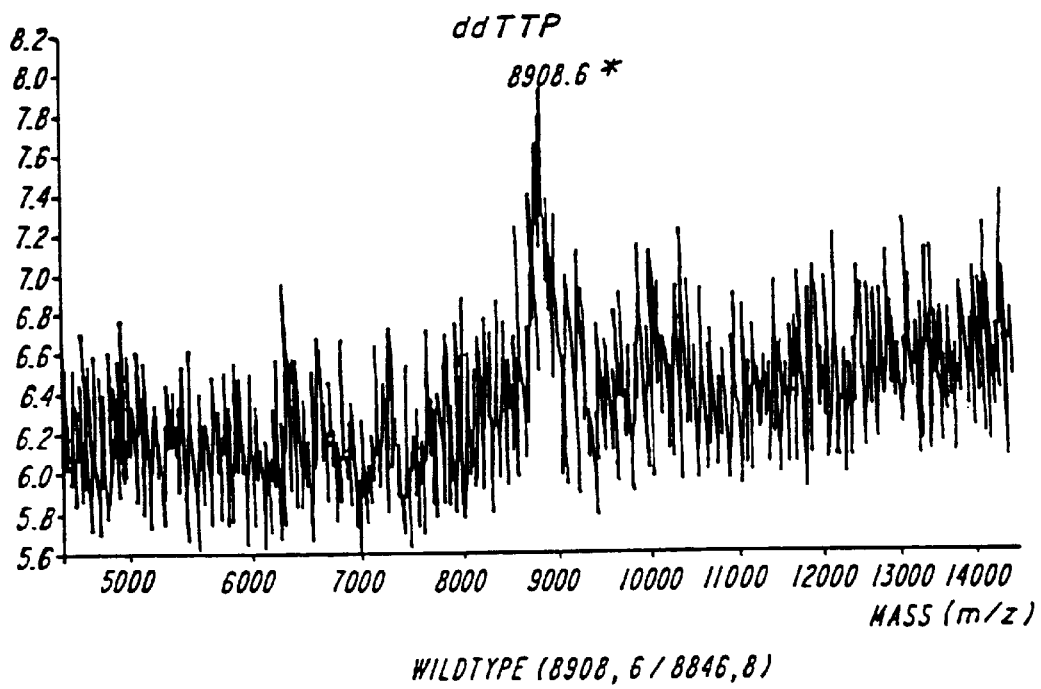
Figure 35D:
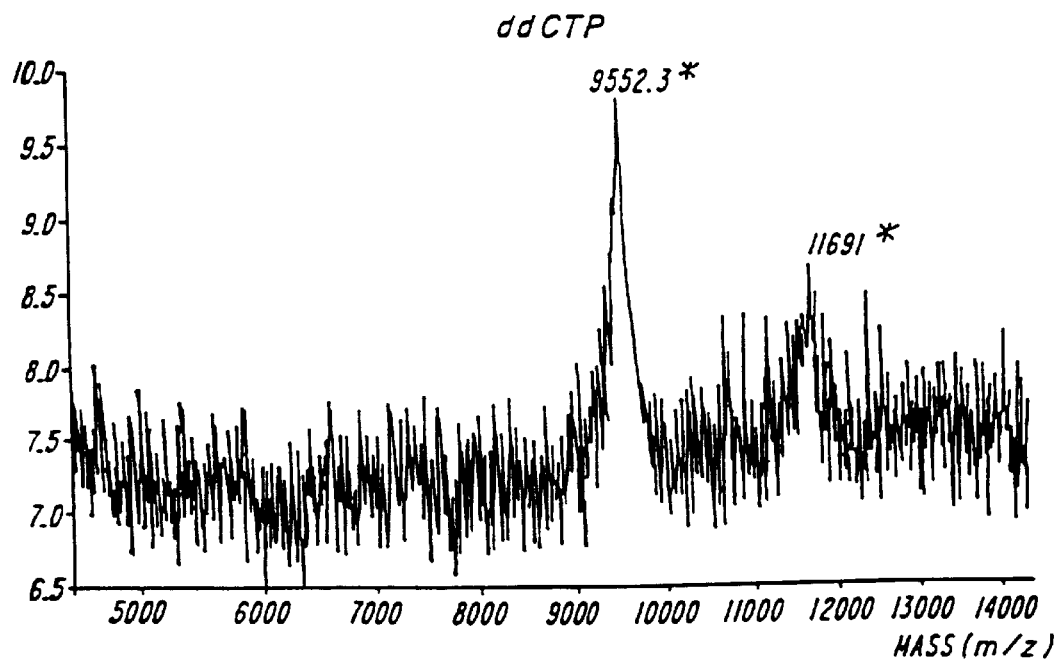
Figure 35E:
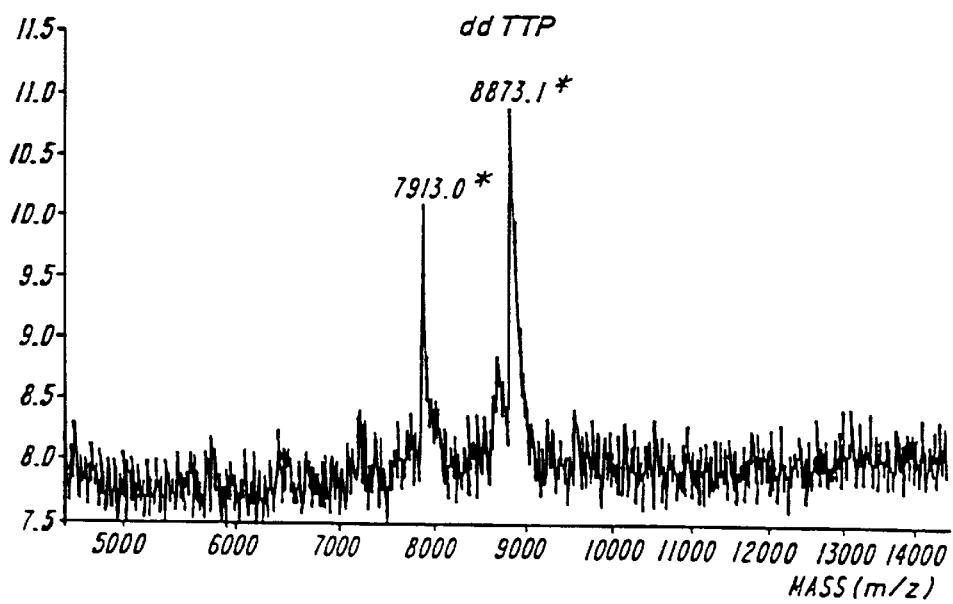
Figure 35F:
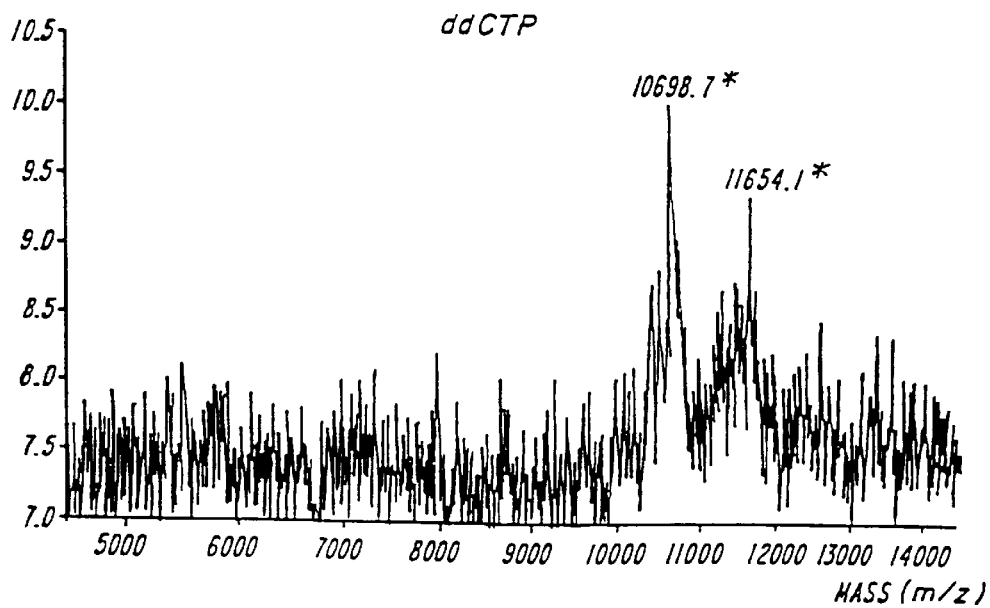
Figure 35G:
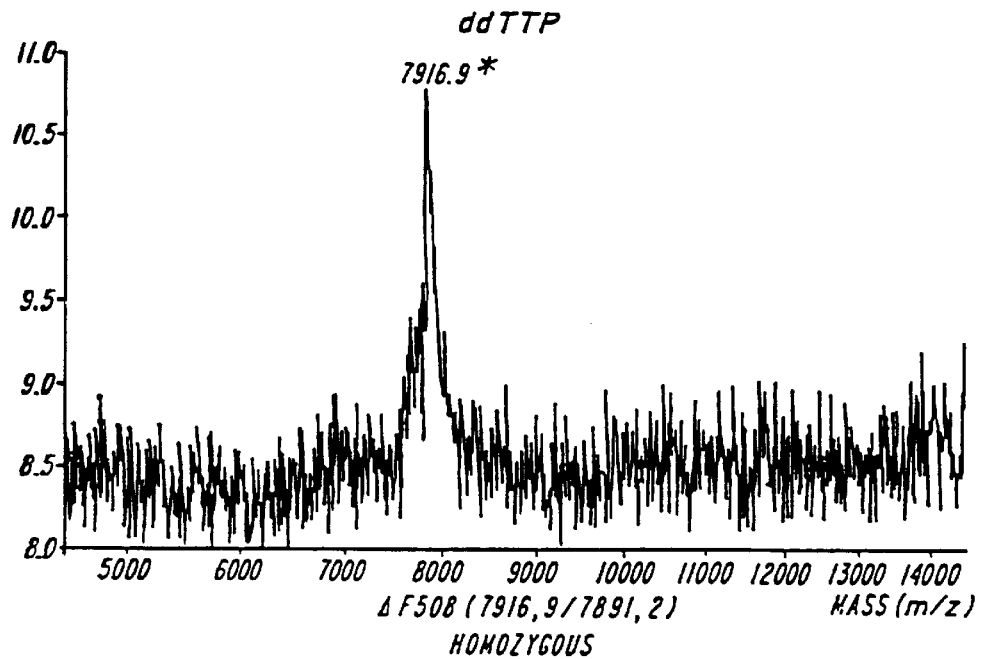
Figure 35H:
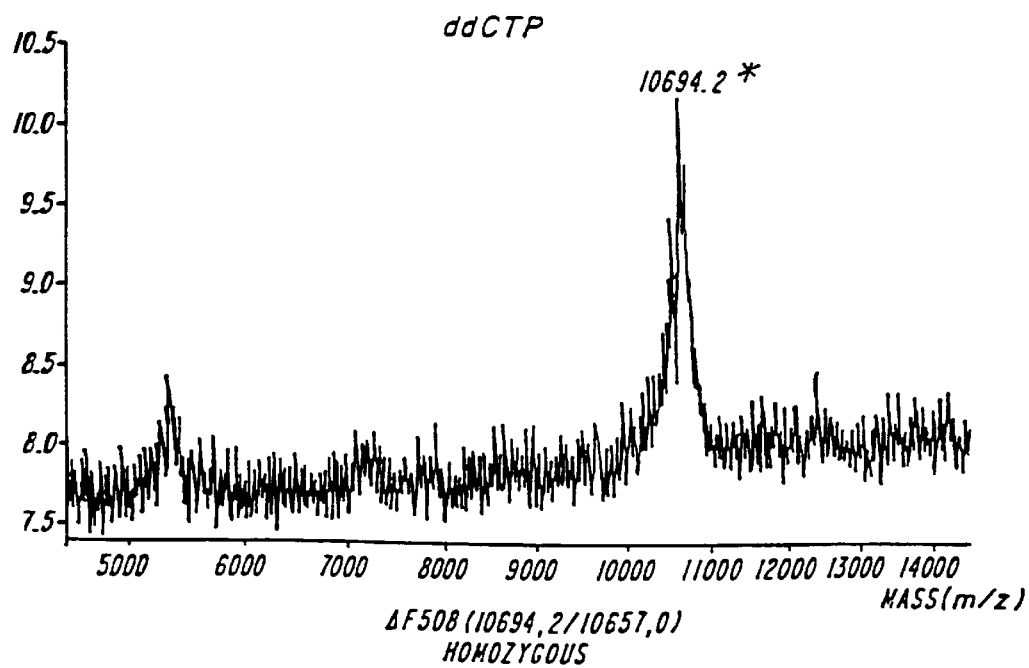

FIG. 33 shows spectra obtained from two pooled positive (33A) and negative (33B) LCRs, respectively. The positive reaction was performed with a chemically synthesized, single strand 50 mer as template with a sequence equivalent to the ligation product of oligo C and D. Oligo C was 5'-biotinylated. Therefore the template was not detected. As expected, only the ligation product of Oligo A and B (calculated mass 15450 Da) could be desorbed from the immobilized and ligated oligo C and D. This newly generated DNA fragment is represented by the mass signal of 15448 Da in FIG. 33A. Compared to FIG. 32A, this spectrum clearly shows that this method of sample preparation produces signals with improved resolution and intensity.

EXAMPLE 7

Mutation Detection by Solid Phase Oligo Base Extension of a Primer and Analysis by MALDI-TOF Mass Spectrometry (Primer Oligo Base Extension=Probe)

SUMMARY

The solid-phase oligo base extension method detects point mutations and small deletions as well as small insertions in amplified DNA. The method is based on the extension of a detection primer that anneals adjacent to a variable nucleotide position on an affinity-captured amplified template, using a DNA polymerase, a mixture of three dNTPs, and the missing one didesoxy nucleotide. The resulting products are evaluated and resolved by MALDI-TOF mass spectrometry without further labeling procedures. The aim of the following experiment was to determine mutant and wildtype alleles in a fast and reliable manner.

Description of the Experiment

The method used a single detection primer followed by a oligonucleotide extension step to give products differing in length by some bases specific for mutant or wildtype alleles which can be easily resolved by MALDI-TOF mass spectrometry. The method is described by using as example the exon 10 of the CFTR-gene. Exon 10 of this gene bears the most common mutation in many ethnic groups ($\Delta$F508) that leads in the homozygous state to the clinical phenotype of cystic fibrosis.

Materials and Methods

Genomic DNA

Genomic DNA were obtained from healthy individuals, individuals homozygous or heterozygous for the $\Delta$F508 mutation, and one individual heterozygous for the 1506S mutation. The wildtype and mutant alleles were confirmed by standard Sanger sequencing.

PCR Amplification of Exon 10 of the CFTR Gene

The primers for PCR amplification were CFEx10-F (5-GCAAGTGAATCCTGAGCGTG-3' (SEQ ID No. 13) located in intron 9 and biotinylated) and CFEx10-R (5'-GTGTGAAGGGCGTG-3', (SEQ ID No. 14) located in intron 10). Primers were used in a concentration of 8 pmol. Taq-polymerase including 10x buffer were purchased from Boehringer-Mannheim and dTNPs were obtained from Pharmacia. The total reaction volume was 50 µl. Cycling conditions for PCR were initially 5 min. at 95° C., followed by 1 min. at 94° C., 45 sec at 53° C., and 30 sec at 72° C. for 40 cycles with a final extension time of 5 min at 72° C.

Purification of the PCR Products

Amplification products were purified by using Qiagen's PCR purification kit (No. 28106) according to manufacturer's instructions. The elution of the purified products from the column was done in 50 µl TE-buffer (10 mM Tris, 1 mM EDTA, pH 7,5).

Affinity-capture and Denaturation of the Double Stranded DNA

10 µL aliquots of the purified PCR product were transferred to one well of a streptavidin-coated microtiter plate (No. 1645684 Boehringer-Mannheim or Noo. 95029262 Labsystems). Subsequently, 10 µl incubation buffer (80 mM sodium phosphate, 400 mM NaCl, 0,4% Tween20, pH 7,5) and 30 µl water were added. After incubation for 1 hour at room temperature the wells were washed three times with 200 µl washing buffer (40 mM Tris, 1 mM EDTA, 50 mM NaCl, 0.1% Tween 20, pH8,8). To denature the double stranded DNA the wells were treated with 100 µl of a 50 mM NaOH solution for 3 min and the wells washed three times with 200 µl washing buffer.

Oligo Base Extension Reaction

The annealing of 25 pmol detection primer (CF508: 5'CTATATTCATCATAGGAAACACCA-3' (SEQ ID No. 15) was performed in 50 µl annealing buffer (20 mM Tris, 10 mM KCl, 10 mM $(NH_4)_2SO_4$, 2 mM MgSO, 1% Triton X-100, pH 8, 75) at 50° C. for 10 min. The wells were washed three times with 200 µl washing buffer and once in 200 µl TE buffer. The extension reaction was performed by using some components of the DNA sequencing kit from USB (No. 70770) and dNTPs or ddNTPs from Pharmacia. The total reaction volume was 45 µl, consisting of 21 µl water, 6 µl Sequenase-buffer, 3 µl 10 mM DTT solution, 4,5 µl, 0,5 mM of three dNTPs, 4,5 µl, 2 mM the missing one ddNTP, 5,5 µl glycerol enzyme diluton buffer, 0,25 µl Sequenase 2.0, and 0,25 pyrophosphatase. The reaction was pipetted on ice and then incubated for 15 min at room temperature and for 5 min at 37° C. Hence, the wells were washed three times with 200 µl washing buffer and once with 60 µl of a 70 mM $NH_4$-Citrate solution.

Denaturation and Precipitation of the Extended Primer

The extended primer was denatured in 50 µl 10%-DMSO (dimethylsufoxide) in water at 80° C. for 10 min. For precipitation, 10 µl $NH_4$-Acetate (pH 6,5), 0,5 µl glycogen (10 mg/ml water, Sigma No. G1765), and 100 µl absolute ethanol were added to the supernatant and incubated for 1 hour at room temperature. After centrifugation at 13,000 g for 10 min the pellet was washed in 70% ethanol and resuspended in 1 µl 18 Mohm/cm $H_2O$ water.

Sample Preparation and Analysis on MALDI-TOF Mass Spectrometry

Sample preparation was performed by mixing 0,3 µl of each of matrix solution (0.7 M 3-hydroxypicolinic acid, 0.07 M dibasic ammonium citrate in 1:1 $H_2O:CH_3CN$) and of resuspended DNA/glycogen pellet on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular mass ($M_r(calc)$) were calculated from atomic compositions; reported experimental Mr ($M_r(exp)$) values are those of the singly-protonated form, determined using external calibration.

Results

The aim of the experiment was to develop a fast and reliable method independent of exact stringencies for mutation detection that leads to high quality and high throughput in the diagnosis of genetic diseases. Therefore a special kind of DNA sequencing (oligo base extension of one mutation detection primer) was combined with the evaluation of the resulting mini-sequencing products by matrix-assisted laser desorption ionization (MALDI) mass spectrometry (MS). The time-of-flight (TOF) reflectron arrangement was chosen as a possible mass measurement system. To prove this hypothesis, the examination was performed with exon 10 of the CFTR-gene, in which some mutations could lead to the clinical phenotype of cystic fibrosis, the most common monogenetic disease in the Caucasian population.

The schematic presentation as given in FIG. 34 shows the expected short sequencing products with the theoretically calculated molecular mass of the wildtype and various mutations of exon 10 of the CFTR-gene. The short sequencing products were produced using either ddTTP (FIG. 34A) or ddCTP (FIG. 34B) to introduce a definitive sequence related stop in the nascent DNA strand. The MALDI-TOF-MS spectra of healthy, mutation heterozygous, and mutation homozygous individuals are presented in FIG. 35. All samples were confirmed by standard Sanger sequencing which showed no discrepancy in comparison to the mass spec analysis. The accuracy of the experimental measurements of the various molecular masses was within a range of minus 21.8 and plus 87.1 dalton (Da) to the range expected. This allows a definitive interpretation of the results in each case. A further advantage of this procedure is the unambiguous detection of the ΔI507 mutation. In the ddTTP reaction, the wildtype allele would be detected, whereas in the ddCTP reaction the three base pair deletion would be disclosed.

The method described is highly suitable for the detection of single point mutations or microlesions of DNA. Careful choice of the mutation detection primers will open the window of multiplexing and lead to a high throughput including high quality in genetic diagnosis without any need for exact stringencies necessary in comparable allele-specific procedures. Because of the uniqueness of the genetic information, the oligo base extension of mutation detection primer is applicable in each disease gene or polymorphic region in the genome like variable number of tandem repeats (VNTR) or other single nucleotide polymorphisms (e.g., apolipoprotein E gene), as also described here.

EXAMPLE 8

Detection of Polymerase Chain Reaction Products Containing 7-Deazapurine Moieties with Matrix-Assisted Laser Desorption/Ionization Time-of-Flight (MALDI-TOF) Mass Spectrometry Materials and Methods PCR Amplifications The following oligodeoxynucleotide primers were either synthesized according to standard phosphoamidite chemistry (Sinha, N. D., et al., (1983) *Tetrahedron Let.* Vol. 24, Pp. 5843–5846; Sinha, N. D., et al., (1984) *Nucleic Acids Res.*, Vol. 12, Pp. 4539–4557) on a MilliGen 7500 DNA synthesizer (Millipore, Bedford, Mass., USA) in 200 nmol scales or purchased from MWG-Biotech (Ebersberg, Germany, primer 3) and Biometra (Goettingen, Germany, primers 6–7).

primer 1: 5'-GTCACCCTCGACCTGCAG (SEQ. ID. NO. 16);
primer 2: 5'-TTGTAAAACGACGGCCAGT (SEQ. ID. NO. 17);
primer 3: 5'-CTTCCACCGCGATGTTGA (SEQ. ID. NO. 18);
primer 4: 5'-CAGGAAACAGCTATGAC (SEQ. ID. NO. 19);
primer 5: 5'-GTAAAACGACGGCCAGT (SEQ. ID. NO. 20);
primer 6: 5'-GTCACCCTCGACCTGCAgC (g: RiboG) (SEQ. ID. NO. 21);
primer 7: 5'-GTTGTAAAACGAGGGCCAgT (g: RiboG) (SEQ. ID. NO. 22);

The 99-mer and 200-mer DNA strands (modified and unmodified) as well as the ribo- and 7-deaza-modified 100-mer were amplified from pRFc1 DNA (10 ng, generously supplied by S. Feyerabend, University of Hamburg) in 100 μL reaction volume containing 10 mmol/L KCl, 10 mmol/L $(NH_4)_2SO_4$, 20 mmol/L Tris HCl (pH=8.8), 2 mmol/L MgSO4, (exo(-)Pseudococcus furiosus (Pfu) -Buffer, Pharmacia, Freiburg, Germany), 0.2 mmol/L each dNTP (Pharmacia, Freiburg, Germany), 1 μmol/L of each primer and 1 unit of exo(-)Pfu DNA polymerase (Stratagene, Heidelberg, Germany).

For the 99-mer primers 1 and 2, for the 200-mer primers 1 and 3 and for the 100-mer primers 6 and 7 were used. To obtain 7-deazapurine modified nucleic acids, during PCR-amplification dATP and dGTP were replaced with 7-deaza-dATP and 7-deaza-dGTP. The reaction was performed in a thermal cycler (OmniGene, MWG-Biotech, Ebersberg, Germany) using the cycle: denaturation at 95° C. for 1 min., annealing at 51 ° C. for 1 min. and extension at 72° C. for 1 min. For all PCRs the number of reaction cycles was 30. The reaction was allowed to extend for additional 10 min. at 72° C. after the last cycle.

The 103-mer DNA strands (modified and unmodified) were amplified from M13mp18 RFI DNA (100 ng, Pharmacia, Freiburg, Germany) in 100 μL reaction volume using primers 4 and 5 all other concentrations were unchanged. The reaction was performed using the cycle: denaturation at 95° C. for 1 min., annealing at 40° C. for 1 min. and extension at 72° C. for 1 min. After 30 cycles for the unmodified and 40 cycles for the modified 103-mer respectively, the samples were incubated for additional 10 min. at 72° C.

Synthesis of 5'-[$^{32}$-P]-labeled PCR-primers

Primers 1 and 4 were 5'-[$^{32}$-P]-labeled employing T4-polynucleotidkinase (Epicentre Technologies) and (γ-$^{32}$P)-ATP. (BLU/NGG/502A, Dupont, Germany) according to the protocols of the manufacturer. The reactions were performed substituting 10% of primer 1 and 4 in PCR with the labeled primers under otherwise unchanged reaction-conditions. The amplified DNAs were separated by gel electrophoresis on a 10% polyacrylamide gel. The appropriate bands were excised and counted on a Packard TRI-CARB 460C liquid scintillation system (Packard, Conn., USA).

Primer-cleavage from Ribo-modified PCR-product

The amplified DNA was purified using Ultrafree-MC filter units (30,000 NMWL), it was then redissolved in 100 μl of 0.2 mol/L NaOH and heated at 95° C. for 25 minutes. The solution was then acidified with HCl (1 mol/L) and further purified for MALDI-TOF analysis employing Ultrafree-MC filter units (10,000 NMWL) as described below.

Purification of PCR Products

All samples were purified and concentrated using Ultrafree-MC units 30000 NMWL (Millipore, Eschborn, Germany) according to the manufacturer's description. After lyophilisation, PCR products were redissolved in 5 μL (3 μL for the 200-mer) of ultrapure water. This analyte solution was directly used for MALDI-TOF measurements.

MALDI-TOF MS

Aliquots of 0.5 μL of analyte solution and 0.5 μL of matrix solution (0.7 mol/L 3-HPA and 0.07 mol/L ammonium citrate in acetonitrile/water (1:1, v/v)) were mixed on a flat metallic sample support. After drying at ambient temperature the sample was introduced into the mass spectrometer for analysis. The MALDI-TOF mass spectrometer used was a Finnigan MAT Vision 2000 (Finnigan MAT, Bremen, Germany). Spectra were recorded in the positive ion reflector mode with a 5 keV ion source and 20 keV postacceleration. The instrument was equipped with a nitrogen laser (337 nm wavelength). The vacuum of the system was $3-4 \cdot 10^{-8}$ hPa in the analyzer region and $1-4 \cdot 10^{-7}$ hPa in the source region. Spectra of modified and unmodified DNA samples were obtained with the same relative laser power; external calibration was performed with a mixture of synthetic oligodeoxynucleotides (7-to50-mer).

Results and Discussion

Enzymatic Synthesis of 7-Deazapurine Nucleotide Containing Nucleic Acids by PCR

Figures 36, 37:
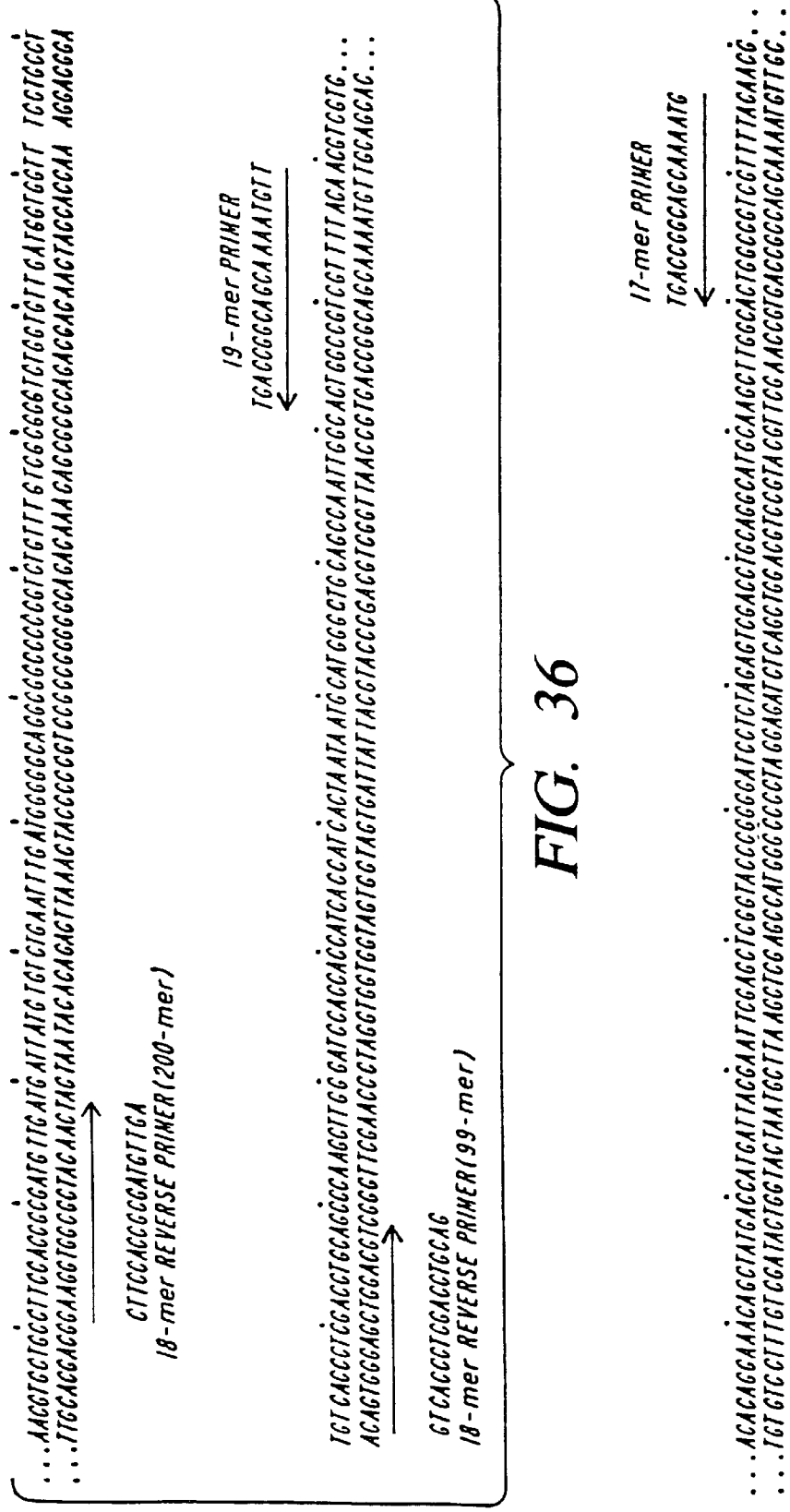
FIG. 36 shows the portion of the sequence of pRFc1 DNA, which was used as template for PCR amplification in Example 8 of unmodified and 7-deazapurine containing 99-mer and 200-mer nucleic acids as well as the sequences of the 19-mer forward primer and the two 18-mer reverse primers.
FIG. 37 shows the portion of the nucleotide sequence of M13mp18 RFI DNA, which was used in Example 8 for PCR amplification of unmodified and 7-deazapurine containing 103-mer nucleic acids. Also shown are nucleotide sequences of the 17-mer primers used in the PCR.

In order to demonstrate the feasibility of MALDI-TOF MS for the rapid, gel-free analysis of short PCR products and to investigate the effect of 7-deazapurine modification of nucleic acids under MALDI-TOF conditions, two different primer-template systems were used to synthesize DNA fragments. Sequences are displayed in FIGS. 36 and 37. While the two single strands of the 103-mer PCR product had nearly equal masses ($\Delta m=8$ u), the two single strands of the 99-mer differed by 526 u.

Considering that 7-deaza purine nucleotide building blocks for chemical DNA synthesis are approximately 160 times more expensive than regular ones (Product Information, Glen Research Corporation, Sterling, Va.) and their application in standard-cyano-phosphoamidite chemistry is not trivial (Product Information, Glen Research Corporation, Sterling, Va.; Schneider, K and B. T. Chait (1995) *Nucleic Acids Res.* 23, 1570) the cost of 7-deaza purine modified primers would be very high. Therefore, to increase the applicability and scope of the method, all PCRs were performed using unmodified oligonucleotide primers which are routinely available. Substituting dATP and dGTP by $c^7$-dATP and $c^7$-dGTP in polymerase chain reaction led to products containing approximately 80% 7-deaza-purine modified nucleosides for the 99-mer and 103-mer; and about 90% for the 200-mer, respectively. Table 1 shows the base composition of all PCR products.

TABLE I

Base composition of the 99-mer, 103-mer and 200-mer PCR amplification products (unmodified and 7-deaza purine modified)

| DNA-fragments[1] | C | T | A | G | $c^7$-deaza-A | $c^7$-deaza-G | rel. modification[2] |
|---|---|---|---|---|---|---|---|
| 200-mers | 54 | 34 | 56 | 56 | — | — | — |
| modified 200-mer s | 54 | 34 | 6 | 5 | 50 | 51 | 90% |
| 200-mer a | 56 | 56 | 34 | 54 | — | — | — |
| modified 200-mer a | 56 | 56 | 3 | 4 | 31 | 50 | 92% |
| 103-mer s | 28 | 23 | 24 | 28 | — | — | — |
| modified 103-mer s | 28 | 23 | 6 | 5 | 18 | 23 | 79% |
| 103-mer a | 28 | 24 | 23 | 28 | — | — | — |
| modified 103-mer a | 28 | 24 | 7 | 4 | 16 | 24 | 78% |
| 99-mer s | 34 | 21 | 24 | 20 | — | — | — |
| modified 99-mer s | 34 | 21 | 6 | 5 | 18 | 15 | 75% |
| 99-mer a | 20 | 24 | 21 | 34 | — | — | — |
| modified 99-mer a | 20 | 24 | 3 | 4 | 18 | 30 | 87% |

[1]"s" and "a" describe "sense" and "antisense" strands of the double-stranded PCR product.
[2]indicates relative modification as percentage of 7-deaza purine modified nucleotides of total amount of purine nucleotides.

Figure 38:
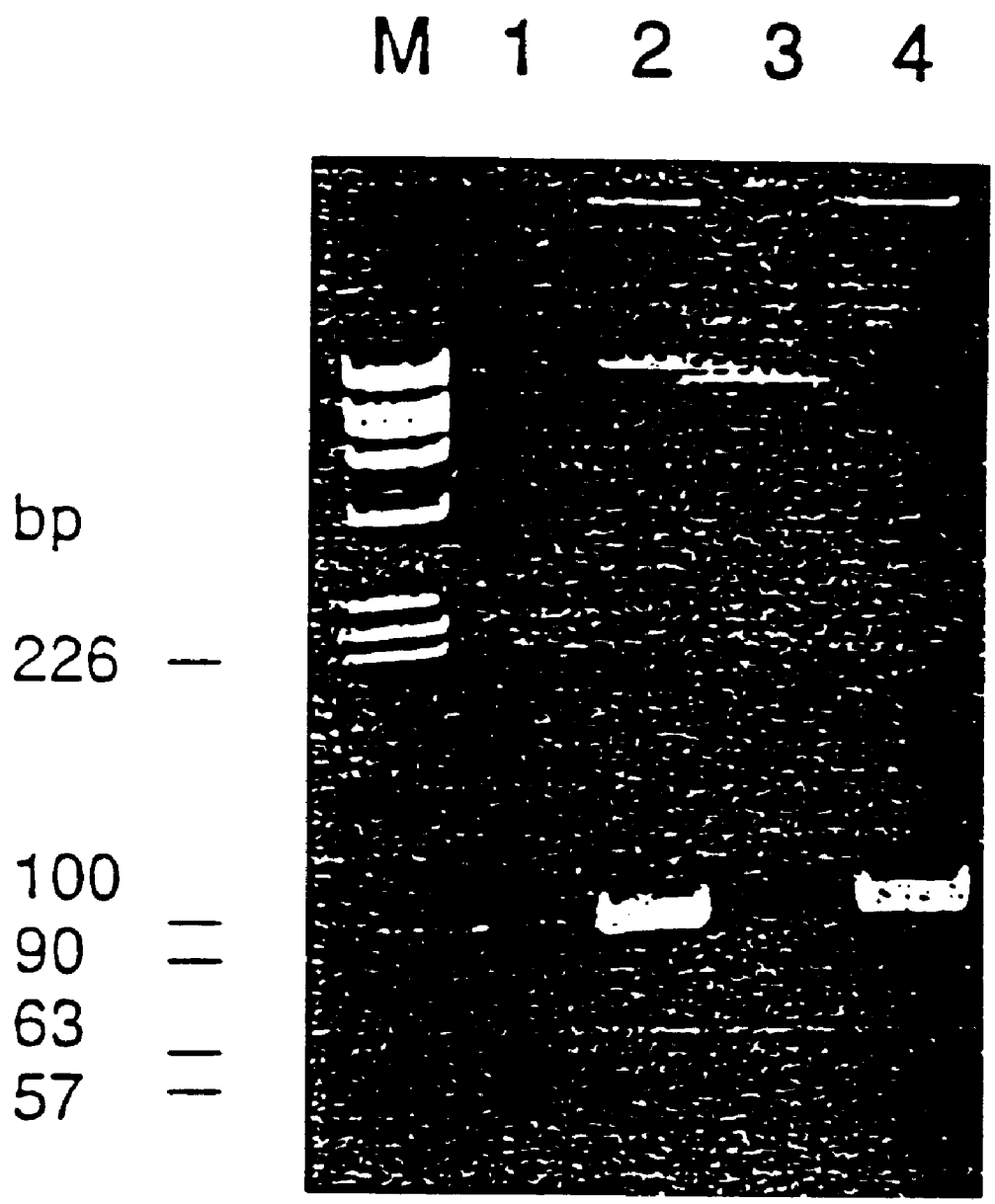
FIG. 38 shows the result of a polyacrylamide gel electrophoresis of PCR products described in Example 8 purified and concentrated for MALDI-TOF MS analysis. M: chain length marker, lane 1: 7-deazapurine containing 99-mer PCR product, lane 2: unmodified 99-mer, lane 3: 7-deazapurine containing 103-mer and lane 4: unmodified 103-mer PCR product.

However, it remained to be determined whether 80–90% 7-deaza-purine modification is sufficient for accurate mass spectrometer detection. It was therefore important to determine whether all purine nucleotides could be substituted during the enzymatic amplification step. This was not trivial since it had been shown that $c^7$-dATP cannot fully replace dATP in PCR if Taq DNA polymerase is employed (Seela, F. and A. Roelling (1992) *Nucleic Acids Res.*, 20,55–61). Fortunately we found that exo(-)Pfu DNA polymerase indeed could accept $c^7$-dATP and $c^7$-dGTP in the absence of unmodified purine nucleoside triphosphates. However, the incorporation was less efficient leading to a lower yield of PCR product (FIG. 38). Ethidium-bromide stains by intercalation with the stacked bases of the DNA-doublestrand. Therefore lower band intensities in the ethidium-bromide stained gel might be artifacts since the modified DNA-strands do not necessarily need to give the same band intensities as the unmodified ones.

Figure 39:
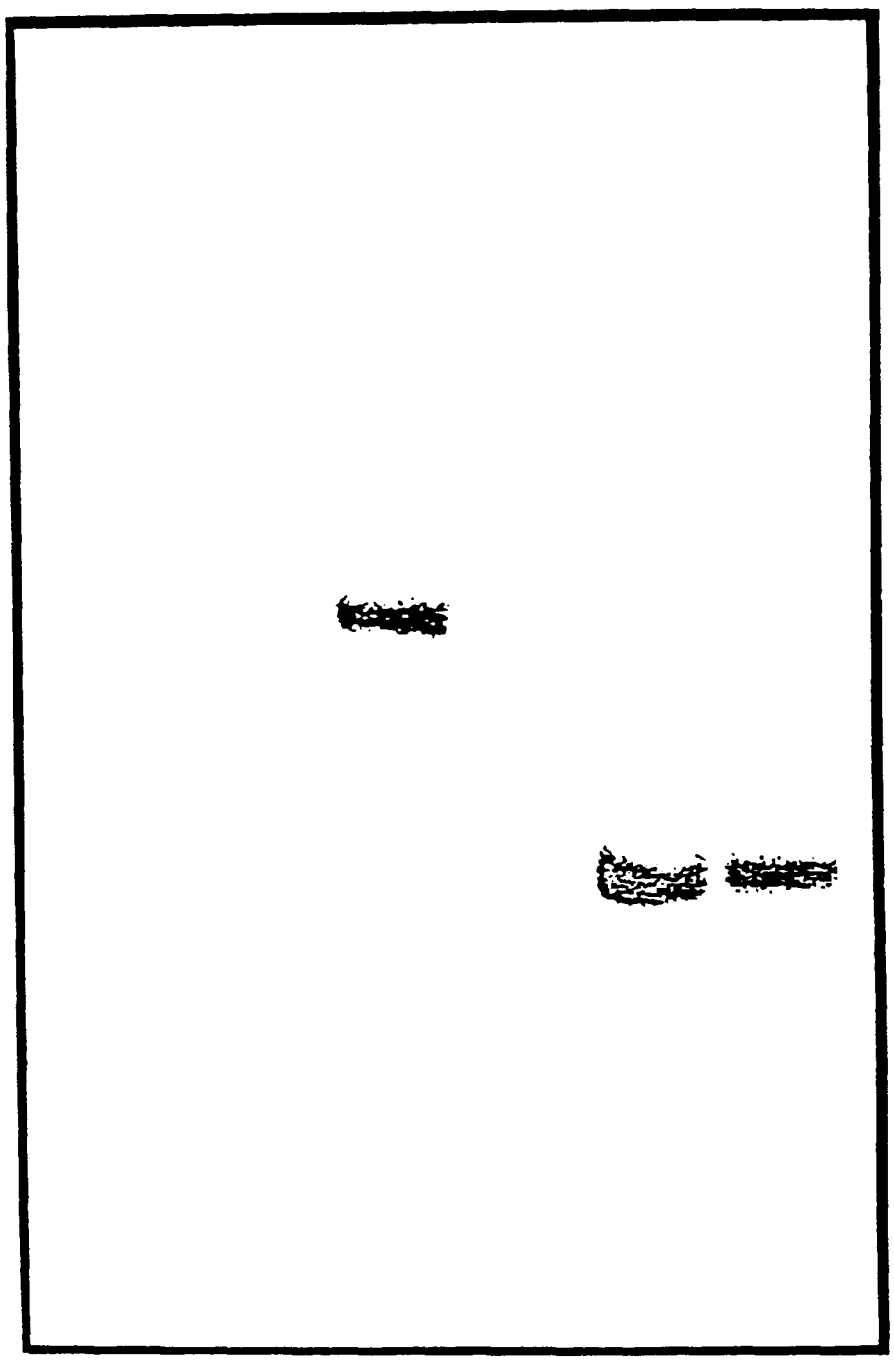
FIG. 39: an autoradiogram of polyacrylamide gel electrophoresis of PCR reactions carried out with 5'-[$^{32}$P]-labeled primers 1 and 4. Lanes 1 and 2: unmodified and 7-deazapurine modified 103-mer PCR product (53321 and 23520 counts), lanes 3 and 4: unmodified and 7-deazapurine modified 200-mer (71123 and 39582 counts) and lanes 5 and 6: unmodified and 7-deazapurine modified 99-mer (173216 and 94400 counts).

To verify these results, the PCRs with [$^{32}$P]-labeled primers were repeated. The autoradiogram (FIG. 39) clearly shows lower yields for the modified PCR-products. The bands were excised from the gel and counted. For all PCR products the yield of the modified nucleic acids was about 50%, referring to the corresponding unmodified amplification product. Further experiments showed that exo(-)Deep Vent and Vent DNA polymerase were able to incorporate $c^7$-dATP and $c^7$-dGTP during PCR as well. The overall performance, however, turned out to be best for the exo(-) Pfu DNA polymerase giving least side products during amplification. Using all three polymerases, it was found that such PCRs employing $c^7$-dATP and $c^7$-dGTP instead of their isosteres showed less side-reactions giving a cleaner PCR-product. Decreased occurrence of amplification side products may be explained by a reduction of primer mismatches due to a lower stability of the complex formed from the primer and the 7-deaza-purine containing template which is synthesized during PCR. Decreased melting point for DNA duplexes containing 7-deaza-purine have been described (Mizusawa, S. et al., (1986) *Nucleic Acids Res.*, 14, 1319–1324). In addition to the three polymerases specified above (exo(-) Deep Vent DNA polymerase, Vent DNA polymerase and exo(-) (Pfu) DNA polymerase), it is anticipated that other polymerases, such as the Large Klenow fragment of *E.coli* DNA polymerase, Sequenase, Taq DNA polymerase and U AmpliTaq DNA polymerase can be used. In addition, where RNA is the template, RNA polymerases, such as the SP6 or the T7 RNA polymerase, must be used MALDI-TOF Mass Spectrometry of Modified and Unmodified PCR Products.

The 99-mer, 103-mer and 200-mer PCR products were analyzed by MALDI-TOF MS. Based on past experience, it was known that the degree of depurination depends on the laser energy used for desorption and ionization of the analyte. Since the influence of 7-deazapurine modification on fragmentation due to depurination was to be investigated, all spectra were measured at the same relative laser energy.

Figure 40A:
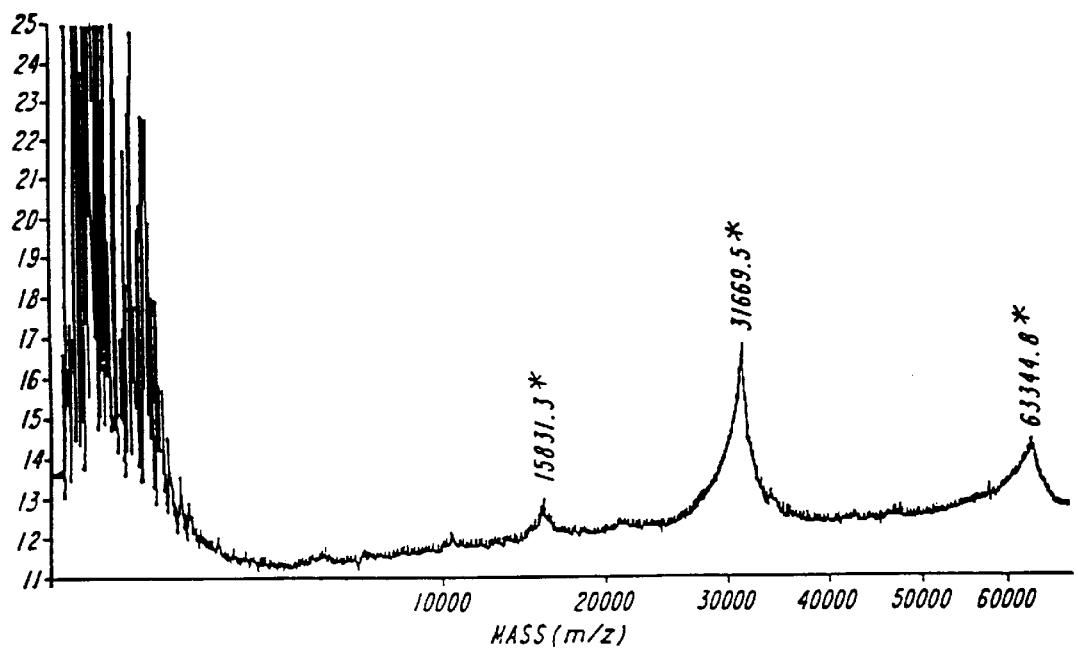
FIG. 40 a) MALDI-TOF mass spectrum of the unmodified 103-mer PCR products (sum of twelve single shot spectra). The mean value of the masses calculated for the two single strands (31768 u and 31759 u) is 31763 u. Mass resolution: 18. b) MALDI-TOF mass spectrum of 7-deazapurine containing 103-mer PCR product (sum of three single shot spectra). The mean value of the masses calculated for the two single strands (31727 u and 31719 u) is 31723 u. Mass resolution: 67.
Figure 40B:
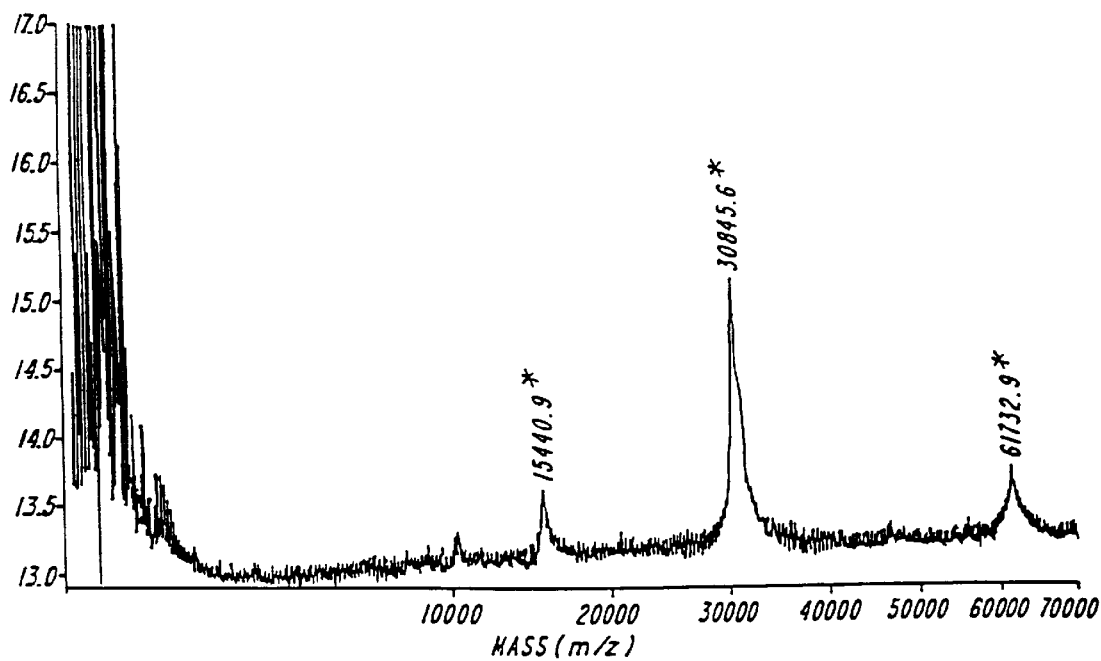

FIGS. 40a and 40b show the mass spectra of the modified and unmodified 103-mer nucleic acids. In case of the modified 103-mer, fragmentation causes a broad $(M+H)^+$ signal. The maximum of the peak is shifted to lower masses so that the assigned mass represents a mean value of $(M+H)^+$ signal and signals of fragmented ions, rather than the $(M+H)^+$ signal itself. Although the modified 103-mer still contains about 20% A and G from the oligonucleotide primers, it shows less fragmentation which is featured by much more narrow and symmetric signals. Especially peak tailing on the lower mass side due to depurination, is substantially reduced. Hence, the difference between measured and calculated mass is strongly reduced although it is still below the expected mass. For the unmodified sample a $(M+H)^+$ signal of 31670 was observed, which is a 97 u or 0.3% difference to the calculated mass. While, in case of the modified sample this mass difference diminished to 10 u or 0.03% (31713 u found, 31723 u calculated). These observations are verified by a significant increase in mass resolution of the $(M+H)^+$ signal of the two signal strands ($m/\Delta m=67$ as opposed to 18 for the unmodified sample with $\Delta m$=full width at half maximum, fwhm). Because of the low mass difference between the two single strands (8 u) their individual signals were not resolved.

Figure 41A:
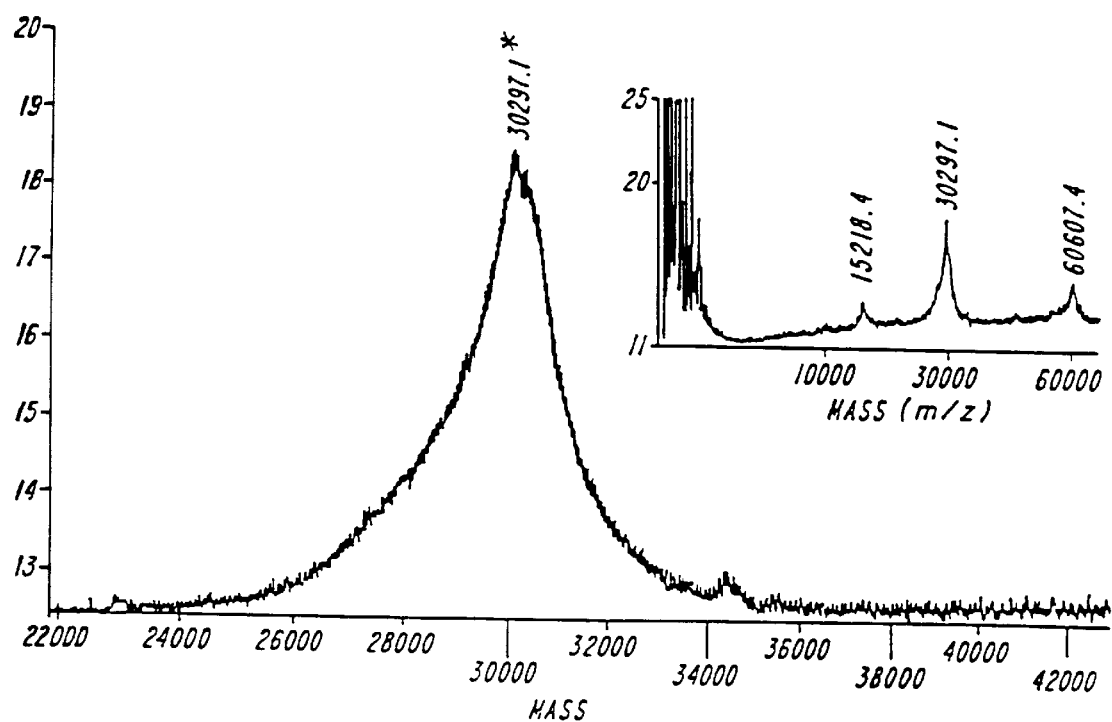
FIG. 41: a) MALDI-TOF mass spectrum of the unmodified 99-mer PCR product (sum of twenty single shot spectra). Values of the masses calculated for the two single strands: 30261 u and 30794 u. b) MALDI-TOF mass spectrum of the 7-deazapurine containing 99-mer PCR product (sum of twelve single shot spectra). Values of the masses calculated for the two single strands: 30224 u and 30750 u.
Figure 41B:
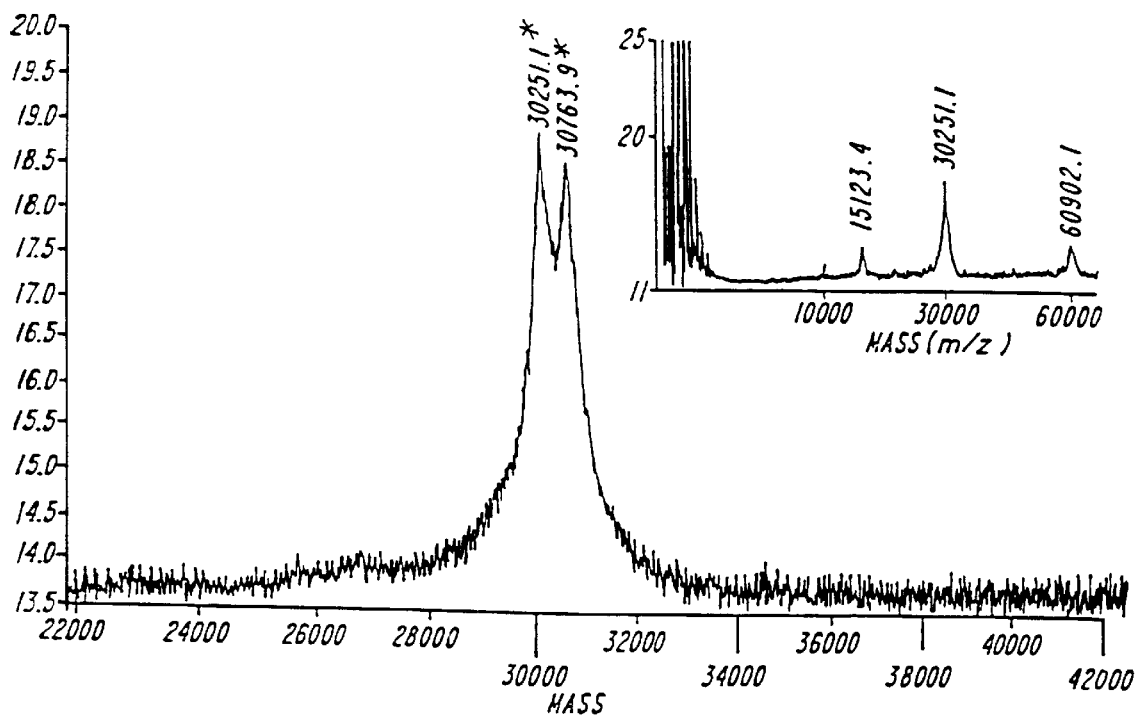

With the results of the 99 base pair DNA fragments the effects of increased mass resolution for 7-deazpurine containing DNA becomes even more evident. The two single strands in the unmodified sample were not resolved even though the mass difference between the two strands of the PCR product was very high with 526 u due to unequal distribution of purines and pyrimidines (FIG. 41a). In contrast to this, the modified DNA showed distinct peaks for the two single strands (FIG. 41b) which demonstrates the superiority of this approach for the determination of molecular weights to gel electrophoretic methods even more profound. Although base line resolution was not obtained the individual masses were abled to be assigned with an accuracy of 0.1%: Δm=27 u for the lighter (calc. mass=30224 u) and Δm=14 u for the heavier strand (calc. mass=30750 u). Again, it was found that the full width at half maximum was substantially decreased for the 7-deazapurine containing sample.

In case of both the 99-mer and 103-mer the 7-deazapurine containing nucleic acids seem to give higher sensitivity despite the fact that they still contain about 20% unmodified purine nucleotides. To get comparable signal-to-noise ratio at similar intensities for the (M+H)$^+$ signals, the unmodified 99-mer required 20 laser shots in contrast to 12 for the modified one and the 103-mer required 12 shots for the unmodified sample as opposed to three for the 7-deazapurine nucleoside-containing PCR product.

Figure 42A:
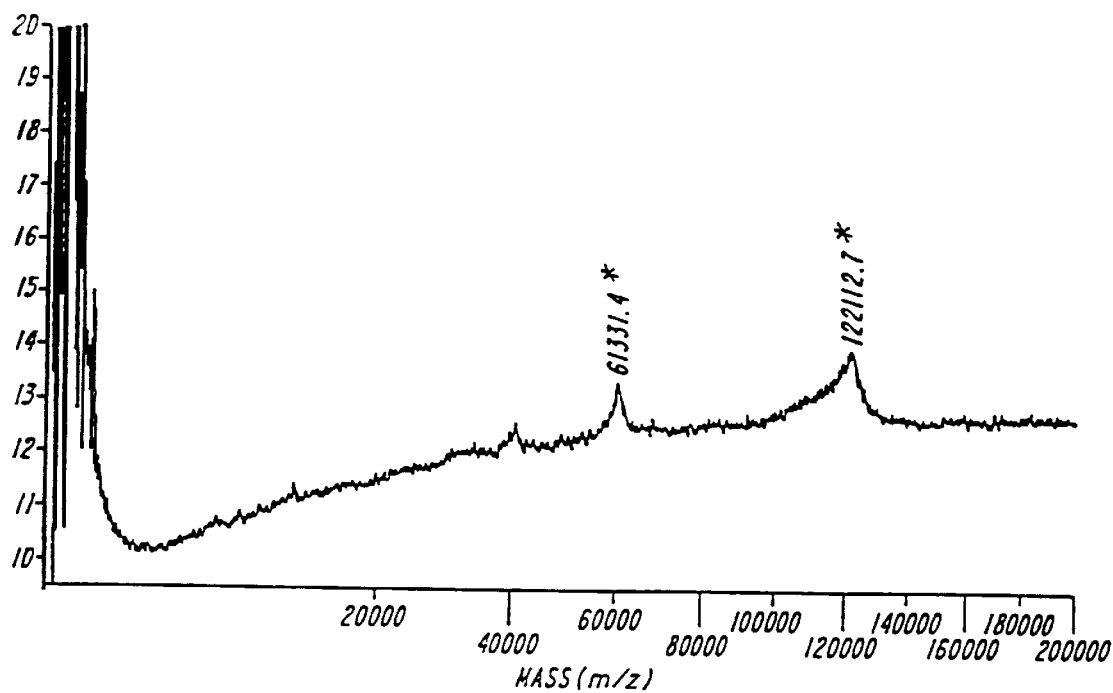
FIG. 42: a) MALDI-TOF mass spectrum of the unmodified 200-mer PCR product (sum of 30 single shot spectra). The mean value of the masses calculated for the two single strands (61873 u and 61595 u) is 61734 u. Mass resolution: 28. b) MALDI-TOF mass spectrum of 7-deazapurine containing 200-mer PCR product (sum of 30 single shot spectra). The mean value of the masses calculated for the two single strands (61772 u and 61514 u) is 61643 u. Mass resolution: 39.
Figure 42B:
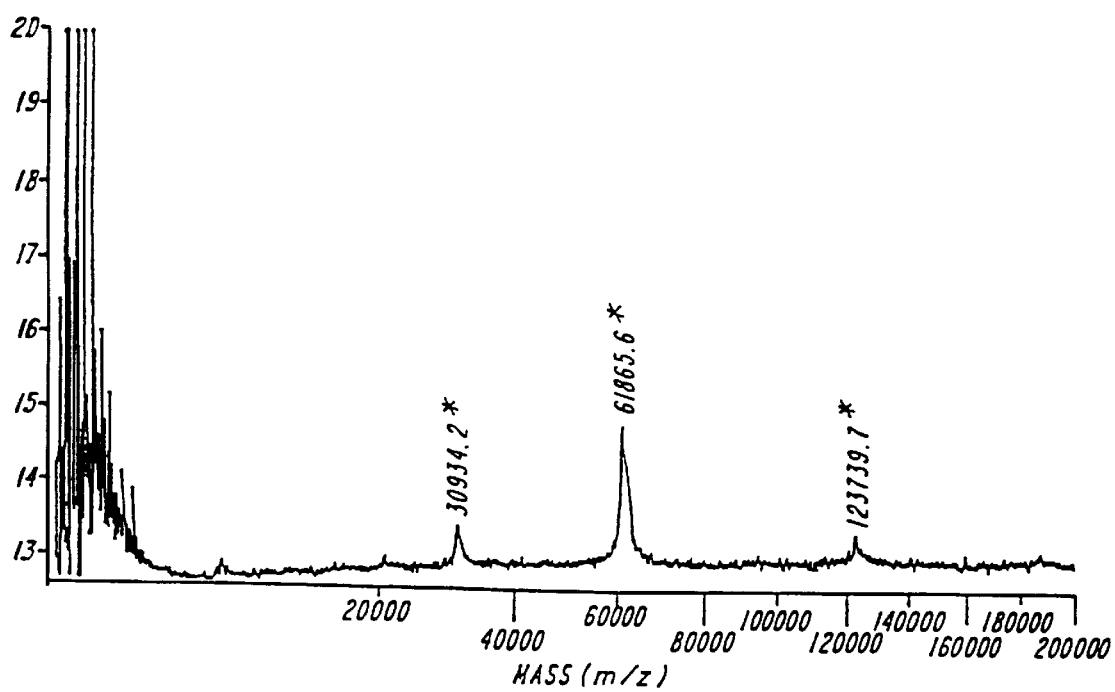

Comparing the spectra of the modified and unmodified 200-mer amplicons, improved mass resolution was again found for the 7-deazapurine containing sample as well as increased signal intensities (FIGS. 42a and 42b). While the signal of the single strands predominates in the spectrum of the modified sample the DNA-duplex and dimers of the single strands gave the strongest signal for the unmodified sample.

Figure 43A:
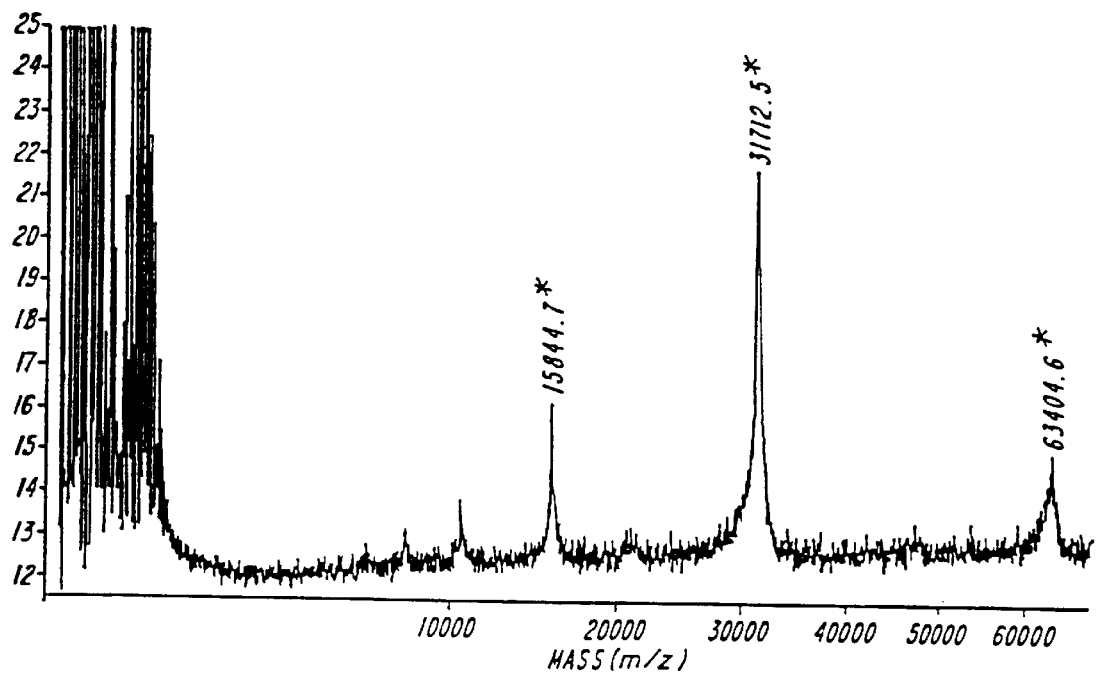
FIG. 43: a) MALDI-TOF mass spectrum of 7-deazapurine containing 100-mer PCR product with ribomodified primers. The mean value of the masses calculated for the two single strands (30529 u and 31095 u) is 30812 u. b) MALDI-TOF mass spectrum of the PCR-product after hydrolytic primer-cleavage. The mean value of the masses calculated for the two single strands (25104 u and 25229 u) is 25167 u. The mean value of the cleaved primers (5437 u and 5918 u) is 5677 u.
Figure 43B:
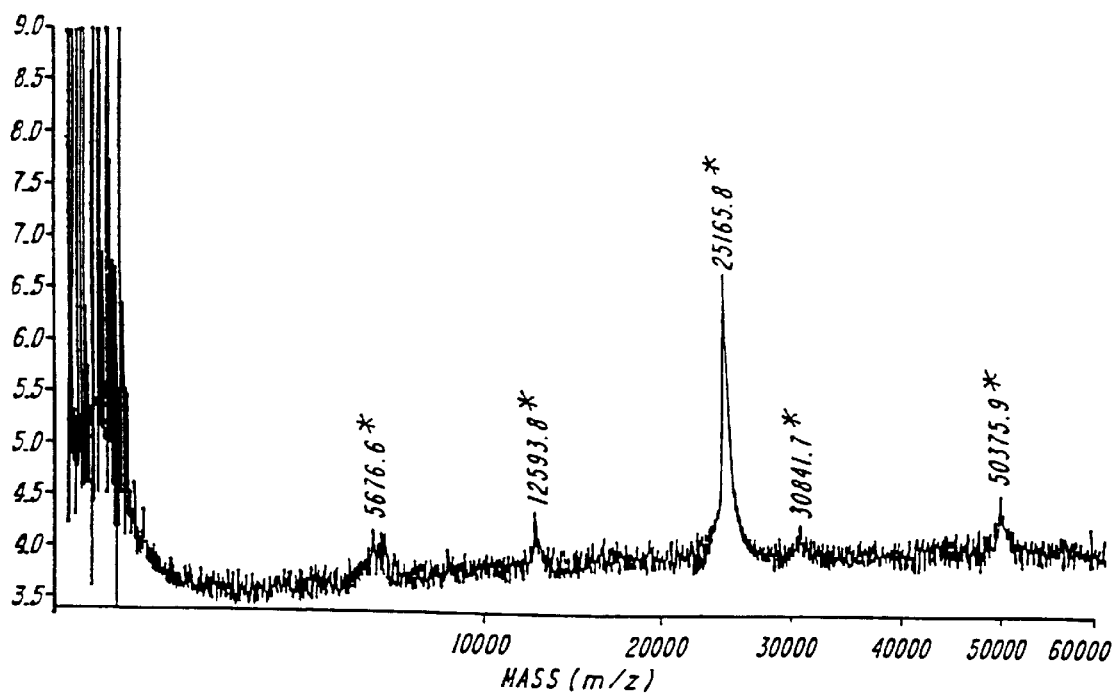
Figure 44A:
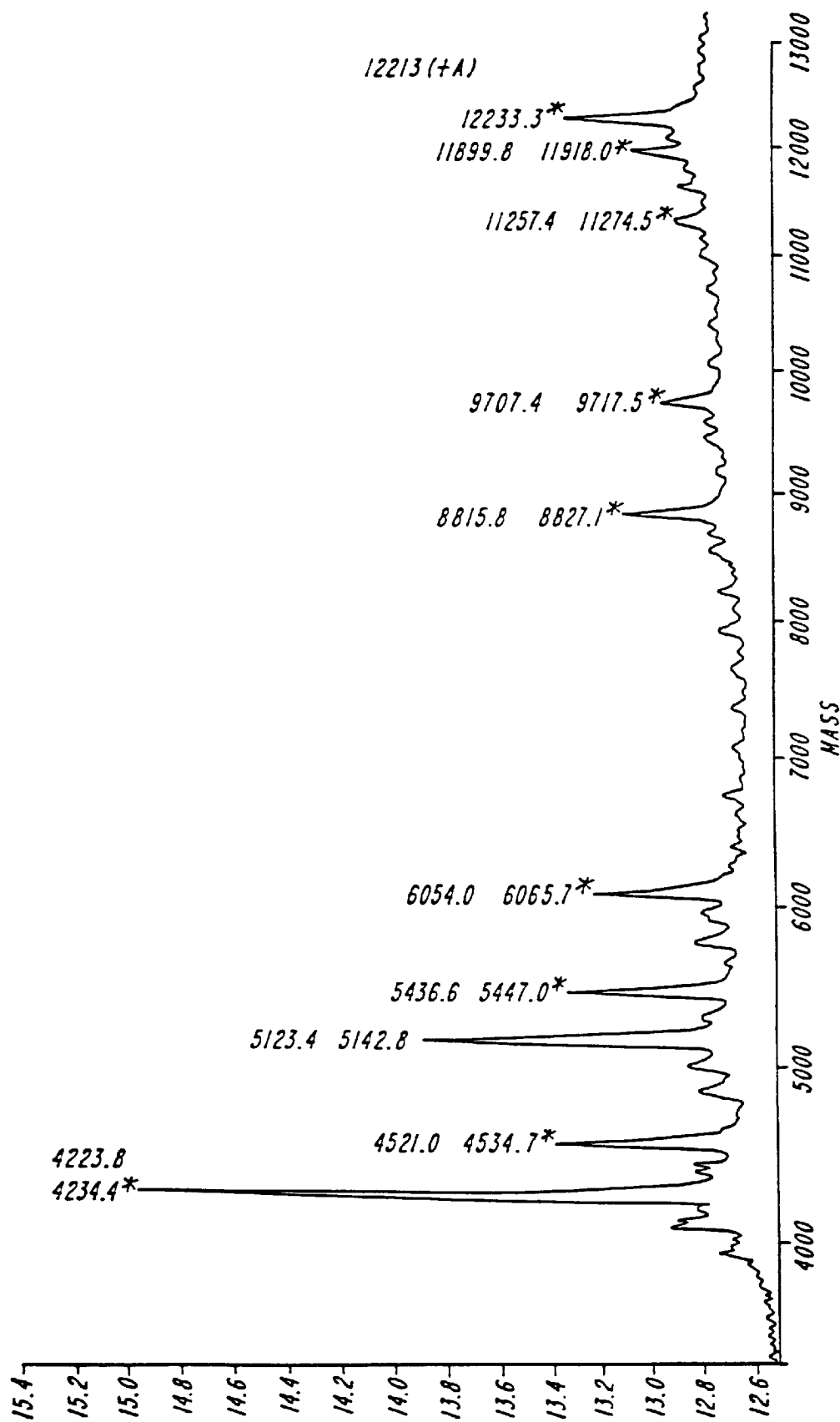
FIG. 44 A–D shows the MALDI-TOF mass spectrum of the four sequencing ladders obtained from a 39-mer template (SEQ. ID. No. 13), which was immobilized to streptavidin beads via a 3' biotinylation. A 14-mer primer (SEQ. ID. NO. 14) was used in the sequencing according to Example 9.
Figure 44B:
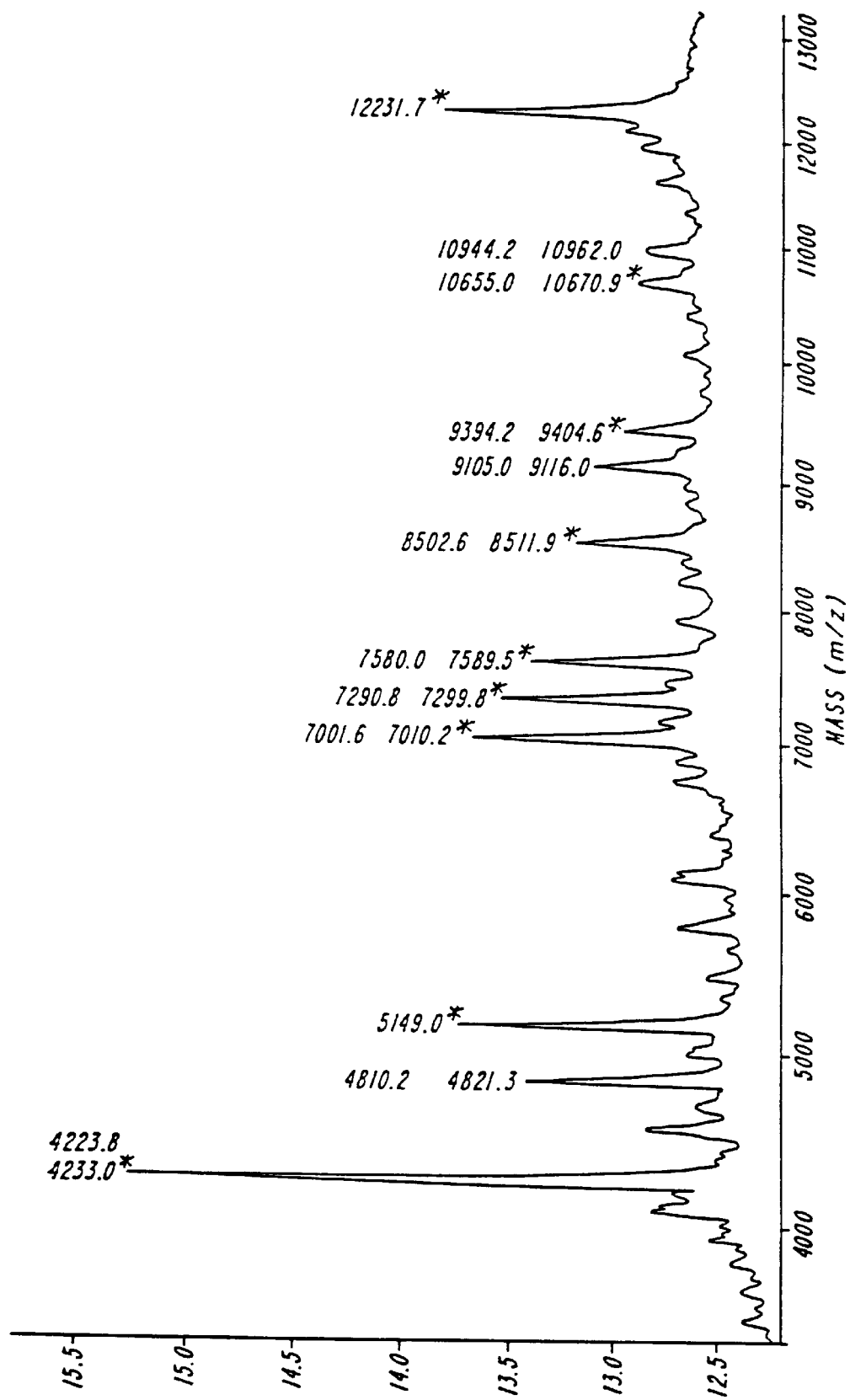
Figure 44C:
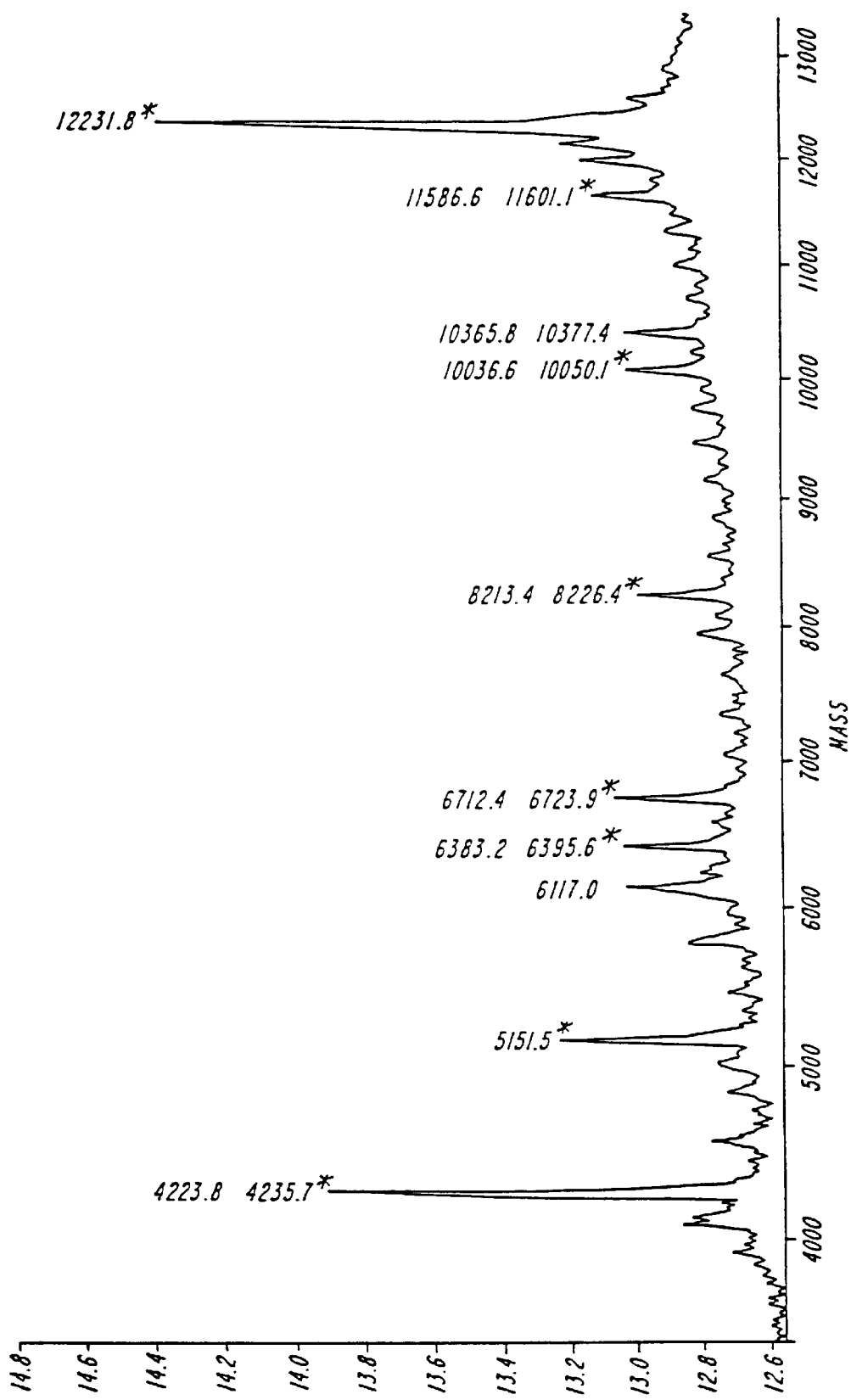
Figure 44D:
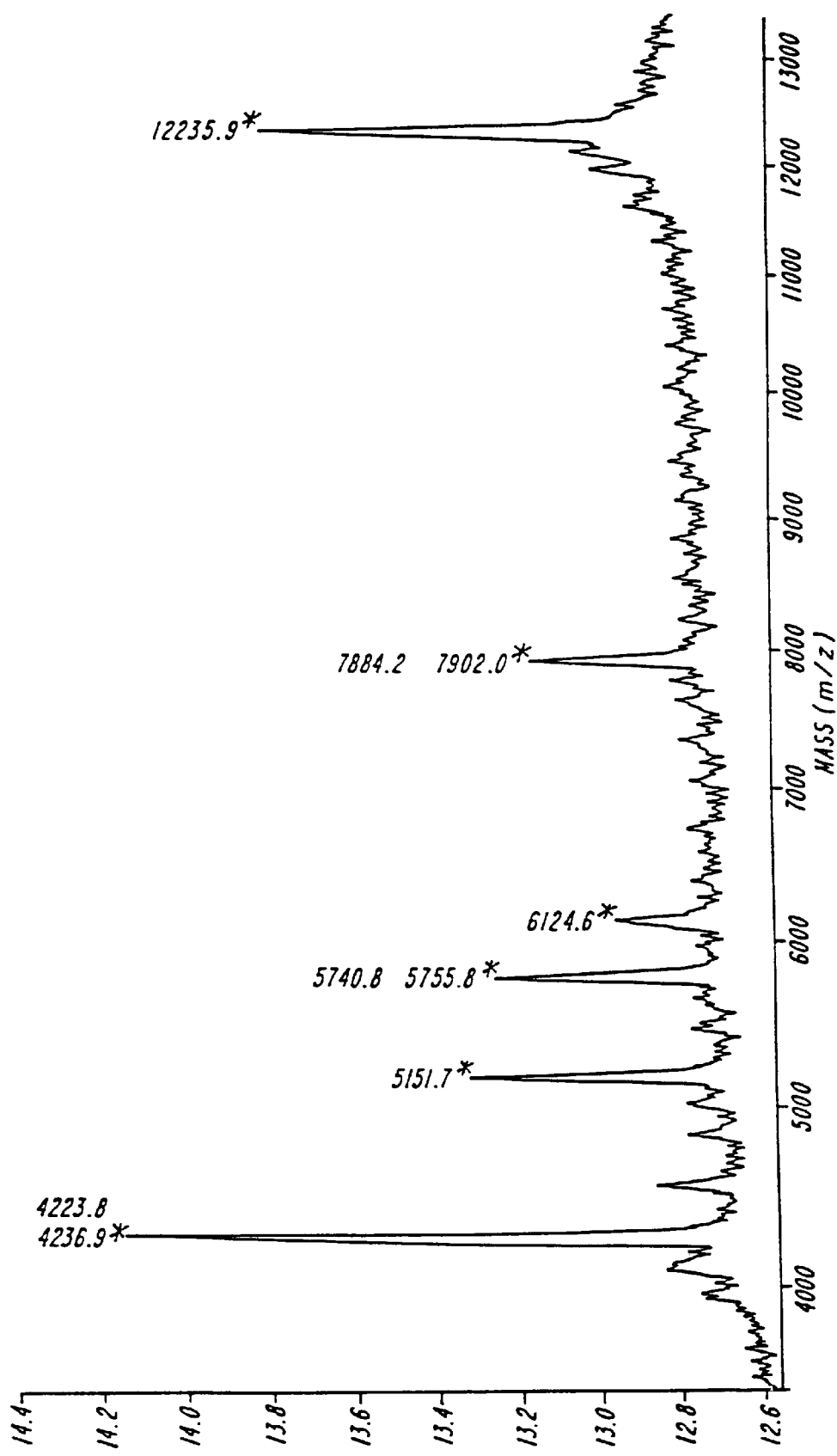

A complete 7-deaza purine modification of nucleic acids may be achieved either using modified primers in PCR or cleaving the unmodified primers from the partially modified PCR product. Since disadvantages are associated with modified primers, as described above, a 100-mer was synthesized using primers with a ribo-modification. The primers were cleaved hydrolytically with NaOH according to a method developed earlier in our laboratory (Koester, H. et al., Z. Physiol. Chem., 359, 1570–1589). FIGS. 43a and 43b display the spectra of the PCR product before and after primer cleavage. FIG. 43b shows that the hydrolysis was successful: Both hydrolyzed PCR product as well as the two released primers could be detected together with a small signal from residual uncleaved 100-mer. This procedure is especially useful for the MALDI-TOF analysis of very short PCR-products since the share of unmodified purines originating from the primer increases with decreasing length of the amplified sequence.

The remarkable properties of 7-deazapurine modified nucleic acids can be explained by either more effective desorption and/or ionization, increased ion stability and/or a lower denaturation energy of the double stranded purine modified nucleic acid. The exchange of the N-7 for a methine group results in the loss of one acceptor for a hydrogen bond which influences the ability of the nucleic acid to form secondary structures due to non-Watson-Crick base pairing (Seela, F. and A. Kehne (1987) Biochemistry, 26, 2232–2238.). In addition to this the aromatic system of 7-deazapurine has a lower electron density that weakens Watson-Crick base pairing resulting in a decreased melting point (Mizusawa, S. et al., (1986) Nucleic Acids Res., 14, 1319–1324) of the double-strand. This effect may decrease the energy needed for denaturation of the duplex in the MALDI process. These aspects as well as the loss of a site which probably will carry a positive charge on the N-7 nitrogen renders the 7-deazapurine modified nucleic acid less polar and may promote the effectiveness of desorption.

Because of the absence of N-7 as proton acceptor and the decreased polarization of the C-N bond in 7-deazapurine nucleosides depurination following the mechanisms established for hydrolysis in solution is prevented. Although a direct correlation of reactions in solution and in the gas phase is problematic, less fragmentation due to depurination of the modified nucleic acids can be expected in the MALDI process. Depurination may either be accompanied by loss of charge which decreases the total yield of charged species or it may produce charged fragmentation products which decreases the intensity of the non fragmented molecular ion signal.

The observation of both increased sensitivity and decreased peak tailing of the (M+H)$^+$ signals on the lower mass side due to decreased fragmentation of the 7-deazapurine containing samples indicate that the N-7 atom indeed is essential for the mechanism of depurination in the MALDI-TOF process. In conclusion, 7-deazapurine containing nucleic acids show distinctly increased ion-stability and sensitivity under MALDI-TOF conditions and therefore provide for higher mass accuracy and mass resolution.

EXAMPLE 9

Solid Phase Sequencing and Mass Spectrometer Detection

Materials and Methods

Oligonucleotides were purchased from Operon Technologies (Alameda, Calif.) in an unpurified form. Sequencing reactions were performed on a solid surface using reagents from the sequencing kit for Sequenase Version 2.0 (Amersham, Arlington Heights, Ill.).

Sequencing a 39-mer Target

Sequencing complex:

5'-TCTGGCCTGGTGCAGGGCCTATTGTAGTTGTGA CGTACA-(A$^b$)$_a$-3' (DNA11683) (SEQ. ID. No. 23)

3'TCAACACTGCATGT-5' (PNA 16/DNA) (SEQ. ID. No. 24)

In order to perform solid-phase DNA sequencing, template strand DNA11683 was 3'-biotinylated by terminal deoxynucleotidyl transferase. A 30 μl reaction, containing 60 pmol of DNA11683, 1.3 nmol of biotin 14-dATP (GIBCO BRL, Grand Island, N.Y.), 30 units of terminal transferase (Amersham, Arlington Heights, Ill.), and 1× reaction buffer (supplied with enzyme), was incubated at 3 7° C. for 1 hour. The reaction was stopped by heat inactivation of the terminal transferase at 70° C. for 10 min. The resulting product was desalted by passing through a TE-10 spin column (Clontech). More than one molecules of biotin-14-dATP could be added to the 3'-end of DNA 11683. The biotinylated DNA 11683 was incubated with 0.3 mg of Dynal streptavidin beads in 30 μl 1× binding and washing buffer at ambient temperature for 30 min. The beads were washed twice with TE and redissolved in 30 μl TE, 10 μl aliquot (containing 0.1 mg of beads) was used for sequencing reactions.

The 0.1 mg beads from previous step were resuspended in a 10 μl volume containing 2 μl of 5×Sequenase buffer (200 mM Tris-HCl, pH 7.5, 100 mM MgCl$_2$, and 250 mM NaCl) from the Sequenase kit and 5 pmol of corresponding primer PNA 16/DNA. The annealing mixture was heated to 70° C. and allowed to cool slowly to room temperature over a 20–30 min time period. Then 1 μl 0.1 M dithiothreitol solution, 1 μl Mn buffer (0.15M sodium isocitrate and 0.1 M MnCl$_2$) and 2 μl of diluted Sequenase (3.25 units) were added. The reaction mixture was divided into four aliquots of 3 μl each and mixed with termination mixes (each consists of 3 μl of the appropriate termination mix: 32 μM c7dATP, 32 μM dCTP, 32 μM c7dGTP, 32 μM dTTP and 3.2 μM of one of the four ddTNPs, in 50 mM NaCl). The reaction mixtures were incubated at 37° C. for 2 min. After the completion of extension, the beads were precipitated and the supernatant was removed. The beads were washed twice and resuspended in TE and kept at 4° C.

Sequencing a 78-mer target

Sequencing complex:

5'-AAGATCTGACCAGGGATTCGGTTAGCGTGA
CTGCTGCTGCTGCTGCTGC
TGGATGATCCGACGCATCAGATCTGG-(A$^b$)$_n$-3
(SEQ. ID. NO. 25) (TNR.PLASM2)

3'-CTACTAGGCTGCGTAGTC-5' (CM 1) (SEQ. ID. NO. 26)

The target TNR.PLASM2 was biotinylated and sequenced using procedures similar to those described in previous section (sequencing a 39-mer target).

Sequencing a 15-mer Target with Partially Duplex Probe

Sequencing complex:

5'-F-GATGATCCGACGCATCACAGCTC$^{3'}$ (SEQ. ID. No.27)

3'-b-CTACTAGGCTGCGTAGTGTCGAGAACCT-TGGCT$^{3'}$ (SEQ. ID. No.28)

CM1B3B was immobilized on Dynabeads M280 with streptavidin (Dynal, Norway) by incubating 60 pmol of CM1B3B with 0.3 magnetic beads in 30 μl 1 M NaCl and TE 1× binding and washing buffer) at room temperature for 30 min. The beads were washed twice with TE and redissolved in 30 μl TE, 10 or 20 μl aliquot (containing 0.1 or 0.2 mg of beads respectively) was used for sequencing reactions.

The duplex was formed by annealing corresponding aliquot of beads from previous step with 10 pmol of DF11a5F (or 20 pmol of DF11a5F for 0.2 mg of beads) in a 9 μl volume containing 2 μl of 5×Sequenase buffer (200 mM Tris-HCl, pH 7.5, 100 mM MgCl$_2$, and 250 mM NaCl) from the Sequenase kit. The annealing mixture was heated to 65° C. and allowed to cool slowly to 37° C. over a 20–30 min time period. The duplex primer was then mixed with 10 pmol of TS10 (20 pmol of TS10 for 0.2 mg of beads) in 1 μl volume, and the resulting mixture was further incubated at 37° C. for 5 min, room temperature for 5–10 min. Then 1 μl 0.1 M dithiothreitol solution, 1 μl Mn buffer (0.15 M sodium isocitrate and 0.1 M MnCl$_2$), and 2 μl of diluted Sequenase (3.25 units) were added. The reaction mixture was divided into four aliquots of 3 μl each and mixed with termination mixes (each consists of 4 μl of the appropriate termination mix: 16 μM dATP, 16 μM dCTP, 16 μM dGTP, 16 μM dTTP and 1.6 μM of one of the four ddNTPs, in 50 mM NaCl). The reaction mixtures were incubated at room temperature for 5 min, and 37° C. for 5 min. After the completion of extension, the beads were precipitated and the supernatant was removed. The beads were resuspended in 20 μl TE and kept at 4° C. An aliquot of 2 μl (out of 20 μl) from each tube was taken and mixed with 8 μl of formamide, the resulting samples were denatured at 90–95° C. for 5 min and 2 μl (out of 10 μl total) was applied to an ALF DNA sequencer (Pharmacia, Piscataway, N.J.) using a 10% polyacrylamide gel containing 7 M urea and 0.6× TBE. The remaining aliquot was used for MALDI-TOFMS analysis.

MALDI Sample Preparation and Instrumentation

Before MALDI analysis, the sequencing ladder loaded magnetic beads were washed twice using 50 mM ammonium citrate and resuspended in 0.5 μl pure water. The suspension was then loaded onto the sample target of the mass spectrometer and 0.5 μl of saturated matrix solution (3-hydroxypicolinic acid (HPA): ammonium citrate=10:1 mole ratio in 50% acetonitrile) was added. The mixture was allowed to dry prior to mass spectometer analysis.

The reflectron TOFMS mass spectrometer (Vision 2000, Finnigan MAT, Bremen, Germany) was used for analysis. 5 kV was applied in the ion source and 20 kV was applied for postacceleration. All spectra were taken in the positive ion mode and a nitrogen laser was used. Normally, each spectrum was averaged for more than 100 shots and a standard 25-point smoothing was applied.

Results and Discussions

Conventional Solid-phase Sequencing

In conventional sequencing methods, a primer is directly annealed to the template and then extended and terminated in a Sanger dideoxy sequencing. Normally, a biotinylated primer is used and the sequencing ladders are captured by streptavidin-coated magnetic beads. After washing, the products are eluted from the beads using EDTA and formamide. However, our previous findings indicated that only the annealed strand of a duplex is desorbed and the immobilized strand remains on the beads. Therefore, it is advantageous to immobilize the template and anneal the primer. After the sequencing reaction and washing, the beads with the immobilized template and annealed sequencing ladder can be loaded directly onto the mass spectrometer target and mix with matrix. In MALDI, only the annealed sequencing ladder will be desorbed and ionized, and the immobilized template will remain on the target.

A 39-mer template (SEQ. ID. No. 23) was first biotinylated at the 3' end by adding biotin-14-dATP with terminal transferase. More than one biotin-14-dATP molecule could be added by the enzyme. However, since the template was immobilized and remained on the beads during MALDI, the number of biotin-14-dATP would not affect the mass spectra. A 14-mer primer (SEQ. ID. No. 29) was used for the solid-state sequencing. MALDI-TOF mass spectra of the four sequencing ladders are shown in FIG. 44 and the expected theoretical values are shown in Table II.

TABLE II

| | |
|---|---|
| 1. | 5'-TCTGGCCTGGTGCAGGGCCTATTGTAGTTGTGACGTACA-(A$^b$)$_n$ -3' |
| 2. | 3'-TCAACACTGCATGT-5' |
| 3. | 3'-ATCAACACTGCATGT-5' |
| 4. | 3'-CATCAACACTGCATGT-5' |
| 5. | 3'-ACATCAACACTGCATGT-5' |

TABLE II-continued

| | |
|---|---|
| 6. | 3'-AACATCAACACTGCATGT-5' |
| 7. | 3'-TAACATCAACACTGCATGT-5' |
| 8. | 3'-ATAACATCAACACTGCATGT-5' |
| 9. | 3'-GATAACATCAACACTGCATGT-5' |
| 10. | 3'-GGATAACATCAACACTGCATGT-5' |
| 11. | 3'-CGGATAACATCAACACTGCATGT-5' |
| 12. | 3'-CCGGATAACATCAACACTGCATGT-5' |
| 13. | 3'-CCCGGATAACATCAACACTGCATGT-5' |
| 14. | 3'-TCCCGGATAACATCAACACTGCATGT-5' |
| 15. | 3'-GTCCCGGATAACATCAACACTGCATGT-5' |
| 16. | 3'-CGTCCCGGATAACATCAACACTGCATGT-5' |
| 17. | 3'-ACGTCCCGGATAACATCAACACTGCATGT-5' |
| 18. | 3'-CACGTCCCGGATAACATCAACACTGCATGT-5' |
| 19. | 3'-CCACGTCCCGGATAACATCAACACTGCATGT-5' |
| 20. | 3'-ACCACGTCCCGGATAACATCAACACTGCATGT-5' |
| 21. | 3'-GACCACGTCCCGGATAACATCAACACTGCATGT-5' |
| 22. | 3'-GGACCACGTCCCGGATAACATCAACACTGCATGT-5' |
| 23. | 3'-CGGACCACGTCCCGGATAACATCAACACTGCATGT-5' |
| 24. | 3'-CCGGACCACGTCCCGGATAACATCAACACTGCATGT-5' |
| 25. | 3'-ACCGGACCACGTCCCGGATAACATCAACACTGCATGT-5' |
| 26. | 3'-GACCGGACCACGTCCCGGATAACATCAACACTGCATGT-5' |
| 27. | 3'-AGACCGGACCACGTCCCGGATAACATCAACACTGCATGT-5' |

| | A-reaction | C-reaction | G-reaction | T-reaction |
|---|---|---|---|---|
| 1. | | | | |
| 2. | 4223.8 | 4223.8 | 4223.8 | 4223.8 |
| 3. | 4521.1 | | | |
| 4. | | 4809.2 | | |
| 5. | 5122.4 | | | |
| 6. | 5434.6 | | | |
| 7. | | | | 5737.8 |
| 8. | 6051.1 | | | |
| 9. | | | 6379.2 | |
| 10. | | | 6704.4 | |
| 11. | | 6995.6 | | |
| 12. | | 7284.8 | | |
| 13. | | 7574.0 | | |
| 14. | | | | 7878.2 |
| 15. | | | 8207.4 | |
| 16. | | 8495.6 | | |
| 17. | 8808.8 | | | |
| 18. | | 9097.0 | | |
| 19. | | 9386.2 | | |
| 20. | 9699.4 | | | |
| 21. | | | 10027.6 | |
| 22. | | | 10355.8 | |
| 23. | | 10644.0 | | |
| 24. | | 10933.2 | | |
| 25. | 11246.4 | | | |
| 26. | | | 11574.6 | |
| 27. | 11886.8 | | | |

The sequencing reaction produced a relatively homogenous ladder, and the full-length sequence was determined easily. One peak around 5150 appeared in all reactions are not identified. A possible explanation is that a small portion of the template formed some kind of secondary structure, such as a loop, which hindered sequenase extension. Misincorporation is of minor importance, since the intensity of these peaks were much lower than that of the sequencing ladders. Although 7-deaza purines were used in the sequencing reaction, which could stabilize the N-glycosidic bond and prevent depurination, minor base losses were still observed since the primer was not substituted by 7-deazapurines. The full length ladder, with a ddA at the 3' end, appeared in the A reaction with an apparent mass of 11899.8. However, a more intense peak of 12333 appeared in all four reactions and is likely due to an addition of an extra nucleotide by the Sequenase enzyme.

Figure 45:
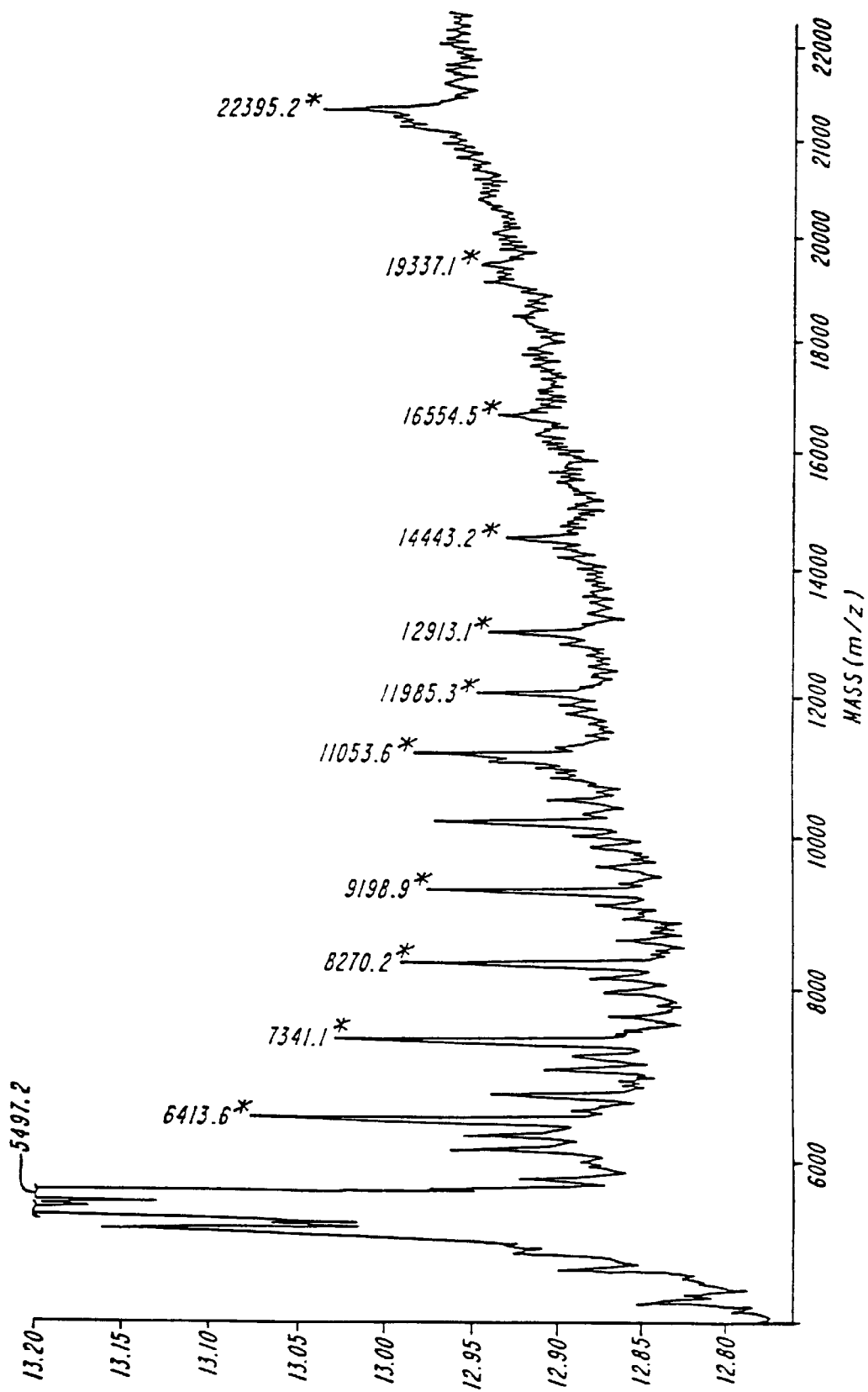
FIG. 45 shows a MALDI-TOF mass spectrum of a solid phase sequencing of a 78-mer template (SEQ. ID. No. 15), which was immobilized to streptavidin beads via a 3' biotinylation. A 18-mer primer (SEQ ID No. 16) and ddGTP were used in the sequencing.

The same technique could be used to sequence longer DNA fragments. A 78-mer template containing a CTG repeat (SEQ. ID. No. 25) was 3'-biotinylated by adding biotin-14-dATP with terminal transferase. An 18-mer primer (SEQ. ID. No. 26) was annealed right outside the CTG repeat so that the repeat could be sequenced immediately after primer extension. The four reactions were washed and analyzed by MALDI-TOFMS as usual. An example of the G-reaction is shown in FIG. 45 and the expected sequencing ladder is shown in Table III with theoretical mass values for each ladder component. All sequencing peaks were well resolved except the last component (theoretical value 20577.4) was indistinguishable from the background. Two neighboring sequencing peaks (a 62-mer and a 63-mer) were also separated indicating that such sequencing analysis could be applicable to longer templates. Again, an addition of an extra nucleotide by the Sequenase enzyme was observed in this spectrum. This addition is not template specific and appeared in all four reactions which makes it easy to be identified. Compared to the primer peak, the sequencing peaks were at much lower intensity in the long template case.

TABLE III

| 5'-AAGATCTGACCAGGGATTCGGTTAGCGTGACTGCTGCTGCTGCTGCTGGATGATCCGACGCATCAGATCTGG-(A^b)_n-3' |
|---|
| 1.  3'-CTACTAGGCTGCGTAGTC-5' |
| 2.  3'-CCTACTAGGCTGCGTAGTC-5' |
| 3.  3'-ACCTACTAGGCTGCGTAGTC-5' |
| 4.  3'-GACCTACTAGGCTGCGTAGTC-5' |
| 5.  3'-CGACCTACTAGGCTGCGTAGTC-5' |
| 6.  3'-ACGACCTACTAGGCTGCGTAGTC-5' |
| 7.  3'-GACGACCTACTAGGCTGCGTAGTC-5' |
| 8.  3'-CGACGACCTACTAGGCTGCGTAGTC-5' |
| 9.  3'-ACGACGACCTACTAGGCTGCGTAGTC-5' |
| 1o. 3'-GACGACGACCTACTAGGCTGCGTAGTC-5' |
| 11. 3'-CGACGACGACCTACTAGGCTGCGTAGTC-5' |
| 12. 3'-ACGACGACGACCTACTAGGCTGCGTAGTC-5' |
| 13. 3'-GACGACGACGACCTACTAGGCTGCGTAGTC-5' |
| 14. 3'-CGACGACGACGACCTACTAGGCTGCGTAGTC-5' |
| 15. 3'-ACGACGACGACGACCTACTAGGCTGCGTAGTC-5' |
| 16. 3'-GACGACGACGACGACCTACTAGGCTGCGTAGTC-5' |
| 17. 3'-CGACGACGACGACGACCTACTAGGCTGCGTAGTC-5' |
| 18. 3'-ACGACGACGACGACGACCTACTAGGCTGCGTAGTC-5' |
| 19. 3'-GACGACGACGACGACGACCTACTAGGCTGCGTAGTC-5' |
| 20. 3'-CGACGACGACGACGACGACCTACTAGGCTGCGTAGTC-5' |
| 21. 3'-ACGACGACGACGACGACGACCTACTAGGCTGCGTAGTC-5' |
| 22. 3'-GACGACGACGACGACGACGACCTACTAGGCTGCGTAGTC-5' |
| 23. 3'-CGACGACGACGACGACGACGACCTACTAGGCTGCGTAGTC-5' |
| 24. 3'-ACGACGACGACGACGACGACGACCTACTAGGCTGCGTAGTC-5' |
| 25. 3'-GACGACGACGACGACGACGACGACCTACTAGGCTGCGTAGTC-5' |
| 26. 3'-TGACGACGACGACGACGACGACGACCTACTAGGCTGCGTAGTC-5' |
| 27. 3'-CTGACGACGACGACGACGACGACGACCTACTAGGCTGCGTAGTC-5' |
| 28. 3'-ACTGACGACGACGACGACGACGACGACCTACTAGGCTGCGTAGTC-5' |
| 29. 3'-CACTGACGACGACGACGACGACGACGACCTACTAGGCTGCGTAGTC-5' |
| 30. 3'-GCACTGACGACGACGACGACGACGACGACCTACTAGGCTGCGTAGTC-5' |
| 31. 3'-CGCACTGACGACGACGACGACGACGACGACCTACTAGGCTGCGTAGTC-5' |
| 32. 3'-TCGCACTGACGACGACGACGACGACGACGACCTACTAGGCTGCGTAGTC-5' |
| 33. 3'-ATCGCACTGACGACGACGACGACGACGACGACCTACTAGGCTGCGTAGTC-5' |
| 34. 3'-AATCGCACTGACGACGACGACGACGACGACGACCTACTAGGCTGCGTAGTC-5' |
| 35. 3'-CAATCGCACTGACGACGACGACGACGACGACGACCTACTAGGCTGCGTAGTC-5' |
| 36. 3'-CCAATCGCACTGACGACGACGACGACGACGACGACCTACTAGGCTGCGTAGTC-5' |
| 37. 3'-GCCAATCGCACTGACGACGACGACGACGACGACGACCTACTAGGCTGCGTAGTC-5' |
| 38. 3'-AGCCAATCGCACTGACGACGACGACGACGACGACGACCTACTAGGCTGCGTAGTC-5' |
| 39. 3'-AAGCCAATCGCACTGACGACGACGACGACGACGACGACCTACTAGGCTGCGTAGTC-5' |
| 40. 3'-TAAGCCAATCGCACTGACGACGACGACGACGACGACGACCTACTAGGCTGCGTAGTC-5' |
| 41. 3'-CTAAGCCAATCGCACTGACGACGACGACGACGACGACGACCTACTAGGCTGCGTAGTC-5' |
| 42. 3'-CCTAAGCCAATCGCACTGACGACGACGACGACGACGACGACCTACTAGGCTGCGTAGTC-5' |
| 43. 3'-CCCTAAGCCAATCGCACTGACGACGACGACGACGACGACGACCTACTAGGCTGCGTAGTC-5' |
| 44. 3'-TCCCTAAGCCAATCGCACTGACGACGACGACGACGACGACGACCTACTAGGCTGCGTAGTC-5' |
| 45. 3'-GTCCCTAAGCCAATCGCACTGACGACGACGACGACGACGACGACCTACTAGGCTGCGTAGTC-5' |
| 46. 3'-GGTCCCTAAGCCAATCGCACTGACGACGACGACGACGACGACGACCTACTAGGCTGCGTAGTC-5' |
| 47. 3'-TGGTCCCTAAGCCAATCGCACTGACGACGACGACGACGACGACGACCTACTAGGCTGCGTAGTC-5' |
| 48. 3'-CTGGTCCCTAAGCCAATCGCACTGACGACGACGACGACGACGACGACCTACTAGGCTGCGTAGTC-5' |
| 49. 3'-ACTGGTCCCTAAGCCAATCGCACTGACGACGACGACGACGACGACGACCTACTAGGCTGCGTAGTC-5' |
| 50. 3'-GACTGGTCCCTAAGCCAATCGCACTGACGACGACGACGACGACGACGACCTACTAGGCTGCGTAGTC-5' |
| 51. 3'-AGACTGGTCCCTAAGCCAATCGCACTGACGACGACGACGACGACGACGACCTACTAGGCTGCGTAGTC-5' |
| 52. 3'-TAGACTGGTCCCTAAGCCAATCGCACTGACGACGACGACGACGACGACGACCTACTAGGCTGCGTAGTC-5' |
| 53. 3'-CTAGACTGGTCCCTAAGCCAATCGCACTGACGACGACGACGACGACGACGACCTACTAGGCTGCGTAGTC-5' |
| 54. 3'-TCTAGACTGGTCCCTAAGCCAATCGCACTGACGACGACGACGACGACGACGACCTACTAGGCTGCGTAGTC-5' |
| 55. 3'-TTCTAGACTGGTCCCTAAGCCAATCGCACTGACGACGACGACGACGACGACGACCTACTAGGCTGCGTAGTC-5' |

|     | ddATP   | ddCTP    | ddGTP   | ddTTP  |
|-----|---------|----------|---------|--------|
| 1.  | 5491.6  | 5491.6   | 5491.6  | 5491.6 |
| 2.  |         | 5764.8   |         |        |
| 3.  | 6078.0  |          |         |        |
| 4.  |         |          | 6407.2  |        |
| 5.  |         | 6696.4   |         |        |
| 6.  | 7009.6  |          |         |        |
| 7.  |         |          | 7338.8  |        |
| 8.  |         | 7628.0   |         |        |
| 9.  | 7941.2  |          |         |        |
| 10. |         |          | 8270.4  |        |
| 11. |         | 8559.6   |         |        |
| 12. | 8872.8  |          |         |        |
| 13. |         |          | 9202.0  |        |
| 14. |         | 9491.2   |         |        |
| 15. | 9804.4  |          |         |        |
| 16. |         |          | 10133.6 |        |
| 17. |         | 10422.88 |         |        |
| 18. | 10736.0 |          |         |        |
| 19. |         |          | 11065.2 |        |

TABLE III-continued

| # | C1 | C2 | C3 | C4 |
|---|---|---|---|---|
| 20. | | 11354.4 | | |
| 21. | 11667.6 | | | |
| 22. | | | 11996.8 | |
| 23. | | 12286.0 | | |
| 24. | 12599.2 | | | |
| 25. | | | 12928.4 | |
| 26. | | | | 13232.6 |
| 27. | | 13521.8 | | |
| 28. | 13835.0 | | | |
| 29. | | 14124.2 | | |
| 30. | | | 14453.4 | |
| 31. | | 14742.6 | | |
| 32. | | | | 15046.8 |
| 33. | 15360.0 | | | |
| 34. | 15673.2 | | | |
| 35. | | 15962.4 | | |
| 36. | | 16251.6 | | |
| 37. | | | 16580.8 | |
| 38. | 16894.0 | | | |
| 39. | 17207.2 | | | |
| 40. | | | | 17511.4 |
| 41. | | 17800.6 | | |
| 42. | | 18089.8 | | |
| 43. | | 18379.0 | | |
| 44. | | | | 18683.2 |
| 45. | | | 19012.4 | |
| 46. | | | 19341.6 | |
| 47. | | | | 19645.8 |
| 48. | | 19935.0 | | |
| 49. | 20248.2 | | | |
| 50. | | | 20577.4 | |
| 51. | 20890.6 | | | |
| 52. | | | | 21194.4 |
| 53. | | 21484.0 | | |
| 54. | | | | 21788.2 |
| 55. | | | | 22092.4 |

Sequencing using Duplex DNA Probes for Capturing and Priming

Figure 46:
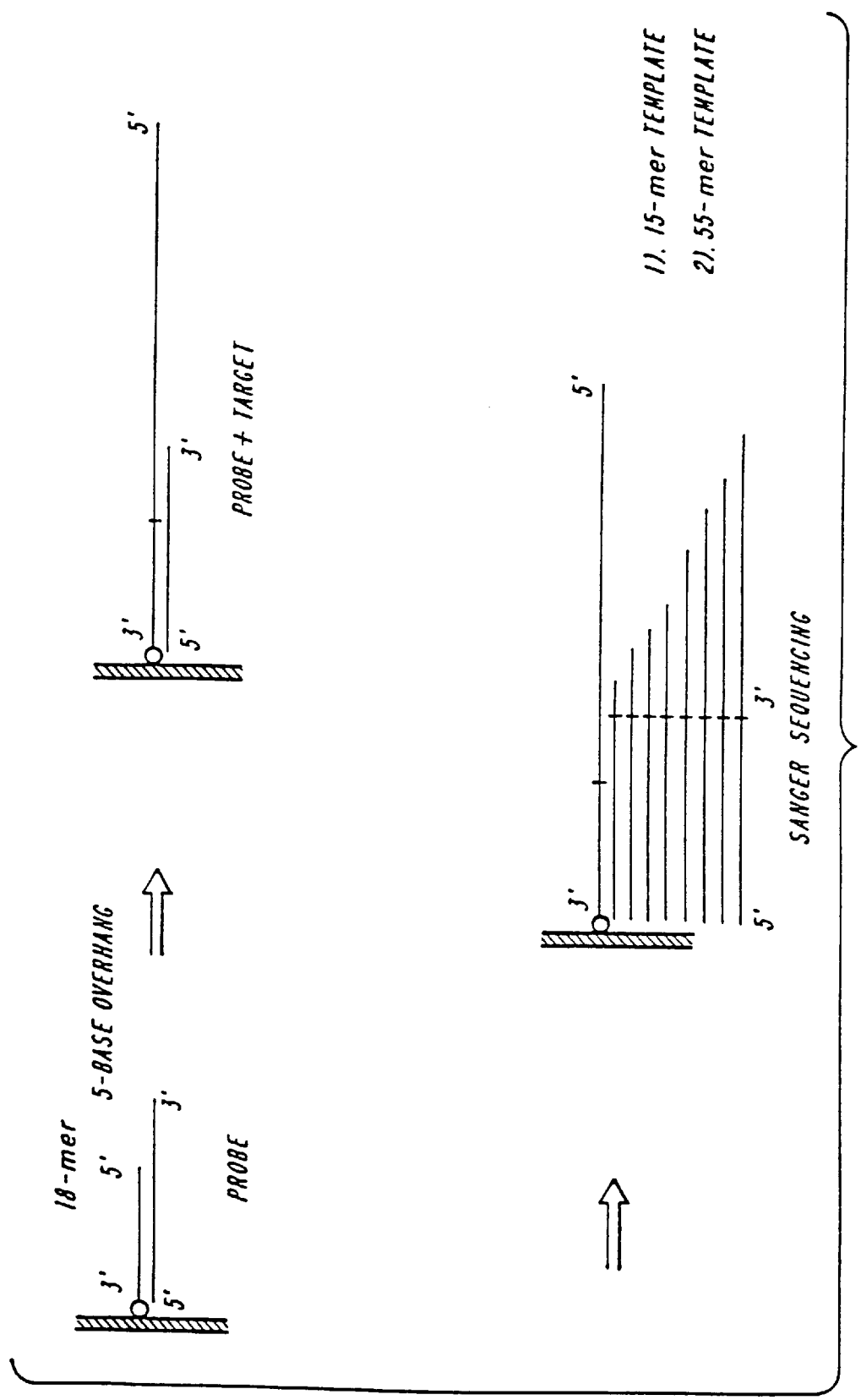
FIG. 46 shows a scheme in which duplex DNA probes with single-stranded overhang capture specific DNA templates and also serve as primers for solid phase sequencing.
Figure 47A:
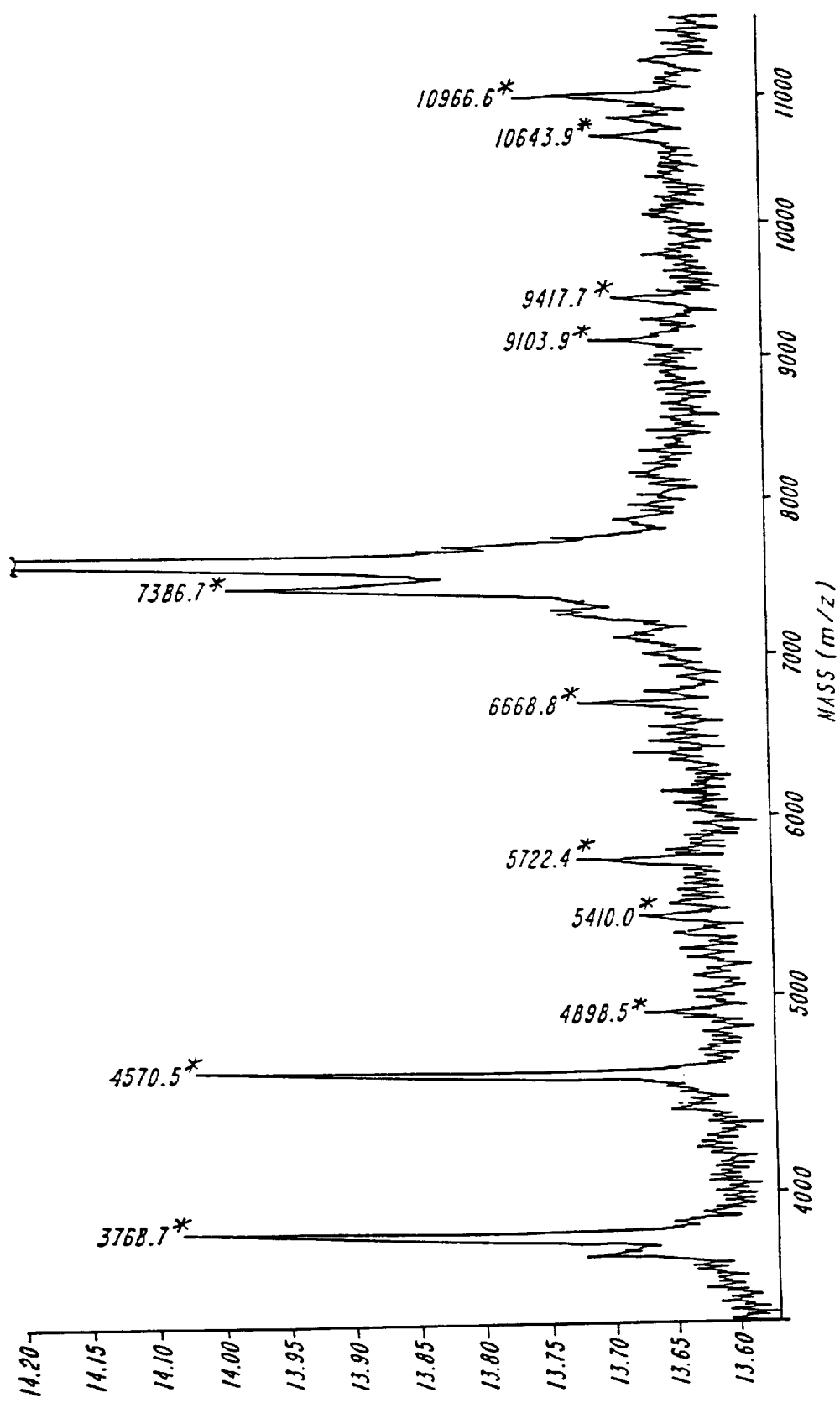
FIG. 47A–D shows MALDI-TOF mass spectra obtained from a sequencing reaction using 5' fluorescent labeled 23-mer (SEQ. ID. No. 19) annealed to a 3'biotinylated 18-mer (SEQ. ID. No. 20), leaving a 5-base overhang, which captured a 15-mer template (SEQ. ID. No. 21) as described in Example 9.
Figure 47B:
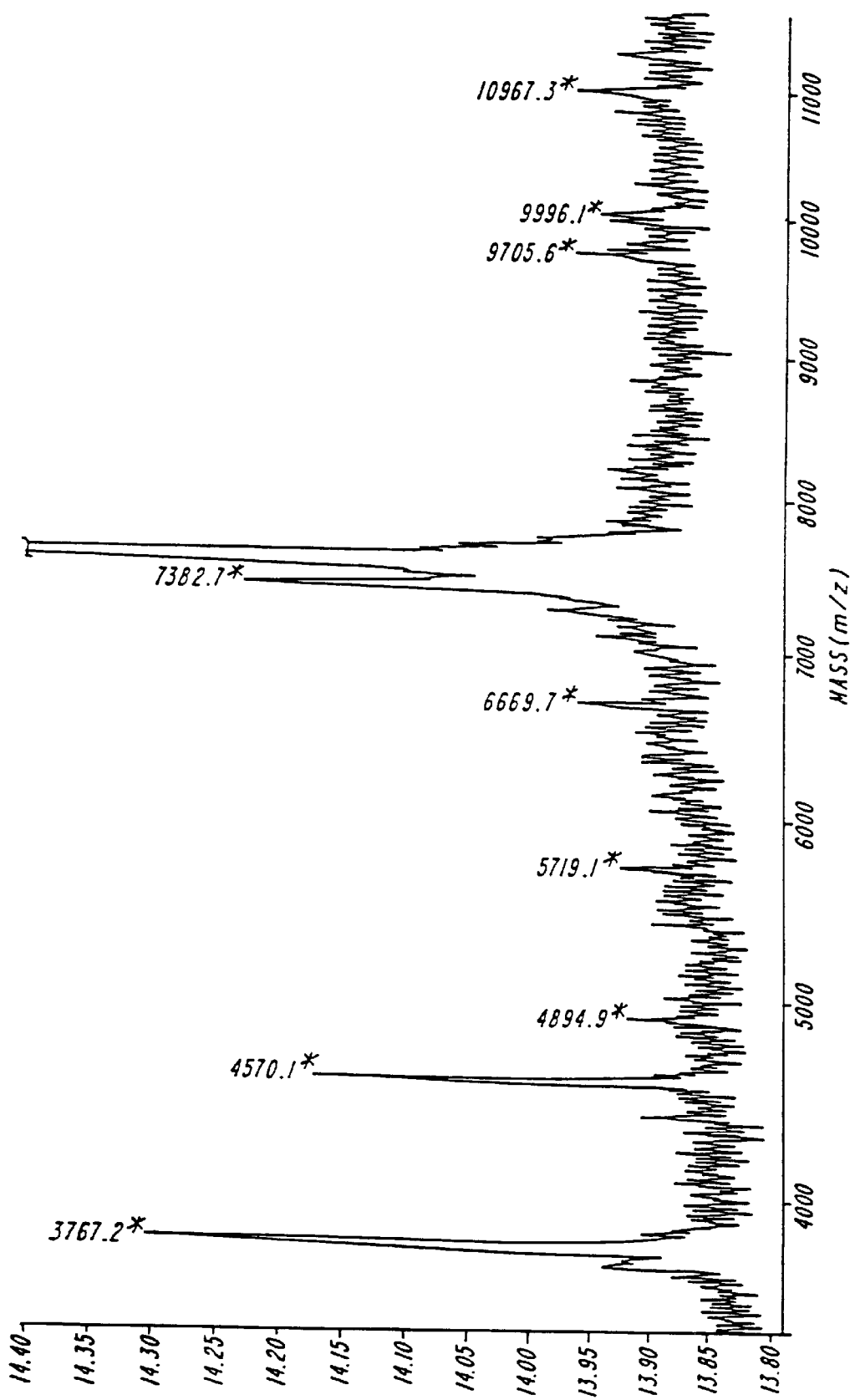
Figure 47C:
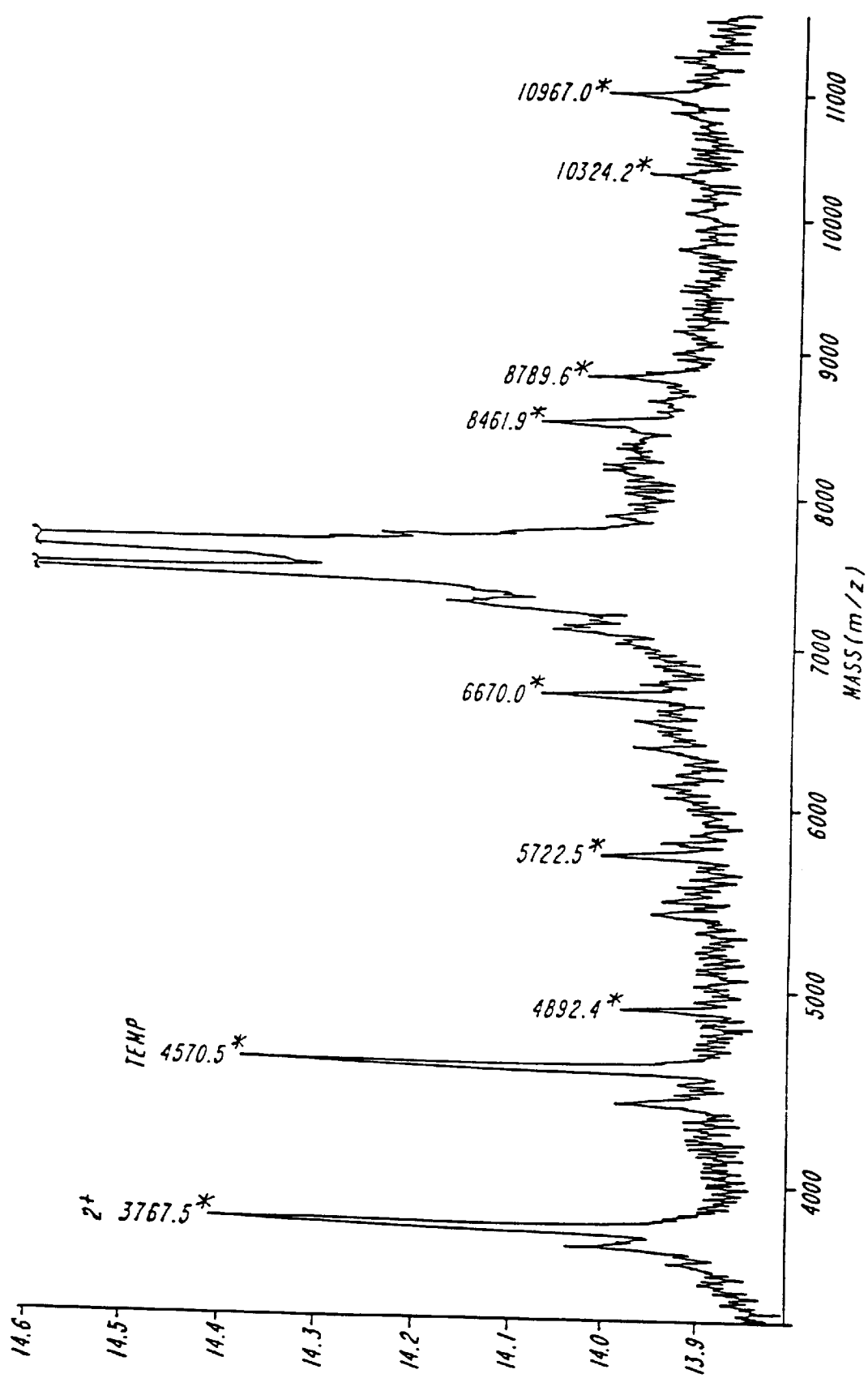
Figure 47D:
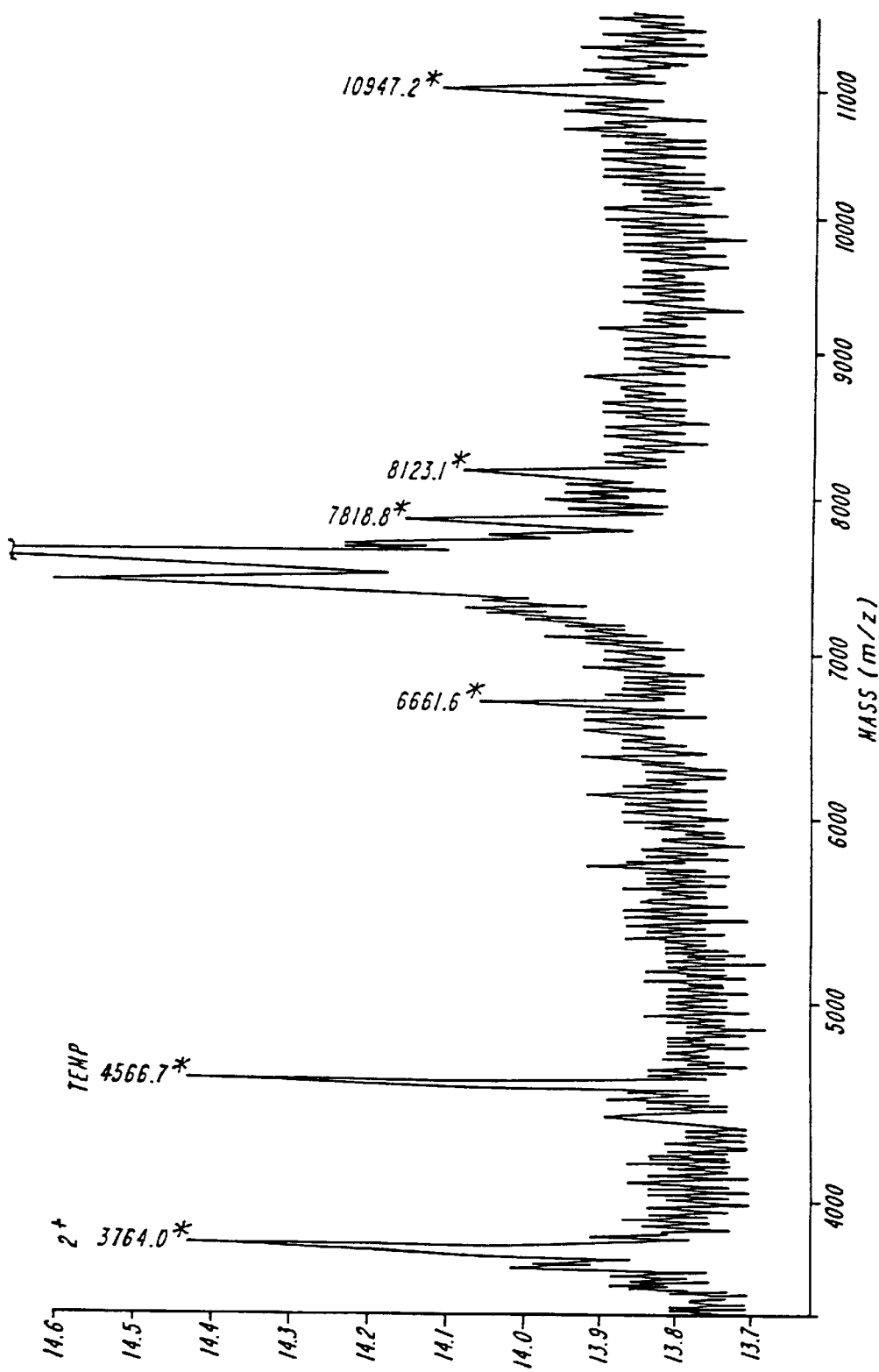
Figure 49A:
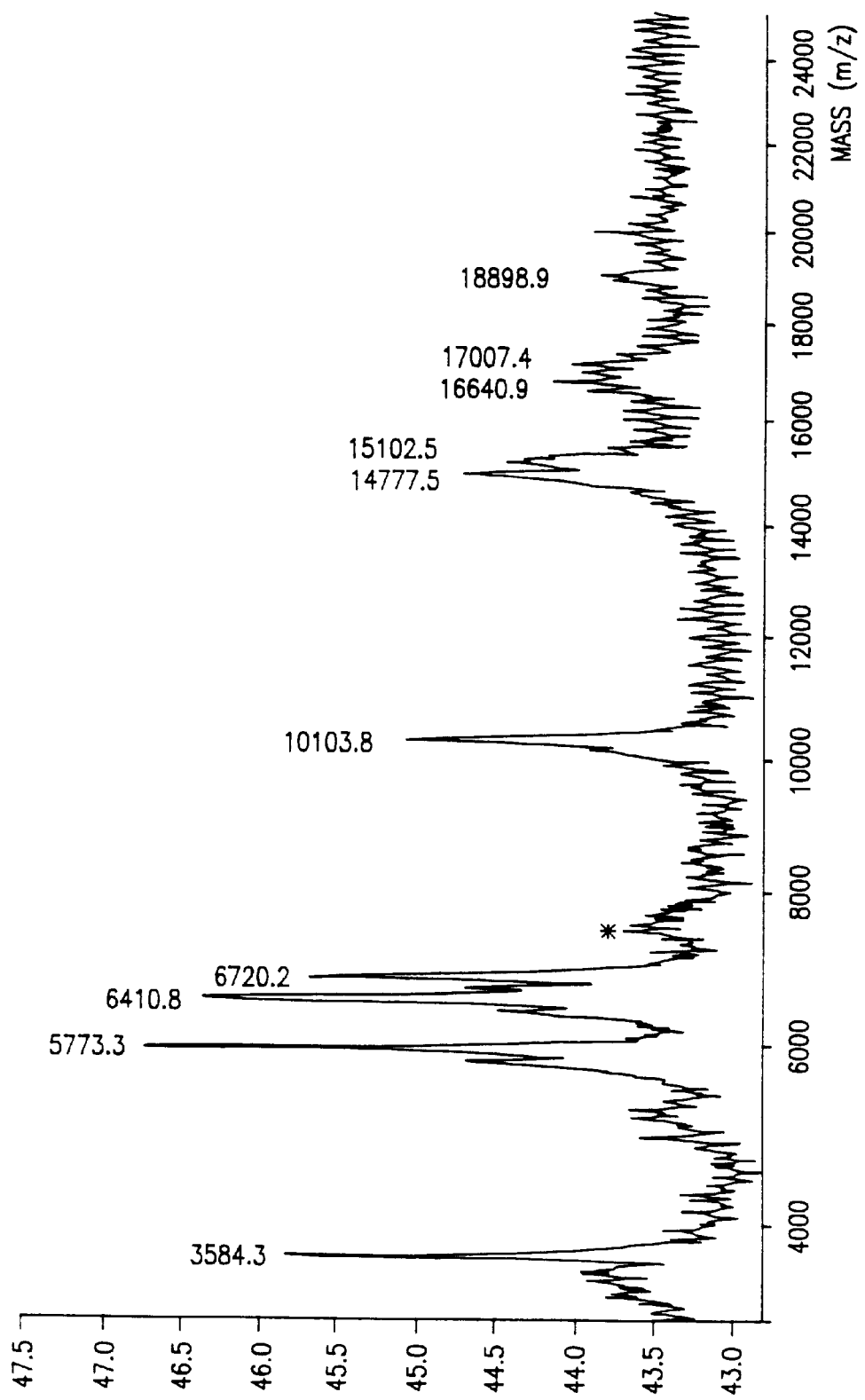
FIG. 49 shows a MALDI-TOF mass spectrum of the sequencing ladder using cycle sequencing as described in Example 1 generated from a biological PCR product as template and a 12 mer (5'-TGC ACC TGA CTC-3' (SEQ ID NO.50)) sequencing primer. The peaks resulting from depurinations and peaks which are not related to the sequence are marked by an asterisk. MALDI-TOF MS measurements were taken on a reflectron TOF MS. A.) Sequencing ladder stopped with ddATP; B.) Sequencing ladder stopped with ddCTP; C.) Sequencing ladder stopped with ddGTP; D.) Sequencing ladder stopped with ddTTP.
Figure 49B:
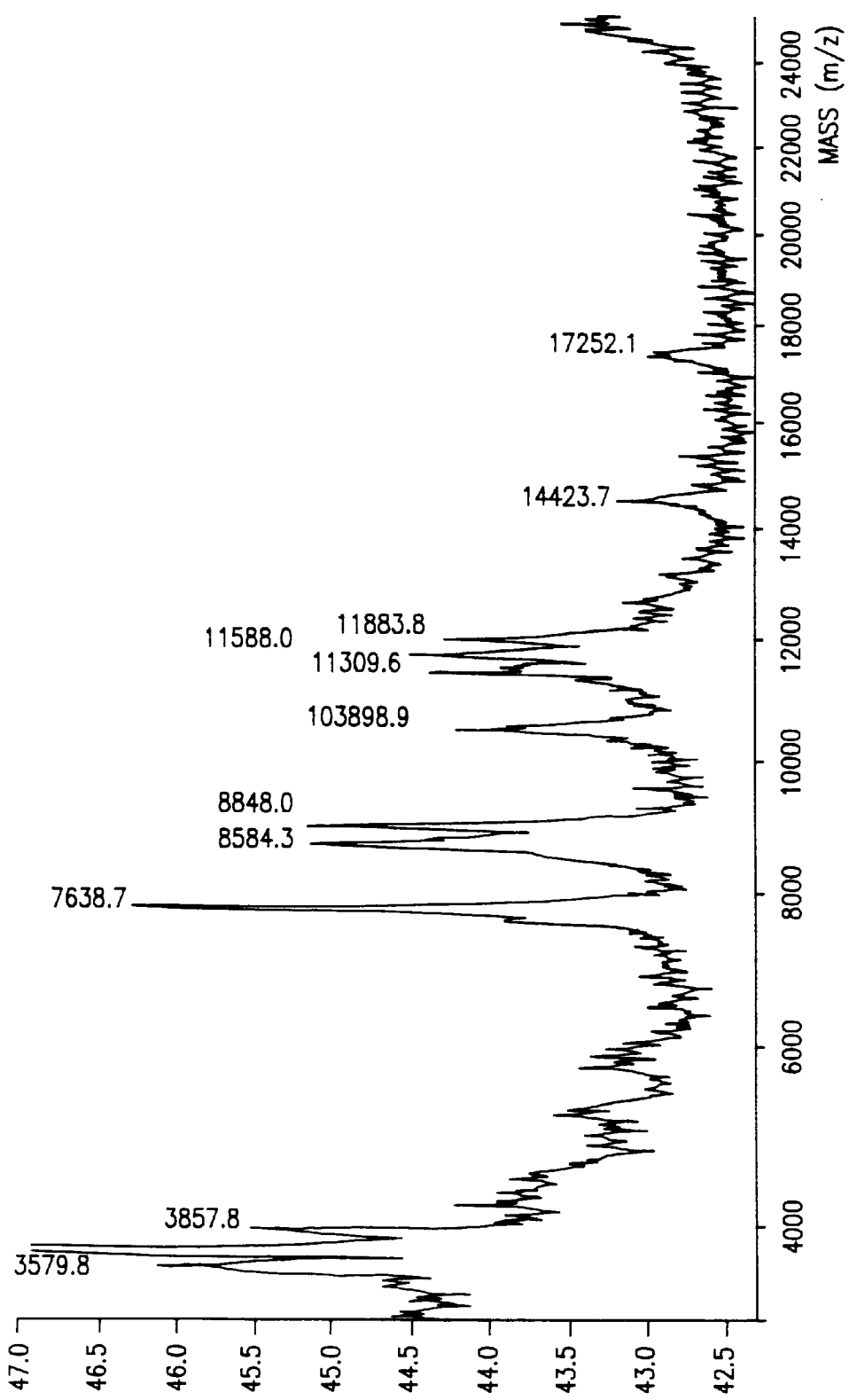
Figure 49C:
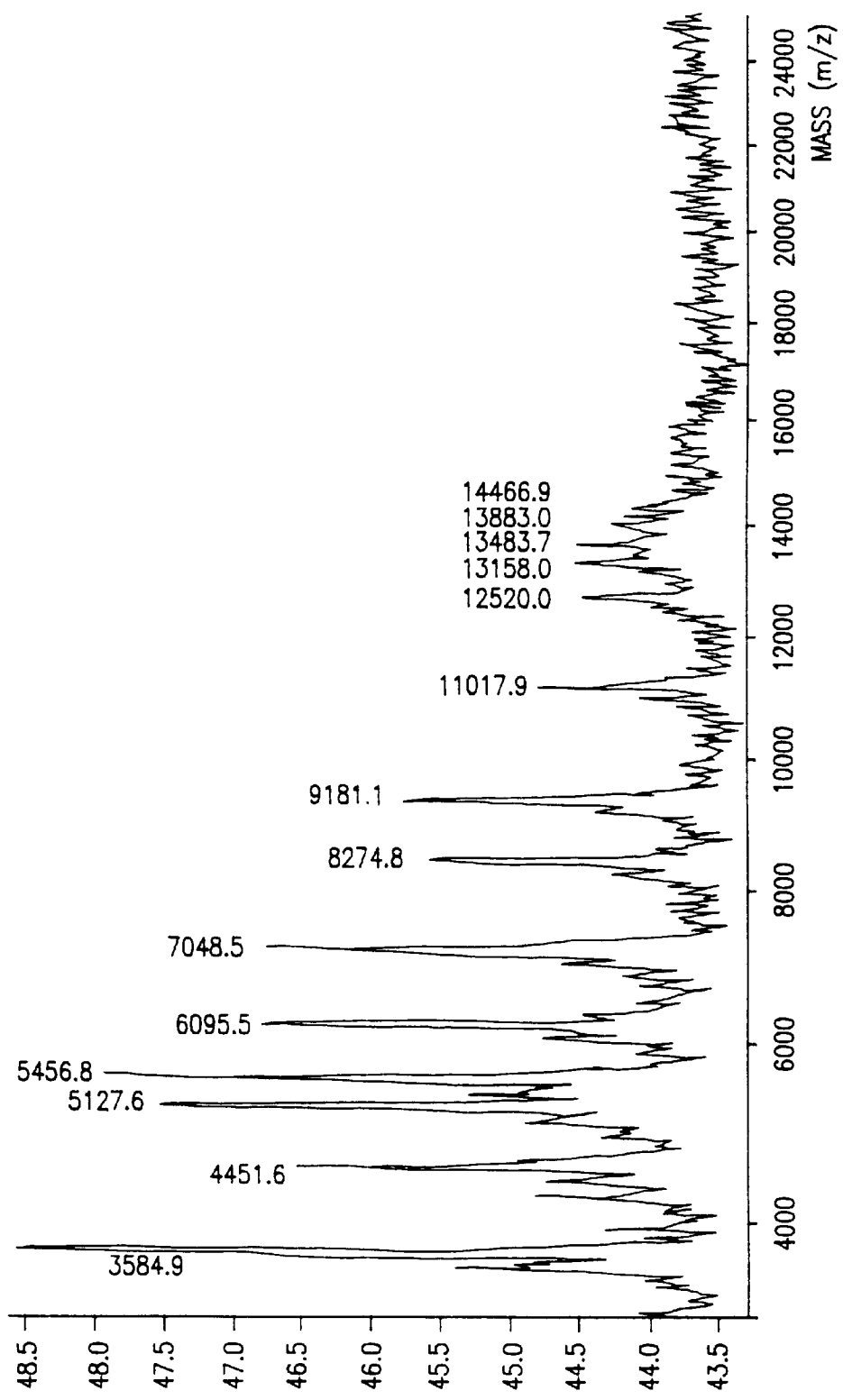
Figure 49D:
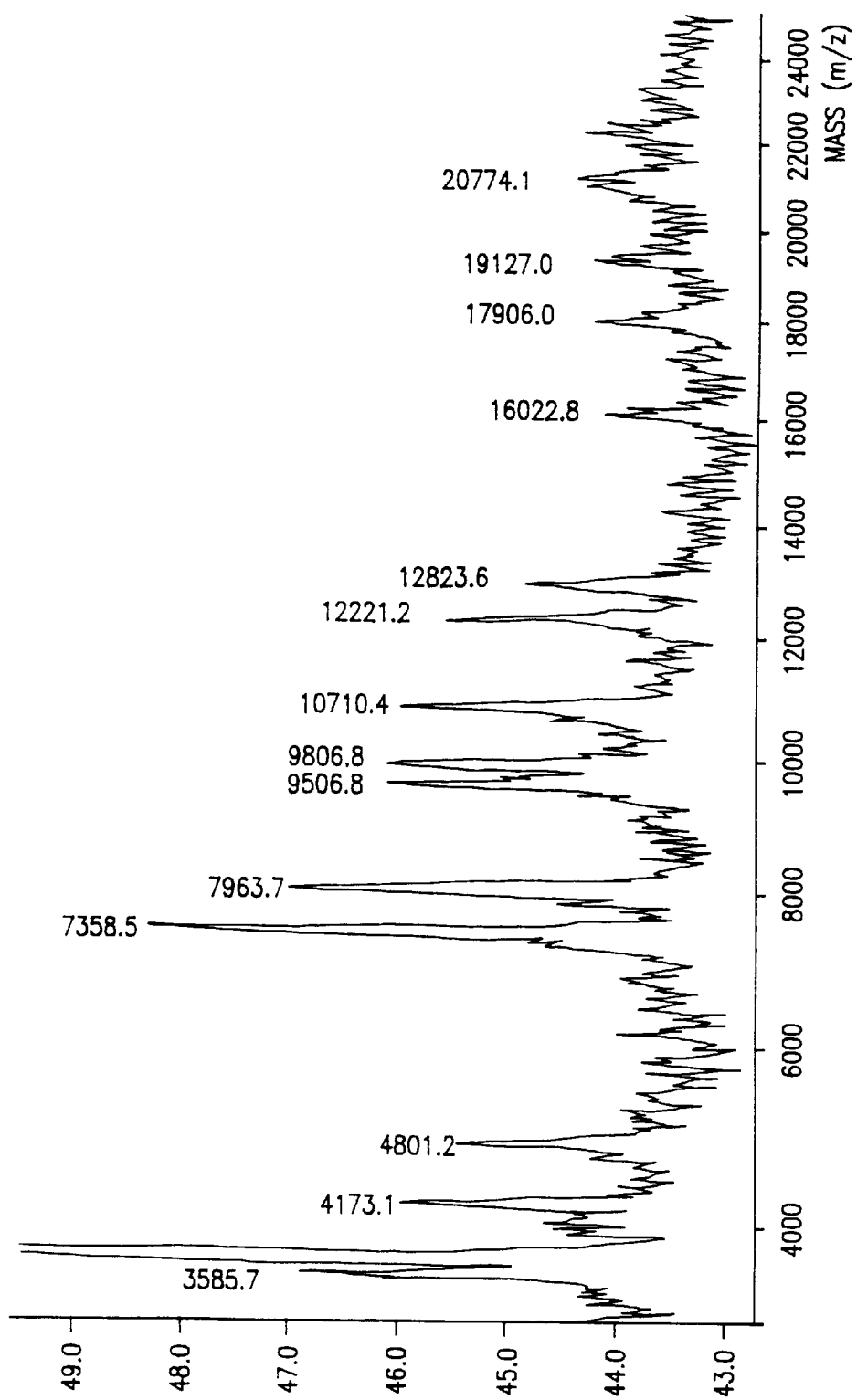
Figure 53A:
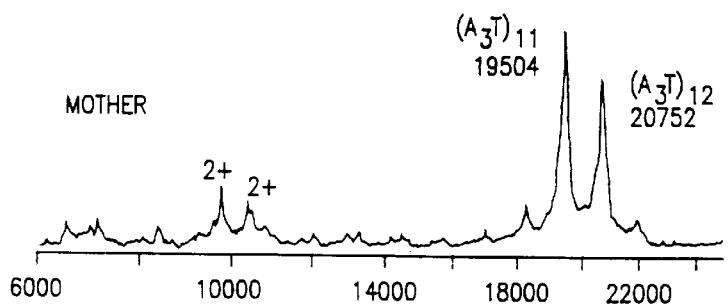
FIG. 53 shows the MALDI-TOF-MS spectra recorded directly form precipitated extended cyclePROBE reaction products. Family study using AluVpA polymorphism in intron 5 of the interferon-a receptor gene (Example 11).
Figure 53B:
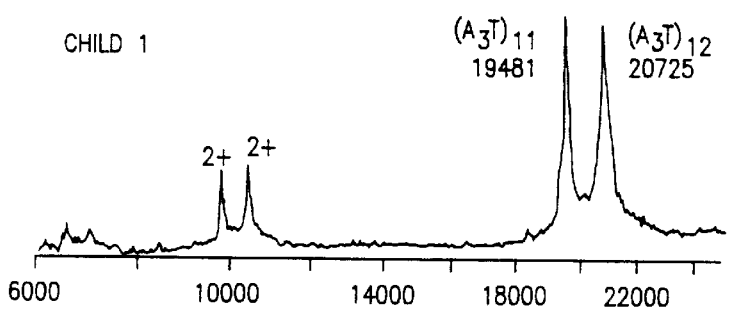
Figure 53C:
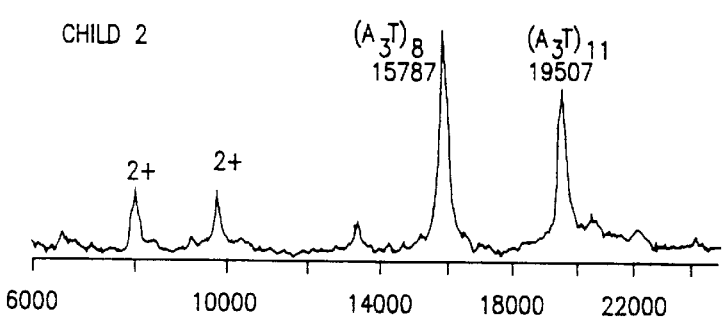
Figure 53D:
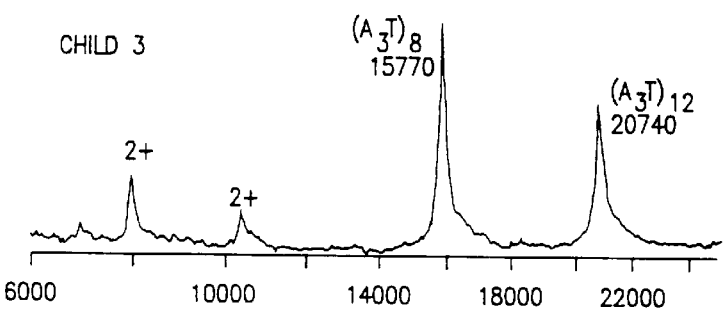
Figure 53E:
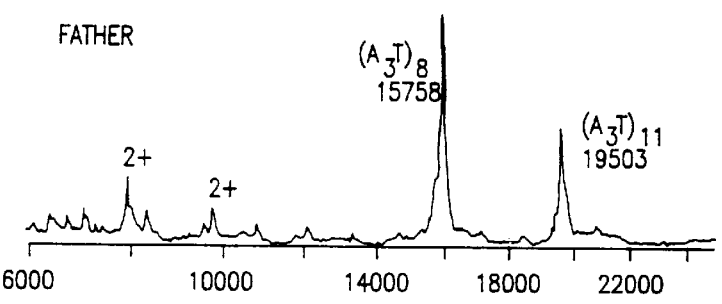

Duplex DNA probes with single-stranded overhang have been demonstrated to be able to capture specific DNA templates and also serve as primers for solid-state sequencing. The scheme is shown in FIG. 46. Stacking interactions between a duplex probe and a single-stranded template allow only a 5-base overhang to be sufficient for capturing. Based on this format, a 5' fluorescent-labeled 23-mer (5'-GAT GAT CCG ACG CAT CAC AGC TC) (SEQ. ID. No. 29) was annealed to a 3'-biotinylated 18-mer (5'-GTG ATG CGT CGG ATC ATC) (SEQ. ID. No.30), leaving a 5-base overhang. A 15-mer template (5'-TCG GTT CCA AGA GCT) (SEQ ID. No.31) was captured by the duplex and sequencing reactions were performed by extension of the 5-base overhang. MALDI-TOF mass spectra of the reactions are shown in FIG. 47A–D. All sequencing peaks were resolved although at relatively low intensities. The last peak in each reaction is due to unspecific addition of one nucleotide to the full length extension product by the Sequenase enzyme. For comparison, the same products were run on a conventional DNA sequencer and a stacking fluorogram of the results is shown in FIG. 48. As can be seen from the Figure, the mass spectra had the same pattern as the fluorogram with sequencing peaks at much lower intensity compared to the 23-mer primer.

EXAMPLE 10

Thermo Sequenase Cycle Sequencing

Materials and Methods

PCR amplification. Human leukocytic genomic DNA was used for PCR amplification. PCR primers to amplify a 209bp fragment of the β-globin gene were the β2 forward primer (5'-CAT TTG CTT CTG ACA CAA CTG-3' SEQ ID. NO.32) and the β11 reverse primer (5'-CTT CTC TGT CTC CAC ATG C-3' SEQ ID. NO.33). Taq polymerase and 10×buffer were purchased from Boehringer-Mannheim (Germany) and dNTPs from Pharmacia (Freiburg, Germany). The total reaction volume was 50 µl including 8 pmol of each primer with approximately 200 ng of genomic DNA used as template and a final dNTP concentration of 200 µM. PCR conditions were: 5 min at 94° C., followed by 40 cycles of 30 sec at 94° C., 45 sec at 53° C., 30 sec at 72° C., and a final extension time of 2 min at 72° C. The generated PCR product was purified and concentrated (2×) with the Qiagen 'Qiaquick' PCR purification kit (#28106) and stored in $H_2O$.

Cycle Sequencing. Sequencing ladders were generated by primer extension with Thermo Sequenase™-DNA Polymerase (Amersham LIFE Science, #E79000Y) under the following conditions: 7 pmol of HPLC purified primer (Cod5 12 mer: 5'-TGC ACC TGA CTC-3') were added to 6 µl purified and concentrated PCR product (ie 12 µl of the original PCR product), 2.5 units Thermo Sequenase and 2.5 ml Thermo Sequenase reaction buffer in a total volume of 25 µl. The final nucleotide concentrations were 30µM of the appropiate ddNTP (ddATP, ddCTP, ddGTP or ddTTP; Pharmacia Biotech, #27–2045–01) and 210 µM of each dNTP (7-deaza-dATP, dCTP, 7-deaza-GTP, dTTP; Pharmacia Biotech). Cycling conditions were: denaturation for 4 min at 94° C., followed by 35 cycles of 30 sec at 94° C., 30 sec at 38° C., 30 sec at 55° C., and a final extension of 2 min at 72°

Sample preparation and analysis by MALDI-TOF MS. After completion of the cycling program, the reaction volume was increased to 50 µl by addition of 25 µl $H_2O$.

Desalting was achieved by shaking 30 μl of ammonium saturated DOWEX (Fluka #44485) cation exchange beads with 50 μl of the analyte for 2 min at room temperature. The Dowex beads, purchased in the protonated form, were pre-treated with 2M NH$_4$OH to convert them to the ammonium form, then washed with H$_2$O until the supernatant was neutral, and finally put in 10 mM ammonium citrate for usage.

After the cation exchange, DNA was purified and concentrated by ethanol precipitation by adding 5 μl 3M ammonium acetate (pH 6.5), 0.5 μl glycogen (10 mg/ml, Sigma), and 110 μl absolute ethanol to the analyte and incubated at room temperature for 1 hour. After 12 min centrifugation at 20,000 g the pellet was washed in 70% ethanol and resuspended in 1 μl 18 Mohm/cm H$_2$O water.

For MALDI-TOF MS analysis 0.35 μl of resuspended DNA was mixed with 0.35–1.3 μl matrix solution (0.7M 3-hydroxypicolinic acid (3-HPA), 0.07M ammonium citrate in 1:1 H$_2$O; CH$_3$CN) on a stainless steel sample target disk and allowed to air dry preceding spectrum acquisition using a Thermo Bioanalysis Vision 2000 MALDI-TOF operated in reflectron mode with 5 and 20 kV on the target and conversion dynode, respectively. External calibration generated from eight peaks (3000–18000 Da) was used for all spectra.

Results

FIG. 49 shows a MALDI-TOF mass spectrum of the sequencing ladder generated from a biological PCR product as template and a 12 mer (5'-TGC ACC TGA CTC-3' (SEQ ID NO.34)) sequencing primer. The peaks resulting from depurinations and peaks which are not related to the sequence are marked by an asterisk. MALDI-TOF MS measurements were taken on a reflectron TOF MS. A.) Sequencing ladder stopped with ddATP; B.) Sequencing ladder stopped with ddCTP; C.) Sequencing ladder stopped with ddGTP; D.) Sequencing ladder stopped with ddTTP.

FIG. 50 shows a schematic representation of the sequencing ladder generated in FIG. 49 with the corresponding calculated molecular masses up to 40 bases after the primer. For the calculation the following masses were used: 3581.4 Da for the primer, 312.2 Da for 7-deaza-dATP, 304.2 Da for dTTP, 289.2 Da for dCTP and 328.2 Da for 7-deaza-dGTP.

FIG. 51 shows the sequence of the amplified 209 bp PCR product within the β-globin gene, which was used as a template for sequencing. The sequences of the appropriate PCR primer and the location of the 12 mer sequencing primer is also shown. This sequence represents a homozygote mutant at the position 4 after the primer. In a wildtype sequence this T would be replaced by an A.

EXAMPLE 11

Microsatellite Analysis Using Primer Oligo Base Extension (PROBE) and MALDI-TOF Mass Spectrometry

Summary

The method uses a single detection primer followed by an oligonucleotide extension step to give products differing in length by a number of bases specific for the number of repeat units or for second site mutations within the repeated region, which can be easily resolved by MALDI-TOF mass spectrometry. The method is demonstrated using as a model system the AluVpA polymorphism in intron 5 of the interferon-a receptor gene located on human chromosome 21, and the poly T tract of the splice acceptor site of intron 8 from the CFTR gene located on human chromosome 7.

Materials and Methods

Genomic DNA was obtained from 28 unrelated individuals and one family consisting of a mother, father, and three children. The repeated region was evaluated conventionally by denaturing gel electrophoresis and results obtained were confirmed by standard Sanger sequencing.

The primers for PCR amplification (8 pmol each) were IFNAR-IVS5–5': (5'-TGC TTA CTT AAC CCA GTG TG-3' SEQ ID. NO.35) and IFNAR-IVS5-3'.2: (5'-CAC ACT ATG TAA TAC TAT GC-3' SEQ ID. NO.36) for a part of the intron 5 of the interferon-α receptor gene, and CFEx9-F: (5'-GAA AAT ATC TGA CAA ACT CAT C-3'3 SEQ ID. NO.37) (5'-biotinylated) and CFEx9-R: (5'-CAT GGA CAC CAA ATT AAG TTC-3' SEQ ID. NO.38) for CFTR exon 9 with flanking intron sequences of the CFTR gene. Taq-polymerase including 10×buffer were purchased from Boehringer-Mannheim and dNTPs were obtained from Pharmacia. The total reaction volume was 50 μl. PCR conditions were 5 min at 94° C. followed by 40 cycles of: 1 min at 94° C., 45 sec at 53° C., and 30 sec at 72° C., and a fin extension time of 5 min at 72° C.

Amplification products were purified using Qiagen's PCR purification kit (No. 28106) according to manufacturer's instructions. Purified products were eluted from the column in 50 μl TE-buffer (10 mM Tris,1 mM EDTA, pH 7,5).

A) Primer Oligo Base Extension Reaction (Thermo Cycling Method)

CyclePROBE was performed with 5 pmol appropriate detection primer (IFN: 5'-TGA GAC TCT GTC TC-3' SEQ ID. NO.39) in a total volume of 25 μl including 1 pmol purified template, 2 units Thermosequenase (Amersharn Life Science, Cat. # E79000Y) 2.5 μl Thermosequenase buffer, 25 μmol of each deoxynucleotide (7-deaza-dATP, dTTP, and in some experiments extra dCTP) and 100 μmol of dideoxyguanine and in some experiments additional ddCTP. Cycling conditions: initial denaturation 94° C. for 5 min followed by 30 cycles with 44° C. annealing temperature for 30 sec and 55° C. extension temperature for 1 min.

B) Primer Oligo Base Extension Reaction (Isothermal Method)

10 μl aliquots of the purified double-stranded PCR product (~3 pmol) were transferred to a streptavidin-coated microtiter plate well (~16 pmol capacity per 50 μl volume; No.1645684 Boehringer-Mannheim), followed by addition of 10 μl incubation buffer (80 mM sodium phosphate, 400 mM NaCI, 0.4% Tween 20, pH 7.5) and 30 μl water. After incubation for 1 hour at room temperature, the wells were washed three times with 200 μl washing buffer A (40 mM Tris, 1 mM EDTA, 50 mM NaCI, 0.1% Tween 20, pH 8.8) and incubated with 100 μl of 50 mM NaOH for 3 min to denature the double-stranded DNA. Finally, the wells were washed three times with 200 μl 70 mM ammonium citrate solution.

The annealing of 100 pmol detection primer (CFpT: 5'-TTC CCC AAA TCC CTG-3' SEQ ID. NO. 40) was performed in 50 μl annealing buffer (50 mM ammonium phosphate buffer, pH 7.0 and 100 mM ammonium chloride) at 65° C. for 2 min, at 37° C. for 10 min, and at room temperature for 10 min. The wells were washed three times with 200 μl washing buffer B (40 mM Tris, 1 mM EDTA, 50 mM NH$_4$Cl, 0.1% Tween 20, pH 8.8) and once in 200 μl TE buffer. The extension reaction was performed using some components of the DNA sequencing kit from USB (No. 70770) and dNTPs or ddNTPs from Pharmacia. Total reaction volume was 45 μl, consisting of 21 μl water, 6 μl Sequenase-buffer, 3 µl 100 mM DTT solution, 50 µmol of 7-deaza-dATP, 20 µmol ddCTP, 5.5 µl glycerol enzyme dilution buffer, 0.25 µl Sequenase 2.0, and 0.25 µl pyrophosphatase. The reaction was pipetted on ice and incubated for 15 min at room temperature and for 5 min at 37° C. Finally, the wells were washed three times with 200 µl washing buffer B.

The extended primer was denatured from the template strand by heating at 80° C. for 10 min in 50 µl of a 50 mM ammonium hydroxide solution.

For precipitation, 10 µl 3M $NH_4$-acetate (pH 6.5), 0.5 µl glycogen (10 mg/ml water, Sigma, Cat. #G1765), and 110 µl absolute ethanol were added to the supernatant and incubated for 1 hour at room temperature. After centrifugation at 13.000 g for 10 min the pellet was washed in 70% ethanol and resuspended in 1 µl 18 Mohm/cm $H_2O$ water.

Sample preparation was performed by mixing 0.6 µl of matrix solution (0.7 M 3-hydroxypicolinic acid, 0.07 M dibasic ammonium citrate in 1:1 $H_2O:CH_3CN$) with 0.3 µl of resuspended DNA/glycogen pellet on a sample target and allowed to air dry. Up to 20 samples were spotted on a probe target disk for introduction into the source region of a Thermo Bioanalysis (formerly Finnigan) Visions 2000 MALDI-TOF operated in reflectron mode with 5 and 20 kV on the target and conversion dynode, respectively. Theoretical average molecular mass ($M_r$(calc)) were calculated from atomic compositions; reported experimental $M_r$($M_r$(exp)) values are those of the singly-protonated form, determined using external calibration.

Results

The aim of the experiments was to develop a fast and reliable method for the exact determination of the number of repeat units in microsatellites or the length of a mononucleotide stretch including the potential to detect second site mutations within the polymorphic region. Therefore, a special kind of DNA sequencing (primer oligo base extension, PROBE) was combined with the evaluation of the resulting products by matrix-assisted laser desorption ionization (MALDI) mass spectrometry (MS). The time-of-flight (TOF) reflectron arrangement was chosen as a possible mass measurement system. As an initial feasibility study, an examination was performed first on an AluVpA repeat polymorphism located in intron 5 of the human interferon-α receptor gene (cyclePROBE reaction) and second on the poly T tract located in intron 8 of the human CFTR gene (isothermal PROBE reaction).

Figure 54A:
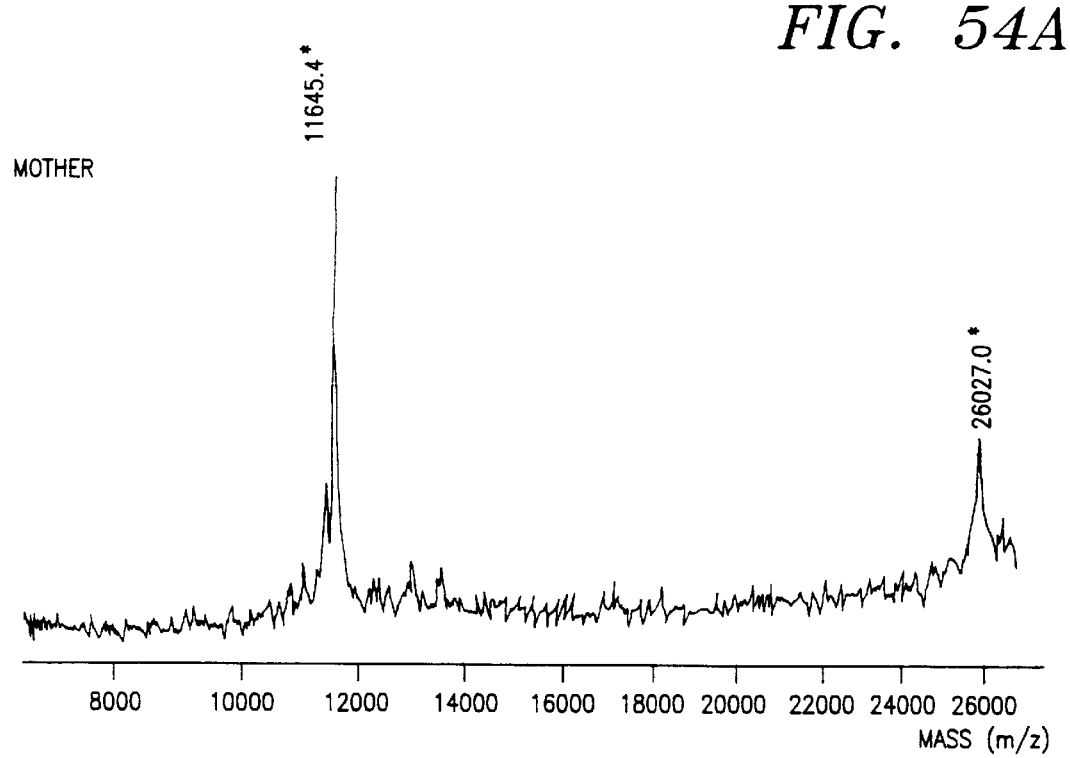
FIG. 54 shows the mass spectra from PROBE products using ddC as termination nucleotide in the reaction mix. The allele with the molecular mass of approximately 11650 da from the DNA of the mother and child 2 is a hint to a second site mutation within one of the repeat units.
Figure 54B:
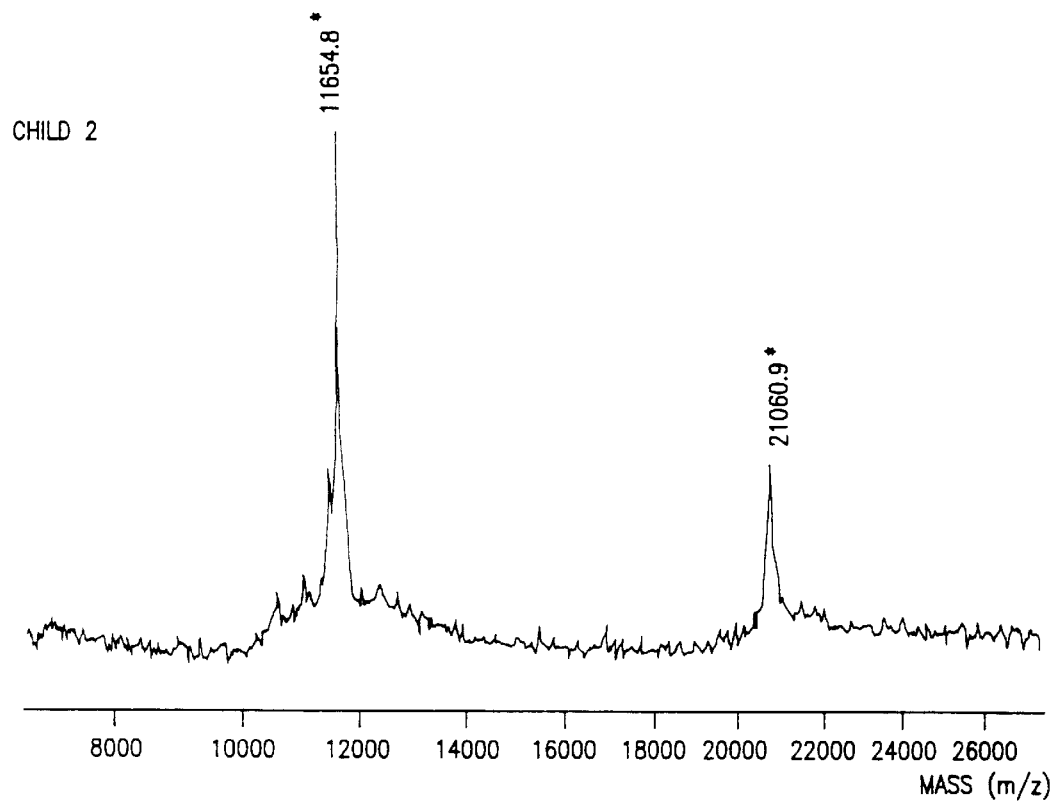

A schematic presentation of the cyclePROBE experiment for the AluVpA repeat polymorphism is given in FIG. 52. The extension of the antisense -strand was performed with the sense strand serving as the template. The detection primer is underlined. In a family study co-dominant segregation of the various alleles could be demonstrated by the electrophoretic procedure as well as by the cyclePROBE method followed by mass spec analysis (FIG. 53). However, those alleles of the mother and child 2, for which direct electrophoresis of the PCR product indicated one of the two copies to have 13 repeat units, were measured using cyclePROBE to have instead only 11 units using ddG as terminator. The replacement of ddG by ddC resulted in a further unexpected short allele with a molecular mass of approximately 11650 in the DNA of the mother and child 2 (FIG. 54). Sequence analysis verified this presence of two second site mutations in the allele with 13 repeat units. The first is a C to T transition in the third repeat unit and the second mutation is a T to G transversion in the ninth repeat unit.

Examination of 28 unrelated individuals shows that the 13 unit allele is spliced into a normal allele and a truncated allele using cyclePROBE. Statistical evaluation shows that the polymorphism is in Hardy-Weinberg equilibrium for both methods, however, using cyclePROBE as detection method the polymorphism information content is increased to 0.734.

We used PROBE also as an isothermic method for the detection of the three common alleles at the intron 8 splice acceptor site of the CFTR gene. FIG. 55 shows a schematic presentation of the expected diagnostic products with the theoretical mass values. The reaction was also performed in the antisense direction.

Figure 56A:
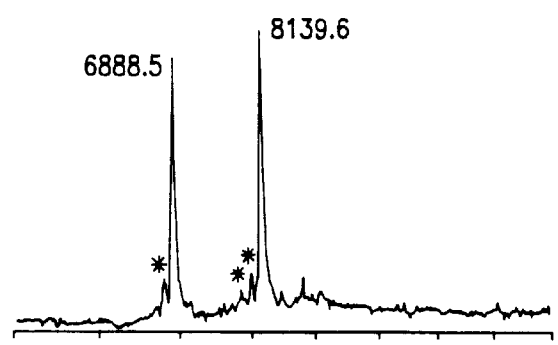
FIG. 56 shows the MALDI-TOF-MS spectra recorded directly from the precipitated extended PROBE reaction products. Detection of all three common alleles of the polyT tract at the 3' end of Intron 8 of the CFTR gene. (a) T5/T9 heterozygous, (b) T7/T9 heterozygous (Example 11).
Figure 56B:
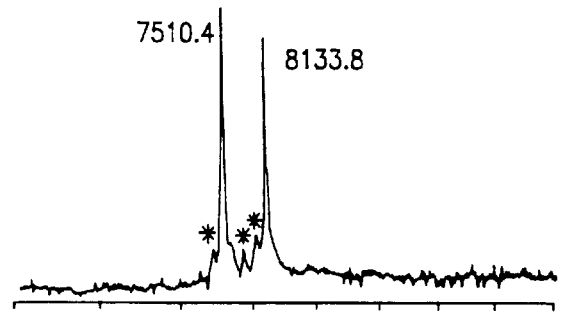

FIG. 56 demonstrates that all three common alleles (T5, T7, and T9, respectively) at this locus could be reliably disclosed by this method. Reference to FIG. 56 indicates that both mass accuracy and precision with the reflectron time of flight used in this study ranged from 0–0.4%, with a relative standard deviation of 0.13%. This corresponds to far better than single base accuracy for the up to <90-mer diagnostic products generated in the IFNAR system. Such high analytical sensitivity is sufficient to detect single or multiple insertion/deletion mutations within the repeat unit or its flanking regions, which would induce >1% mass shifts in a 90-mer. This is analogous to the FIG. 56 polyT tract analysis. However, other mutations (i.e. an A to T or a T to A mutation within the IFNAR gene A3T repeat) which do not cause premature product termination are not detectable using any dNTP/ddNTP combination with PROBE and low performance MS instrumentation; a 9 Da shift in a 90-mer corresponds to a 0.03% mass shift. Achieving the accuracy and precision required to detect such minor mass shifts has been demonstrated with higher performance instrumentation such as Fourier transform (FT)MS, for which single Da accuracy is obtained up to 100-mers. Further, tandem FTMS, in which a mass shifted fragment can be isolated within the instrument and dissociated to generate sequence specific fragments, has been demonstrated to locate point mutations to the base in comparably sized products. Thus the combination of PROBE with higher performance instrumentation will have an analytical sensitivity which can be matched only by cumbersome full sequencing of the repeat region.

EXAMPLE 12

Improved Apolipoprotein E Genotyping Using Primer Oligo Base Extension (PROBE) and MALDI-TOF Mass Spectrometry Materials and Methods PCR Amplification.

Human leukocytic genomic DNA from 100 anonymous individuals from a previously published study (Braun, A et al., (1992) *Human Genet* 89:401–406) were screened for apolipoprotein E genotypes using conventional methods. PCR primers to amplify a portion of exon 4 of the apo E gene were delineated according to the published sequence (Das, H K et al., (1985) *J Biol Chem* 260:6240–6247) (forward primer, apoE-F: 5'-GGC ACG GCT GTC CAA GGA G-3' SEQ ID. NO.41; reverse, apoE-R: 5'-AGG CCG CGC TCG GCG CCC TC-3' SEQ ID. NO.42). Taq polymerase and 10× buffer were purchased from Boehringer-Mannheim (Germany) and dNTPs from Pharmacia (Freiburg, Germany). The total reaction volume was 50 µL including 8 pmol of each primer and 10% DMSO (dimethylsulfoxide, Sigma) with approximately 200 ng of genomic DNA used as template. Solutions were heated to 80° C. before the addition of 1 U polymerase; PCR conditions were: 2 min at 94° C., followed by 40 cycles of 30 sec at 94° C., 45 sec at 63° C., 30 sec at 72° C., and a final extension time of 2 min at 72° C.

Restriction Enzyme Digestion and Polyacrylamide Electrophoresis.

CfoI and Rsa I and reaction buffer L were purchased from Boehringer-Mannheim, and Hha I from Pharmacia (Freiburg, Germany). For CfoI alone and simultaneous CfoI/RsaI digestion, 20 pL of PCR products were diluted with 15 μL water and 4 pL Boehringer-Mannheim buffer L; after addition of 10 units of appropriate restriction enzyme (s) the samples were incubated for 60 min at 37° C. The procedure for simultaneous HhaI/RsaI digestion required first digestion by RsaI in buffer L for one hour followed by addition of NaCl (50 mM end concentration) and HhaI, and additional incubation for one hour. 20 pL of the restriction digest were analyzed on a 12% polyacrylamide gel as described elsewhere (Hixson, J E (1990) J Lipid Res 31:545–548). Recognition sequences of RsaI and CfoI (HhaI) are GT/AC and GCG/C, respectively; masses of expected digestion fragments from the 252-mer PCR product with CfoI alone and the simultaneous double digest with CfoI (or HhaI) and RsaI are given in Table IV.

Thermo-PROBE.

PCR amplification was performed as described above, but with products purified with the Qiagen 'Qiaquick' kit to remove unincorporated primers. Multiplex Thermo-PROBE was performed with 35 μL PCR product and 8 pmol each of the codon 112 (5'-GCG GAC ATG GAG GAC GTG-3' SEQ ID. NO.43) and 158 (5'-GAT GCC GAT GAC CTG CAG AAG-3' SEQ ID. NO.44) detection primers in 20 μL including ~1 pmol purified biotinylated antisense template immobilized on streptavidin coated magnetic beads, 2.5 units Thermosequenase, 2 μL Thermosequenase buffer, 50 μM of each dNTP and 200 μM of ddXTP, with the base identity of N and X as described in the text. Cycling conditions were: denaturation (94° C., 30 sec) followed by 30 cycles at 94° C. (10 min) and 60° C. (45 sec).

Sample Preparation and Analysis by MALDI-TOF MS.

For precipitation (Stults, J T et al., (1991) *Rapid Commun Mass Spectrom* 5: 359–363) of both digests and PROBE products, 5 μL 3M ammonium acetate (pH 6.5), 0.5 μL glycogen (10 mg/ml, Sigma), and 110 μL absolute ethanol were added to 50 μL of the analyte solutions and stored for 1 hour at room temperature. After 10 min centrifugation at 13,000 g the pellet was washed in 70% ethanol and resuspended in 1 μL 18 Mohm/cm $H_2O$ water. Where noted in the text, additional desalting was achieved by shaking 10–20 μL of ammonium saturated DOWEX (Fluka #44485) cation exchange beads in 40 μL of analyte. The beads, purchased in the protonated form, were pre-treated with three 5 min spin-decant steps in 2M $NH_4OH$, followed with $H_2O$ and 10 mM ammonium citrate.

0.35 μL of resuspended DNA was mixed with 0.35–1.3 μL matrix solutions (Wu, K J et al., (1993) *Rapid Commun Mass Spectrom* 7:142–146) 0.7M 3-hydroxypicolinic acid (3-HPA), 0.07M ammonium citrate in 1:1 $H_2O:CH_3CN$) on a stainless steel sample target disk and allowed to air dry preceding spectrum acquisition using a Thermo Bioanalysis Vision 2000 MALDI-TOF operated in reflectron mode with 5 and 20 kV on the target and conversion dynode, respectively. Theoretical average molecular masses ($M_r$(calc)) of the fragments were calculated from atomic compositions; the mass of a proton (1.08 Da) is subtracted from raw data values in reporting experimental molecular masses ($M_r$ (exp)) as neutral basis. An external calibration generated from eight peaks (3000–18000 Da) was applied to all spectra.

Results

Digestion with CfoI Alone.

Figure 57A:
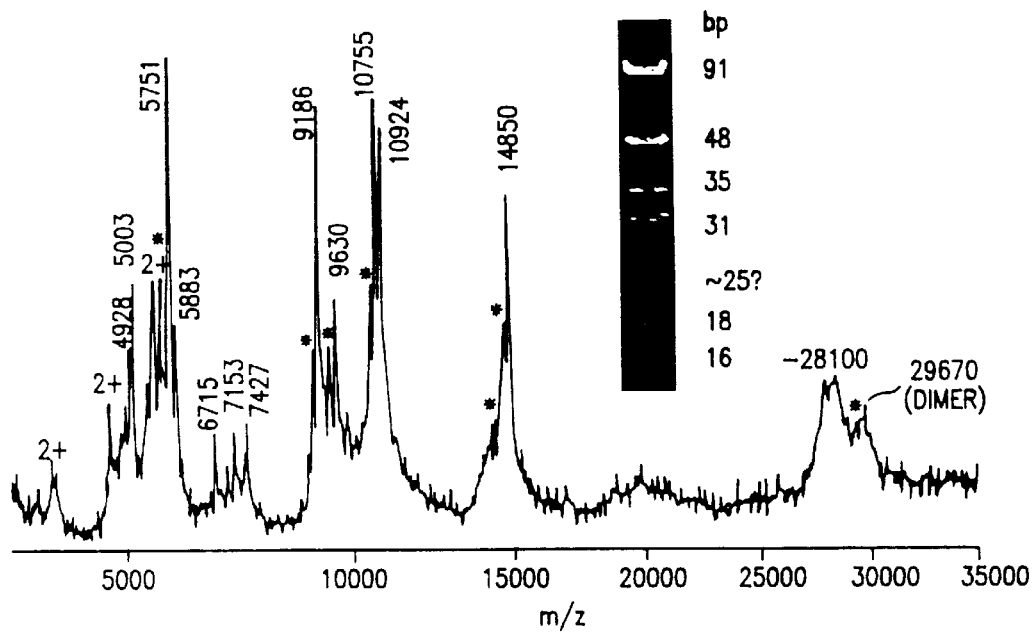
FIG. 57 shows a mass spectrum of the digestion of a 252-mer ApoE gene PCR product ($\epsilon3/\epsilon3$ genotype) as described in Example 12 using a) CfoI alone and b) CfoI plus RsaI. Asterisks: depurination peaks.

The inset to FIG. 57a shows a 12% polyacrylamide gel electrophoretic separation of an ε3/ε3 genotype after digestion of the 252 bp apo E PCR product with CfoI. Comparison of the electrophoretic bands with a molecular weight ladder shows the cutting pattern to be as mostly as expected (Table IV) for the ε3/ε3 genotype. Differences are that the faint band at approximately 25 bp is not expected, and the smallest fragments are not observed. The accompanying mass spectrum of precipitated digest products shows a similar pattern, albeit at higher resolution. Comparison with Table IV shows that the observed masses are consistent with those of single-stranded DNA; the combination of an acidic matrix environment (3-HPA, $pK_a$ 3) and the absorption of thermal energy via interactions with the 337 nm absorbing 3-HPA upon ionization is known to denature short stretches of dsDNA under normal MALDI conditions (Tang, K et al., (1994) *Rapid Commun Mass Spectrom* 8:183–186).

The approximately 25-mers, unresolved with electrophoresis, are resolved by MS as three single stranded fragments; while the largest (7427 Da) of these may represent a doubly charged ion from the 14.8 kDa fragments (m=14850, z=2; m/z=7425), the 6715 and 7153 Da fragments could result from PCR artifacts or primer impurities; all three peaks are not observed when PCR products are purified with Qiagen purification kits prior to digestion. The Table 1V 8871 Da 29-mer sense strand 3'-terminal fragment is not observed; the species detected at 9186 Da is consistent with the addition of an extra base (9187−8871=316, consistent with A) by the Taq-polymerase during PCR amplification (Hu, G et al., (1993) *DNA and Cell Biol* 12:763–770). The individual single strands of each double strand with <35 bases (11 kDa) are resolved as single peaks; the 48-base single strands ($M_r$(calc) 14845 and 14858), however, are observed as an unresolved single peak at 14850 Da. Separating these into single peaks would require a mass resolution (m/Δm, the ratio of the mass to the peak width at half height) of 14850/13=1140, nearly an order of magnitude greater than what is routine with the standard reflectron time-of-flight instrumentation used in this study; resolving such small mass differences with high performance instrumentation such as Fourier transform MS, which provides up to three orders of magnitude higher resolution in this mass range, has been demonstrated. The 91-mer single strands ($M_r$(calc) 27849 and 28436) are also not resolved, even though this requires a resolution of only <50. The dramatic decrease in peak quality at higher masses is due to metastable fragmentation (i.e. depurination) resulting from excess internal energy absorbed during and subsequent to laser irradiation.

Simultaneous Digestion with CfoI and RsaI.

Figure 57B:
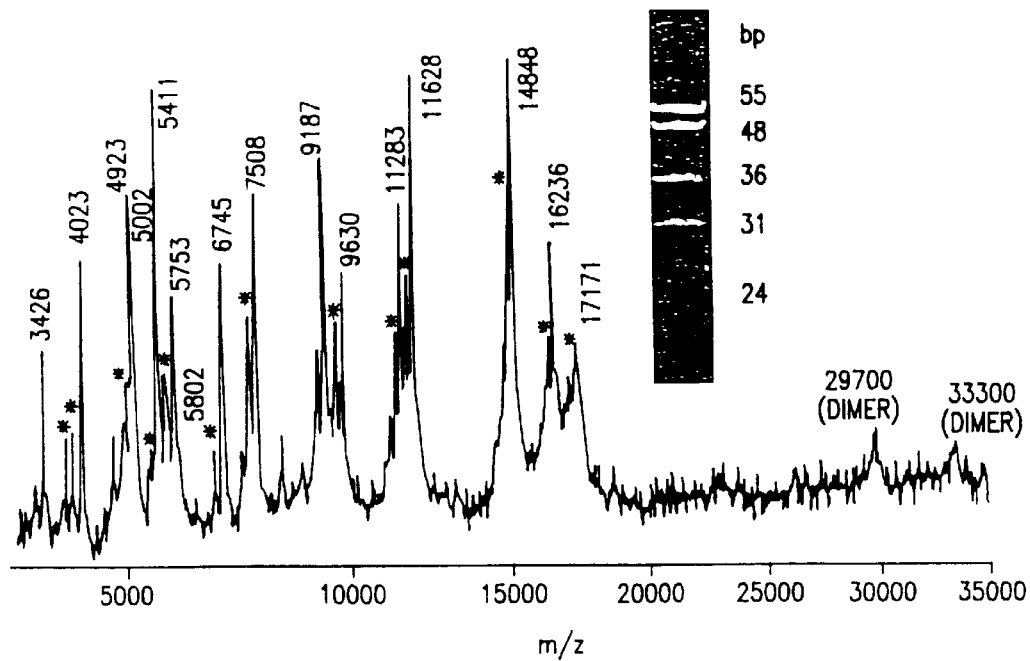

FIG. 57b (inset) shows a 12% polyacrylamide gel electrophoresis separation of ε3/ε3 double digest products, with bands consistent with dsDNA with 24, 31, 36, 48, and 55 base pairs, but not for the smaller fragments. Although more peaks are generated (Table IV) than with CfoI alone, the corresponding mass spectrum is more easily interpreted and reproducible since all fragments contain <60 bases, a size range far more appropriate for MALDI-MS if reasonably accurate $M_r$ values (e.g. 0.1%) are desired. For fragments in this mass range, the mass measuring accuracy using external calibration is ~0.1% (i.e. ≦±10 Da at 10 kDa). Significant depurination (indicated in Figure by asterisk) is observed for all peaks above 10 kDa, but even the largest peak at 17171 Da is clearly resolved from its depurination peak so that an accurate $M_r$ can be measured. Although molar concentrations of digest products should be identical, some discrimination against those fragments with ≦11 bases is observed, probably due to their loss in the ethanol/glycogen precipitation step. The quality of MS results from simultaneous digestion with CfoI (or HhaI) and RsaI is superior to those with CfoI (or HhaI) alone, since the smaller fragments generated are good for higher mass accuracy measurements, and with all genotypes there is no possibility for dimer peaks overlapping with high mass diagnostic peaks. Since digestion by RsaI/CfoI and RsaI/HhaI produce the same restriction fragments but the former may be performed as a simultaneous digest since their buffer requirements are the same, we used this enzyme mixture for all subsequent genotyping by restriction digest protocols.

TABLE IV

Mass and Copy Number of Expected Restriction Digest Products

| (+) | (−) | e2/e2 | e2/e3 | e2/e4 | e3/e3 | e3/e4 | e4/e4 |
|---|---|---|---|---|---|---|---|
| Table IVa. CfoI Digestion* | | | | | | | |
| 5781, 5999 | | — | — | 1 | — | 1 | 2 |
| 10752, 10921 | | — | 1 | 1 | 2 | 2 | 2 |
| 14845, 14858 | | — | 1 | 1 | 2 | 2 | 2 |
| 22102, 22440 | | — | — | 1 | — | 1 | 2 |
| 25575, 25763 | | 2 | 1 | 1 | — | — | — |
| 27849, 28436 | | 2 | 2 | 1 | 2 | 1 | — |
| Table IVb. CfoI/RsaI Digestion* | | | | | | | |
| 3428, 4025 | | — | 1 | 1 | 2 | 2 | 2 |
| 5283, 5880 | | — | — | 1 | — | 1 | 2 |
| 5781, 5999 | | — | — | 1 | — | 1 | 2 |
| 11279, 11627 | | 2 | 2 | 1 | 2 | 1 | — |
| 14845, 14858 | | — | 1 | 1 | 2 | 2 | 2 |
| 18269, 18848 | | 2 | 1 | 1 | — | — | — |

[a]CfoI Ivariant fragment masses: 1848, 2177, 2186, 2435, 4924, 5004, 5412, 5750, 8871, 9628 Da.
[b]CfoI/RsaI Invariant fragment masses: 1848, 2177, 2186, 2436, 4924, 5004, 5412, 5750, 6745, 7510, 8871, 9628, 16240, 17175 Da.

TABLE V

| | ddT $M_r$ (calc) | ddT $M_r$ (exp) | ddC $M_r$ (calc) | ddC $M_r$ (exp) |
|---|---|---|---|---|
| ε2/ε2 | [a]5918, [b]6768 | — | [a]6536, [b]7387 | — |
| ε2/ε3 | [a]5918, [b]6768, [b]7965 | 5919, 6769, 7967 | [a]6536, [b]6753, [b]7387 | 6542, 6752, 7393 |
| ε2/ε4 | [a]5918, [b]6768, [b]7965, [a]8970 | — | [a]5903, [b]6536, [b]6753, [b]7387 | — |
| ε3/ε3 | [a]5918, [b]7965 | 5918, 7966 | [a]6536, [b]6753 | 6542, 6756 |
| ε3/ε4 | [a]5918, [b]7965, [a]8970 | 5914, 7959, 8965 | [a]5903, [a]6536, [b]6753 | 5898, 6533, 6747 |
| ε4/ε4 | [b]7965, [a]8970 | 7966, 8969 | [a]5903, [b]6753 | 5900, 6752 |

[a]From codon 112 detection primer (unextended 5629.7 Da).
[b]From codon 158 detection primer (unextended 6480.3 Da).
Dashed lines: this genotype not available from the analyzed pool of 100 patients.

Figure 58A:
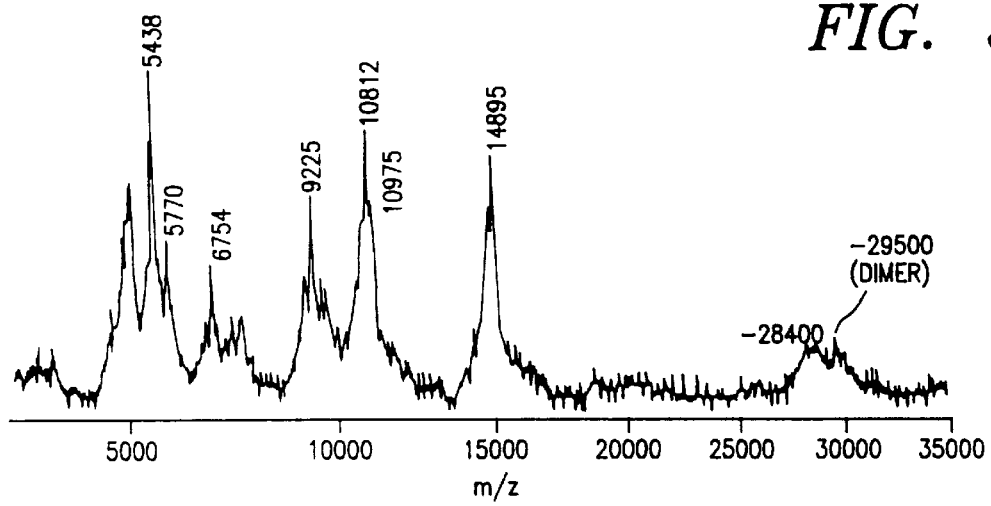
FIG. 58 shows a mass spectrum of the ApoE gene PCR product ($\epsilon3/\epsilon3$ genotype) digested by CfoI and purified by a) single and b) double ethanol/glycogen and c) double isopropyl alcohol/glycogen precipitations.
Figure 58B:
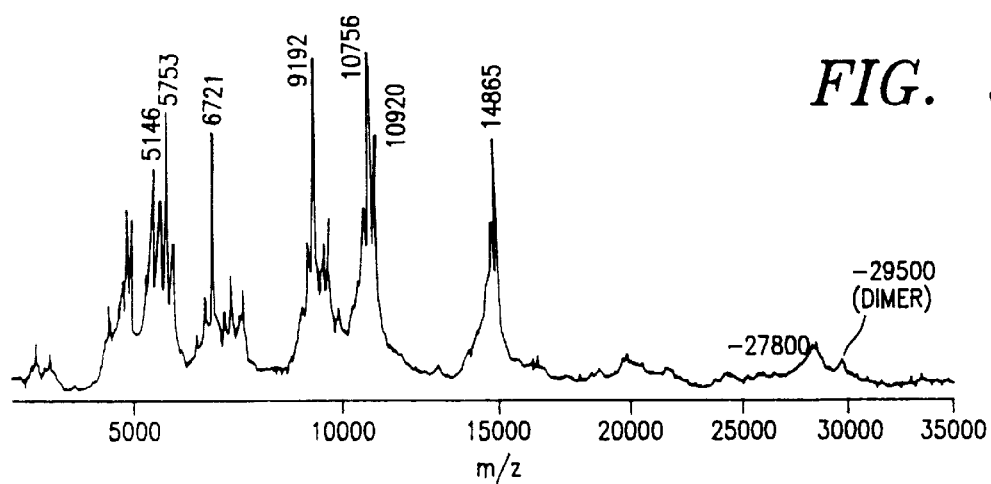
Figure 58C:
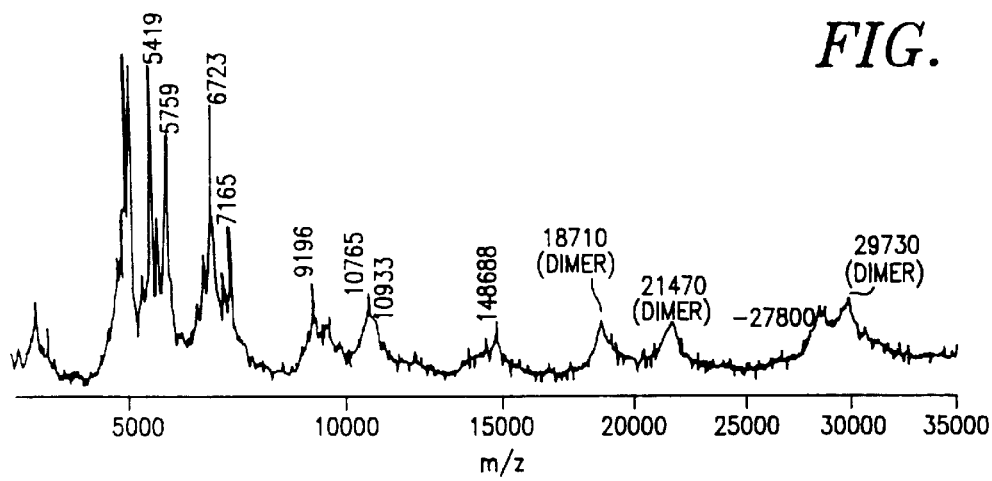

FIG. 58a–c shows the ApoE ε3/ε3 genotype after digestion with CfoI and a variety of precipitation schemes; equal volume aliquots of the same PCR product were used for each. The sample treated with a single precipitation (FIG. 58a) from an ammonium acetate/ethanol/glycogen solution results in a mass spectrum characterized by broad peaks, especially at high mass. The masses for intense peaks at 5.4, 10.7, and 14.9 kDa are 26 Da (0.5%), 61 Da (0.6%), and 45 Da (0.3%) Da higher, respectively, than the expected values; the resolution (the ratio of a peak width at half its total intensity to the measured mass of the peak) for each of these is ~50, and decreases with increasing mass. Such observations are consistent with a high level of nonvolatile cation adduction; for the 10.8 kDa fragment, the observed mass shift is consistent with a greater than unit ratio of adducted:nonadducted molecular ions.

MS peaks from a sample redissolved and precipitated a second time are far sharper (FIG. 58b), with resolution values nearly double those of the corresponding FIG. 58a peaks. Mass accuracy values are also considerably improved; each is within 0.07% of its respective calculated values, close to the independently determined instrumental limits for DNA measurement using 3-HPA as a matrix. Single (not shown) and double (FIG. 58C) precipitations with isopropyl alcohol (IPA) instead of ethanol result in resolution and mass accuracy values comparable to those for corresponding ethanol precipitations, but enhanced levels of dimerization are observed, again potentially confusing measurements when such dimers overlap with higher mass 'diagnostics' monomers present in the solution. EtOH/ammonium acetate precipitation with glycogen as a nucleation agent results in nearly quantitative recovery of fragments except for the 7-mers, serving as a simultaneous concentration and desalting step prior to MS detection. Precipitation from the same EtOH/ammonium acetate solutions in the absence of glycogen results in far poorer recovery, especially at low mass.

The results indicate that to obtain accurate $M_r$(exp) values after either 1 PA and EtOH precipitations, a second precipitation is necessary to maintain high mass accuracy and resolution.

The ratio of matrix:digest product also affects spectral quality; severe suppression of higher mass fragments (not shown) observed with 1:1 volume matrix: digest product (redissolved in 1 µL) is alleviated by using a 3–5 fold volume excess of matrix.

Apo E genotyping by enzymatic digestion. Codon 112 and 158 polymorphisms both fall within CfoI (but not RsaI) recognition sequences. In the 252 bp PCR product studied here, invariant (i.e. cut in all genotypes) sites cause cuts after bases 31, 47, 138, 156, 239, and 246. The cutting site after base 66 is only present for ε4, while that after base 204 is present in both ε3 and ε4; the ε2 genotype is cut at neither of these sites. These differences in the restriction pattern can be demonstrated as variations in mass spectra. FIG. 59 shows mass spectra from several ApoE genotypes available from a pool of 100 patients (Braun, A et al., (1992) *Hum Genet* 89:401–406). Vertical dashed lines are drawn through those masses corresponding to the expected Table IV diagnostic fragments; other labeled fragments are invariant. Referring to Table IV, note that a fragment is only considered 'invariant' if it is present in duplicate copies for a given allele; to satisfy this requirement, such a fragment must be generated in each of the ε2, ε3, and ε4 alleles.

Figures 59A, 59B:
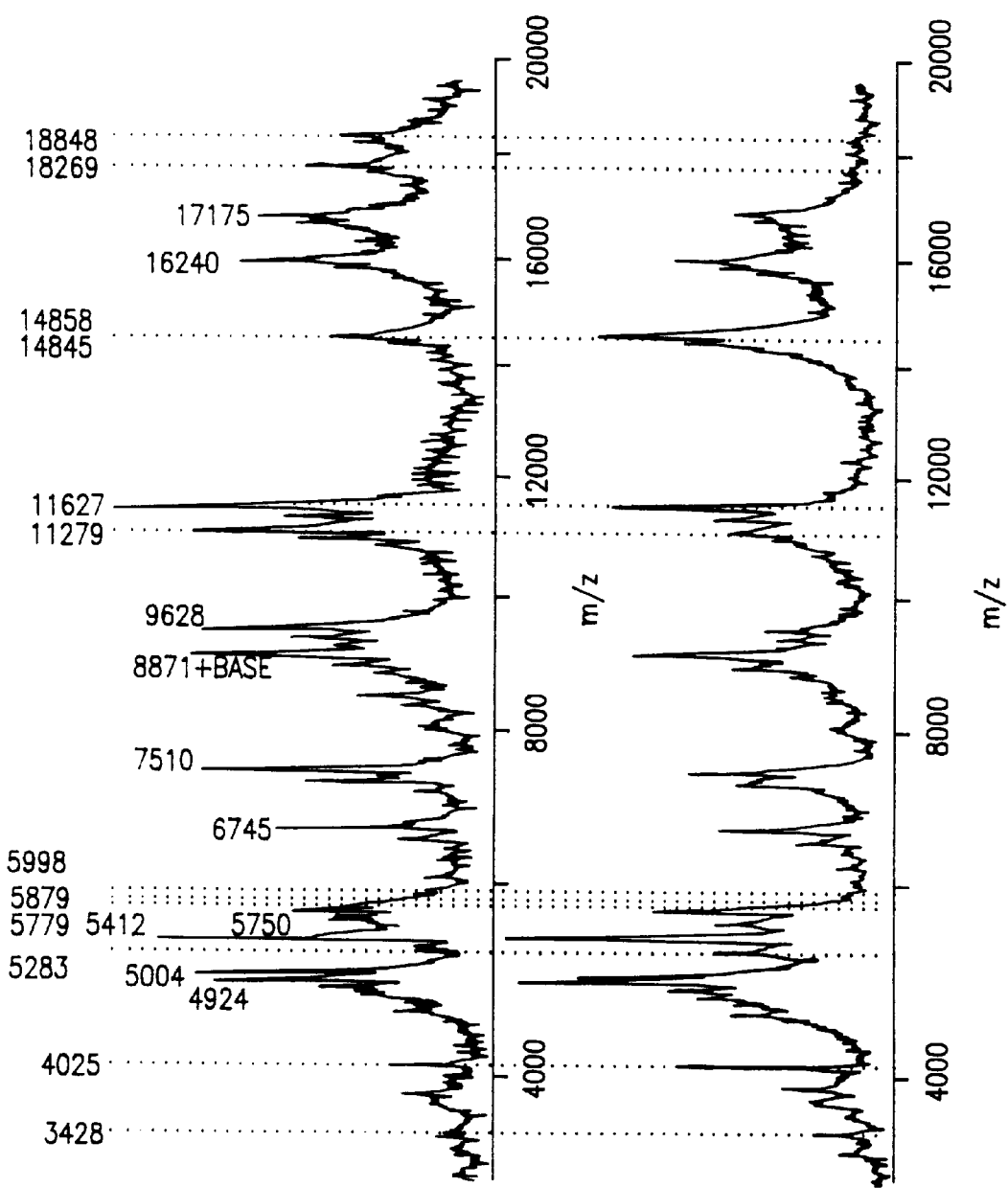
FIG. 59 shows a mass spectrum of the CfoI/RsaI digest products from a) $\epsilon2/\epsilon3$, b) $\epsilon3/\epsilon3$, c) $\epsilon3/\epsilon4$, and d) $\epsilon4/\epsilon4$ genotypes. Dashed lines are drawn through diagnostic fragments.

The spectrum in FIG. 59a contains all of the expected invariant fragments above 3 kDa, as well as diagnostic peaks at 3428 and 4021 (both weak), 11276 and 11627 (both intense), 14845, 18271, and 18865 Da. The spectrum in FIG. 59b is nearly identical except that the pair of peaks at 18 kDa is not detected, and the relative peak intensities, most notably among the 11–18 kDa fragments, are different. The spectrum in FIG. 59c also has no 18 kDa fragments, but instead has new low intensity peaks between 5–6 kDa. The intensity ratios for fragments above 9 kDa are similar to those of FIG. 59b except for a relatively lower 11 kDa fragment pair. FIG. 59d, which again contains the 5–6 kDa cluster of peaks, is the only spectrum with no 11 kDa fragments, and like the previous two also has no 18 kDa fragment.

Despite the myriad of peaks in each spectrum, each genotype can be identified by the presence and absence of only a few of the Table IVb diagnostic peaks. Due to the limited resolution of the MALDI-TOF instrumentation employed, the most difficult genotypes to differentiate are those based upon the presence or absence of the four diagnostic fragments between 5.2 and 6.0 kDa characteristic of the E4 allele, since these fragments nearly overlap with several invariant peaks. We have observed that the 5283 Da diagnostic fragment overlaps with a depurination peak from the 5412 Da invariant fragment, and that the 5781 Da diagnostic peak is normally not completely resolved from the 5750 Da invariant fragment. Thus, distinguishing between an $\epsilon 2/\epsilon 4$ and $\epsilon 2/\epsilon 3$, or between an $\epsilon 3/\epsilon 4$ and an $\epsilon 3/\epsilon 3$ allele, relies upon the presence or absence of the 5880 and 5999 Da fragments. Each of these is present in FIGS. 59c and 59d, but not in 59a or 59b.

Figures 59C, 59D:
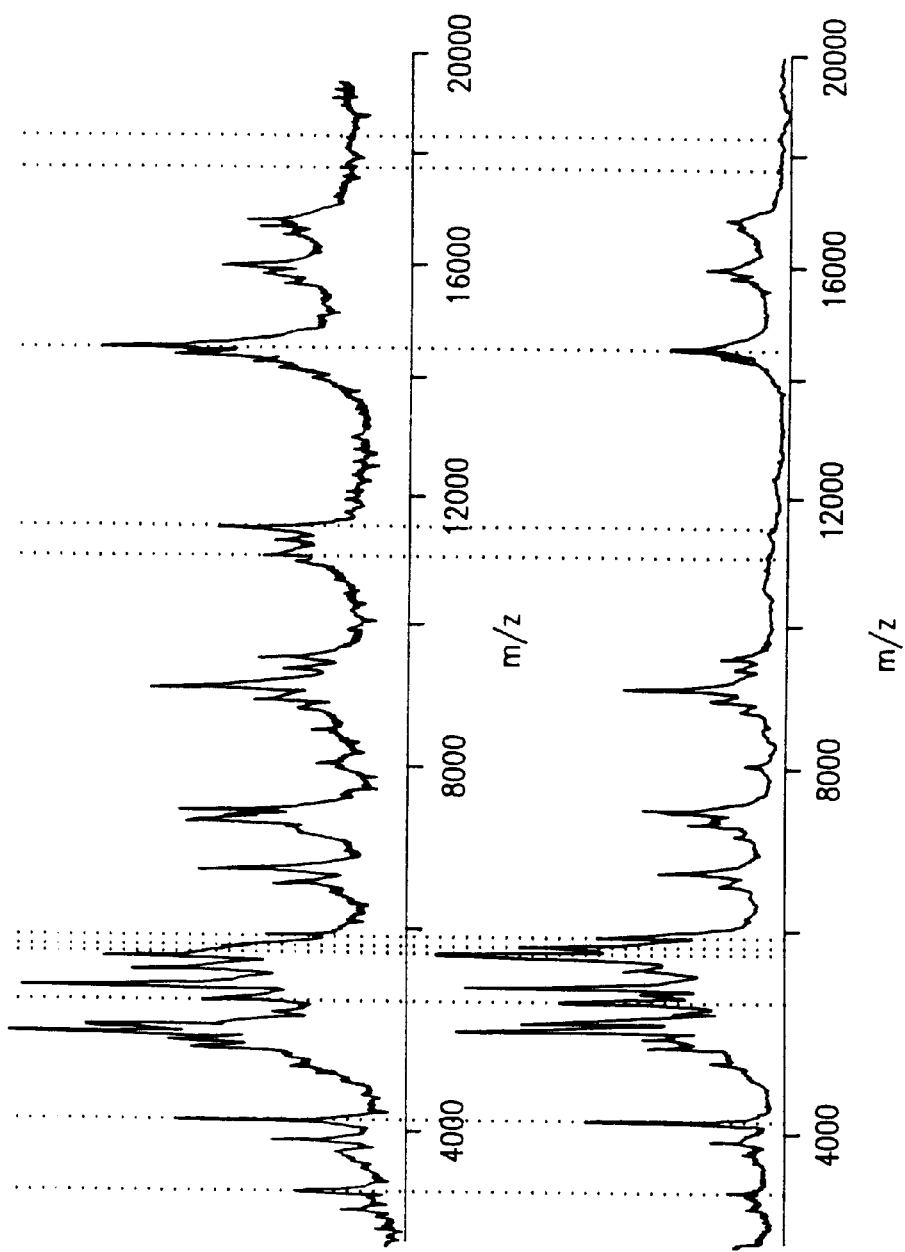
Figure 60:
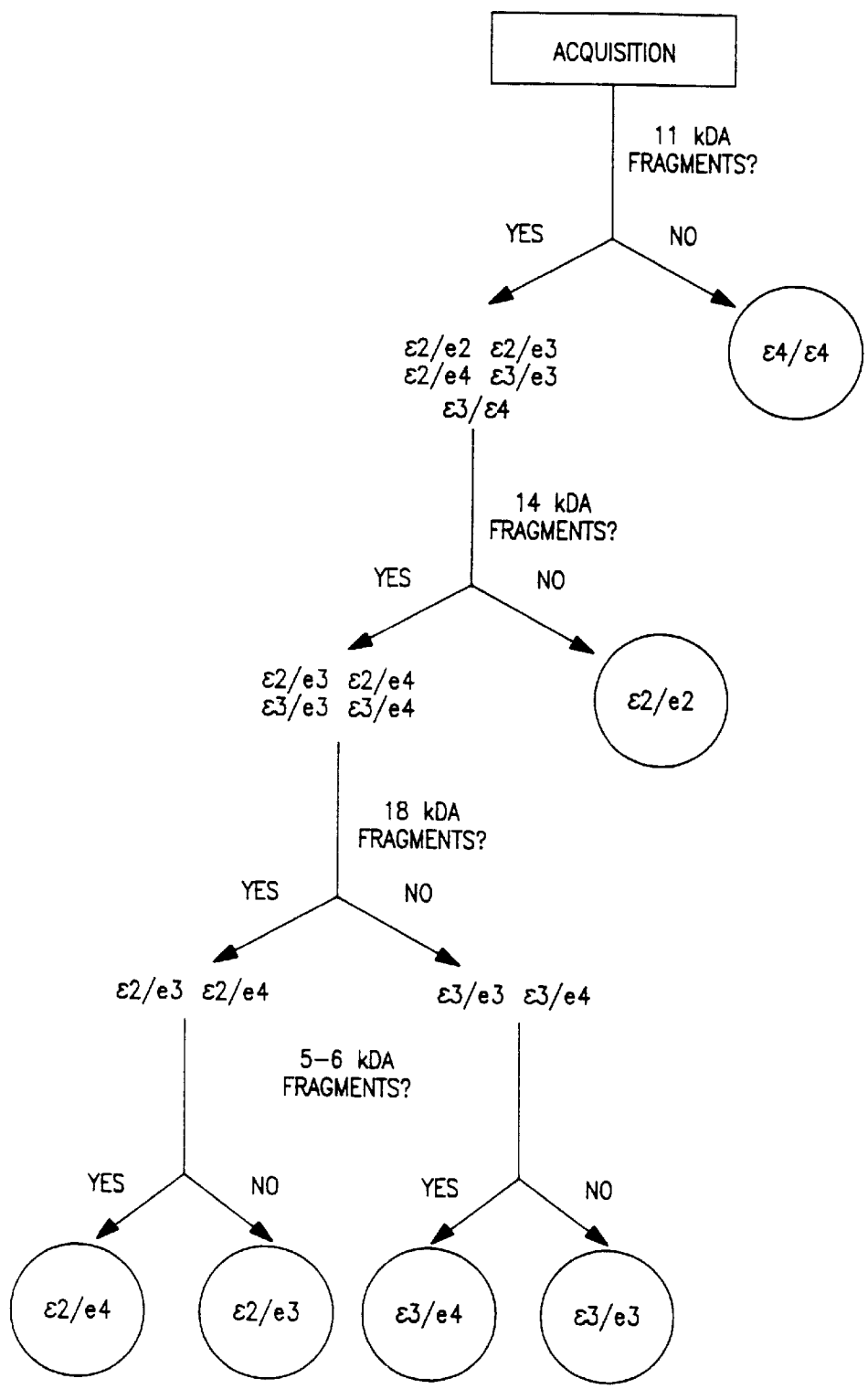
FIG. 60 shows a scheme for rapid identification of unknown ApoE genotypes following simultaneous digestion of a 252-mer apo E gene PCR product by the restriction enzymes CfoI and RsaI.

The genotype of each of the patients in FIG. 59 can be more rapidly identified by reference to the flowchart in FIG. 60. Consider the FIG. 59a spectrum. The intense pair of peaks at 11 kDa discounts the possibility of homozygous 64, but does not differentiate between the other five genotypes. Likewise, the presence of the unresolved 14.8 kDa fragments is inconsistent with homozygous $\epsilon 2$, but leaves four possibilities ($\epsilon 2/\epsilon 3$, $\epsilon 2/\epsilon 4$, $\epsilon 3/\epsilon 3$, $\epsilon 3/\epsilon 4$). Of these only $\epsilon 2/\epsilon 3$ and $\epsilon 2/\epsilon 4$ are consistent with the 18 kDa peaks; the lack of peaks at 5283, 5879, 5779, and 5998, Da indicate that the FIG. 59a sample is $\epsilon 2/\epsilon 3$. Using the same procedure, the FIGS. 59b–d genotypes can be identified as $\epsilon 3/\epsilon 3$, $\epsilon 3/\epsilon 4$, and $\epsilon 4/\epsilon 4$, respectively. To date, all allele identifications by this method have been consistent with, and in many cases more easily interpreted than, those attained via conventional methods. The assignment can be further confirmed by assuring that fragment intensity ratios are consistent with the copy numbers of Table IV. For instance, the 14.8 kDa fragments are of lower intensity than those at 16–17 kDa in FIG. 59a, but the opposite is seen in FIGS. 59b–d. This is as expected, since in the latter three genotypes the 14.8 kDa fragments are present in duplicate, but the first is a heterozygote containing $\epsilon 2$, so that half of the PCR products do not contribute to the 14.8 kDa signal. Likewise, comparison of the 11 kDa fragment intensify to those at 9.6 and 14.8 kDa indicate that this fragment is double, double, single, and zero copy in FIGS. 59a, d, respectively. These data confirm that MALDI can perform in a semi-quantitative way under these conditions.

ApoE genotyping by Primer Oligo Base Extension (PROBE). The PROBE reaction was also tested as a means of simultaneous detection of the codon 112 and 158 polymorphisms. A detection primer is annealed to a single-stranded PCR-amplified template so that its 3' terminus is just downstream of the variable site. Extension of this primer by a DNA polymerase in the presence of three dNTPs and one ddXTP (that is not present as a dNTP) results in products whose length and mass depend upon the identity of the polymorphic base. Unlike standard Sanger type sequencing, in which a particular base-specific tube contains ~99% dXTP and ~1% ddXTP, the PROBE mixture contains 100% of a particular ddXTP combined with the other three dNTPs. Thus with PROBE a full stop of all detection primers is achieved after the first base complementary to the ddXTP is reached.

For the $\epsilon 2/\epsilon 3$ genotype, the PROBE reaction (mixture of ddTTP, dATP, dCTP, dGTP) causes a $M_r(exp)$ shift of the codon 112 primer to 5919 Da, and of the codon 158 primer to 6769 and 7967 Da (Table V); a pair of extension products results from the single codon 158 primer because the $\epsilon 2/\epsilon 3$ genotype is heterozygous at this position. Three extension products (one from codon 158, two from 112) are also observed from the heterozygote $\epsilon 3/\epsilon 4$ (FIG. 61c and Table V), while only two products (one from each primer) are observed from the FIG. 61b ($\epsilon 3/\epsilon 3$) and FIG. 59d ($\epsilon 4/\epsilon 4$) homozygote alleles. Referring to Table V, each of the available alleles result in all expected ddT reaction product masses within 0.1% of the theoretical mass, and thus each is unambiguously characterized by this data alone. Further configuration of the allele identities may be obtained by repeating the reaction with ddCTP (plus dATP, dTTP, dGTP); these results, summarized also in Table V, unambiguously confirm the ddT results.

Appropriateness of the methods. Comparison of FIGS. 59 (restriction digestion) and 61 (PROBE) indicates that the PROBE method provides far more easily interpreted spectra for the multiplex analysis of codon 112 and 158 polymorphisms than does the restriction digest analysis. While the digests generate up to ~25 peaks per mass spectrum and in some case diagnostic fragments overlapping with invariant fragments, the PROBE reaction generates a maximum of only two peaks per detection primer (i.e. polymorphism). Automated peak detection, spectrum analysis, and allele identification would clearly be far more straightforward for the latter. Spectra for highly multiplexed PROBE, in which several polymorphic sites from the same or different PCR products are measured from one tube, are also potentially simple to analyze. Underscoring its flexibility, PROBE data analysis can be further simplified by judicious a priori choice of primer lengths, which can be designed so that no primers or products can overlap in mass.

Thus while PROBE is the method of choice for large scale clinical testing of previously well characterized polymorphic sites, the restriction digest analysis as described here is ideally suited to screening for new mutations. The identity of each of the two polymorphisms discussed in this study affects the fragment pattern; if this is the only information used, then the MS detection is a faster alternative to conventional electrophoretic separation of restriction fragment length polymorphism products. However, the exact measurement of fragment $M_r$values can also give information on about sites completely remote from the enzyme recognition site since other single point mutations necessarily alter the mass of each of the single strands of the double stranded fragment containing the mutation. The 252 bp PCR product could also contain allelic variants resulting in, for example, previously described Gly127Asp (Weisgraber, K H et al, (1984) *J Clin Invest* 73:1024–1033), Arg136Ser (Wardell, M R et al., (1987) *J Clin Invest* 80:483–490), Arg142Cys (Horie, Y et al., (1992) *J Biol Chem* 267:1962–1968), Arg145Cys (Rall S C Jr et al., (1982) *Proc Natl Acad Sci USA* 79:4696–4700), Lys146Glu (Mann, W A et al., (1995) *J Clin Invest* 96:1100–1107), or Lys146Gln (Smit, M et al., (1990) *J Lipid Res* 31:45–53) substitutions. The G→A base substitution which codes for the Gly127Asp amino acid substitution would result in a −16 Da shift in the sense strand, and in a +15 Da (C→T) shift in the antisense strand, but not in a change in the restriction pattern. Such a minor change would be virtually invisible by electrophoresis; however, with accurate mass determination the substitution could be detected; the invariant 55-mer fragment at 16240 (sense) and 17175 Da would shift to 16224 and 17190 Da, respectively. Obtaining the mass accuracy required to detect such minor mass shifts using current MALDI-TOF instrumentation, even with internal calibration, is not routine since minor unresolved adducts and/or poorly defined peaks limit the ability for accurate mass calling. With high performance electrospray ionization Fourier transform (ESI-FTMS) single Da accuracy has been achieved with synthetic oligonucleotides (Little, D P et al., (1995) *Proc Natl Acad Sci USA* 92:2318–2322) up to 100-mers (Little, D P et al., (1994) *J Am Chem Soc* 116:4893–4897), and similar results have recently been achieved with up to 25-mers using MALDI-FTMS (Li, Y et al., (1996) *Anal Chem* 68:2090–2096).

EXAMPLE 13

A Method for Mass Spectrometric Detection of DNA Fragments Associated With Telomerase Activity Introduction One-fourth of all deaths in the United States are due to malignant tumors (R. K. Jain, (1996) *Science*, 271, 1079–1080). For diagnostic and therapeutic purposes there is a high interest in reliable and sensitive methods of tumor cell detection.

Malignant cells can be distinguished from normal cells by different properties. One of those is the immortalization of malignant cells which enables uncontrolled cell-proliferation. Normal diploid mammalian cells undergo a finite number of population doublings in culture, before they undergo senescence. It is supposed that the number of population doublings is related to the shortening of chromosome ends, called telomers, in every cell division. The reason for said shortening is based on the properties of the conventional semiconservative replication machinery. DNA polymerases only work in 5' to 3' direction and need an RNA primer.

Immortalization is thought to be associated with the expression of active telomerase. Said telomerase is a ribonucleoprotein catalyzing repetitive elongation of templates. This activity can be detected in a native protein extract of telomerase containing cells by a special PCR-system (N. W. Kim et al. (1994) *Science*, 266, 2011–2015) known as telomeric repeat amplification protocol (TRAP). The assay, as used herein, is based on the telomerase specific extension of a substrate primer (TS) and a subsequent amplification of the telomerase specific extension products by a PCR step using a second primer (bioCX) complementary to the repeat structure. The characteristic ladder fragments of those assays are conventionally detected by the use of gel electrophoretic and labeling or staining systems. These methods can be replaced by MALDI-TOF mass spectrometry leading to faster accurate and automated detection.

Materials and Methods

Preparation of Cells $1 \times 10^6$ cultured telomerase-positive cells were pelleted, washed once with PBS (137 mM NaCl, 2.7 mM KCl, 4.3 mM $Na_2HPO_4 \cdot 7$ $H_2O$, 1.4 mM $KH_2PO_4$ in sterile DEPC water). The prepared cells may be stored at −75° C. Tissue samples have to be homogenized, according to procedures well known in the art, before extraction.

Telomerase Extraction

Pellet was resuspended in 200 μl CHAPS lysis buffer (10 mM Tris-HCl pH 7.5, 1 mM $MgCl_2$, 1 mM EGTA, 0.1 mM benzamidine, 5 mM β-mercaptoethanol, 0.5% CHAPS, 10% glycerol) and incubated on ice for 30 min. The sample was centrifuged at 12,000 g for 30 min at 4° C. The supernatant was transferred into a fresh tube and stored at −75° C. until use.

TRAP-assay

2 μl of telomerase extract were added to a mixture of 10×TRAP buffer (200 mM Tris-HCl pH 8.3, 15 mM $MgCl_2$, 630 mM KCl, 0.05% Tween 20, 10 mM EGTA) 50×dNTP-mix (2.5 mM each dATP, dTTP, dGTP and dCTP), 10 pmol of TS primer and 50 pmol of bioCX primer in a final volume of 50 μl. The mixture was incubated at 30° C. for 10 minutes and 5 min. at 94° C., 2 units of Taq Polymerase were added and a PCR was performed with 30 cycles of 94° C. for 30 seconds, 50° C. for 30 seconds and 72° C. for 45 seconds.

Purification of TRAP-assay Products

For every TRAP-assay to be purified, 50 μl Streptavidin M-280 Dynabeads (10 mg/ml) were washed twice with 1×BW buffer (5 mM Tris-HCl, pH 7.5, 0.5 mM EDTA, 1 M NaCl). 50 μl of 2×BW buffer were added to the PCR mix and the beads were resuspended in this mixture. The beads were incubated under gentle shaking for 15 min. at ambient temperature. The supernatant was removed and the beads were washed twice with 1×BW buffer. To the beads 50 μl 25% ammonium hydroxide were added and incubated at 60° C. for 10 min. The supernatant was saved, the procedure repeated, both supernatants were pooled and 300 μl ethanol (100%) were added. After 30 min. the DNA was pelleted at 13,000 rpm for 12 min., the pellet was air-dried and resuspended in 600 nl ultrapure water.

MALDI-TOF MS of TRAP-assay Products 300 nl sample were mixed with 500 nl of saturated matrix-solution (3-HPA: ammonium citrate=10:1 molar ratio in 50% aqueous acetonitril), dried at ambient temperature and introduced into the mass spectrometer (Vision 2000, Finigan MAT). All spectra were collected in reflector mode using external calibration.

Sequences and Masses bioCX: d(bio-CCC TTA CCC TTA CCC TTA CCC TAA SEQ ID NO.45), mass: 7540 Da.

TS: d(AAT CCG TGC AGC AGA GTT SEQ ID NO.46), mass: 5523 Da.

Telomeric-repeat structure: $(TTAGGG)_n$, mass of one repeat: 1909.2

Amplification products:

TS elongated by three telomeric repeats (first amplification product): 12452 Da. (N3)

TS elongated by four telomeric repeats: 14361 Da. (N4)

TS elongated by seven telomeric repeats: 20088 Da. (N7)

Results

Figure 62:
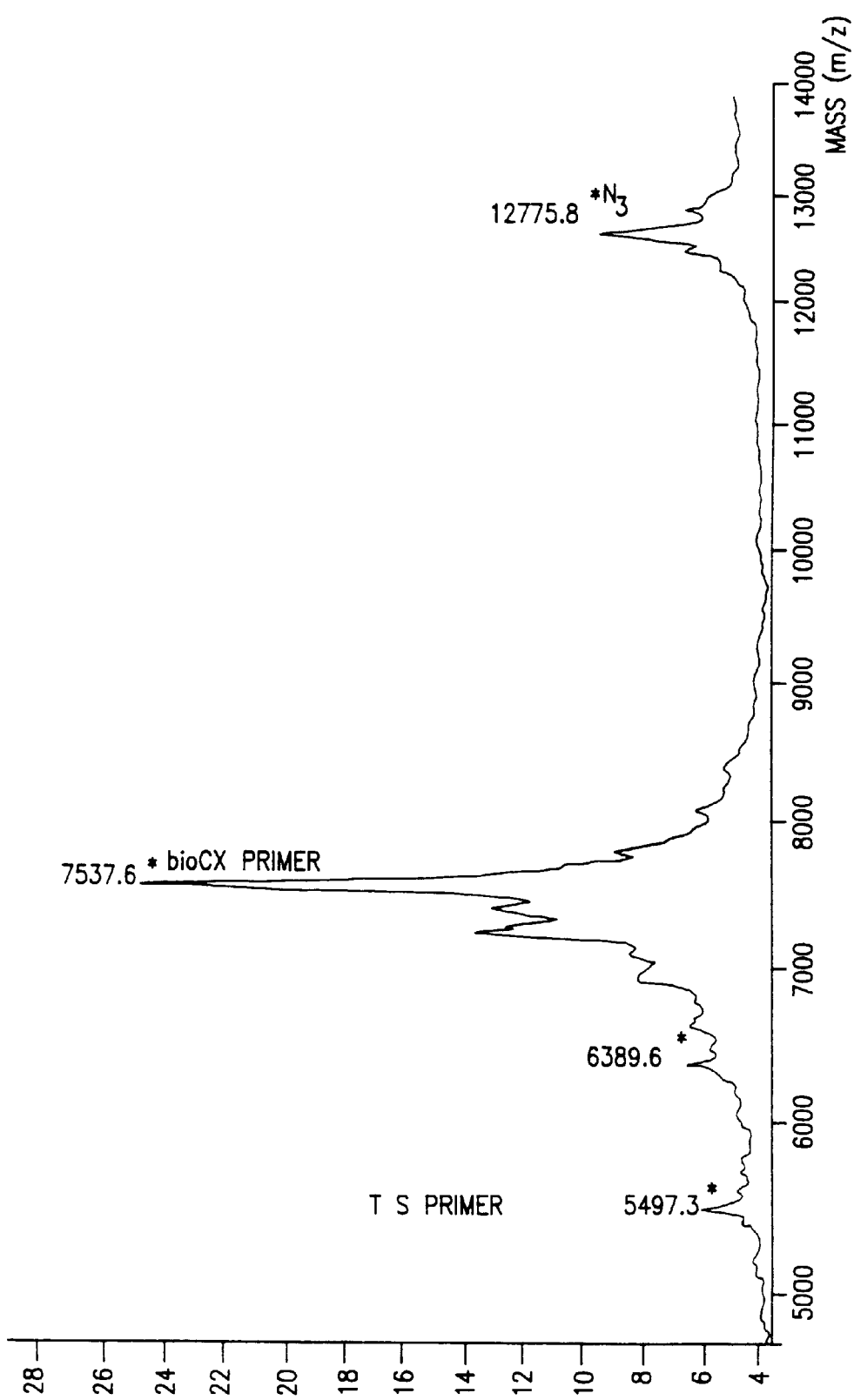
FIG. 62 shows a mass spectrum of a TRAP assay to detect telomerase activity (Example 13). The spectrum shows two of the primer signals of the PCR product TS primer at 5,497.3 Da (calc. 5523 Da) and the biotinylated bioCX primer at 7,537.6 Da (calc. 7,537 Da) and the first telomerase-specific assay product containing three telomeric repeats at 12,775.8 Da (calc. 12,452 Da) its mass is larger by one dA nucleotide (12,765Da) due to extendase activity of Taq DNA polymerase.
Figure 63:
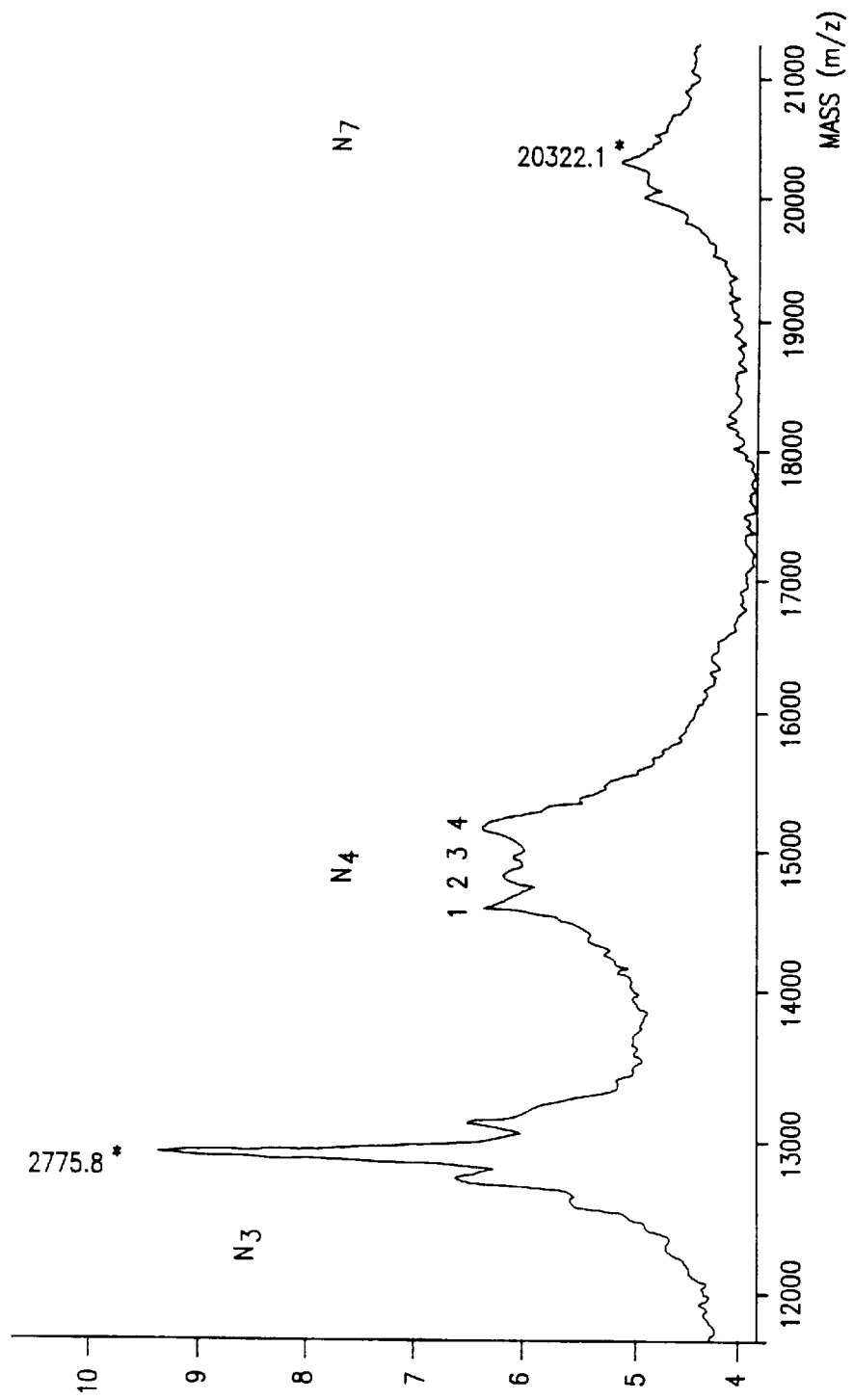
FIG. 63 depicts the higher mass range of FIG. 62, i.e. the peak at 12,775.6 Da represents the products with these telomeric repeats. The peaks at 20,322.1 Da is the result of a telomerase activity to form seven telomeric repeats (calc. 20,395 Da including the extension by one dA nucleotide). The peaks marked 1, 2, 3 and 4 contain a four telomeric repeats at 14,674 Da as well as secondary ion product.

FIG. 62 depicts a section of a TRAP-assay MALDI-TOF mass spectrum. Assigned are the primers TS and bioCX at 5497 and 7537 Da, respectively (calculated 5523 and 7540 Da). The signal marked by an asterisk represents n-1 primer product of chemical DNA synthesis. The first telomerase specific TRAP-assay product is assigned at 12775 Da. This product represents a 40 mer containing three telomeric repeats. Due to primer sequences this is the first expected amplification product of a positive TRAP-assay. The product is elongated by an additional nucleotide due to extendase activity of Taq DNA polymerase (calculated non-extended product: 12452 Da, by A extended product: 12765 Da). The signal at 6389 Da represents the doubly charged ion of this product (calculated: 6387 Da). FIG. 63 shows a section of higher masses of the same spectrum as depicted in FIG. 62, therefore the signal at 12775 Da is identical to that in FIG. 62. The TRAP-assay product containing seven telomeric repeats, representing a 64 mer also elongated by an additional nucleotide, is detected at 20322 Da (calculated: 20395

Da). The signals marked 1, 2, 3 and 4 cannot be base-line resolved. This region consists of: 1. signal of dimeric n-1 primer, 2. second TRAP-assay amplification product, containing 4 telomeric repeats and therefore representing a 46 mer (calculated: 14361 Da/14674 Da for extendase elongated product) and 3. dimeric primer-ion and furthermore all their corresponding depurination signals. There is a gap observed between the signals of the second and fifth extension product. This signal gap corresponds to the reduced band intensities observed in some cases for the third and fourth extension product in autoradiographic analysis of TRAP-assays (N. W. Kim et al. (1994), Science, 266, page 2013).

In future applications, the above-mentioned problems, caused by the dimeric primer and related signals, can be overcome using an ultrafiltration step employing a molecular weight cut-off membrane for primer removal prior to MALDI-TOF-MS analysis. This will enable an unambiguous assignment of the second amplification product.

EXAMPLE 14

A Method for Detecting Neuroblastoma-Specific Nested RT-PCR Products Via MALDI-TOF Mass Spectrometry

Introduction

Neuroblastoma is predominantly a tumor of early childhood with 66% of the cases presenting in children younger than 5 years of age. The most common symptoms are those due to tumor mass, bone pain, or those caused by excessive catecholamine secretion. In rare cases, neuroblastoma can be identified prenatally (R. W. Jennings et al., (1993) *J Ped. Surgery*, 28, 1168–1174). Approximately 70% of all patients with neuroblastoma have metastatic disease at diagnosis. The prognosis is dependent on age at diagnosis, clinical stage and other parameters.

For diagnostic purposes there is a high interest in reliable and sensitive methods of tumor cell detection, e.g. in control of autologous bone marrow transplants or on-going therapy.

Since catecholamine synthesis is a characteristic property of neuroblastoma cells and bone marrow cells lack this activity (H. Naito et al., (1991) *Eur. J Cancer*, 27, 762–765), neuroblastoma cells or metastasis in bone marrow can be identified by detection of human tyrosine 3-hydroxylase (E.C. 1.14.16.2, hTH) which catalyzes the first step in biosynthesis of catecholamines.

The expression of hTH can be detected via reverse transcription (RT) polymerase chain reaction (PCR) and the PCR product can be analyzed via MALDI-TOF mass spectrometry.

Materials and Methods

Cell- or Tissue-treatment

Cultured cells were pelleted (10 min. 8000 rpm) and washed twice with PBS (137 mM NaCl, 2.7 mM KCl, 4.3 mM $Na_2HPO_4 \cdot 7 H_2O$, 1.4 mM $KH_2PO_4$ in sterile PEPC water). The pellet was resuspended in 1 ml lysis/binding buffer (100 mM Tris-HCl, pH 8.0, 500 mM LiCl, 10 mM EDTA, 1% Li-dodecyl sulfate, 5 mM DTT) until the solution becomes viscose. Viscosity was reduced by a DNA-shear step using a 1 ml syringe. The lysate may be stored in −75° C. or processed further directly. Solid tissues (e.g. patient samples) have to be homogenized before lysis.

Preparation of Magnetic Oligo-dT(25) Beads

100 μL beads per $1 \times 10^6$ cells were separated from the storage buffer and washed twice with 200 μL lysis/binding buffer.

Isolation of Poly $A^+$RNA

The cell lysate was added to the prepared beads and incubated for 5 min. at ambient temperature. The beads were separated magnetically for 2–5 min. and washed twice with 0.5 ml LDS (10 mM Tris-HCl, pH 8.0, 0.15 M LiCl, 1 mM EDTA, 0.1% LiDS).

Solid-phase First-strand cDNA Synthesis

The poly $A^+$RNA containing beads were resuspended in 20 μL of reverse transcription mix (50 mM Tris-HCl, pH 8.3, 8 mM $MgCl_2$, 30 mM KCl, 10 mM DTT, 1.7 mM dNTPs, 3 U AMV reverse transcriptase) and incubated for 1 hour at 45° C. (with a resuspension step all ten min.). The beads were separated from the reverse transcription mix, resuspended in 50 μL of elution buffer (2 mM EDTA pH 8.0) and heated to 95° C. for 1 min. for elution of the RNA. The beads with the cDNA first-strand can be stored in TB (0.089 M Tris-base, 0.089 M boric acid, 0.2 mM EDTA pH 8.0), TE (10 mM Tris-HCl, 0.1 mM EDTA, pH 8.0) or 70% ethanol for further processing.

Nested Polymerase Chain Reaction

Beads containing cDNA first-strand were washed twice with 1×PCR buffer (20 mM Tris-HCl pH 8.75, 10 mM KCl, 10 mM $(NH_4)_2SO_4$, 2 mM $MgSO_4$, 0.1% Triton X-100, 0.1 mg bovine serum albumin) and resuspended in PCR mix (containing 100 pmol of each outer primer, 2.5 u Pfu (exo-) DNA polymerase, 200 μM of each dNTP and PCR buffer in a final volume of 50 μL). The mixture was incubated at 72° C. 1 min and amplified by PCR for 30 cycles. For the nested reaction: 1 μL of the first PCR was added as template to a PCR mix (as above but nested primers instead of outer primers) and subjected to the following temperature program:

94° C. 1 min., 65° C. 1 min and 72° C. 1 min for 20 cycles.

Purification of Nested PCR Products

Primers and low-molecular reaction by-products are removed using 10,000 Da cut-off ultrafiltration-unit. Ultrafiltration was performed at 7,500 g for 25 minutes. For every PCR to be purified, 50 μL Strepravidin M-280 Dynabeads (10 mg/ml) were washed twice with 1×BW buffer (5 mM Tris-HCl, pH 7.5, 0.5 mM EDTA, 1 M NaCl), added to the ultrafiltration membrane and incubated under gentle shaking for 15 min. at ambient temperature. The supernatant was removed and the beads were washed twice with 1×BW buffer. 50 μL 25% ammonium hydroxide were added to the beads and incubated at ambient temperature for 10 min. The supernatant was saved, the procedure repeated, both supernatants were pooled and 300 μL ethanol (100%) were added. After 30 min. the DNA was pelleted at 13,000 rpm for 12 min., the pellet was air-dried and resuspended in 600 nl ultrapure water.

MALDI-TOF MS of Nested PCR Products 300 nl sample was mixed with 500 nl of saturated matrix-solution (3-HPA: ammonium citrate=10:1 molar ratio in 50% aqueous acetonitril), dried at ambient temperature and introduced into the mass spectrometer (Vision 2000, Finigan MAT). All spectra were collected in reflector mode using external calibration.

Outer Primers:

hTH1: d(TGT CAG AGC TGG ACA AGT GT SEQ ID NO:47)

hTH2: d(GAT ATT GTC TTC CCG GTA GC SEQ ID NO:48)

Figure 64:
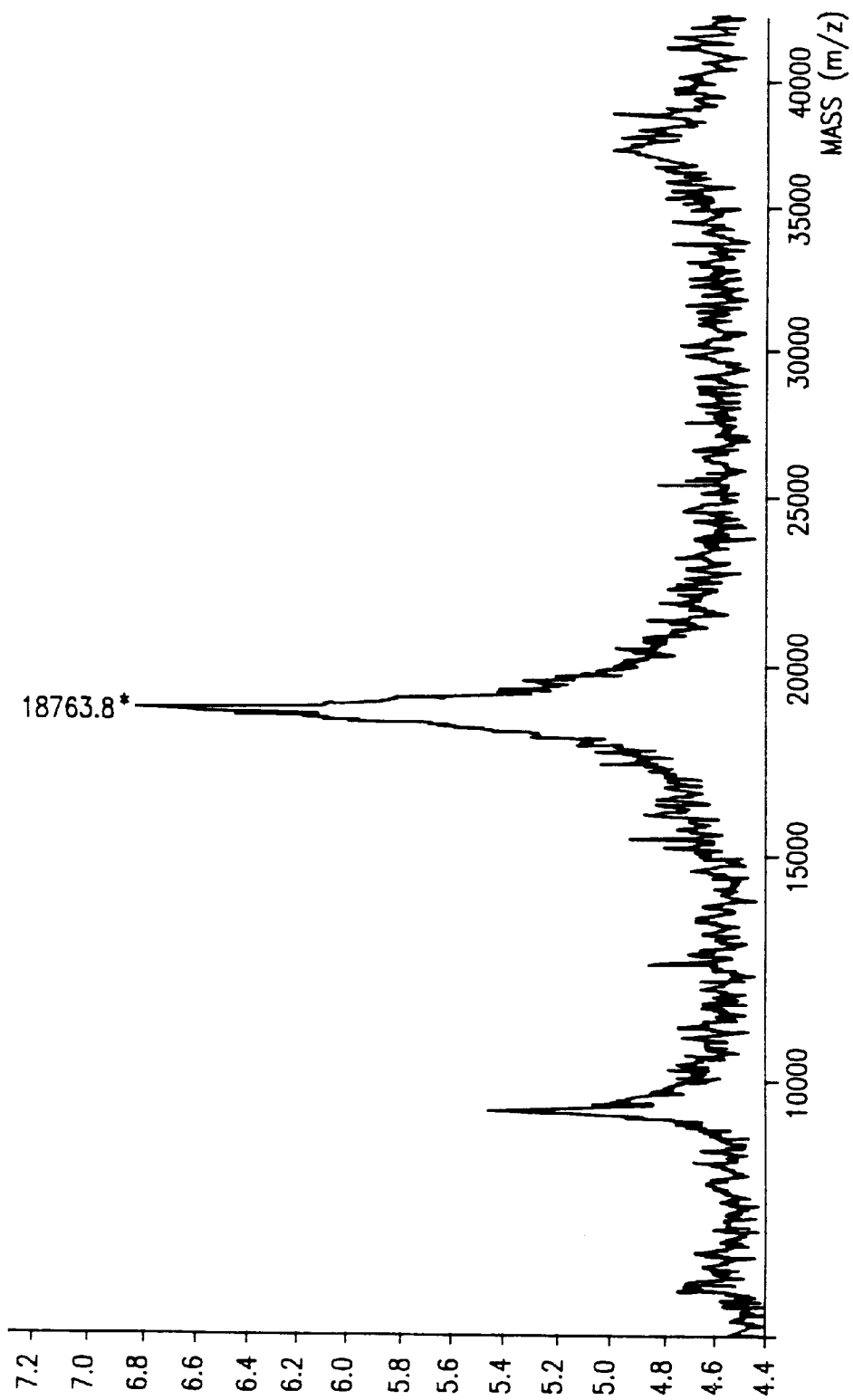
FIG. 64 displays a MALDI-TOF spectrum of the RT-PCR product of the human tyrosine hydroxylase mRNA indicating the presence of neuroblastoma cells (Example 14). The signal at 18,763.8 Da represents the non-biotinylated single-stranded 61 mer of the nested PCR product (calc. 18,758.2 Da).

Nested Primers:

bio-hTH d(bio-CTC GGA CCA GGT GTA CCG CC SEQ ID NO:49), mass: 6485 Da hTH6; d(CCT GTA CTG GAA GGC GAT CTC SEQ ID NO:50), mass: 6422 21 Da mass of biotinylated single strand PCR product: 19253.6 Da mass of nonbiotinylated single strand PCR product: 18758.2 Da Results A MALDI-TOF mass spectrum of a human tyrosine 3-hydroxylase (hTH) specific nested PCR product (61 mer) is depicted in FIG. 64. The signal at 18763 Da corresponds to non-biotinylated strand of the PCR product (calculated: 18758.2 Da, mass error: 0.02 Da). The signals below 10,000 and above 35,000 Da are due to multiply charged and dimeric PCR product-ions, respectively.

The product was obtained from a solid phase cDNA derived in a reverse transcription reaction from $1 \times 10^6$ cells of a neuroblastoma cell-line (L-A-N-1) as described above. The cDNA first-strand was subjected to a first PCR using outer primers (hTH1 and hTH2), an aliquot of this PCR was used as template in a second PCR using nested primers (biohTH and hTH6). The nested PCR product was purified and MALDI-TOF MS analyzed:

The spectrum in FIG. 64 demonstrates the possibility of neuroblastoma cell detection using nested RT-PCR and MALDI-TOF MS analysis.

EXAMPLE 15

Rapid Detection of the RET Proto-oncogene Codon 634 Mutation Using Mass Spectrometry Materials and Methods Probe The identity of codon 634 in each of the three alleles was confirmed by RsaI enzymatic digestion, single strand conformational polymorphism or Sanger sequencing. Exon 11 of the RET gene was PCR amplified (40 cycles) from genomic DNA using Taq-Polymerase (Boehringer-Mannheim) with 8 pmol each of 5'-biotinylated forward (5'-biotin-CAT GAG GCA GAG CAT ACG CA SEQ ID NO:51) and unmodified reverse (5'-GAC AGC AGC ACC GAG ACG AT SEQ ID NO:52) primer per tube; PCR products were purified using the Qiagen "QIAquick" kit to remove unincorporated primers. 15 μl of PCR product were immobilized on 10 μL (10 mg/mL) Dynal streptavidin coated magnetic beads, denatured using the manufacturer's protocol, and the supernatant containing antisense strand discarded. The PROBE reaction was performed using ThermoSequenase (TS) DNA Polymerase (Amersham) and Pharmacia dNTP/ddNTPs. 8 pmol of extension primer (5'-CGG CTG CGA TCA CCG TGC GG-3' SEQ ID NO:53) was added to 13μL $H_2O$, 2 μL TS-buffer, 2 μL 2mM ddATP (or ddTTP), and 2 μL of 0.5 mM dGTP/dCTP/dTTP (or dGTP/dCTP/dATP), and the mixture heated for 30 sec @ 94° C., followed by 30 cycles of 10 sec @ 94° C. and 45 sec @ 50° C.; after a 5 min incubation @ 95 ° C., the supernatant was decanted, and products were desalted by ethanol precipitation with the addition of 0.5 μL of 10 mg/mL glycogen. The resulting pellet was washed in 70% ethanol, air dried, and suspended in 1 μL $H_2O$. 300 nL of this was mixed with the MALDI matrix (0.7 M 3-hydroxypicolinic acid, 0.07 M ammonium citrate in 1:1 $H_2O:CH_3CN$) on a stainless steel sample probe and air dried. Mass, spectra were collected on a Thermo Bioanalysis Vision 2000 MALDI-TOF operated in reflectron mode with 5 and 20 kV on the target and conversion dynode, respectively. Experimental masses ($M_r$(exp)) reported are those of the neutral molecules as measured using external calibration.

Direct Measurement of Diagnostic Products

PCR amplifications conditions for a 44 bp region containing codon 634 were the same as above but using Pfu polymerase; the forward primer contained a ribonucleotide at its 3'-terminus (forward, 5'-GAT CCA CTG TGC GAC GAG C (SEQ ID NO:54) -ribo; reverse, 5'-GCG GCT GCG ATC ACC GTG C (SEQ ID NO:55). After product immobilization and washing, 80 μL of 12.5% $NH_4OH$ was added and heated at 80° C. overnight to cleave the primer from 44-mer (sense strand) to give a 25-mer. Supernatant was pipetted off while still hot, dried, resuspended in 50 μL $H_2O$, precipitated, resuspended, and measured by MALDI-TOF as above. MALDI-FTMS spectra of 25-mer synthetic analogs were collected as previously described (Li, Y. et al., (1996) Anal. Chem. 68:2090–2096); briefly, 1–10 pmol DNA was mixed 1:1 with matrix on a direct insertion probe, admitted into the external ion source (positive ion mode), ionized upon irradiance with a 337 nm wavelength laser pulse, and transferred via rf-only quadrupole rods into a 6.5 Tesla magnetic field where they were trapped collisionally. After a 15 second delay, ions were excited by a broadband chirp pulse and detected using 256K data points, resulting in time domain signals of 5 s duration. Reported (neutral) masses are those of the most abundant isotope peak after subtracting the mass of the charge carrying proton (1.01 Da).

Results

The first scheme presented utilizes the PROBE reaction shown schematically in FIG. 65. A 20-mer primer is designed to bind specifically to a region on the complementary template downstream of the mutation site; upon annealing to the template, which is labeled with biotin and immobilized to streptavidin coated magnetic beads, the PROBE primer is presented with a mixture of three deoxynucleotide triphosphates (dNTPs), a di-dNTP (ddNTP), and a DNA polymerase (FIG. 65). The primer is extended by a series of bases specific to the identity of the variable base in codon 634; for any reaction mixture (e.g. ddA+dT+dC+dG), three possible extension products representing the three alleles are possible (FIG. 65).

For the negative control (FIG. 66), the PROBE reaction with ddATP+dNTPs (N=T, C, G) causes a $M_r$(exp) shift of the primer from 6135 to 6726 Da (Δm=591). The absence of a peak at 6432 rules out a C→A mutation (FIG. 65); the mass of the single observed peak is more consistent with extension by C-ddA ($M_r$(calc) 6721, +0.07% error) than by T-ddA ($M_r$(calc ) 6736, −0.15% error). The PROBE reaction with ddT yields a single peak at 8248 Da, far more consistent with addition of $A_2TC_3G$ as expected for wildtype ($M_r$ (calc)=8246, +0.02% error) than of $A_3TC_2G$ expected for C→A mutant. Combining the ddA and ddT reaction data, it is clear that the negative control is as expected homozygous normal at codon 634.

Figures 65A, 65B:
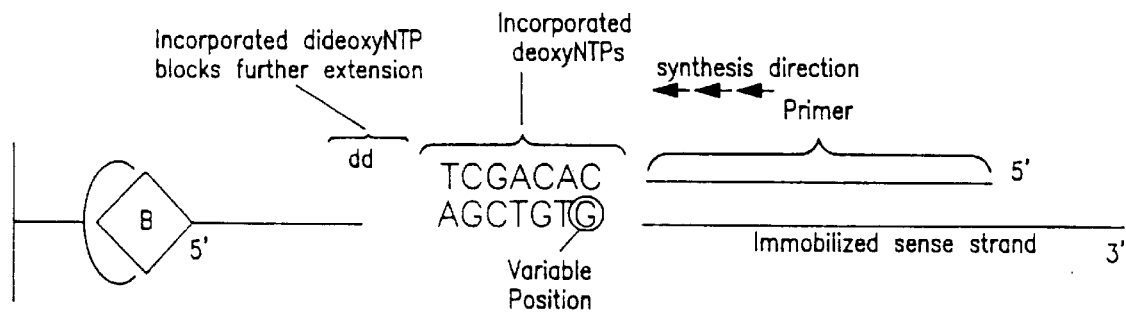
FIG. 65 (a) shows a schematic representaion of a PROBE reaction for the RET proto-oncogene with a mixture of dATP, dCTP, dGTP, and ddTTP (Example 15). B represents biotin, through which the sense template strand is bound through streptavidin to a solid support.
Figure 66A:
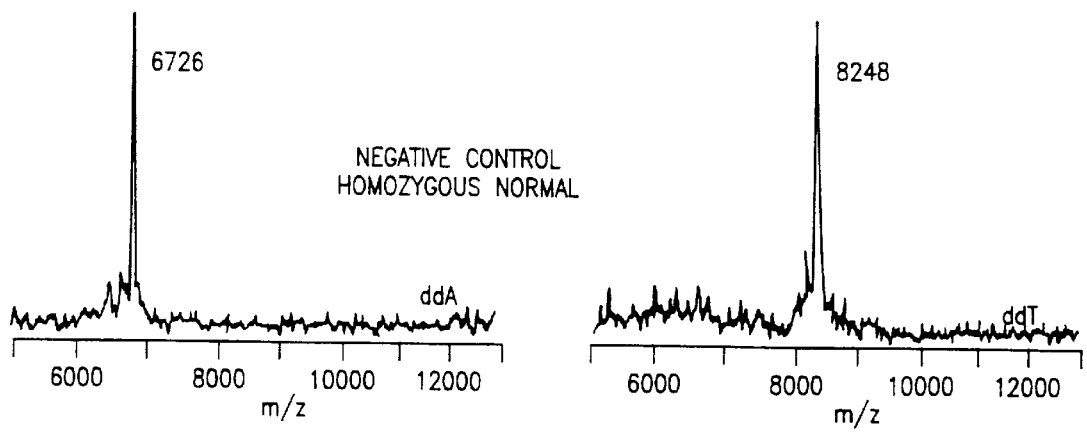
FIG. 66 shows the PROBE product mass spectra for (a) negative control, (b) Patient 1 being heterozygote (Wt/C→T) and (c) Patient 2 being heterozygote (Wt/C→A), reporting average $M_r$ values.
Figure 66B:
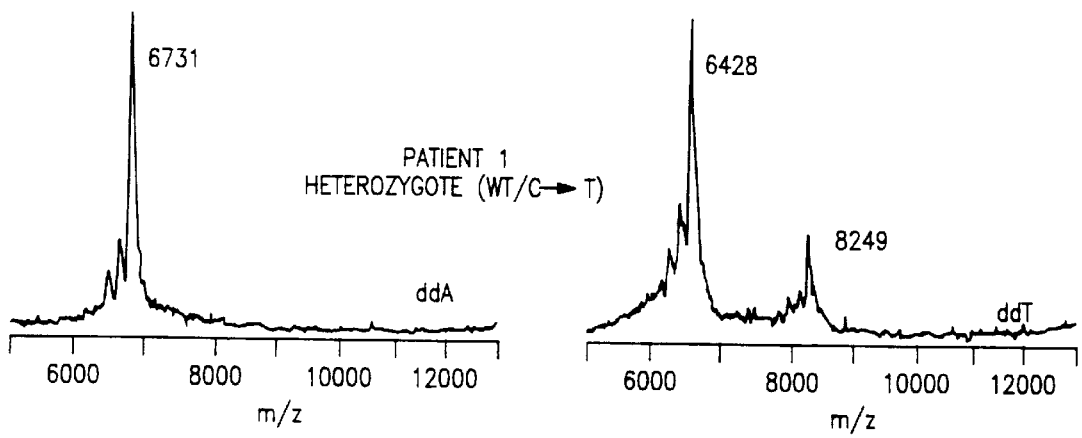
Figure 66C:
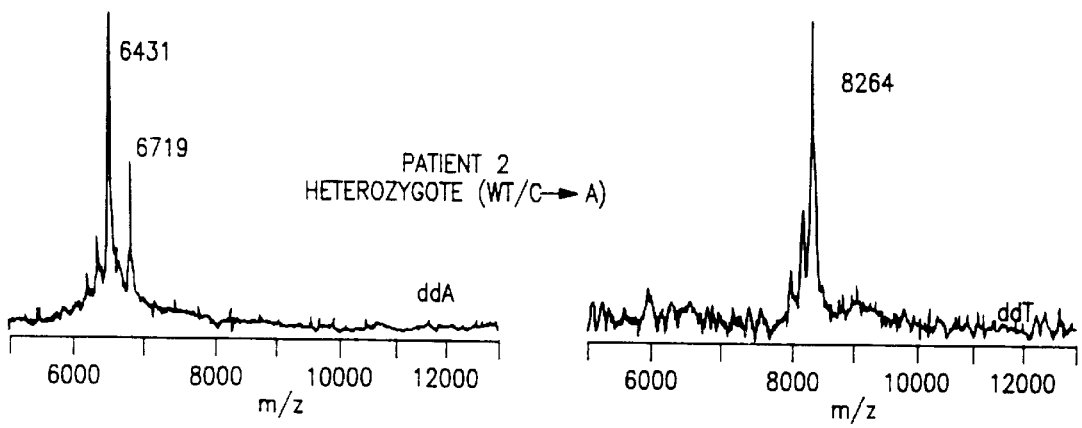
Figure 67A:
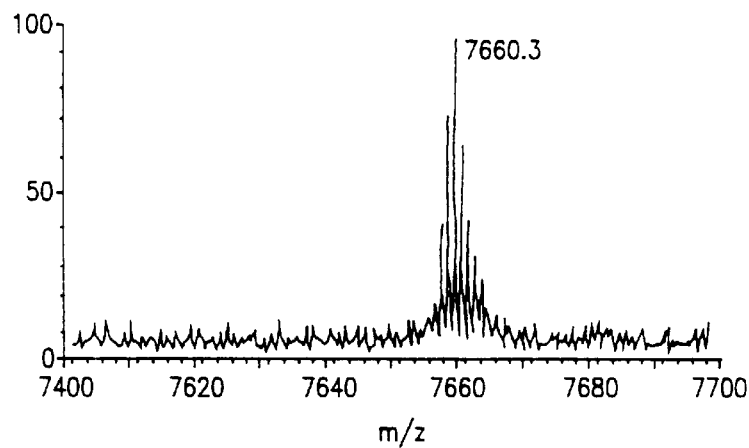
FIG. 67 shows the MALDI-FTMS spectra for synthetic analogs representing ribo-cleaved RET proto-oncogene PCR products from (a) wildtype, (b) G→A, and (c) G→T homozygotes, and (d) wildtype/G→A, (e) wildtype/G→T, and (f) G→A/G→T heterozygotes, reporting masses of most abundant isotope peaks.
Figure 67B:
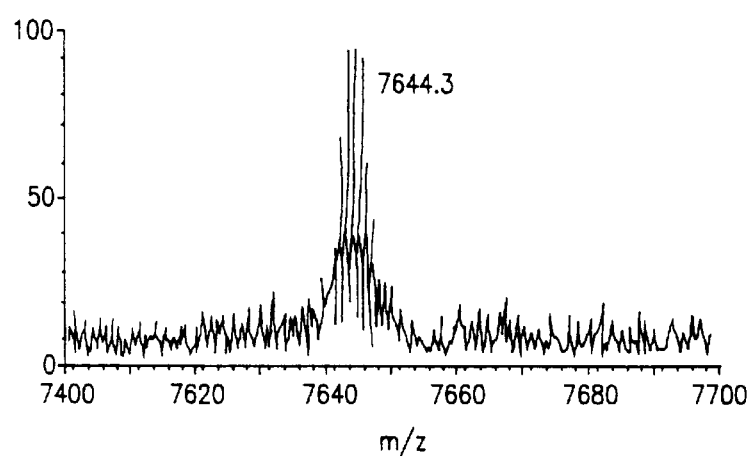
Figure 67C:
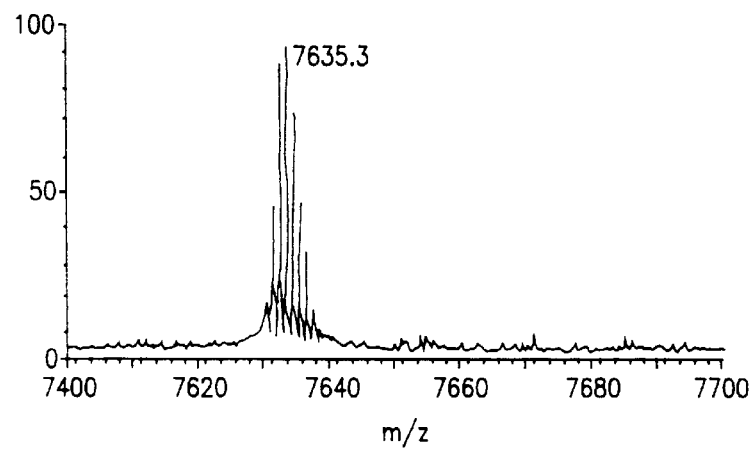
Figure 67D:
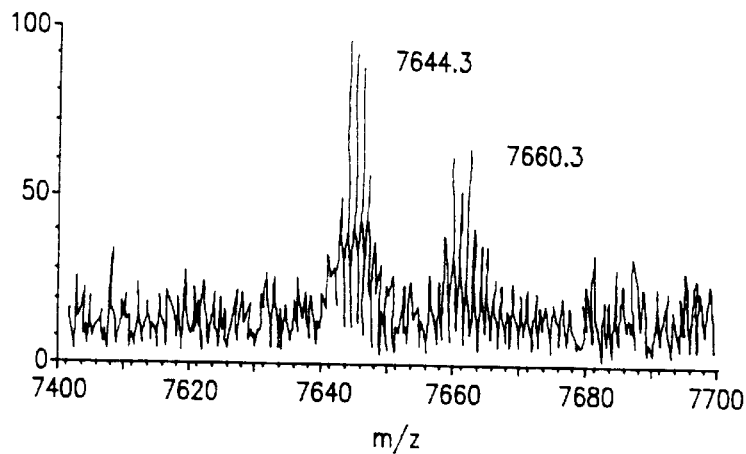
Figure 67E:
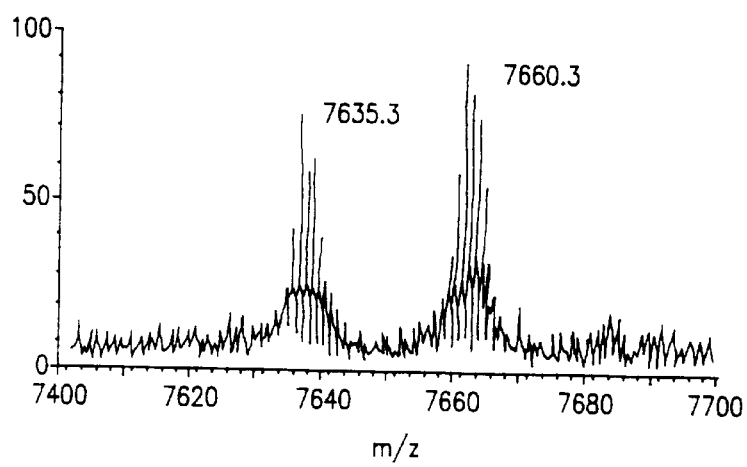
Figure 67F:
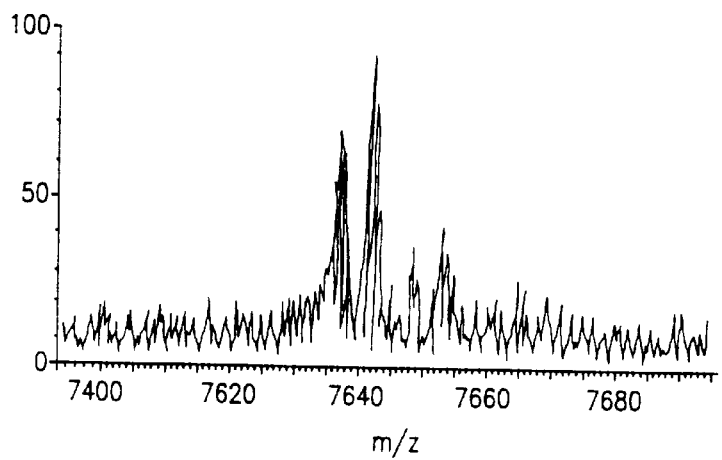

The ddA reaction for patient 1 also results in a single peak ($M_r$(exp)=6731) between expected values for wildtype C→T mutation (FIG. 65*b*). The ddT reaction, however, results in two clearly resolved peaks consistent with a heterozygote wildtype ($M_r$(exp) 8249, +0.04% mass error)/C→T mutant ($M_r$(calc)=8270, 0.27% error); the absence of a peak at 6423 Da excludes the possibility of the aforementioned C→T mutant. Combining the ddA and ddT reaction data, it is clear that the negative control is as expected homozygous normal at codon 634.

The ddA reaction for patient 1 also results in a single peak ($M_r$(exp)=6731) between expected values for wildtype and C→T mutation (FIG. 65b). The ddT reaction, however, results in two clearly resolved peaks consistent with a heterozygote wildtype ($M_r$(exp) 8249, +0.04% mass error)/ C→T mutant ($M_r$(exp) 6428 Da, +0.08% mass error). For patient 2, the pair of FIG. 66c ddA products represent a heterozygote C→A ($M_r$(exp) 6431, −0.06% mass error)/ normal ($M_r$(exp) 6719, −0.03% mass error) allele. The ddT reaction confirms this, with a single peak measured at 8264 Da consistent with unresolved wildtype and C→A alleles. The value of duplicate experiments is seen by comparing FIGS. 66a and 66b; while for patient 1 the peak at 6726 from the ddA reaction represents only one species, a similar peak from patient 1 is actually a pair of unresolved peaks differing in mass by 15 Da.

An alternate scheme for point mutation detection is differentiation of alleles by direct measurement of diagnostic product masses. A 44-mer containing the RET634 site was generated by the PCR, and the 19-mer sense primer removed by $NH_4OH$ cleavage at a ribonucleotide at its 3' terminus.

FIG. 67 shows a series of MALDI-FTMS spectra of synthetic analogs of short PCR products containing the RET634 mutant site. FIGS. 67a–c and 67d–f are homozygous and heterozygous genotypes, respectively. An internal calibration was done using the most abundant isotope peak for the wildtype allele; application of this (external) calibration to the five other spectra resulted in better than 20 ppm mass accuracy for each. Differentiation by mass alone of the alleles is straightforward, even for heterozygote mixtures whose components differ by 16.00 (FIG. 67d), 25.01 (FIG. 67e), or 9.01 Da (FIG. 67f). The value of high performance MS is clear when recognition of small DNA mass shifts is the basis for diagnosis of the presence or absence of a mutation. The recent reintroduction of delayed extraction (DE) techniques has improved the performance of MALDI-TOF with short DNAs (Roskey, M. T. et al., (1996) Anal. Chem. 68:941–946); a resolving power (RP) of >$10^3$ has been reported for a mixed-base 50-mer, and a pair of 31-mere with a C or a T ($\Delta$m 15 Da) at a variable position resolved nearly to baseline. Thus DE-TOF-MS has demonstrated the RP required for separation of the individual components of heterozygotes. Even with DE, however, the precision of DNA mass measurement with TOF is typically 0.1% (8 Da at 8 kDa) using external calibration, sufficiently high to result in incorrect diagnoses. Despite the possibility of space charge induced frequency shifts (Marshall, A. G. and Grosshans, P. B. (1991) Anal. Chem. 63:215A–229A), MALDI-FTMS mass errors are rarely as high as 0.005% (0.4 Da at 8 kDa), making internal calibration unnecessary.

The methods for DNA point mutation presented here are not only applicable to the analysis of single base mutations, but also to less demanding detection of single or multiple base insertions or deletions, and quantification of tandem two, three, or four base repeats. The PROBE reaction yields products amenable to analysis by relatively low performance ESI or MALDI instrumentation; direct measurement of short PCR product masses is an even more direct means of mutation detection, and will likely become more widespread with the increasing interest in high performance MS available with FTMS.

EXAMPLE 16

Efficiency and Specificity Assay for Base-Specific Ribonucleases.

Figure 68:
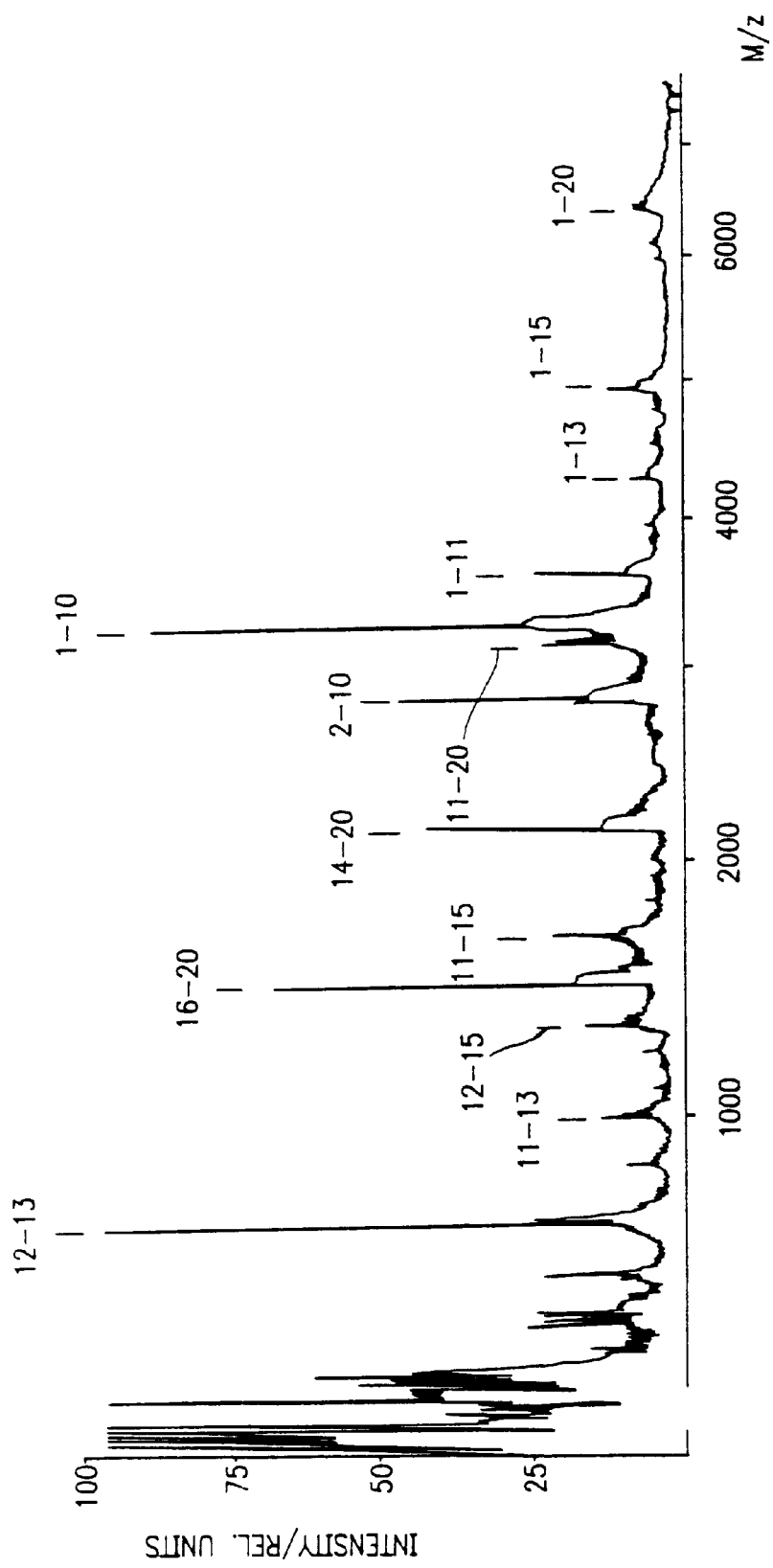
FIG. 68 is a MALDI mass spectrum of an aliquot sampled after a $T_1$ digest of a synthetic 20-mer RNA.
Figure 69:
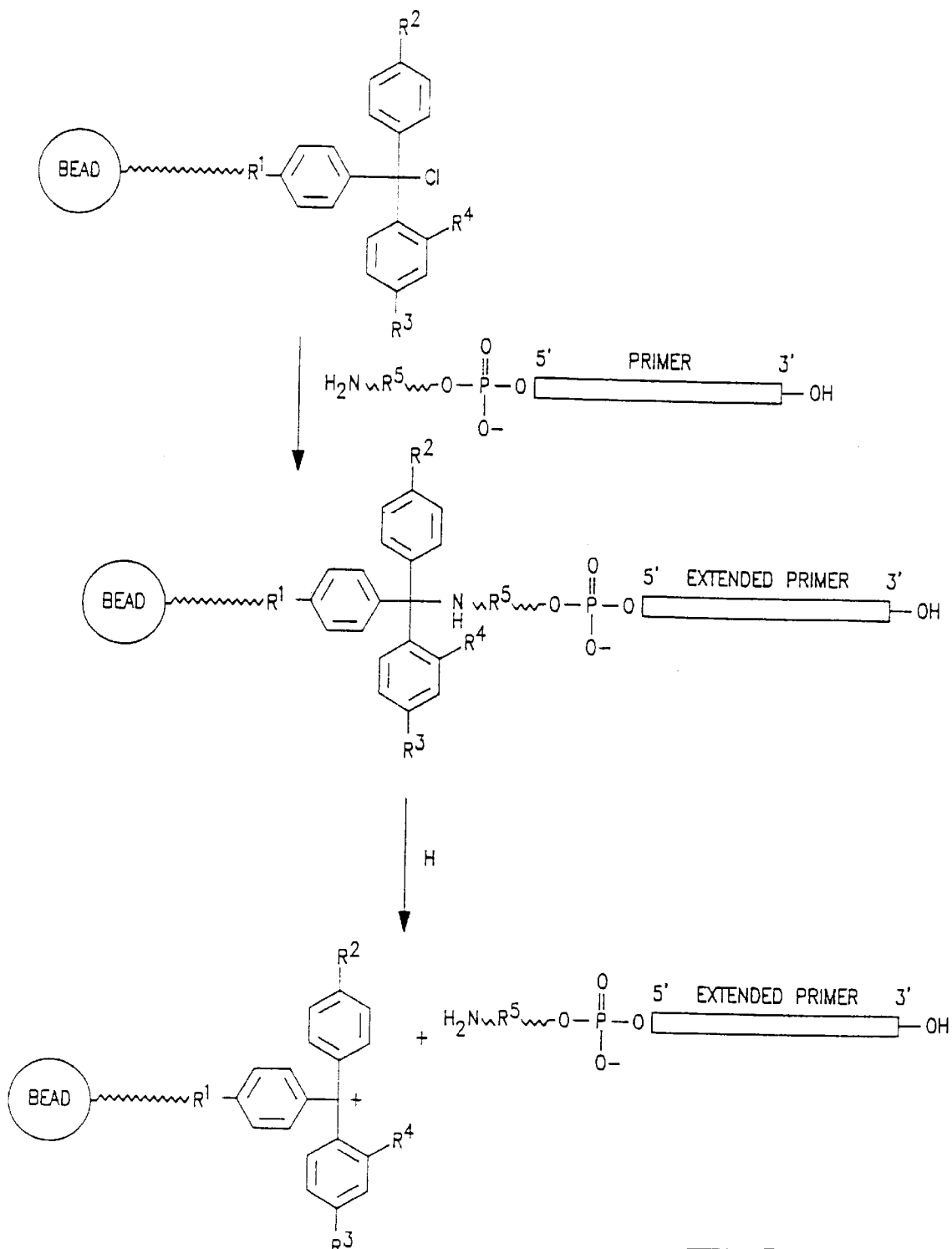
FIG. 69 is a schematic representation of nucleic acid immobilization via covalent bifunctional trityl linkers.
Figure 70:
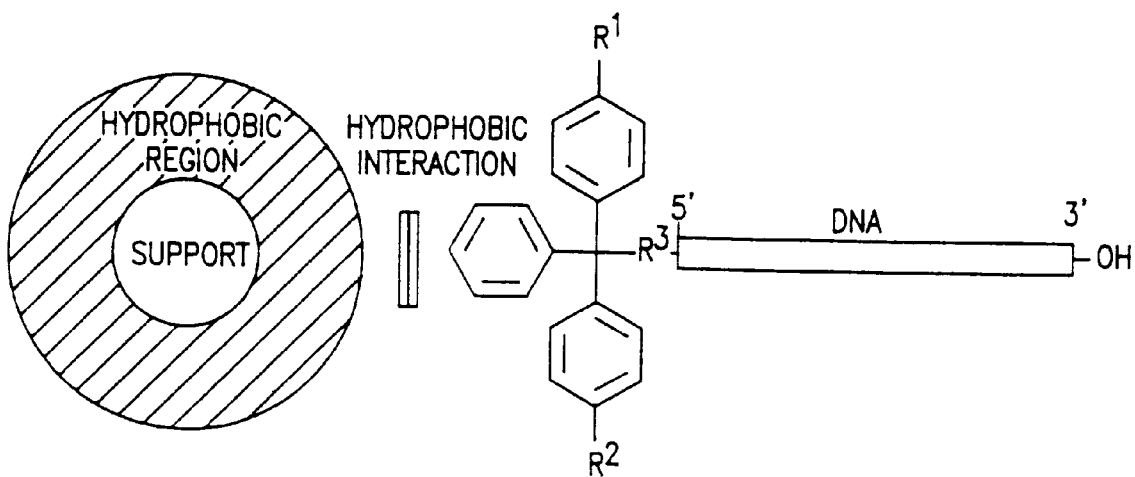
FIG. 70 is a schematic representation of nucleic acid immobilization via hydrophobic trityl linkers.

Aliquots sampled at regular time intervals during digestion of selected synthetic 20 to 25 mers were analyzed by mass spectrometry. Three of the RNAses were found to be both efficient and specific. These include: the G-specific $T_1$, the A-specific $U_2$ and the A/U- specific PhyM. The ribonucleases presumed to be C-specific were found to be less reliable, e.g. did not cleave at every C or also cleaved at U in an unpredictable manner. The three promising RNAses all yielded cleavage at all of the predicted positions and a complete sequence coverage was obtained. In addition, the presence of cleavage products containing one or several uncleaved positions (short incubation times), allowed alignment of the cleavage products. An example of the MALDI-spectrum of an aliquot sampled after a $T_1$ digest of a synthetic 20-mer RNA is shown in FIG. 68.

EXAMPLE 17

Immobilization of Nucleic Acids on Solid Supports via an Acid-labile Covalent Bifunctional Trityl Linker Aminolink DNA was prepared and purified according to standard methods. A portion (10 eq) was evaporated to dryness on a speedvac and suspended in anhydrous DMF/ pyridine (9:1; 0.1 ml). To this was added the chlorotrityl chloride resin (1 eq, 1.05 $\mu$mol/mg loading) and the mixture was shaken for 24 hours. The loading was checked by taking a sample of the resin, detritylating this using 80% AcOH, and measuring the absorbance at 260 nm. Loading was ca. 150 pmol/mg resin.

In 80% acetic acid, the half-life of cleavage was found to be substantially less than 5 minutes—this compares with trityl ether-based approaches of half-lives of 105 and 39 minutes for para and meta substituted bifunctional dimethoxytrityl linkers respectively. Preliminary results have also indicated that the hydroxy picolinic acid matrix alone is sufficient to cleave the DNA from the chlorotrityl resin.

EXAMPLE 18

Immobilization of Nucleic Acids on Solid Supports via Hydrophobic Trityl Linker

The primer contained a 5'-dimethoxytrityl group attached using routine trityl-on DNA synthesis.

C18 beads from an oligo purification cartridge (0.2 mg) placed in a filter tip was washed with acetonitrile, then the solution of DNA (50 ng in 25 $\mu$l) was flushed through. This was then washed with 5% acetonitrile in ammonium citrate buffer (70 mM, 250 $\mu$l). To remove the DNA from the C18, the beads were washed with 40% acetonitrile in water (10 $\mu$l) and concentrated to ca 2 $\mu$l on the Speedvac. The sample was then submitted to MALDI.

The results showed that acetonitrile/water at levels of ca.>30% are enough to dissociate the hydrophobic interaction. Since the matrix used in MALDI contains 50% acetonitrile, the DNA can be released from the support and MALDIed successfully (with the trityl group removed during the MALDI process).

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

We claim:

1. A process for detecting a target nucleic acid sequence present in a biological sample, comprising the steps of:
   a) obtaining a nucleic acid molecule from a biological sample;
   b) immobilizing the nucleic acid molecule onto a solid suppor to produce an immobilized nucleic acid molecule, wherein immobilization is accomplished by hybridization between a complementary capture nucleic acid molecule, which has been previously immobilized to a solid support, and a portion of the nucleic acid molecule, which is distinct from the target nucleic acid sequence;
   c) hybridizing a detector oligonucleotide with the immobilized nucleic acid molecule and removing unhybridized detector oligonucleotide;
   d) ionizing and volatizing the product of step c); and
   e) detecting the detector oligonucleotide by mass spectrometry, wherein detection of the detector oligonucleotide indicates the presence of the target nucleic acid sequence in the biological sample.

2. A process for detecting a target nucleic acid sequence present in a biological sample, comprising the steps of:
   a) obtaining a nucleic acid molecule from a biological sample;
   b) immobilizing the nucleic acid molecule onto a solid suppor to produce an immobilized nucleic acid molecule, wherein immobilization is accomplished via direct bonding between the solid support and a portion of the nucleic acid molecule, which is distinct from the target nucleic acid sequence;
   c) hybridizing a detector oligonucleotide with the immobilized nucleic acid molecule and removing unhybridized detector oligonucleotide;
   d) ionizing and volatizing the product of step c); and
   e) detecting the detector oligonucleotide by mass spectrometry, wherein detection of the detector oligonucleotide indicates the presence of the target nucleic acid sequence in the biological sample.

3. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein prior to step c), the target nucleic acid sequence is amplified.

4. A process of claim 3, wherein the target nucleic acid sequence is amplified by an amplification procedure selected from the group consisting of: cloning, transcription, the polymerase chain reaction, the ligase chain reaction, and strand displacement amplification.

5. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the solid support is selected from the group consisting of: beads, flat surfaces, pins, and combs.

6. A process of claim 5, wherein in step b), immobilization is accomplished by hybridization between an array of complementary capture nucleic acid molecules, which have been previously immobilized to a solid support, and a portion of the nucleic acid molecule, which is distinct from the target nucleic acid sequence.

7. A process of claim 6, wherein the complementary capture nucleic acid molecules are oligonucleotides or oligonucleotide mimetics.

8. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the immobilization is reversible.

9. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the mass spectrometer is selected from the group consisting of: Matrix-Assisted Laser Desorption/Ionization Time-of-Flight, Electrospray, Ion Cyclotron Resonance, and Fourier Transform.

10. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the nucleic acid molecule obtained from a biological sample is replicated into DNA using mass modified deoxynucleoside triphosphates and RNA dependent polymerase prior to mass spectrometric detection.

11. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the nucleic acid molecule obtained from a biological sample is replicated into RNA using mass modified ribonucleoside triphosphates and DNA dependent RNA polymerase prior to mass spectrometric detection.

12. A process for detecting a target nucleic acid sequence present in a biological sample, comprising the steps of:

a) obtaining a nucleic acid molecule from a biological sample;

b) immobilizing the nucleic acid molecule onto a solid suppor to produce an immobilized nucleic acid molecule;

c) hybridizing a detector oligonucleotide with the immobilized nucleic acid molecule and removing unhybridized detector oligonucleotide;

d) ionizing and volatizing the product of step c); and e) detecting the detector oligonucleotide by mass spectrometry, wherein detection of the detector oligonucleotide indicates the presence of the target nucleic acid sequence in the biological sample, wherein the target nucleic acid sequence is indicative of a disease or condition selected from the group consisting of a genetic disease, a chromosomal abnormality, a genetic predisposition, a viral infection, a fungal infection, a bacterial infection and a protist infection.

13. A process for detecting a target nucleic acid sequence present in a biological sample, comprising the steps of:
   a) obtaining nucleic acid molecules potentially containing a target nucleic acid sequence from a biological sample;
   b) amplifying any target nucleic acid sequence in the molecules, thereby obtaining an amplified target nucleic acid sequence;
   c) hybridizing a detector oligonucleotide with the nucleic acid molecules and removing unhybridized detector oligonucleotide;
   d) ionizing and volatizing the product of step c); and
   e) detecting the detector oligonucleotide by mass spectrometry, wherein detection of the detector oligonucleotide indicates the presence of the target nucleic acid sequence in the biological sample.

14. A process of claim 13, wherein the target nucleic acid is amplified by an amplification procedure selected from the group consisting of: cloning, transcription, the polymerase chain reaction, the ligase chain reaction, and strand displacement amplification.

15. A process of claim 13, wherein the nucleic acid molecules comprise DNA.

16. A process of claim 13, wherein the nucleic acid molecules comprise RNA.

17. A process of claim 13, wherein prior to step c) amplified nucleic acid molecules are immobilized onto a solid support to produce immobilized target nucleic acid sequences.

18. A process for detecting a target nucleic acid sequence present in a biological sample, comprising the steps of:
   a) obtaining a nucleic acid molecule from a biological sample;
   b) immobilizing the nucleic acid molecule onto a solid suppor to produce an immobilized nucleic acid molecule;
   c) hybridizing a detector oligonucleotide with the immobilized nucleic acid molecule and removing unhybridized detector oligonucleotide;
   d) ionizing and volatizing the product of step c); and
   e) detecting the detector oligonucleotide by mass spectrometry, wherein detection of the detector oligonucleotide indicates the presence of the target nucleic acid sequence in the biological sample, wherein the target nucleic acid sequence serves as a DNA fingerprint for identifying an individual.

* * * * *

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

Title page,
Item [75], please delete "Kai Tang, Dong-Jing Fu, Carsten W. Siegert, Daniel P. Little, Andreas Braun, Brigitte Darnhofer-Demar, Christian Jurinke and Dirk van den Boom" as inventors.

Item [*] Notice, please insert the following:

-- This patent is subject to a terminal disclaimer. --

Item [56], References Cited, please add the following to the
U.S. PATENT DOCUMENTS:

| | | | | |
|---|---|---|---|---|
| -- 4214159 | 01/22/80 | Hillenkamp et al. | 250 | 288 |
| 4778993 | 10/18/88 | Waugh | 250 | 287 |
| 4920264 | 04/24/94 | Becker | 250 | 282 |
| 5062935 | 11/05/91 | Schlag et al. | 204 | 157.41 |
| 5118605 | 06/02/92 | Urdea | 435 | 6 |
| 5202561 | 04/13/93 | Giessmann et al. | 250 | 281 |
| 5373156 | 12/13/94 | Franzen | 250 | 288 |
| 5376788 | 12/27/94 | Standing et al. | 250 | 287 |
| 5382793 | 01/17/95 | Weinberger et al. | 250 | 288 |
| 5510613 | 04/23/96 | Reilly et al. | 250 | 287 |
| 5625184 | 04/29/97 | Vestal et al. | 250 | 287 |
| 5627369 | 05/06/97 | Vestal et al. | 250 | 287 |
| 5760393 | 06/02/98 | Vestal et al. | 250 | 282 |
| 5777324 | 07/07/98 | Hillenkamp | 250 | 288 |
| 5777325 | 07/07/98 | Weinberger et al. | 250 | 287 |
| 5821063 | 10/13/98 | Patterson et al. | 435 | 6 |
| 5864137 | 06/26/99 | Becker et al. | 250 | 287 |
| 5888775 | 03/23/99 | Haff et al. | 435 | 6 -- |

Please add the following to the FOREIGN PATENT DOCUMENTS:

| | | |
|---|---|---|
| -- 9507361 | 03/16/96 | PCT |
| 9636986 | 11/21/96 | PCT |
| 9636987 | 11/21/96 | PCT |
| 9820019 | 05/14/98 | PCT -- |

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

Column 2,
Line 12, replace "artefacts" with -- artifacts --

Column 3,
Line 56, replace "artherosclerosis" with -- arteriosclerosis --

Column 5,
Line 61, replace "squnce" with -- sequence --

Column 6,
Line 51, replace "capure" with -- capture --

Column 10,
Line 52, in "Tween20" insert a space between "Tween" and "20"

Column 12,
Line 36, replace "flurogram" with -- fluorogram --

Column 14,
Line 5, replace "representaion" with -- representation --

Column 16,
Line 9, replace "dithioerythrol" with -- dithiothreitol --
Line 16, replace "levulinyl" with -- leuvinyl --
Line 50, replace "volatization" with -- volatilization --

Column 21,
Line 10, replace "spectometer" with -- spectrometer --

Column 22,
Line 49, replace "hepatits" with -- hepatitis --
Line 59, replace "ribsomal" with -- ribosomal --
Line 60, replace "indentification" with -- identification --

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

Column 26,
Line 12, replace "umol" with -- $\mu$mol --
Line 17, replace "HCI" with -- HCl --
Line 18, replace "MgCI$_2$" with -- MgCl$_2$ --
Line 18, replace "NaCI" with -- NaCl --
Line 23, in "ammoniumcitrate" insert a space between "ammonium" and "citrate"
Line 26, replace "acetonitril" with -- acetonitrile --
Line 33, replace "ul" with -- $\mu$l --
Line 34, in "ammoniumcarbonate" insert a space between "ammonium" and "carbonate"

Column 27,
Line 9, replace "Perseptive" with -- PerSeptive --

Column 28,
Line 29, replace "choloform" with -- chloroform --
Line 39, replace "HC1" with -- HCl --
Line 39, replace "KC1" with -- KCl --
Line 54, replace "Tris-HC1" with -- Tris-HCl --
Line 54, replace "KC1" with -- KCl --

Column 29,
Line 11, replace "Tris-HC1" with -- KCl --
Line 11, replace "NaC1" with -- NaCl --

Column 30,
Line 29, replace "anlaysis" with -- analysis --

Column 32,
Line 38, in "with30" insert a space between "with" and "30"

Column 33,
Line 44, in "Tween20" insert a space between "Tween" and "20"

Column 34,
Lines 35 and 39, in "Tween20" insert a space between "Tween" and "20"

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

Column 35,
Line 5, replace "didesoxy nucleotide." with -- dideoxynucleotide --.
Line 51, replace "Noo." with -- No. --
Line 53, in "Tween20" insert a space between "Tween" and "20"
Line 53, replace "pH8,8" with -- pH 8.8 --
Line 67, replace "8,75" with -- 8.75 --

Column 36,
Line 17, replace "6,5" with -- 6.5 --
Line 17, replace "0,5" with -- 0.5 --

Column 38,
Line 19, replace "5'-[$^{32}$-P]-labeled" with -- 5'-[$^{32}$P]-labeled --
Line 43, replace "lyophilisation" with -- lyophilization --

Column 41,
Line 4, insert a -- , -- after "obtained"
Line 5, replace "abled" with -- able --
Line 35, replace "Koester" with -- Köster --

Column 44,
Line 16, replace "spectometer" with -- spectrometer --

Column 45,
Line 56, replace "deaza purines" with -- deazapurines --

Column 50,
Line 59, replace "appropiate" with -- appropriate --

Column 52,
Lines 47 and 50, replace "NaCI" with -- NaCl --

Column 56,
Line 4, replace "polyacrylarnide" with -- polyacrylamide --

Column 62,
Line 30, replace "acetonitril" with -- acetonitrile --

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

<u>Column 64,</u>
Line 42, replace "Strepravidin" with -- Streptavidin --
Line 58, replace "acetonitril" with -- acetonitrile --

<u>Column 68,</u>
Line 34, replace "hydroxy picolinic" with -- hydroxypicolinic --

Please amend the claims 1-3, 5, 8-13 and 18 as follows:

1. A process for detecting a target nucleic acid sequence present in a biological sample, comprising the steps of:
a) obtaining a nucleic acid molecule from a biological sample;
b) immobilizing the nucleic acid molecule onto a solid support to
   produce an immobilized nucleic acid molecule, wherein immobilization is
   accomplished by hybridization between a complementary capture nucleic acid
   molecule, which has been previously immobilized to a solid support, and a portion
   of the nucleic acid molecule, which is distinct from the target nucleic acid sequence;
c) hybridizing a detector oligonucleotide with the immobilized nucleic acid
   molecule and removing unhybridized detector oligonucleotide;
d) ionizing and volatilizing the product of step c); and
e) detecting the detector oligonucleotide by mass spectrometry,
   wherein detection of the detector oligonucleotide indicates the
   presence of the target nucleic acid sequence in the biological sample.
2. A process for detecting a target nucleic acid sequence present in a biological sample, comprising the steps of:
a) obtaining a nucleic acid molecule from a biological sample;
b) immobilizing the nucleic acid molecule onto a solid support to
   produce an immobilized nucleic acid molecule, wherein immobilization is
   accomplished via direct bonding between the solid support and a portion of the
   nucleic acid molecule, which is distinct from the target nucleic acid sequence;
c) hybridizing a detector oligonucleotide with the immobilized nucleic acid
   molecule and removing unhybridized detector oligonucleotide;
d) ionizing and volatilizing the product of step c); and
e) detecting the detector oligonucleotide by mass spectrometry,
   wherein detection of the detector oligonucleotide indicates the
   presence of the target nucleic acid sequence in the biological sample.
3. A process for detecting a target nucleic acid sequence present in a biological sample, comprising the steps of:
a) obtaining a nucleic acid molecule from a biological sample;
b) immobilizing the nucleic acid molecule onto a solid support to
   produce an immobilized nucleic acid molecule;

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

c) hybridizing a detector oligonucleotide with the immobilized nucleic acid molecule and removing unhybridized detector oligonucleotide;
d) ionizing and volatilizing the product of step c); and
e) detecting the detector oligonucleotide by mass spectrometry, wherein detection of the detector oligonucleotide indicates the presence of the target nucleic acid sequence in the biological sample, wherein prior to step c), the target nucleic acid sequence is amplified.
5. A process for detecting a target nucleic acid sequence present in a biological sample, comprising the steps of:
a) obtaining a nucleic acid molecule from a biological sample;
b) immobilizing the nucleic acid molecule onto a solid support to produce an immobilized nucleic acid molecule;
c) hybridizing a detector oligonucleotide with the immobilized nucleic acid molecule and removing unhybridized detector oligonucleotide;
d) ionizing and volatilizing the product of step c); and
e) detecting the detector oligonucleotide by mass spectrometry, wherein detection of the detector oligonucleotide indicates the presence of the target nucleic acid sequence in the biological sample, wherein the solid support is selected from the group consisting of: beads, flat surfaces, pins, and combs.
8. A process for detecting a target nucleic acid sequence present in a biological sample, comprising the steps of:
a) obtaining a nucleic acid molecule from a biological sample;
b) immobilizing the nucleic acid molecule onto a solid support to produce an immobilized nucleic acid molecule;
c) hybridizing a detector oligonucleotide with the immobilized nucleic acid molecule and removing unhybridized detector oligonucleotide;
d) ionizing and volatilizing the product of step c); and
e) detecting the detector oligonucleotide by mass spectrometry, wherein detection of the detector oligonucleotide indicates the presence of the target nucleic acid sequence in the biological sample, wherein the immobilization is reversible.
9. A process for detecting a target nucleic acid sequence present in a biological sample, comprising the steps of:
a) obtaining a nucleic acid molecule from a biological sample;
b) immobilizing the nucleic acid molecule onto a solid support to produce an immobilized nucleic acid molecule;

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

c) hybridizing a detector oligonucleotide with the immobilized nucleic acid molecule and removing unhybridized detector oligonucleotide;
   d) ionizing and volatilizing the product of step c); and
   e) detecting the detector oligonucleotide by mass spectrometry, wherein detection of the detector oligonucleotide indicates the presence of the target nucleic acid sequence in the biological sample, wherein the mass spectrometer is selected from the group consisting of: Matrix-Assisted Laser Desorption/Ionization Time-of-Flight, Electrospray, Ion Cyclotron Resonance, and Fourier Transform.

10. A process for detecting a target nucleic acid sequence present in a biological sample, comprising the steps of:
  a) obtaining a nucleic acid molecule from a biological sample;
  b) immobilizing the nucleic acid molecule onto a solid support to produce an immobilized nucleic acid molecule;
  c) hybridizing a detector oligonucleotide with the immobilized nucleic acid molecule and removing unhybridized detector oligonucleotide;
  d) ionizing and volatilizing the product of step c); and
  e) detecting the detector oligonucleotide by mass spectrometry, wherein detection of the detector oligonucleotide indicates the presence of the target nucleic acid sequence in the biological sample, wherein the nucleic acid molecule obtained from a biological sample is replicated into DNA using mass modified deoxynucleoside triphosphates and RNA dependent polymerase prior to mass spectrometric detection.

11. A process for detecting a target nucleic acid sequence present in a biological sample, comprising the steps of:
  a) obtaining a nucleic acid molecule from a biological sample;
  b) immobilizing the nucleic acid molecule onto a solid support to produce an immobilized nucleic acid molecule;
  c) hybridizing a detector oligonucleotide with the immobilized nucleic acid molecule and removing unhybridized detector oligonucleotide;
  d) ionizing and volatilizing the product of step c); and
  e) detecting the detector oligonucleotide by mass spectrometry, wherein detection of the detector oligonucleotide indicates the presence of the target nucleic acid sequence in the biological sample, wherein the nucleic acid molecule obtained from a biological sample is replicated into RNA using mass modified ribonucleoside triphosphates and DNA dependent RNA polymerase prior to mass spectrometric detection.

UNITED STATES PATENT AND TRADEMARK OFFICE
CERTIFICATE OF CORRECTION

PATENT NO. : 6,428,955 B1
DATED : August 6, 2002
INVENTOR(S) : Köster, H.

It is certified that error appears in the above-identified patent and that said Letters Patent is hereby corrected as shown below:

12. A process for detecting a target nucleic acid sequence present in a
 biological sample, comprising the steps of:
  a) obtaining a nucleic acid molecule from a biological sample;
  b) immobilizing the nucleic acid molecule onto a solid support to produce
     an immobilized nucleic acid molecule;
  c) hybridizing a detector oligonucleotide with the immobilized nucleic acid
     molecule and removing unhybridized detector oligonucleotide;
  d) ionizing and volatilizing the product of step c); and
  e) detecting the detector oligonucleotide by mass spectrometry, wherein detection of
the detector oligonucleotide indicates the presence of the target nucleic acid sequence in
the biological sample, wherein the target nucleic acid sequence is indicative of a disease
or condition selected from the group consisting of a genetic disease, a chromosomal abnormality, a genetic predisposition, a viral infection, a fungal infection, a bacterial infection and a protist infection.
13. A process for detecting a target nucleic acid sequence present in a biological sample,
comprising the steps of:
  a) obtaining nucleic acid molecules potentially containing a target nucleic acid
     sequence from a biological sample;
  b) amplifying any target nucleic acid sequence in the molecules, thereby obtaining
     an amplified target nucleic acid sequence;
  c) hybridizing a detector oligonucleotide with the nucleic acid molecules and
     removing unhybridized detector oligonucleotide;
  d) ionizing and volatilizing the product of step c); and
  e) detecting the detector oligonucleotide by mass spectrometry, wherein
     detection of the detector oligonucleotide indicates the presence of the
     target nucleic acid sequence in the biological sample.
18. A process for detecting a target nucleic acid sequence present in a biological sample,
comprising the steps of:
  a) obtaining a nucleic acid molecule from a biological sample;
  b) immobilizing the nucleic acid molecule onto a solid support to produce
     an immobilized nucleic acid molecule;
  c) hybridizing a detector oligonucleotide with the immobilized nucleic acid
     molecule and removing unhybridized detector oligonucleotide;
  d) ionizing and volatilizing the product of step c); and

UNITED STATES PATENT AND TRADEMARK OFFICE
CERTIFICATE OF CORRECTION

PATENT NO.    : 6,428,955 B1
DATED         : August 6, 2002
INVENTOR(S)   : Köster, H.

It is certified that error appears in the above-identified patent and that said Letters Patent is hereby corrected as shown below:

e) detecting the detector oligonucleotide by mass spectrometry,
  wherein detection of the detector oligonucleotide indicates the presence of the target nucleic acid sequence in the biological sample, wherein the target nucleic acid sequence serves as a DNA fingerprint for identifying an individual.

Signed and Sealed this

Twenty-second Day of October, 2002

Attest:

JAMES E. ROGAN
Attesting Officer                Director of the United States Patent and Trademark Office